United States Patent
Duroy et al.

(10) Patent No.: US 12,404,527 B2
(45) Date of Patent: Sep. 2, 2025

(54) CHARACTERIZATION AND INACTIVATION OF ENDOGENOUS RETROVIRUSES IN CHINESE HAMSTER OVARY CELLS

(71) Applicant: Selexis S.A., Plan-les-Ouates (CH)

(72) Inventors: Pierre-Olivier Duroy, Plan-les-Ouates (CH); Sandra Bosshard, Plan-les-Ouates (CH); Philippe Le Mercier, Plan-les-Ouates (CH); Emanuel Schmid-Siegert, Plan-les-Ouates (CH); Nicolas Mermod, Plan-les-Ouates (CH)

(73) Assignee: Selexs S.A., Plan-les-Ouates (CH)

( * ) Notice: Subject to any disclaimer, the term of this patent is extended or adjusted under 35 U.S.C. 154(b) by 954 days.

(21) Appl. No.: 17/417,131

(22) PCT Filed: Dec. 20, 2019

(86) PCT No.: PCT/EP2019/086873
§ 371 (c)(1),
(2) Date: Jun. 22, 2021

(87) PCT Pub. No.: WO2020/136149
PCT Pub. Date: Jul. 2, 2020

(65) Prior Publication Data
US 2022/0090144 A1   Mar. 24, 2022

Related U.S. Application Data

(60) Provisional application No. 62/784,566, filed on Dec. 24, 2018.

(51) Int. Cl.
*C12N 15/90* (2006.01)
*C07K 14/005* (2006.01)
*C12N 15/67* (2006.01)

(52) U.S. Cl.
CPC .......... *C12N 15/907* (2013.01); *C07K 14/005* (2013.01); *C12N 15/67* (2013.01);
(Continued)

(58) Field of Classification Search
CPC .................. C12N 15/907; C12N 15/67; C12N 2740/13021; C07K 14/005
See application file for complete search history.

(56) References Cited

FOREIGN PATENT DOCUMENTS

| WO | 2007130543 A2 | 11/2007 | |
|---|---|---|---|
| WO | WO-2017109177 A1 * | 6/2017 | ........... C07K 14/005 |

OTHER PUBLICATIONS

Gifford, et al., Retrovirology (Aug. 28, 2018) 15:59 p. 2-11 (Year: 2018).*

(Continued)

*Primary Examiner* — Evelyn Y Pyla
*Assistant Examiner* — Katherine R Small
(74) *Attorney, Agent, or Firm* — Agris & von Natzmer LLP; Joyce von Natzmer

(57) ABSTRACT

Type-C endogenous retroviruses (ERVs) embedded in Chinese hamster ovary (CHO) cells were altered to modify the release of retroviral and/or retroviral-like particles in the culture supernatant. Although evidence for the infectivity of these particles is missing, their presence has raised safety concerns. 173 type-C ERV sequences that clustered into functionally conserved groups were identified. Transcripts from one type-C ERV group were identified to be full-length with intact open reading frames, and to have corresponding viral RNA genomes that were loaded into retroviral-like particles. Also, sequence analysis of the genomic RNA from viral particles indicated that they may result from few expressed ERV sequences. Disclosed herein is the disruption/alteration of the gag gene of the expressed ERV group using CRISPR-Cas9 genome editing. Comparison of CRISPR-derived mutations at the DNA and mRNA level led to the identification of a single ERV locus responsible for the release of viral RNA-loaded particles from CHO cells. Clones bearing a Gag loss-of-function mutation in this particular ERV locus showed a reduction of viral RNA-containing particles in the cell supernatant by over 250-fold. Notably, ERV mutagenesis did not compromise cell growth, cell size or recombinant protein production. Provided herein is a new strategy and cells, in particular engineered CHO cells, to mitigate potential contaminations from CHO endogenous retroviruses during biopharmaceutical manufacturing.

23 Claims, 16 Drawing Sheets

Specification includes a Sequence Listing.

(52) U.S. Cl.
 CPC .............. *C12N 2740/10023* (2013.01); *C12N 2740/13021* (2013.01); *C12N 2740/13022* (2013.01)

(56) References Cited

OTHER PUBLICATIONS

L. Yang et al, "Genome-wide inactivation of porcine endogenous retroviruses (PERVs)", Science, vol. 350, No. 6264, Nov. 27, 2015 (Nov. 27, 2015), p. 1101-1104.

Lie Y S et al, "Chinese hamster ovary cells contain transcriptionally active full-length type C proviruses", Journal of Virology, the American Society for Microbiology, US,vol. 68, No. 12, Dec. 1, 1994 (Dec. 1, 1994), p. 7840-7849.

Pierre-Olivier Duroy et al, "Characterization and mutagenesis of Chinese hamster ovary cells endogenous retroviruses to inactivate viral particle release", Biotechnology and Bioengineering, vol. 117, No. 2, Oct. 21, 2019 (Oct. 21, 2019), p. 466-485.

\* cited by examiner

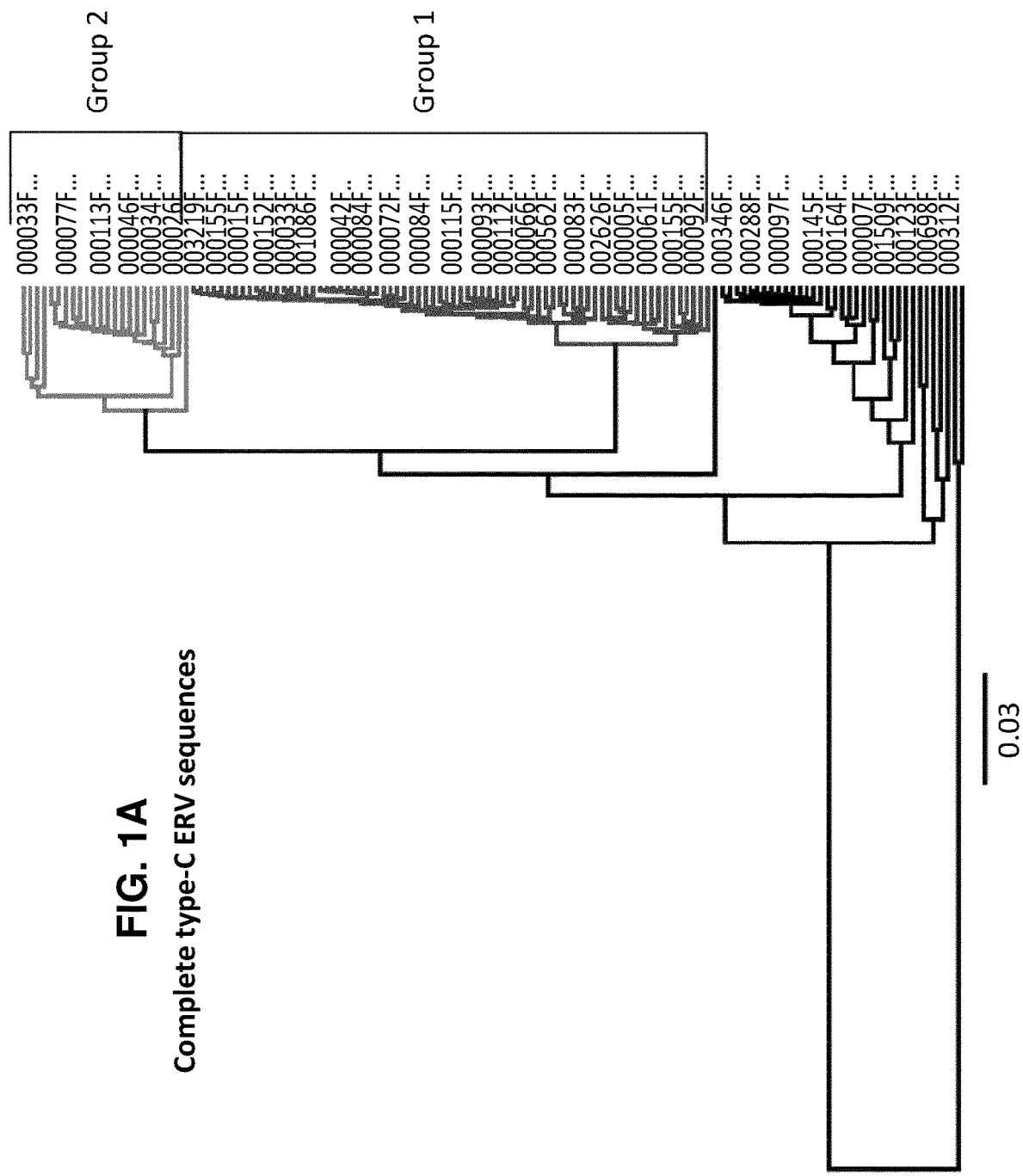

Gag phylogeny

Pol phylogeny

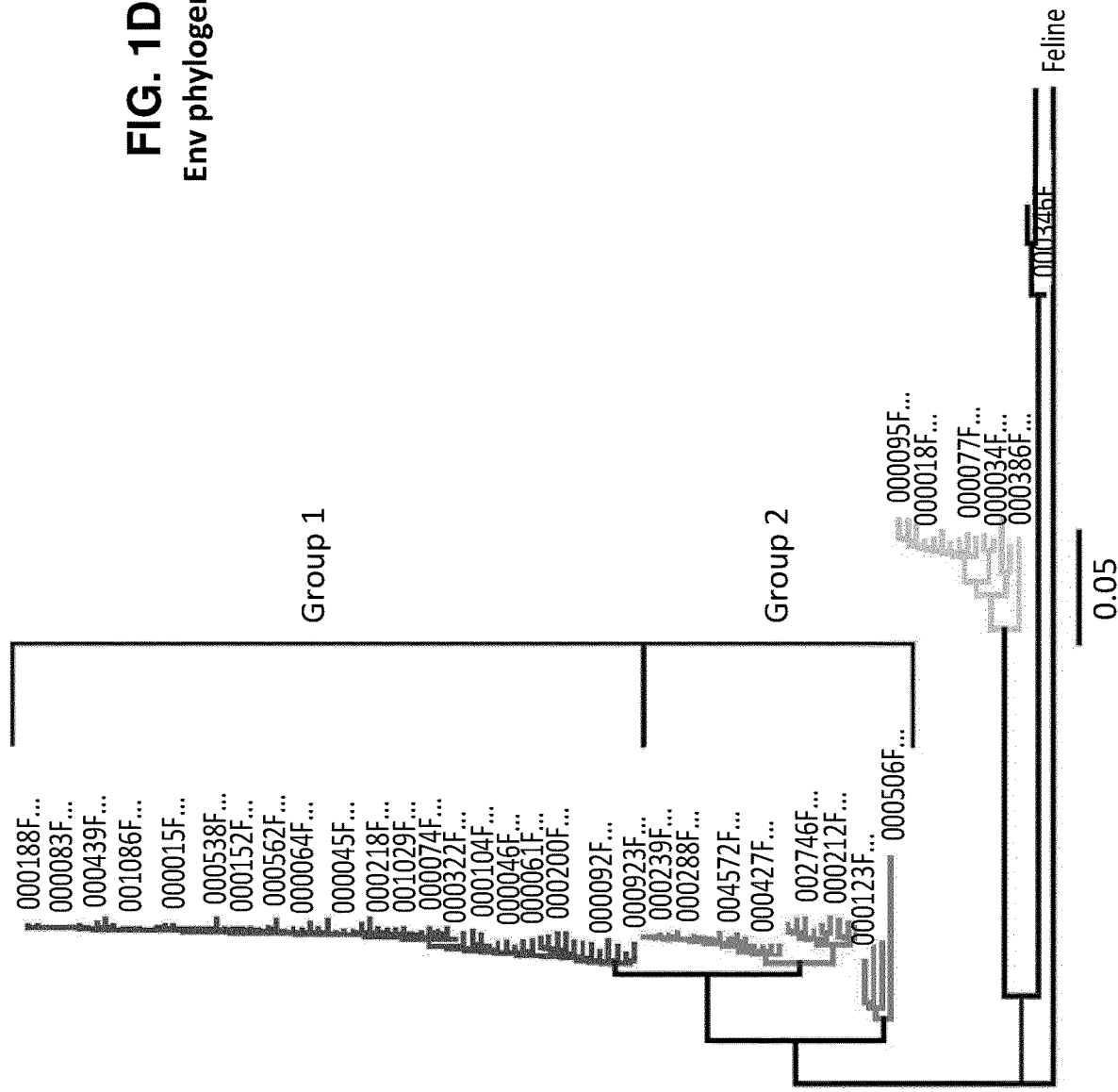

CHARACTERIZATION AND INACTIVATION OF ENDOGENOUS RETROVIRUSES IN CHINESE HAMSTER OVARY CELLS

CROSS-REFERENCE TO RELATED APPLICATIONS

This is the U.S. national stage of international application no. PCT/EP2019/086873, filed Dec. 20, 2019, designating the United States and claiming the benefit of U.S. provisional patent appl. No. 62/784,566, filed Dec. 24, 2018.

INCORPORATION OF SEQUENCE LISTING

The sequence listing was filed as a text file as part of international application no. PCT/EP2019/086873, filed Dec. 20, 2019, is hereby incorporated by reference. An extra copy of this text file named "P100579WO-seg1-000001.txt", which is 268 kilobytes (measured in MS-WINDOWS), dated Jun. 21, 2021 was downloaded from WIPO and is submitted herewith via the USPTO EFS system.

BACKGROUND AND INTRODUCTION

Contamination of biopharmaceutical products by adventitious agents such as viruses can interrupt drug supply and thereby imperil patient safety. Although viral contaminations of biopharmaceuticals are rare, they still occur (1), and mitigating the risk of viral contaminations in therapeutic protein preparations remains a top priority.

Chinese hamster ovary (CHO) cells are the most widely used mammalian expression system for biopharmaceutical products. Among others, CHO cells became a preferred production host in view of their superior safety profile compared to other cell lines used for recombinant protein production. For instance, it was shown that CHO cells possess reduced susceptibility to certain viral infections (1), including resistance to infections elicited by many human as well as murine retroviruses, with some of the latter being known to infect other mammalian cells (2, 3). In addition, CHO cells, unlike other rodent cells, appeared to be unable to produce infective retroviruses that could replicate in mammalian cells, notably in human cells (3-6). However, viral-like particles (VLPs) have been detected both within CHO cells as well as budding off in the culture medium (7-11). The presence of such VLPs raises safety and regulatory concerns, not only because there is a remaining risk of a possible hamster to human endogenous retrovirus (ERV) transmission, but also because they interfere with and reduce the sensitivity of the detection of other adventitious agents.

The publications and other materials, including patents and patent applications, used herein to illustrate the invention and, in particular, to provide additional details respecting the practice the invention are incorporated herein by reference in their entirety. For convenience, the publications are referenced in the following text either by a number for reference to the appended bibliography, by the name of the authors and year published or by the patent/patent publication number.

VLPs were detected independently by several laboratories, suggesting that they result from ERVs that stably integrated into the CHO genome, rather than from an exogenous infection (12). CHO cells possess two classes of ERVs: the intracisternal type-A ERVs (IAP), a defective ERV class forming immature particles in the cisternae of the endoplasmic reticulum (13), and the budding type-C ERVs (6, 12). Although type-C ERV sequences remain incompletely characterized, a previous study estimated that approximately 100-300 type-C ERV sequences may be present in the CHO genome (6). Some of them seemed to be full-length and actively transcribed proviruses, such as the ML2G retrovirus (10, 12). However, the ML2G ERV sequences described by Lie et al., contain frameshift mutations in each of its gene (Gag, Pol and Env), indicating that the specific ERV sequence at this locus is not producing any VLP (12). Nevertheless, this publication indicated that other members of this type of ERV sequence are transcribed and may produce VLP. The ML2G transcript shares approximately 64% sequence identity to the murine leukemia virus (MLV) family.

CHO cells are generally believed to produce non-infective retroviral particles, as their infectivity could not be demonstrated. Nevertheless, the risk that at least one of the uncountable predicted type-C ERV proviruses in the CHO genome is or becomes infective cannot be excluded. This may happen if epigenetically silenced ERVs become expressed, as was observed upon some chemical treatments (14), if dysfunctional ERVs may acquire gain-of-function mutations or if ERVs recombine or trans complement each other. Such genetic changes are more likely to occur in immortalized cell lines, such as CHO cells, which have an overall increased genetic instability (15). Notably, the close similarity of CHO type-C ERVs to the MLV family, a retrovirus family known to cross the species barrier and to infect even primate cells (16), further indicates that CHO particles may have the potential to become pathogenic for humans, as seen for other retroviruses (17). Finally, CHO cell VLP were reported to contain viral genomic RNA sequences related to type-C retroviruses, as expected of viral particles (VP) (De Wit, C., Fautz, C., & Xu, Y. (2000). Real-time quantitative PCR for retrovirus-like particle quantification in CHO cell culture. *Biologicals,* 28(3), 137-148). However, the ERV sequences responsible for the release of the VLPs and VPs by CHO cells have remained uncharacterized. Hence strategies to avoid viral contaminations originating from CHO endogenous sources are highly desirable.

The most promising strategy to efficiently prevent hamster ERV transmission is to inactivate retroviruses using CRISPR-Cas9-mediated mutagenesis. The programmable CRISPR-Cas9 RNA-guided nuclease system has already been employed to introduce DNA double strand breaks (DSBs) into proviral sequences in human and porcine cells (18, 19). Imprecise DSB repair may lead to insertions and deletions within the viral sequences and inhibit viral activity. In a seminal paper, Yang et al. demonstrated that the CRISPR-Cas9 technology can be used to knock-out all 62 genomic porcine ERV sequences resulting in a more than 1000-fold reduction of ERV infectivity (19). Although successful, viral inactivation remains technically challenging, due to high cytotoxicity, frequent genomic rearrangements and low editing efficiency (19, 20). One explanation for the reduced editing efficiency of multi-loci sites compared to conventional editing of single genes might be the sheer number of ERV-like sequences that could serve as repair templates for precise, mutation-free repair, so antagonizing ERV mutagenesis and promoting chromosomal rearrangements. However, the incomplete characterization of type-C ERV sequences in CHO cells, as well as the absence of a clear link between the genomic type-C ERV sequences and viral particles, have hampered the establishment of a similar ERV inactivation strategy in CHO cells.

US Patent Publication 2019/0194694 A1, filed Dec. 23, 2016 discloses mammalian cells and mammalian cell lines that have a reduced load of remnants of past viral/retroviral infections and methods of producing and using the same. Engineered cells such as engineered CHO-K1 were disclosed therein. The engineering aimed at altering the genome by introducing alterations, preferably a high number of alterations, into ERVs in the genome of the cells to suppress or eliminate the release of VLPs and/or VPs. The complete consensus DNA sequence of functional Group 1 ERVs is shown in SEQ ID NO. 1 of US Patent Publication 2019/0194694 A1. The disclosure of US Patent Publication 2019/0194694 A1 is specifically incorporated herein by reference in its entirety.

There is a need in the art to engineer cells, such as CHO cells, so that they do not release or release substantially no potentially functional VPs. This is in particular of importance when the cells are designed to express any transgene product, in particular proteins with therapeutic activity. There is a need that the resulting engineered cells display little or none decrease in their transgene product production. There is a need in the art to provide such engineered cells, in particular for transgene product production. There is also a need to limit or abolish the presence of incompletely characterized retroviral nucleic acids in CHO culture supernatants. This and other needs are addressed herein.

SUMMARY OF THE INVENTION

The budding type-C ERV sequences at the genome, transcriptome and viral particle level using CHO-K1 cells was characterized in-depth. In contrast to previous studies, transcribed type-C ERV group 1 sequences yielding full-length transcripts with open reading frames were identified, suggesting that this ERV group results in potentially functional retroviruses. Using CRISPR-Cas9 genome editing, the expressed group 1 type-C ERV sequences were mutated, and it could be shown that specific loss-of-function mutations within the gag gene of a single ERV suffices to decrease the release of functional viral RNA-loaded particles more than 250-fold. This indicated that a single ERV locus is responsible for most type-C viral particles released from CHO cells. Altogether, provided herein is a novel strategy to further improve the safety profile of CHO cells, paving the way to a complete eradication of endogenous viral contaminations in cultures of CHO cells producing biotherapeutics (also referred to herein as therapeutic products).

The invention is, in one embodiment, directed at an engineered cell, preferably of a mammalian cell line such as an engineered CHO cell, including an engineered CHO-K1, comprising: a genome of the cell comprising group 1 type-C ERV sequences including at least one full-length group 1 type-C ERV sequence(s) integrated into the genome, wherein the genome comprises one or more, but not more than twenty, including 19, 18, 17, 16, 15, 14, 13, 12, 11, 10, 9, 8, 7, 6, 5, 4, 3, 2 or 1 alteration(s) within one or more gag sequences of the group 1 type-C ERV sequences resulting in one or more altered group 1 type-C ERV sequences, wherein at least one of the alterations is within a gag gene of the at least one full-length group 1 type-C ERV sequence resulting in at least one altered full-length group 1 type-C ERV sequence.

The genome may comprise more than 100, more than 120, 140, 160, 180, 200, 220, 240, 260, 280 or 300 group 1 type-C ERV sequences, including at least one full-length group 1 type-C ERV sequence(s) integrated into the genome.

The at least one full-length group 1 type-C ERV sequence(s) integrated into the genome may correspond to SEQ ID 3 or sequences having more than 90%, 95%, 96%, 97%, 98% or 99% sequence identity therewith.

Of the more than 100, more than 120, 140, 160, 180, 200, 220, 240, 260, 280 or 300 group 1 type-C ERV sequences, more than 10, 20, 30, 40, 50, 60, 70 80, 90, 100 may be full-length group 1 type-C ERV sequence(s).

At least one of the at least one alteration within a gag gene of the at least one full-length group 1 type-C ERV sequence(s) may be a loss-of-function mutation.

The alteration(s) in the at least one full-length group 1 type-C ERV sequence(s) may block(s) translation initiation or may introduce a frameshift in the gag gene downstream of a PPYP motif.

The alteration(s) may be within the gag gene of not more than one of the full-length group 1 type-C ERV sequence(s), preferably within SEQ ID No. 3 more preferably within the Myr and/or PPYP Gag budding motifs or a sequence up to 5, 10, 15, 20, 25, 30, 35, 40, 45 or 50 nucleotides, including consecutive nucleotides, 5' and/or 3' of the Myr and/or PPYP Gag budding motifs.

The alteration(s) may comprise(s) a deletion of equal to or more than 1, 2, 3, 4, 5, 6, 7, 8, 9, 10 nucleotide(s), equal to or more than 1%, 2%, 3%, 4%, 5%, 10%, 20%, 30%, 40%, 50%, 60%, 70%, 80%, 90% or 100% consecutive nucleotides of SEQ ID NO: 3 or a sequence having more than 95%, 96%, 97%, 98%, 99% sequence identity therewith from the genome and optionally alterations in, including deletions of, nucleotide 1 to 30020, and 39348 to 59558 of Seq ID NO: 1.

Disclosed herein is also an engineered cell, preferably of a mammalian cell line such as an engineered CHO cell, including an engineered CHO-K1 cell, comprising:
  a genome of the cell comprising:
  a sequence comprising a gag gene, an env gene, a pol gene and long terminal repeats (LTR), and comprising at least one alteration in the gag gene, env gene, pol gene and/or the LTRs, wherein the sequence is selected from:
  (i) SEQ ID NO: 3,
  (ii) SEQ ID NO: 1,
  (iii) a variant of (i) or (ii); or
  (iv) a sequence having more than 95%, 96%, 97%, 98%, 99% sequence identity with (i) and/or (ii) outside the gag, env, pol gene and/or the LTRs,
said at least one alteration being selected from the group consisting of insertions, deletions, substitutions and combinations thereof.

The at least one alteration may be in the gag, env, pol gene and/or the LTRs is in not more than 100, 90, 80, 70, 60, 50, 40, 30, 20, 15, 10, 5, 4, 3, 2 nucleotides including consecutive nucleotides, or 1 nucleotide of the gag, env, pol gene and/or the LTRs.

Also disclosed herein is an engineered cell preferably of a mammalian cell line such as an engineered CHO cell, including an engineered CHO-K1 cell, wherein the genome comprises:
(i) not more than 10%, 20%, 30%, 40%, 50% consecutive nucleotides of SEQ ID NO: 3, or
(ii) a sequence having more than 90% sequence identity with (i).

The alteration(s) in the at least one full-length group 1 type-C ERV sequence(s) may be in the gag gene, that comprises a PPYP motif and wherein (i) sequences encoding the PPYP motif and/or a sequence up to 5, 10, 15, 20, 25, 30, 35, 40, 45 or 50 nucleotides, including consecutive nucleotides, 5' and/or 3' flanking the sequences in (i) may comprise the alteration(s).

The genome may comprise not more than 15, 14, 13, 12, 11, 10, 9, 8, 7, 6, 5, 4, 3, 2, 1 alteration(s) in the group 1 type-C ERV sequences.

The genome may comprise not more than 15, 14, 13, 12, 11, 10, 9, 8, 7, 6, 5, 4, 3, 2, 1 altered group 1 type-C ERV sequences.

The alteration(s) may be deletions, insertions, substitutions or combinations thereof, preferably alterations of the N-terminal Myr motif-encoding DNA sequence, such as one or several mutations that may inhibit the myristoylation of the GAG protein by removing or substituting the amino-terminal glycine residue, or a PPYP mutation that may inhibit the release of viral particles from the host cell, or one or several frameshift mutations that may infer with a translation of the gag mRNA into a full-length GAG protein.

The alteration(s) may be frameshift mutation(s).

The invention is, in a further embodiment, directed at an engineered cell, preferably of a mammalian cell line such as an engineered CHO cell, including an engineered CHO-K1, comprising:
a genome of the cell comprising group 1 type-C ERV sequences integrated into the genome, wherein at least one, including a singular, full-length group 1 type-C ERV sequence, such as SEQ ID NO: 3 or at least 10%, 20%, 30%, 40%, 50%, 60%, 70% 80% 90% or 100% consecutive nucleotides of SEQ ID NO: 3, and
optionally, 5' and/or 3' flanking regions of SEQ ID NO: 3 (i.e., sequences located 5' and/or 3' of SEQ ID NO: 3 in the genome), including 1-50, 30-100, 50-150, 100-200 or more than 200, 300, 400 or more than 500 consecutive nucleotides flanking SEQ ID NO: 3 are deleted from the genome.

The flanking regions may be SEQ ID NO: 4 and SEQ ID NO:5, respectively.

The genome of the cell may comprise: (i) at least 80%, 90%, 95%, 98%, 99% or 100% consecutive nucleotides of SEQ ID NO: 4 or sequences having at least 90%, 95%, 98% or 99% sequence identity therewith and, directly adjacent thereto, at least 80%, 90%, 95%, 98%, 99% or 100% consecutive nucleotides of SEQ ID NO: 5 or sequences having at least 90%, 95%, 98% or 99% sequence identity therewith. Preferably, SEQ ID NO: 4 is 5' of SEQ ID NO: 5 in the resulting sequence.

The alteration(s) may be insertions of at least 5, 10, 15, 20, 25, 30, 50 or 100 nucleotides, deletions of at least 5, 10, 15, 20, 25, 30, 50 or 100 nucleotides, including consecutive nucleotides, or combinations thereof or combinations of insertions, substitution and/or deletions resulting together in an addition and/or removal of at least 5, 10, 15, 20, 25, 30, 50 or 100 nucleotides.

The ERV elements may be from gamma or beta retroviral ERVs, including Intracisternal Leukemia Virus, Koala epidemic viral (KoRV), Mouse Mammary Tumor Viral (MMTV), Mouse Leukemia Viral (MLV) ERVs, Feline Leukemia Virus, Gibbon Ape Leukemia Virus, Porcine Type-C Endogenous Retrovirus and/or Intracisternal Leukemia Virus.

The engineered cell may release a number of viral particles (VPs), viral like particles (VLPs) and/or retroviral (like) particles (RV(L)Ps) per unit of time, the number being reduced, preferably more than 2-fold, more preferably more than 10-fold, even more preferably more than 50-fold, more than 100-fold, more than 150-fold, more than 200-fold or more than 250-fold relative to the VPs, VLPs and/or RV(L) Ps per unit of time released by its non-engineered counterpart.

The engineered cell may release no or substantially no VPs and/or VLPs, in particular substantially no RVPs and/or RVLPs.

The engineered cell may further comprise a transgene, preferably integrated into the genome.

The transgene may be a marker gene encoding a marker protein such as GFP (green fluorescent protein), a biotherapeutic and/or a non-coding RNA.

The invention is, in a further embodiment, directed at an engineered cell, preferably of a mammalian cell line such as an engineered CHO cell, including an engineered CHO-K1, comprising:
a genome of the cell comprising SEQ ID NO: 3 or a variant thereof, and further comprising a sequence encoding a siRNA, wherein a target sequence of the siRNA is located within SEQ ID NO:3, preferably within a sequence of SEQ ID NO:3 or a variant thereof, more preferably within sequence of SEQ ID NO: 3 encoding the Gag precursor protein or a variant thereof.

The invention is, in a further embodiment, directed at a method for producing a transgene product comprising:
providing the engineered cell(s) of any one of the preceding claims,
introducing at least one transgene encoding the transgene product, such as a biotherapeutic, into the engineered cell, and
expressing the at least one transgene in the cell, wherein said engineered cell releases no or substantially no VLPs.

Disclosed is also a detection kit and its use comprising:
(i) at least one primer against SEQ ID NO: 3, and/or
(ii) at least one primer against SEQ ID NO: 4 or 5, and instructions how to use the primers of (i) and/or (ii) to detect the presence or absence of SEQ ID NO: 1, of SEQ ID NO: 3 from a genome of a CHO cell or a mutation within SEQ ID NO: 3 of the genome of the CHO cell.

Indel mutation analysis of polyclonal PCR products obtained from reverse-transcribed cellular mRNA of bulk-sorted CRISPR-treated polyclonal populations using the indicated group 1 type-C specific primers. The mutation frequency was estimated by decomposition of the Sanger chromatogram (28). The predicted mutation frequency relative to the untreated wild-type control sample is shown on the right of the chromatograms. The DSB site for each sgRNA is shown with a black line and the decomposition window, downstream of the DSB site relative to the sequencing direction indicated by an arrow, is shaded in grey. The Myr motif shown corresponds to nucleotides 10-71 of SEQ ID NO: 86. The PPYP motif shown corresponds to nucleotides 21-98 of SEQ ID NO: 76.

Figure 9:
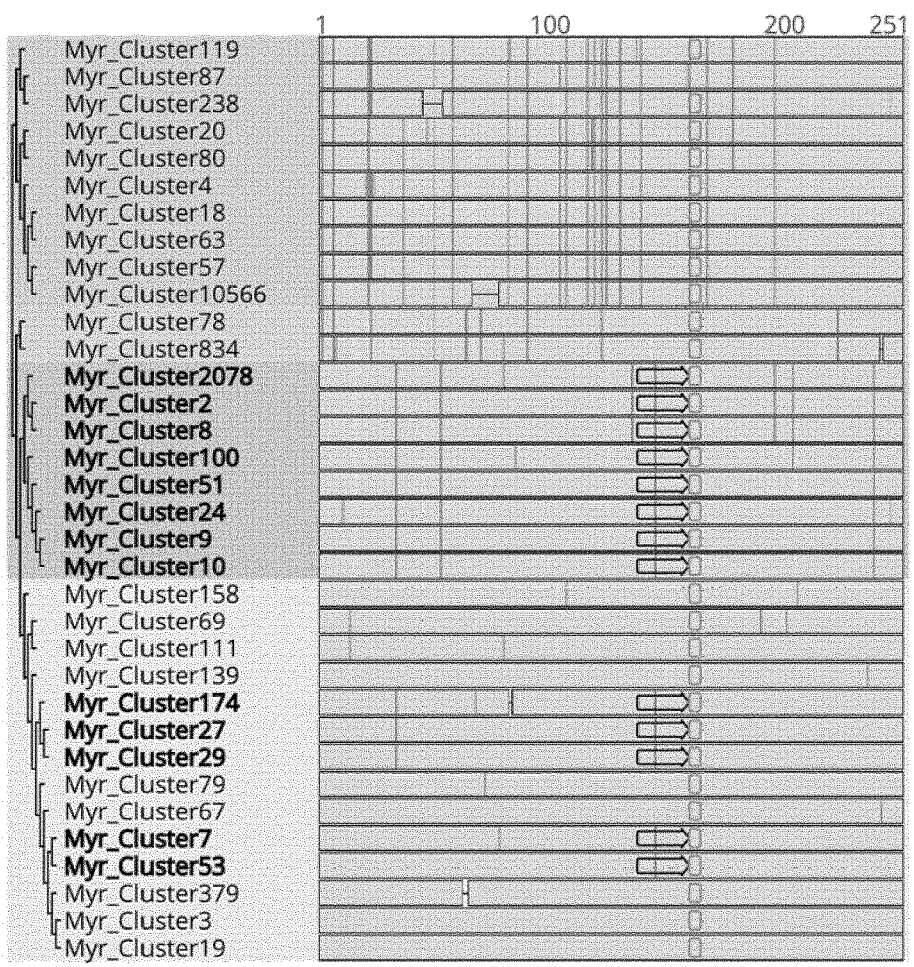
Figure 9:
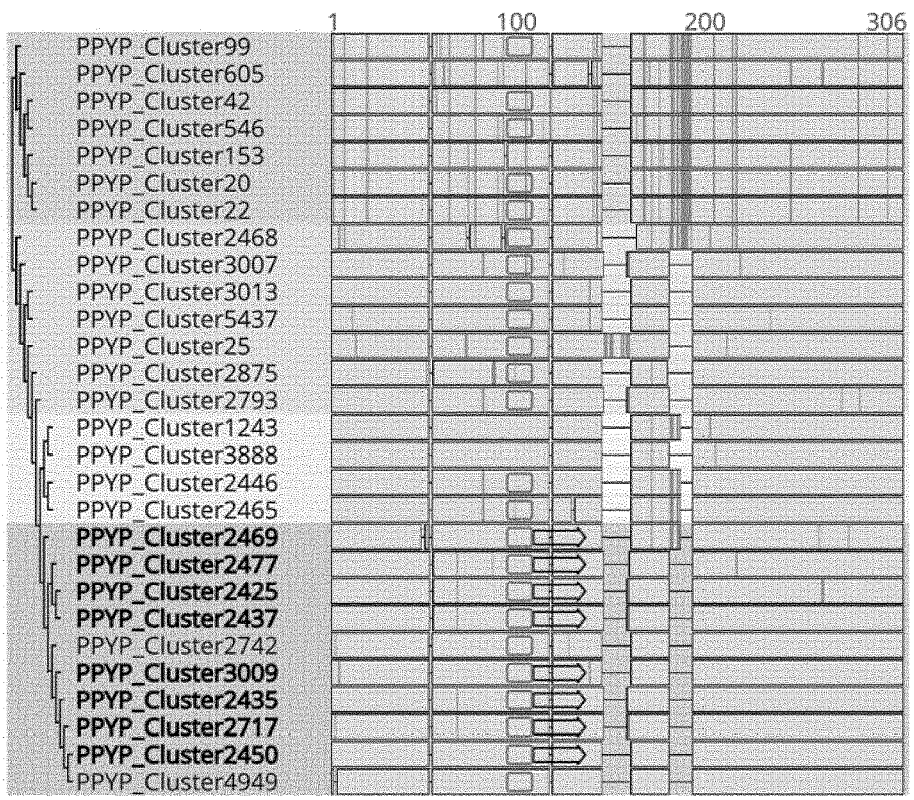

FIG. 9. Wild-type CHO consensus sequences of Myr and PPYP diversity clusters. Cluster sequences of Myr (A) and PPYP (B) flanking regions of deep-sequenced wild-type CHO cells. Shades correspond to the phylogenetic groups depicted in FIGS. 4A and 4B. Myr and PPYP clusters containing a sgRNA recognition site (black outlined arrow) with an adjacent PAM sequence are written in bold letters. Myr and PPYP motifs are indicated with very light grey and dark grey outlined boxes, respectively. The higher sequence complexity of the PPYP flanking region relative to the Myr flanking region is illustrated by missing sequences or lines depicting deletions or insertions and single nucleotide variants, respectively.

Figure 10:
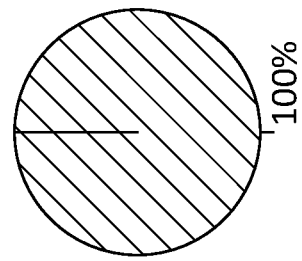
Figure 10:
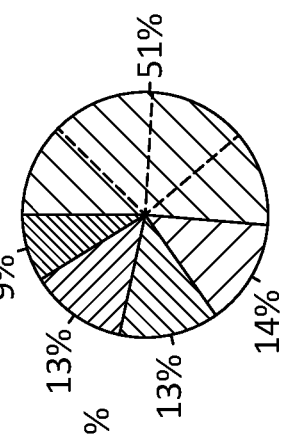
Figure 10:
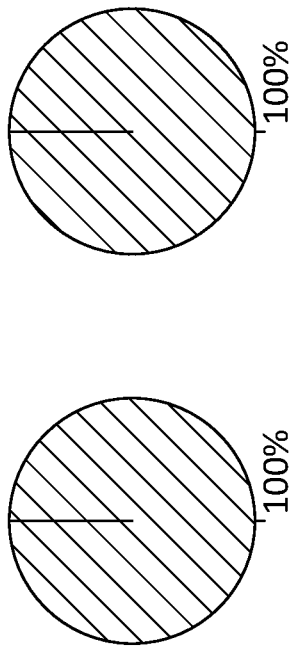
Figure 10:
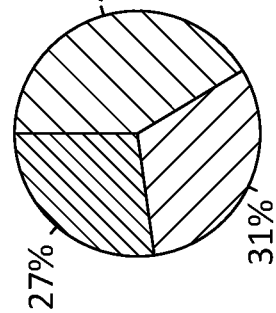

FIG. 10. Characterization of ERV locus-specific mutations and their frequencies within clonal populations. Analysis of Illumina raw reads of mutations detected at normal (0.2-0.4%) or high (>0.4%) read frequencies in different clones. Pie charts represent number and frequency of identified groups with identical CRISPR-derived mutation but distinct mutation flanking sequences (e.g. in D12_1_1 and G09_1_1). The 51% marked part of the pie provides 4 about equal sections indicating the number of predicted ERV loci that could not be distinguished based on their flanking sequences.

Figure 11:
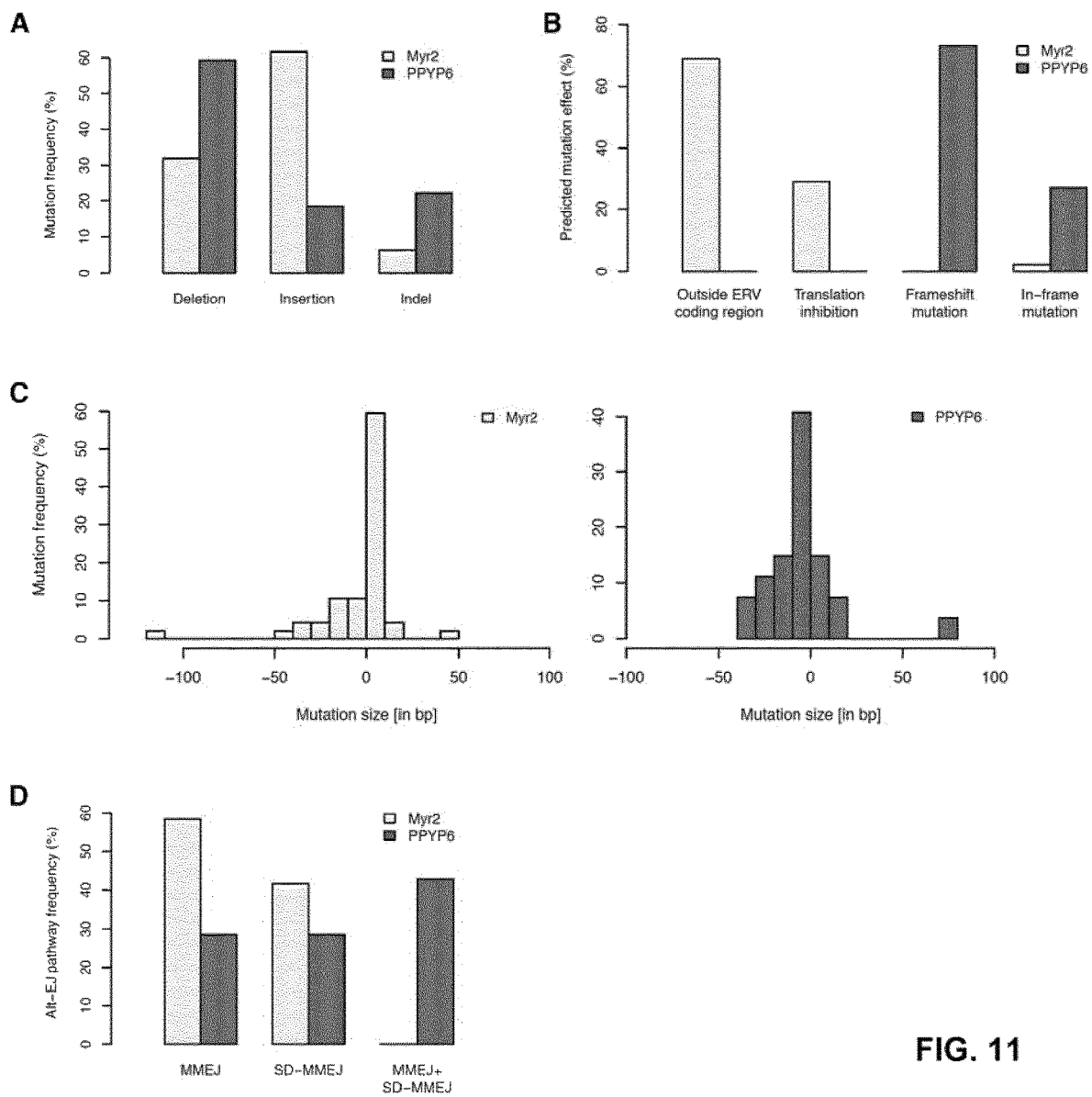

FIG. 11. Characterization of Myr2 sgRNA- and PPYP6 sgRNA-mediated mutations and repair junctions. 47 Myr2- and 27 PPYP6-derived repair junctions were analyzed for sgRNA specific mutation signatures, including the elicited mutation type (Deletion, Insertion, Indel) (A), the mutation effect on Gag and ERV function (Outside ERV coding region, Translational inhibition, Frameshift mutation, In-frame mutation) (B), the mutation size distribution (C) and MMEJ and SD-MMEJ alt-EJ repair pathway activities. Indel mutations are defined in this figure and throughout this specification as deletions coupled to insertions. Repair junctions compatible with both MMEJ and SD-MMEJ repair mechanisms are classified as "MMEJ+SD-MMEJ". Repair junctions were obtained from both Sanger mRNA and Illumina DNA deep sequencing.

Figure 12:
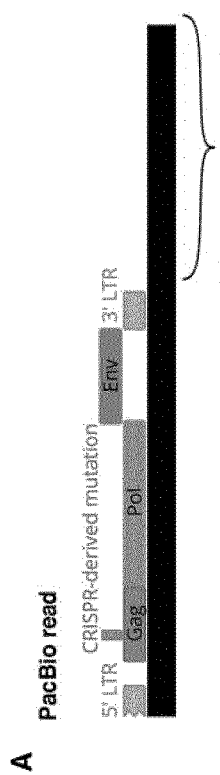
Figure 12:
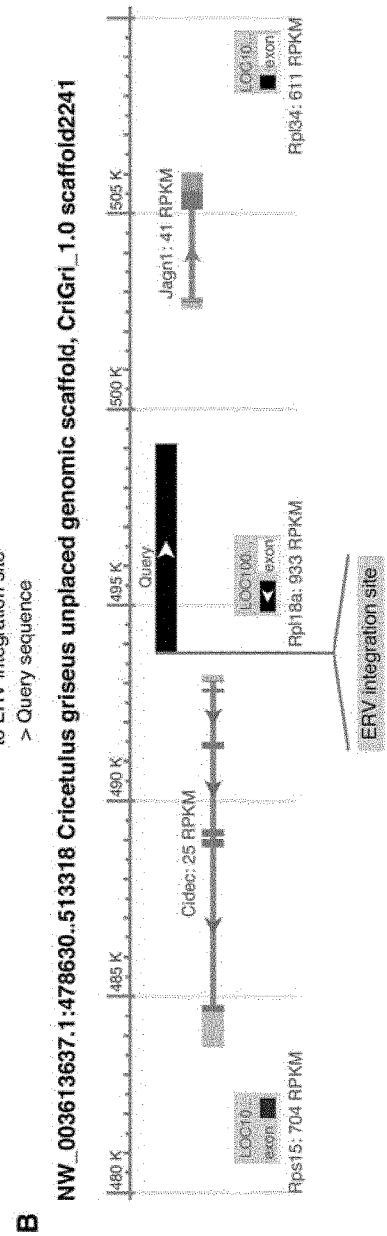
Figure 12:
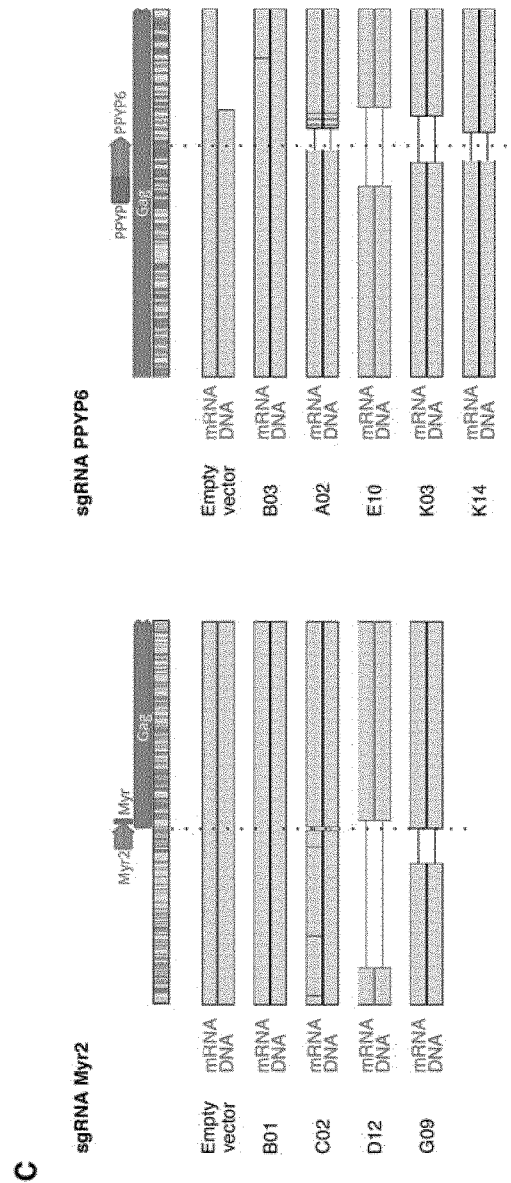

FIG. 12. Identification of a unique functionally active group 1 type-C ERV locus. (A) Schematic representation of a 15 kb PacBio read obtained following whole-genome sequencing of the E10 (PPYP6 sgRNA) clone. The read contains full-length gag, pol, env and full-length 3' LTR sequences as well as the E10-specific CRISPR-mutation in the gag gene and extends into the CHO genome. (B) Alignment of the PacBio CHO genome-specific sequence against the publicly available NCBI CHO genome. The NCBI scaffold identifier is shown on top. The predicted group 1 type-C ERV integration site is indicated. The genomic region surrounding the ERV integration site contains two protein-coding genes (Cidec, Jagn1) as well as three pseudogenes (Rps15, Rpl18a, Rpl34; shown with light grey backgrounds), as annotated by the NCBI. Cidec (cell death inducing DFFA like effector c) encodes for a lipid droplet protein involved in lipid metabolism (65), Jagn1 (jagunal homolog 1) encodes for an endoplasmatic reticulum protein involved in the early secretory pathway (66) and Rps15, Rpl18a, Rpl34 encode for ribosomal proteins. The predicted mRNA expression levels for each gene are estimated by RNA sequencing data and expressed as Reads Per Kilobase Million (RPKM). (C) Sanger sequencing results of the Myr2 and PPYP6 sgRNA flanking regions. Sanger sequencing was performed on PCR amplicons obtained from total cellular mRNA using group 1 specific primers ("mRNA" in the figure) or genomic DNA using primers specific to the expressed group 1 type-C ERV ("DNA" in the figure). Clones C02, D12, G09, A02, E10, K03, K14 contain mutations in the functionally active group 1 type-C ERV locus, but clones (B01 and B03) as well as the empty vector controls do not. The predicted Myr2 and PPYP6 DSB sites are marked with a dotted line.

Figure 13:
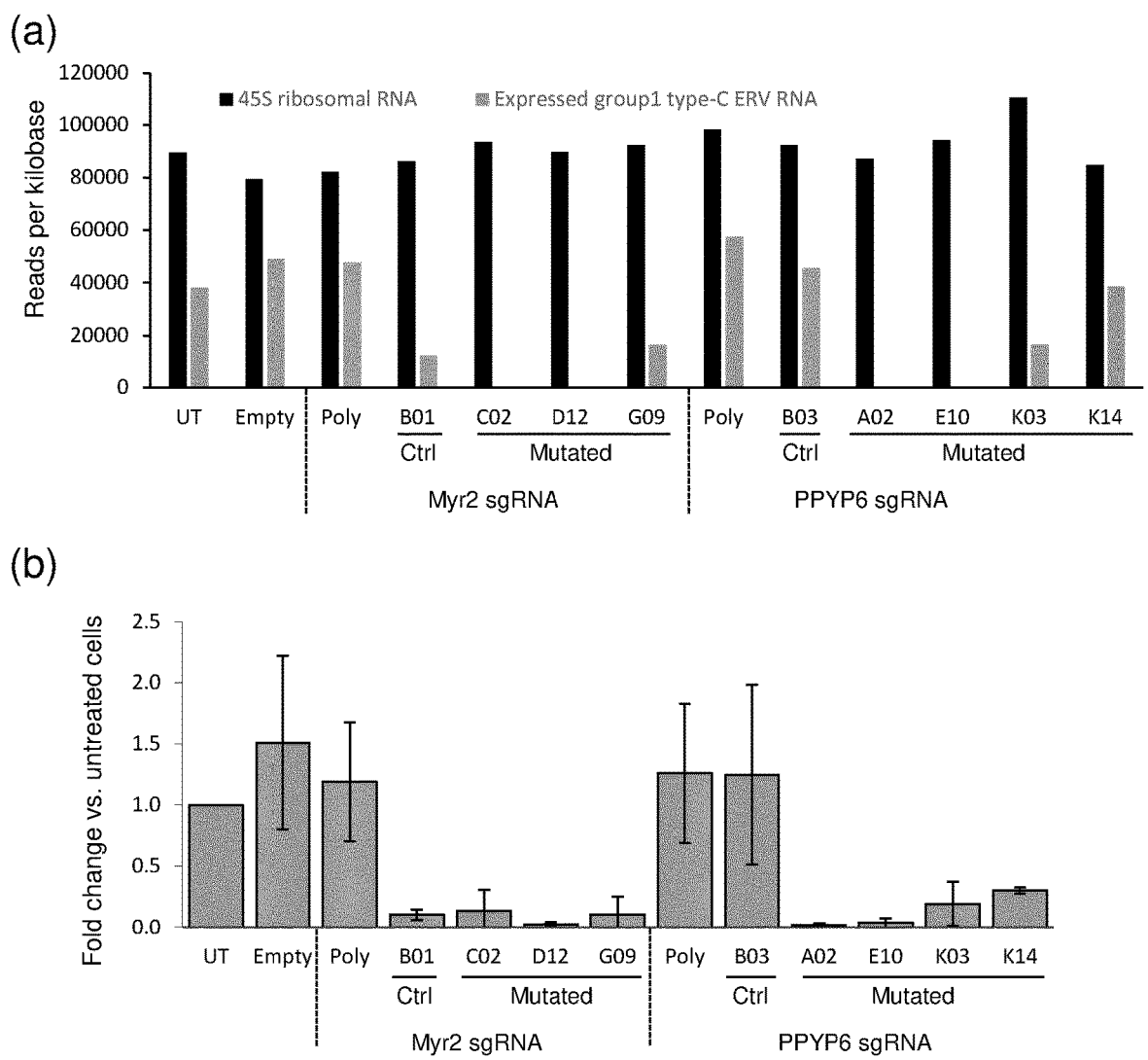

FIG. 13. Assessment of viral RNA amounts released in VP by ERV-mutated CHO cells. The retroviral RNA genomes were isolated from viral particles present within the supernatants of five-day cultures of untreated cells (UT), empty sgRNA vector-treated cells (Empty), bulk-sorted polyclonal CRISPR-treated cells (Poly), as well as clones containing mutations in the expressed type-C group 1 ERV locus (C02, D12, G09, A02, E10, K03 and K14) or without a detected ERV mutation (B01, B03). (A) The RNA was processed for Illumina sequencing and the obtained reads were mapped onto the group 1 type-C ERV locus of SEQ ID NO: 3. The ERV reads were mapped to the sequences of the expressed group 1 ERV locus of SEQ ID NO: 3 (grey bars) and to the 45S ribosomal RNA (black bars) sequences of CHO cells used as a control. The y-axis represents the number of reads per kilobases for each sequencing reaction. (B) Quantitative PCR (q-PCR) analysis of the reverse-transcribed total RNA isolated from VP released in cell culture supernatants. Reverse transcription and q-PCR analysis was performed in triplicates from samples obtained from 3 independent CHO cell cultures. The genomic retroviral sequences were quantified using group 1 ERV LTR-specific primers. Data were normalized to the number of analyzed cells and are represented as the average and standard deviation of the fold change relative to those of UT cells.

DETAILED DESCRIPTION OF VARIOUS AND PREFERRED EMBODIMENTS

A cell, preferably a mammalian cell/eukaryotic cell, that according to the present invention includes an engineered cell, is capable of being maintained under cell culture conditions. Standard cell culture conditions are from 30 to 40° C., preferably at or at about 37° C., for instance in fully synthetic culture medium as used in the production of recombinant proteins. Non-limiting examples of this type of cell are non-primate eukaryotic cells such as Chinese hamster ovary (CHOs) cells including the CHO-K1 (ATCC CCL 61), DG44 and CHO-S cells and SURE CHO-M cells (derivative of CHO-K1), and baby hamster kidney cells (BHK, ATCC CCL 10). Primate eukaryotic host cells include, e.g., human cervical carcinoma cells (HELA, ATCC CCL 2) and 293 [ATCC CRL 1573] as well as 3T3 [ATCC CCL 163] and monkey kidney CV1 line [ATCC CCL 70], also transformed with SV40 (COS-7, ATCC CRL-1587). The term engineered signifies that the genome of the cell has been altered, e.g., by insertion(s), deletion(s) and/or substitution(s). As the person skilled in the art will readily understand the cells that are being engineered, even prior to engineering as described herein, are non-naturally occurring cells. The above-mentioned cells, in particular, the various CHO cells, are commonly used in biotechnological applications, such as for the production of therapeutic proteins. As the person skilled in the art will also readily understand, other cells than the ones mentioned above might be engineered as long as they are used or can be used in biotechnological applications, in particular for the expression of, e.g., therapeutic proteins.

Endogenous retroviruses (ERVs) are sequences that derived from ancient retroviral infections of germ cells and integrated in mammal and other vertebrate cells millions of years ago. These ERVs are inherited according to Mendelian laws. The size of a complete endogenous retrovirus is between 6-12 kb on average and it contains gag, pol and env genes that always occur in the same order. Coding sequences are flanked by two LTRs (Long Terminal Repeat sequences). Most ERVs are defective, as they are carrying a multitude of inactivating mutations. In addition, they can be inactivated (i.e. not transcribed) by epigenetic silencing effects. However, some ERVs still have open reading frames in their genome and/or they may be transcriptionally active. The ERVs of mammals bear strong similarities and may originate from the genus of gammaretroviruses and betaretroviruses, including Intracisternal Leukemia Virus, Feline leukemia virus (FeLV), Mouse Leukemia Virus (MLV), Koala epidemic virus (KoRV), Mouse Mammary Tumor Virus (MMTV). ERVs are maintained in the genomes and may have certain advantages for the cells into whose genome they are integrated, including providing a source of genetic diversity and protection against other viral pathogens. However, they can become infectious and carry risks in in the context of transgene, i.e. protein, expression described elsewhere herein, in particular, as a result of ERV awakening due to cancer, cellular stress and/or epigenetic modifications.

The three major proteins encoded within the retroviral genome are Gag, Pol, and Env. Gag (Group Antigens) encoded by the gag gene is a polyprotein, which is processed to matrix and other core proteins, including the nucleoprotein core particle, that determines the retroviral core. Pol is the reverse transcriptase, encoded by the pol gene and has RNase H and integrase function. Its activity results in the double-stranded DNA pre-integrated form of the virus and, via the integrase function, for the integration into the host genome, and also via the RNase function, the reverse transcription after integration into the genome of the host. Env is the envelope protein, encoded by the env gene, and resides in the lipid layer of the virus determining the viral tropism.

US Patent Publication 2019/0194694 A1, filed Dec. 23, 2016 demonstrated the three classes of gammaretroviruses that might be integrated into the genome of the cells to form gammaretrovirus-related ERVs. 159 IAP (Intracisternal A-type particles) sequences and 144 type C murine ERV-like sequences were previously reported, as well as 6 sequences related to GALV (Gibbon Ape Leukemia Virus).

A neighbor-joining consensus tree based on 121 GAG sequences of the gamma retrovirus-like ERVs from a CHO genome was also discussed in US Patent Publication 2019/0194694 A1, filed Dec. 23, 2016. Both group 1 and 2 ERVs were shown to contain transcriptionally active ERVs. One sequence in the group 2 ERVs was found to be active, but contained stop codons. In contrast multiple sequences in group 1 were found to be active and not to contain a stop codon in the coding sequence. A Gag and Pol cDNA analysis was consistent with the existence of expressed ERVs encoded by full-length ERV sequences. Based on those sequences, a consensus sequence of group 1 viruses was determined as gcccccgcca tatccgccac tgccgccccc accagaggca gaagcgg [SEQ ID NO: 6]. Compare FIG. 1A, B, C and D.

Full length ERV sequences, in particular full-length group 1 type-C ERV sequences, are sequences that are integrated into the genome of a cell and, prior to introducing an alteration, can be expressed, that is, transcribed into functional transcripts with intact open reading frames of the gag, pol and env genes. Thus, a full-length ERV sequence, in particular full-length group 1 type-C ERV sequence, will encode, at a minimum, a Gag-precursor protein, a Pol encoded reverse transcriptase, and an Env protein. In preferred embodiments a full-length ERV sequence also includes one or both long terminal repeats (LTRs) or portions thereof, such as 10, 20, 30, 40, 50, 60, 70, 80% consecutive nucleotides thereof. In an even more preferred embodiment, the full-length and expressed ERV sequence corresponds to SEQ ID NO: 3 or a sequence having more than 90%, 95%, 98% or 99% sequence identity therewith.

Some of the full-length group 1 type-C ERV sequences might lead to the formation and release of viral particles (VPs) that might comprise the full-length viral genomic RNA packaged into the viral particles. In the context of the present application VPs refer to viral particles that contain at least a part of a viral genome. In some instances, the VPs may comprise the full-length viral genomic RNA and thus may be functional VPs. VLPs as used in the context of the present invention are particles that appear to be VPs, but lack any part of the viral genome.

A loss of function mutation interferes with proper protein synthesis, ergo no functional protein is synthesized if such a mutation occurs. In the case of a loss of function mutation in, e.g., a gag gene, the Gag-precursor protein or one of its cleavage products is compromised so that ERV budding does not take place.

The engineered cell according to the present invention, may comprise a genome that, in most parts, is identical to the genome of the cell it is derived from, such as a CHO-K1 cell. However, at least one and not more than 20, including 19, 18, 17, 16, 14, 13, 12, 11, 10, 9, 8, 7, 6, 5, 4, 3, 2, 1 ERV sequences, including group 1 type-C ERV sequences, which are part of these genomes will contain alterations as described herein.

The gag gene gives rise to a Gag precursor protein, which is expressed from the unspliced viral mRNA. The Gag precursor protein is cleaved by the virally encoded protease (a product of the pol gene) during the process of viral maturation into generally four smaller proteins designated MA (matrix), CA (capsid), NC (nucleocapsid), and a further protein domain (e.g. pp12 in murine leukemia virus (MLV) or p6 in HIV). A gag sequence as referenced herein may or may not give rise to a Gag precursor protein.

The gag gene encodes an N-terminal Myr motif, located downstream of the ATG translation initiation codon. Alterations in the Myr motif are part of the present invention. Such alterations generally interfere with Gag myristoylation and, e.g., block translation or create a loss-of-function mutated gag transcript. As a result, the proper viral particle assembly at the plasma membrane and/or retroviral particle release may, in certain embodiments of the invention, be blocked. The Myr motif of SEQ ID NO: 3 is encoded by sequences located at 1334-1336 (atg ggg caa). The Myr motif is also referred to herein as the Myr budding motif.

The PPxY motif of the gag gene also contributes to retrovirus budding. Alterations in the PPXY motif are also part of the present invention. Such alterations may strongly inhibit viral particle release. The PPxY motif may overlap with a PPYP motif (or the PPYP budding motif) that is conserved in group 1 and group 2 CHO ERVs, which is termed PPYP hereafter to refer to this CHO-specific PPxY-related budding motif. The PPYP is encoded by the sequences located at 1851-1868 (ccc ccg cca tat ccg cca) of SEQ ID NO: 3.

The MA polypeptide is derived from the N-terminal, myristoylated end of the precursor protein. Most MA molecules remain attached to the inner surface of the virion lipid bilayer, stabilizing the particle.

The CA protein forms the conical core of viral particles.

The NC region of Gag is responsible for specifically recognizing the so-called packaging signal of the retrovirus. The packaging signal comprises four stem loop structures located near the 5' end of the viral RNA, and is sufficient to mediate the incorporation of a heterologous RNA into virions. NC binds to the packaging signal through interactions mediated by two zinc-finger motifs.

Another protein domain mediates interactions between precursor protein Gag and the accessory protein Vpr, leads to the incorporation of Vpr into assembling virions. The p6 region in HIV also contains a so-called late domain which is required for the efficient release of budding virions from an infected cell. (Hope & Trono, 2000).

The viral protease (Pro), integrase (IN), RNase H, and reverse transcriptase (RT) are expressed within the context of a Gag-Pol fusion protein. The Gag-Pol precursor is generally generated by a ribosomal frame shifting event, which is triggered by a specific cis-acting RNA motif (a heptanucleotide sequence followed by a short stem loop in the distal region of the Gag RNA). When ribosomes encounter this motif, they shift approximately 5% of the time to the pol reading frame without interrupting translation. The frequency of ribosomal frameshifting explains why the Gag and the Gag-Pol precursor are produced at a ratio of approximately 20:1.

During viral maturation, the virally encoded protease cleaves the Pol polypeptide away from Gag and further digests it to separate the protease, RT, RNase H, and integrase activities. These cleavages do not all occur efficiently, for example, roughly 50% of the RT protein remains linked to RNase H as a single polypeptide (p65) (Hope & Trono, 2000).

The pol gene encodes the reverse transcriptase. During the process of reverse transcription, the polymerase makes a double-stranded DNA copy of the dimer of single-stranded genomic RNA present in the virion. RNase H removes the original RNA template from the first DNA strand, allowing synthesis of the complementary strand of DNA. The predominant functional species of the polymerase is a heterodimer. All of the pol gene products can be found within the capsid of released virions.

The IN protein mediates the insertion of the proviral DNA into the genomic DNA of an infected cell. This process is mediated by three distinct functions of IN.

The Env protein is expressed from singly spliced mRNA. First synthesized in the endoplasmic reticulum, Env migrates through the Golgi complex where it undergoes glycosylation. Env glycosylation is generally required for infectivity. A cellular protease cleaves the protein into a transmembrane domain and a surface domain. (Hope & Trono, 2000).

The viral genomic RNA expressed from some ERVs of a genome can be released from the cells in the form of VPs. Other expressed ERVs may cause the formation of RVLPs but not of VPs, and thus may not be released in the form of a viral genomic RNA. However, generally the ones that are released have a higher potential to become infectious.

Thus, it is generally advantageous to have cells engineered, as described herein, that can express and release no or substantially no VPs, preferably also no VLPs, preferably under both standard or stressful culturing conditions. Substantially no VPs/VLPs are released if a cell culture comprising the so engineered cell releases less than 50%, less than 40%, less than 30%, less than 20%, less than 10%, preferably less than 5% of VPs/VLPs than their counterpart that has not been subjected to the VPs/VLP release reducing procedures described herein. Such a counterpart would, e.g., be a commercially available CHO-K1 cell. No or substantially no expression means that less than 50%, less than 40%, less than 30%, less than 20%, less than 10%, preferably less than 5%, unmutated Gag mRNA sequence can be detected by PCR and sequencing analysis. No release means that no, or substantially no detectable viral sequence release occurs as assessed via a PureLink Viral RNA/DNA extraction Kit® INVITROGEN and a cDNA PCR assay, or as obtained from QIAGEN, QuantiTect Rev. Transcription Kit 6®.

Alteration(s) to a sequence or gene include addition(s)/insertion(s), deletion(s) and/or substitution(s) that do not occur in the cells, in particular in one or more, including one or more specific, ERVs of the cell, prior to engineering as described herein. In certain embodiments the alteration(s) might encompass the excision of at least one, in certain embodiments just one, that is a singular, entire ERV including optionally flanking regions 5' and/or 3' of the ERV. The alteration may include, for example, at least one alteration in the gag, env, pol gene and/or the LTRs. In certain embodiments the alteration comprises not more than 100, 90, 80, 70, 60, 50, 40, 30, 20, 15, 10, 5, 4, 3, 2 nucleotides including consecutive nucleotides, or 1 nucleotide of the gag, env, pol gene and/or the LTRs, of in particular one or more ERV sequences such as a full length ERV sequences and/or one or more specific sequences disclosed herein.

A heterologous nucleic acid sequence is a nucleic acid sequence that does not occur in the cells prior to engineering according to the present invention, while related types of nucleic acid sequences may very well exist in the cell. A transgene as used in the context of the present invention is such a heterologous nucleic acid sequence, in particular a deoxyribonucleotide (DNA) sequence coding for a given mature protein (also referred to herein as a DNA encoding a protein), for a precursor protein or for a functional RNA that does not encode a protein (non-coding RNA). A transgene is isolated and introduced into a cell to produce the transgene product. Some preferred transgenes according to the present invention encode marker proteins such as GFP (green fluorescent protein). Those can be used to detect successful integration into, ergo alteration/inactivation of, ERV elements. Other transgenes are those that encode, e.g., proteins that shall ultimately be produced by the cell in question such as immunoglobulins (Igs) and Fc-fusion proteins and other proteins, in particular proteins with therapeutic activity ("biotherapeutics").

As used herein, "genome editing" refers to the modification ("editing") of genomic sequences and may comprise a deletion of at least one nucleotide, an addition/insertion of at least one nucleotide, or a substitution of at least one nucleotide. The genomic sequence edited is referred to herein as target nucleic acid sequence. Targeted insertions are insertions that occur at a specific predetermined target site. Genome editing tools introduce double or single stranded breaks into the genome, e.g., via nucleases or nickases, and rely at least in part on the cellular recombination mechanisms (see discussion below) to repair these breaks. These tools also contain generally sequence specific DNA binding modules.

ZFNs (Zinc-Finger Nucleases) and TALENs (transcription activator-like effector nucleases) enable a broad range of genetic modifications by inducing DNA double-strand breaks (DSBs) that stimulate error-prone non-homologous end joining (NHEJ) or homology-directed repair (HDR) at specific genomic locations.

The sequence specificity of CRISPR (clustered, regularly interspaced, short palindromic repeats) systems is determined by small RNAs. CRISPR loci are composed of a series of repeats separated by 'spacer' sequences that match the genomes of bacteriophages and other mobile genetic elements. The repeat-spacer array is transcribed as a long precursor and processed within repeat sequences to generate small crRNA that specify the target sequences (also known as protospacers) cleaved by CRISPR systems. For cleavage, the presence of a sequence motif immediately downstream of the target region is often required, known as the protospacer-adjacent motif (PAM). CRISPR-associated (cas) genes usually flank the repeat-spacer array and encode the enzymatic machinery responsible for crRNA (CRISPR RNA) biogenesis and targeting. Cas9 is a dsDNA endonuclease that uses a crRNA guide to specify the site of cleavage. Loading of the crRNA guide onto Cas9 occurs during the processing of the crRNA precursor and requires a small RNA antisense to the precursor, the tracrRNA, and RNAse III. In contrast to genome editing with ZFNs or TALENs, changing Cas9 target specificity does not require protein engineering but only the design of the short crRNA guide, also termed sgRNA.

To date, three different variants of the Cas9 nuclease have been adopted in genome-editing protocols. The first is wild-type Cas9, which can site-specifically cleave double-stranded DNA, resulting in the activation of the doublestrand break (DSB) repair machinery. DSBs can be repaired by the cellular Non-Homologous End Joining (NHEJ) pathway, resulting in insertions and/or deletions (indels) which disrupt the targeted locus. Alternatively, if a donor template with homology to the targeted locus is supplied, the DSB may be repaired by the homology-directed repair (HDR) pathway allowing for precise replacement mutations to be made.

The Cas9 system was further engineered towards increased precision by developing a mutant form, known as Cas9D10A, with only nickase activity. This means it cleaves only one DNA strand, and does not activate NHEJ. Instead, when provided with a homologous repair template, DNA repairs are conducted via the high-fidelity HDR pathway only, resulting in reduced indel mutations. Cas9D10A is therefore in many applications more appealing in terms of target specificity when loci are targeted by paired Cas9 complexes designed to generate adjacent DNA nicks.

In the context of the present invention, a specific sequence or a consensus sequence of ERV elements are determined to specify the site of cleavage via, e.g., one of the systems above. Such a specific or consensus sequence is preferably between 5 and 50 base pairs long, preferably between 10 and 50 or between 15 and 25 or between 25 and 50 or 30 and 50. The consensus sequences may contain, e.g., 1, 2, 3, 4 or 5 mismatches (have more than 60%, 70%, 80%, 90% or 95% complementarity relative to each other), as long as cleave can still be performed. See, e.g, FIG. 3 and Table 1 that show specific target sites for Myr- and PPYP-specific sgRNAs in the CHO-K1 genome. The above systems are called non-naturally occurring systems or heterologous systems, which means that they are introduced to the cell rather than being a part of the cell prior to engineering according to the present invention. The specific DNA cleavage events lead, in certain embodiments, to transcriptional silencing of expressed ERVs.

A vector according to the present invention is a nucleic acid molecule capable of transporting another nucleic acid, such as a transgene that is to be expressed by this vector, to which it has been linked, generally into which it has been integrated. For example, a plasmid is a type of vector, a retrovirus or lentivirus is another type of vector. In a preferred embodiment of the invention, the vector is linearized prior to transfection. An expression vector comprises heterologous regulatory elements or is under the control of such regulatory elements that are designed to further the transcription and/or expression of a nucleic acid sequence, such as a transgene, carried by the expression vector. Regulatory elements comprise enhancers and/or promoters, but also a variety of other elements described herein.

Among non-viral vectors, transposons are particularly attractive because of their ability to integrate single copies of DNA sequences with high frequency at multiple loci within the host genome (integrating vector). Unlike viral vectors, some transposons were reported not to integrate preferentially close to cellular genes, and they are thus less likely to introduce deleterious mutations. Moreover, transposons are readily produced and handled, comprising generally of a transposon donor vector containing the cargo DNA flanked by inverted repeat sequences and of a transposase-expressing helper plasmid or mRNA. Several transposon systems were developed to mobilize DNA in a variety of cell lines without interfering with endogenous transposon copies. For instance, the PiggyBac (PB) transposon originally isolated from the cabbage looper moth efficiently transposes cargo DNA into a variety of mammalian cells.

In the context of the present invention, vectors, in particular non-integrating vectors, may also be used for transient expression of a gene or a functional RNA. Transient expression is an expression for a limited amount of time and the time period of expression depends on the vector design and culturing conditions. However, transient expression means expression over a period of at least 24 hours but generally not more than 7 days.

Epigenetic regulatory elements can be used to protect the cargo DNA from unwanted epigenetic effects when placed near the transgene on plasmid vectors. For example, elements called matrix attachment region (MARs) were proposed to increase cargo DNA genomic integration and transcription while preventing heterochromatin silencing, as exemplified by the potent human MAR 1-68. They can also act as insulators and thereby prevent the activation of neighboring cellular genes. MAR elements have thus been used to mediate high and sustained expression in the context of plasmid or viral vectors. For transient gene expression, non-integrating vectors (sometimes referred to as episomal vectors) such as plasmids or non-integrating lentiviral (NIL) vectors may be used. They may be stably or transiently maintained and replicated within the host cell.

The vector sequence of a vector is the DNA or RNA sequence of the vector excluding any "other" nucleic acids such as transgenes as well as genetic elements such as MAR elements.

The term sequence identity refers to a measure of the identity of nucleotide sequences or amino acid sequences. In general, the sequences are aligned so that the highest order match is obtained. "Identity", per se, has a recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans as defining identical nucleotides or amino acids at a given position in the sequence (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, the gammaretrovirus-like sequences of SEQ ID NOs. 1, 2, 3, 4, 5 or a part thereof can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments.

Whether the amino acid sequence is at least 50%, 60%, 70%, 75%, 80%, 85%, 90%, 95%, 96%, 97%, 98% or 99% identical to, for instance a protein expressed by SEQ ID NOs:1, 2, 3, 4, 5 or a part thereof, can be determined conventionally using known computer programs such the BESTFIT program (Wisconsin Sequence Analysis Package®, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences.

When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

Another preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

For example, a polynucleotide having 95% "identity" to a reference nucleotide sequence of the present invention, is identical to the reference sequence except that the polynucleotide sequence may include on average up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

The NCBI Basic Local Alignment Search Tool (BLAST) (Altschul et al. J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity and sequence similarities using this program.

The invention is not only directly to sequence having a certain sequence identity with the sequences disclosed herein but is, equally, directed to sequence variants of any of the sequences disclosed herein. The invention is thus also directed to sequence variants in any context in which a certain sequence identity is mentioned and vice versa. A "sequence variant" refers to a polynucleotide or polypeptide differing from the sequences disclosed herein (polynucleotide or polypeptide sequences), but retaining essential properties thereof. Generally, variants are overall closely similar and in many regions, identical to the sequences disclosed herein.

The variants may contain alterations in the coding regions, non-coding regions, or both. Especially preferred are sequence variants containing alterations which produce silent substitutions, additions, or deletions, but do not alter the properties or activities of, e.g., the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4 or 5 by an insertion or deletion of one or more amino acid residues and/or the substitution of one or more amino acid residues by different amino acid residues. Preferably, amino acid changes are of a minor nature, that is conservative amino acid substitutions that do not significantly affect, e.g., the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

A certain percentile of "consecutive nucleotides" means nucleotides directly following each other. Thus 10% of the nucleotides of SEQ ID NO:2, which contains 60000 nucleotides could be nucleotide 1-6000 or nucleotide 2-6001 etc.

If a sequence is said to be "directly adjacent" to another, this means that there are no intervening sequences. Flanking regions are directly adjacent to a particular sequence and denotes 5' and 3' regions of a specific nucleic acid sequence.

Gene silencing via, e.g., siRNAs has been described elsewhere, for example in US Patent Publication 20180016583, which is incorporated herein by reference in its entirety, and specifically for its disclosure and gene silencing.

CHO cells are the most widely used expression system for therapeutic proteins, but also a recognized source of adventitious viral-like particles for more than 40 years (7-10). Although these particles were never shown to be infectious, their genomic origin and possible evolution remain mostly unknown. Thus, safety concerns have persisted, and ample precautions must be taken when purifying therapeutic proteins. Here, this issue was approached by characterizing CHO endogenous retroviral elements at the genome, transcriptome and viral particle level, showing that CHO cells are able to release intact viral particles loaded with viral RNA genomes of group 1 type-C ERVs. The sequence encodes a full-length open reading frame, thus likely producing functional viral proteins. This finding challenges the only available study on CHO viral particle sequences, published in 1994, in which the authors detected only defective DNA sequences with numerous mutations in the ERV genes (12). Using this updated viral particle RNA sequence, the number of possible ERV loci responsible for the expression and release of CHO viral particles was limited to a group of up to 30 well-conserved group 1 type-C ERV sequences in the CHO genome.

Next, the Myr and PPYP budding motifs of the functionally relevant group 1 type-C ERV sequences were mutated using CRISPR-Cas9, to seek to prevent ERV budding. After transient CRISPR-Cas9 expression, 10-15% of the isolated clones contained mutations in the expressed group 1 sequences, some of which causing Gag loss-of-function effects. Having introduced unique mutations into defined ERV sequences a single genomic ERV locus as the origin of viral type-C particle formation in CHO cells could be pinpointed. Most interestingly, site-specific mutagenesis of this particular locus was sufficient to avoid release of viral particle carrying the viral genomic RNA. This indicated that the other ERVs present in the CHO genome may be unable to complement the Gag loss-of-function, nor become reactivated upon CRISPR-Cas9 mutagenesis.

A common technical challenge for multi-locus genome editing is the presence of extensive DNA damage. This damage may be elicited by the multiple Cas9-induced DSBs, which usually activate p53 signaling and cause cell death (20, 47-50). The sgRNAs designed in this study were predicted to perfectly recognize roughly 60 distinct group 1 type-C ERV loci in the CHO genome, although only some of them should be transcribed and may thus be preferentially cleaved by Cas9. Indeed, CRISPR-Cas9 treated clones possessed between 1 to 14 different mutation sites following a single transient transfection, suggesting that CHO cells are able to handle the DNA damage response and repair of up to 14 separate DSBs. In comparison to primary cells where sometimes a single DSB break results in cell death (50), transformed cell lines such as CHO cells typically encounter higher levels of endogenous DNA damage, and they are more likely to be able to handle and survive multi-loci genome editing, as seen here (51). However, even in CHO cells, a drop in cell proliferation and/or viability following a rather mild transient treatment with ERV-targeting sgRNAs was observed, which correlated well with the predicted number of target sites. An elevated cytotoxicity might have prevented the isolation of even more highly mutated clones. This would explain why a recent study reporting the isolation of primary porcine cells containing mutations in up to 62 endogenous viral elements required anti-apoptotic treatments to suppress p53-mediated cell death (20).

Another challenge in multi-locus editing is the plurality of repetitive ERV sequences present in the CHO genome that could be used as template for HR (homologous recombination) repair, which may counteract efficient gene knock-out mediated by C-NHEJ (canonical non-homologous end-joining repair) and alt-EJ (alternative end-joining) repair pathways. In CHO cells, HR activity is believed to be rather low compared to other cell (52, 53). Typically, HR may precisely repair DSBs (double strand breaks), but imprecise repair outcomes also occur (54). Here it was found that roughly 10% of the analyzed repair junctions at both sgRNA sites contained HR-compatible signatures, such as templated insertions from other ERV loci. Thus, it was hypothesized that HR repair is active and possibly opposes efficient ERV mutagenesis.

The genome editing strategy used in this study aimed primarily at introducing Gag loss-of-function mutations that interfere with proper Gag protein synthesis and thereby prevent ERV budding. However, as the person skilled in the art will appreciate that loss of function mutations in the pol gene or env gene and/or in at least one of the LTRs can also be introduced by appropriate procedures. As expected, clones mutated in the expressed group 1 type-C ERV sequence showed unchanged mRNA expression levels of group 1 and group 2 ERVs (data not shown), while being strongly impaired in releasing encapsulated viral RNA. In addition, ERV-mutated clones did not consistently differ in cell growth, cell size or therapeutic protein production compared to control samples. Hence, the differences between clones may be clone-specific. Clonal variation is a common phenomenon when isolating clones from polyclonal populations and has even been noticed during clone subcloning (57, 58). Clone-specific variability arises not only from genetic heterogeneity between the clones, for instance due to the acquisition of random and/or CRISPR-derived mutations, exposure to different stress responses, notably during CRISPR treatment, but also from stochastic fluctuations in protein expression and/or epigenetic effects (49, 58, 59). Furthermore, the accumulation of untranslated or nonsense mRNAs as well as of truncated and usually dysfunctional proteins in the cell cytoplasm has been associated with unclear side effects (60).

The present disclosure shows that a functionally active ERV locus can be selectively mutated using group 1 type-C specific sgRNAs. This offers novel avenues to improve the safety profile of CHO cells and thereby substantially reducing the number of virus inactivation and removal steps needed for viral clearance during biopharmaceutical production. The finding that a single ERV locus may be responsible for ERV expression and viral particle release by CHO cells enables to excise the entire 10 kb long proviral genome using two site-specific sgRNAs, as it has been done for HIV-infected human cells (61). This approach for ERV mutagenesis might reduce the elicited DNA damage response, possibly avoiding the accumulation of defective ERV RNAs in the cytoplasm and/or other detrimental side-effect arising from the mutation of other elements of the CHO genome, and consequently leading to less confounded effects on-target phenotypes.

Materials and Methods

Cell Culture

Suspension-adapted Chinese hamster ovary (CHO-K1) derived cells were maintained in serum-free HyClone SFM4CHO medium supplemented with HyClone Cell boost 5 supplement (GE HEALTHCARE), L-glutamine (GIBCO), HT supplement (GIBCO) and antibiotic-antimycotic solution (GIBCO). CHO cell viability was assessed by Erythrosin B dye (SIGMA-ALDRICH) and viable cell density and cell size were quantified using the LUNA-FL Dual Fluorescence Cell Counter (LOGOS BIOSYSTEMS). The cells were cultivated in 50 ml TubeSpin bioreactor tubes (TPP, Switzerland) at 37° C., 5% CO2 in a humidified incubator with 180 rpm agitation rate and passed every 3-4 days.

Plasmid Construction

The mammalian codon-optimized *Streptococcus pyogenes* Cas9 (SpCas9) nuclease expression plasmid JDS246 (ADDGENE plasmid #43861) (21) was used to introduce site-specific DSBs. The CRISPRseek R package (22) was applied to design single guide RNA (sgRNA) sequences that target the myristoylation (Myr) or PPYP motifs in the gag consensus sequence of group 1 ERVs.

Among all potential sgRNAs, three Myr (Myr2, Myr4, Myr8)- and five PPYP (PPYP5, PPYP6, PPYP7, PPYP13, PPYP20)-specific sgRNA sequences were selected as they mediate DSB cleavage no more than 25 bp apart from the target motif, and as they were predicted to have high sgRNA efficiency using various scoring tools (CRISPRseek, (22); Sequence Scan for CRISPR, (23); sgRNA scorer 1.0, (24)) (TABLE 1).

TABLE 1

Predicted number of ERV target sites for Myr- and PPYP-specific sgRNAs in the CHO-K1 genome.

| sgRNA name | sgRNA sequence (5'-3') | PAM sequence* | Number of mismatches allowed | | | | |
|---|---|---|---|---|---|---|---|
| | | | 0 | 1 | 2 | 3 | Total |
| Myr2 | TCCTAAGCCTAGAAACTATG (SEQ ID NO: 7) | Canonical Non-canonical | 59 — | 29 — | 16 1 | 26 16 | 147 |
| Myr4 | CATAGTTTCTAGGCTTAGGA (SEQ ID NO: 8) | Canonical Non-canonical | 33 — | — — | — 1 | 9 11 | 54 |
| Myr8 | GAGTGTTAGGGACAAAGGAG (SEQ ID NO: 9) | Canonical Non-canonical | 117 — | 30 — | — 2 | 36 33 | 218 |
| PPYP5 | GTTGGTTGATCTATTAACGG (SEQ ID NO: 10) | Canonical Non-canonical | 61 — | 30 — | 12 — | 5 6 | 114 |
| PPYP6 | GCCACTGCCGCCCCCACCAG (SEQ ID NO: 11) | Canonical Non-canonical | 55 1 | 16 — | 9 — | 36 16 | 133 |
| PPYP7 | GCCCCCACCAGAGGCAGAAG (SEQ ID NO: 12) | Canonical Non-canonical | 69 3 | 65 3 | 41 3 | 60 39 | 283 |
| PPYP13 | GGCAGTGGCGGATATGGCGG (SEQ ID NO: 13) | Canonical Non-canonical | 58 1 | 16 2 | 14 1 | 42 8 | 142 |
| PPYP20 | GCTTCTGCCTCTGGTGGGGG (SEQ ID NO: 14) | Canonical Non-canonical | 70 3 | 63 4 | 8 5 | 47 17 | 217 |

*The canonical PAM sequence of SpCas9 is NGG

Genome-wide off-target cleavage analysis for these sgRNA sequences was performed using the CRISPRseekR® package using the CHO-K1 cell genome as reference sequence. sgRNA oligonucleotides were designed using the Zinc Finger TARGETER software support tool (25, 26), and annealed sgRNA oligonucleotides were subsequently cloned into the mammalian sgRNA expression vector MLM3636 (ADDGENE plasmid #43860) as previously described (21). For sgRNA sequences lacking a guanine (G) nucleotide at the 5' end, an additional, non-pairing G was appended to improve transcription from the sgRNA expression plasmid (27). All primers used were purchased from MICROSYNTH AG (Balgach, Switzerland) and are listed in TABLE 2.

TABLE 2A

Sequences of the sgRNAs and corresponding primers used in this study.

| sgRNA name | Orientation | 5'-3 target site (without PAM) | Addition of G at 5' end for better U6 expression |
|---|---|---|---|
| Myr2 | Forward strand | TCCTAAGCCTAGAAACTATG (SEQ ID NO: 7) Oligo 1 ACACCGTCCTAAGCCTAGAAACTATGG (SEQ ID NO: 16) | GTCCTAAGCCTAGAAACTATG (SEQ ID NO: 15) Oligo 2 AAAACCATAGTTTCTAGGCTTAGGACG (SEQ ID NO: 17) |
| Myr4 | Reverse strand | CATAGTTTCTAGGCTTAGGA (SEQ ID NO: 8) Oligo 1 ACACCGCATAGTTTCTAGGCTTAGGAG (SEQ ID NO: 19) | GCATAGTTTCTAGGCTTAGGA (SEQ ID NO: 18) Oligo 2 AAAACTCCTAAGCCTAGAAACTATGCG (SEQ ID NO: 20) |
| Myr8 | Reverse strand | GAGTGTTAGGGACAAAGGAG (SEQ ID NO: 9) Oligo 1 ACACCGAGTGTTAGGGACAAAGGAGG (SEQ ID NO: 21) | — Oligo 2 AAAACCTCCTTTGTCCCTAACACTCG (SEQ ID NO: 22) |
| PPYP5 | Forward strand | GTTGGTTGATCTATTAACGG (SEQ ID NO: 10) Oligo 1 ACACCGTTGGTTGATCTATTAACGGG (SEQ ID NO: 23) | — Oligo 2 AAAACCCGTTAATAGATCAACCAACG (SEQ ID NO: 24) |
| PPYP6 | Forward strand | GCCACTGCCGCCCCCACCAG (SEQ ID NO: 11) Oligo 1 ACACCGCCACTGCCGCCCCCACCAGG (SEQ ID NO: 25) | — Oligo 2 AAAACCTGGTGGGGGCGGCAGTGGCG (SEQ ID NO: 26) |
| PPYP7 | Forward strand | GCCCCCACCAGAGGCAGAAG (SEQ ID NO: 12) Oligo 1 ACACCGCCCCCACCAGAGGCAGAAGG (SEQ ID NO: 27) | — Oligo 2 AAAACCTTCTGCCTCTGGTGGGGGCG (SEQ ID NO: 28) |
| PPYP13 | Reverse strand | GGCAGTGGCGGATATGGCGG (SEQ ID NO: 13) Oligo 1 ACACCGGCAGTGGCGGATATGGCGGG (SEQ ID NO: 29) | — Oligo 2 AAAACCCGCCATATCCGCCACTGCCG (SEQ ID NO: 30) |
| PPYP20 | Reverse strand | GCTTCTGCCTCTGGTGGGGG (SEQ ID NO: 14) Oligo 1 ACACCGCTTCTGCCTCTGGTGGGGG (SEQ ID NO: 31) | — Oligo 2 AAAACCCCCCACCAGAGGCAGAAGCG (SEQ ID NO: 32) |

TABLE 2B

Sequences of the PCR and Illumina sequencing primers used to characterize corresponding genomic loci of edited CHO cells.

| Primer Name | Full sequence (5'-3') | SEQ ID NO: |
|---|---|---|
| Myr Forward Primers | | |
| Myr_Fa_3 | TCGTCGGCAGCGTCAGATGTGTATAAGAGACAGACCGCTTGAAGGATTTGCAATC | 33 |
| Myr_Fb_0 | TCGTCGGCAGCGTCAGATGTGTATAAGAGACAGGCTTGAGGGATTTGCAATC | 34 |
| Myr_Fb_1 | TCGTCGGCAGCGTCAGATGTGTATAAGAGACAGTGCTTGAGGGATTTGCAATC | 35 |

TABLE 2B-continued

Sequences of the PCR and Illumina sequencing primers used to characterize corresponding genomic loci of edited CHO cells.

| | | |
|---|---|---|
| Myr_Fb_2 | TCGTCGGCAGCGTCAGATGTGTATAAGAGACAGTTGCTTGAGGGATTTGCAATC | 36 |
| Myr_Fb_3 | TCGTCGGCAGCGTCAGATGTGTATAAGAGACAGACTGCTTGAGGGATTTGCAATC | 37 |
| Myr_Fc_2 | TCGTCGGCAGCGTCAGATGTGTATAAGAGACAGGTGCTTGAGGGATTTGTAATC | 38 |

Myr Reverse Primers

| | | |
|---|---|---|
| Myr_R_0 | GTCTCGTGGGCTCGGAGATGTGTATAAGAGACAGACAAAGAGTAATCCATTTGCG | 39 |
| Myr_R_1 | GTCTCGTGGGCTCGGAGATGTGTATAAGAGACAGGACAAAGAGTAATCCATTTGCG | 40 |
| Myr_R_2 | GTCTCGTGGGCTCGGAGATGTGTATAAGAGACAGCGACAAAGAGTAATCCATTTGCG | 41 |
| Myr_R_3 | GTCTCGTGGGCTCGGAGATGTGTATAAGAGACAGAAGACAAAGAGTAATCCATTTGCG | 42 |

PPYP Forward Primers

| | | |
|---|---|---|
| PPYP_Fa_0 | TCGTCGGCAGCGTCAGATGTGTATAAGAGACAGACTCCAGCCTTTACCCTAC | 43 |
| PPYP_Fa_1 | TCGTCGGCAGCGTCAGATGTGTATAAGAGACAGAACTCCAGCCTTTACCCTAC | 44 |
| PPYP_Fb_0 | TCGTCGGCAGCGTCAGATGTGTATAAGAGACAGATTCCAACCTTTACCCTAC | 45 |
| PPYP_Fb_1 | TCGTCGGCAGCGTCAGATGTGTATAAGAGACAGGATTCCAACCTTTACCCTAC | 46 |
| PPYP_Fb_2 | TCGTCGGCAGCGTCAGATGTGTATAAGAGACAGTGATTCCAACCTTTACCCTAC | 47 |
| PPYP_Fb_3 | TCGTCGGCAGCGTCAGATGTGTATAAGAGACAGCTTATTCCAACCTTTACCCTAC | 48 |

PPYP Reverse Primers

| | | |
|---|---|---|
| PPYP_Ra_1 | GTCTCGTGGGCTCGGAGATGTGTATAAGAGACAGGGGTCTGATGCTGAGAATG | 49 |
| PPYP_Rb_0 | GTCTCGTGGGCTCGGAGATGTGTATAAGAGACAGGGTCCGATGCTGAGAATG | 50 |
| PPYP_Rb_1 | GTCTCGTGGGCTCGGAGATGTGTATAAGAGACAGTGGTCCGATGCTGAGAATG | 51 |
| PPYP_Rb_2 | GTCTCGTGGGCTCGGAGATGTGTATAAGAGACAGGTGGTCCGATGCTGAGAATG | 52 |
| PPYP_Rb_3 | GTCTCGTGGGCTCGGAGATGTGTATAAGAGACAGAAGGGTCCGATGCTGAGAATG | 53 |

| Ilumina Adapter | Spacer | Gene-specific Primer | SEQ ID NO: | PR |
|---|---|---|---|---|
| TCGTCGGCAGCGTCAGATGTGTATAAGAGACAG | ACC | GCTTGAAGGATTTGCAATC | 33 | 0.15 |
| TCGTCGGCAGCGTCAGATGTGTATAAGAGACAG | | GCTTGAGGGATTTGCAATC | 34 | 0.2 |
| TCGTCGGCAGCGTCAGATGTGTATAAGAGACAG | T | GCTTGAGGGATTTGCAATC | 35 | 0.2 |
| TCGTCGGCAGCGTCAGATGTGTATAAGAGACAG | TT | GCTTGAGGGATTTGCAATC | 36 | 0.2 |
| TCGTCGGCAGCGTCAGATGTGTATAAGAGACAG | ACT | GCTTGAGGGATTTGCAATC | 37 | 0.2 |
| TCGTCGGCAGCGTCAGATGTGTATAAGAGACAG | GT | GCTTGAGGGATTTGTAATC | 38 | 0.05 |
| | | | | 1 |
| GTCTCGTGGGCTCGGAGATGTGTATAAGAGACAG | | ACAAAGAGTAATCCATTTGCG | 39 | 0.25 |
| GTCTCGTGGGCTCGGAGATGTGTATAAGAGACAG | G | ACAAAGAGTAATCCATTTGCG | 40 | 0.25 |
| GTCTCGTGGGCTCGGAGATGTGTATAAGAGACAG | CG | ACAAAGAGTAATCCATTTGCG | 41 | 0.25 |
| GTCTCGTGGGCTCGGAGATGTGTATAAGAGACAG | MG | ACAAAGAGTAATCCATTTGCG | 42 | 0.25 |
| | | | | 1 |
| TCGTCGGCAGCGTCAGATGTGTATAAGAGACAG | | ACTCCAGCCTTTACCCTAC | 43 | 0.1 |
| TCGTCGGCAGCGTCAGATGTGTATAAGAGACAG | A | ACTCCAGCCTTTACCCTAC | 44 | 0.1 |
| TCGTCGGCAGCGTCAGATGTGTATAAGAGACAG | | ATTCCAACCTTTACCCTAC | 45 | 0.2 |
| TCGTCGGCAGCGTCAGATGTGTATAAGAGACAG | G | ATTCCAACCTTTACCCTAC | 46 | 0.2 |
| TCGTCGGCAGCGTCAGATGTGTATAAGAGACAG | TG | ATTCCAACCTTTACCCTAC | 47 | 0.2 |
| TCGTCGGCAGCGTCAGATGTGTATAAGAGACAG | CTT | ATTCCAACCTTTACCCTAC | 48 | 0.2 |
| | | | | 1 |
| GTCTCGTGGGCTCGGAGATGTGTATAAGAGACAG | G | GGTCTGATGCTGAGAATG | 49 | 0.04 |
| GTCTCGTGGGCTCGGAGATGTGTATAAGAGACAG | | GGTCCGATGCTGAGAATG | 50 | 0.24 |
| GTCTCGTGGGCTCGGAGATGTGTATAAGAGACAG | T | GGTCCGATGCTGAGAATG | 51 | 0.24 |

TABLE 2B-continued

Sequences of the PCR and Illumina sequencing primers used to characterize corresponding genomic loci of edited CHO cells.

| | | | | |
|---|---|---|---|---|
| GTCTCGTGGGCTCGGAGATGTGTATAAGAGACAG | GT | GGTCCGATGCTGAGAATG | 52 | 0.24 |
| GTCTCGTGGGCTCGGAGATGTGTATAAGAGACAG | MG | GGTCCGATGCTGAGAATG | 53 | 0.24 |
| | | | | 1 |

PR = Primer ratio acc. to expected % of ERVs (total = 1)

TABLE 2C

Sequences of the PCR and qPCR primers used to characterize and validate ERV loci and expression

| Amplification type | Oligo 1 | Oligo 2 |
|---|---|---|
| Locus ERV Type 1 validation1 | CTCTGGTTCTTGCCTGCTGAGCT (SEQ ID NO: 54) | TGGTCAATGTATATGAGGCGCT (SEQ ID NO: 55) |
| qPCR Type1 ERV specific LTR | GGGAATTGAGTCTGCTGTACCA (SEQ ID NO: 56) | ACAGAGTCTTTCAAATGAGGCG (SEQ ID NO: 57) |
| qPCR ref GAPDH | GCGACTTCAACAGTGACTCCCA (SEQ ID NO: 58) | TGAGGTCCACCACTCTGTTGCT (SEQ ID NO: 59) |
| qPCR Type2 ERV specific | GAATAAAAGGTCAGGGCGTTGG (SEQ ID NO: 60) | CTGACTTGGCTCTATCTTGGGT (SEQ ID NO: 61) |
| qPCR Type1 ERV specific Gag | TGACGATATAAGCCACTTGA (SEQ ID NO: 62) | ACCCCCAGACTATATTCCAGATA (SEQ ID NO: 63) |
| qPCR Type1 ERV specific Env | CTATGTGCTGCCCTCAAGGA (SEQ ID NO: 64) | GCCTCTCCCTAAGTTTGGCC (SEQ ID NO: 65) |
| Locus ERV type 1 validation2 | CTCTGGTTCTTGCCTGCTGAGCT (SEQ ID NO: 54) | TAAGCCATTGGTGAAGGGTCA (SEQ ID NO: 66) |
| Locus ERV type 1 validation3 | CTCTGGTTCTTGCCTGCTGAGCT (SEQ ID NO: 54) | TGACGATATAAGCCACTTGA (SEQ ID NO: 62) |
| Locus ERV type 1 validation4 | TTTTCTGGTGCCCTCTTGCCTGG (SEQ ID NO: 67) | TAAGCCATTGGTGAAGGGTCA (SEQ ID NO: 66) |
| Locus ERV type 1 validation without ERV | CTCTGGTTCTTGCCTGCTGAGCT (SEQ ID NO: 54) | TTGTGGAGCTGTGTGAGTGGTGG (SEQ ID NO: 68) |

RNA Extraction from VP and VLP

Total RNA was extracted from the VPs and VLPs isolated CHO culture supernatants using the Invitrogen PureLink® Viral RNA/DNA mini kit (THERMO FISHER SCIENTIFIC) according to the manufacturer's protocol with some modifications. The supernatants were used freshly prepared, or after only one freezing and thawing cycle. 50 µl of supernatant was loaded on a Corning Costar Spin-X column centrifuge tube with 0.22 µm membrane filter and centrifuged at 16000 g for 1 minute. Approximately 12.5 units of RNase free DNase (MACHEREY-NAGEL) were added to 500 µl of CHO cell culture supernatants, which were incubated for 15 min at 37° C. to digest the residual DNA possibly present. The resulting extracts were then treated as described in the PureLink® Viral RNA/DNA mini kit protocol. The RNA recovered from the spin columns was resuspended in 34l of RNase free water, followed by another DNase treatment using 10 units of RNase free DNase (MACHEREY-NAGEL) for 30 min at 37° C. After the addition of EDTA at a 5 mM final concentration, a DNase denaturation step was made by incubating the extracts at 70° C. for 15 min. The samples were after place on a MICRODIALYSIS MF-MILLIPORE Membrane Filter (MERK-MILLIPORE) type VSWP 0.025 µm pore for 15 min in order to remove salts such as EDTA remaining in the samples.

Inactivation of ERV Sequences, Fluorescent Cells Enrichment and Single Cell Isolation CHO-K1 cells were seeded at 300,000 cells/ml one day prior to transfection. On the day of transfection, 700,000 cells were electroporated with 3700 ng of CRISPR-Cas9 and 1110 ng of Myr- or PPYP-specific sgRNA expression plasmids using the NEON transfection system (THERMO FISHER SCIENTIFIC), according to the manufacturer's instructions. CRISPR-Cas9 and sgRNA expression plasmids were used at equimolar ratio. 200 ng of pCMV-DsRed-Express plasmid (CLONETECH) was added to each transfection condition as transfection control. For CRISPR control experiments, the Myr or PPYP-specific sgRNA plasmids were substituted with the empty sgRNA expression vector (empty vector control).

To enrich for transfected and ERV mutated CHO cells, at least 70,000 cells were bulk-sorted for the highest 30-40% of transfected dsRed expressing cell population 48-72 h after transfection using the MOFLO ASTRIOS EQ or FACSAria II cell sorters (BECKMAN COULTER). Cells were then briefly centrifuged to exchange medium and expanded. To isolate single cell clones, CRISPR-treated cells were incubated at room temperature with DAPI viability dye (BD BIOSCIENCES) for 15 min. Viable cells were single cell sorted into 96 well plates using the FACSAria Fusion cell Sorter® (BECKMAN COULTER). Cell clones were recovered in HyClone® SFM4CHO medium supplemented with L-glutamine, HT supplement, antibiotic-antimycotic solution and ClonaCell-CHO ACF Supplement (STEMCELL TECHNOLOGIES) to increase post-sort survival. Flow cytometry data were analyzed using FlowJo® software v10.4.2. Cells were first gated using side scatter (SSC) versus forward scatter (FSC) to separate the intact cell population from debris, and then selected for single cells in the SSC-H/SSC-W and FSC-H/FSC-W plots. This single cell population was then gated for dsRed+ cells with non-fluorescent cells as gating control.

ERV Mutation Efficiency

To assess the cleavage efficiency of ERV-specific sgRNAs, the frequency of ERV mutations was determined among the transcribed ERV sequences. Total RNA from CRISPR-treated polyclonal cell populations was extracted using the NUCLEOSPIN RNA kit (MACHEREY NAGEL) and reverse transcribed into cDNA using oligo(dT)$_{15}$ primers and the GoScript® Reverse Transcription System (PROMEGA). For CRISPR-treated single cell clones, total RNA was isolated using the SV 96 Total RNA Isolation System (PROMEGA) and reverse transcribed using GoScript® Reverse Transcription Mix, Oligo(dT) (PROMEGA). PCR amplification of the CRISPR target regions was carried out using One Taq® DNA polymerase (NEW ENGLAND BIOLABS) with group 1 ERV-specific primers (TABLE 2B). PCR products were analyzed by Sanger sequencing and analyzed for mutations. The mutagenesis frequency in CRISPR-treated polyclonal populations was determined by decomposition of the mixed Sanger sequencing chromatograms and comparison to untreated (wild-type) cells using the TIDE software (28).

Deep Amplicon Sequencing Analysis of CRISPR-Targeted Genomic Regions

To assess the number of CRISPR-induced ERV mutations at the genome level, DNA was extracted from ERV-edited CHO clones using the DNeasy Blood & Tissue Kit® (QIAGEN). This extracted genomic DNA was used to prepare sequencing libraries in a two-step PCR approach as described in the Illumina "16S Metagenomic Sequencing Library Preparation" protocol with some modifications. Briefly, degenerate primers were designed using the Primer Design-M tool (29) to amplify approximately 300 bp of the genomic region flanking the Myr2 and PPYP6 sgRNA target sites of all predicted type-C ERV sequences (290 bp amplicon for Myr, 314 bp amplicon for PPYP, TABLE 2). Degenerate primers contained various 0-3 bp heterogeneity spacers to increase template complexity (30) and Myr or PPYP primers were mixed at the predicted genomic frequency. In the first PCR round, 100 ng of isolated genomic DNA was used to PCR amplify the Myr and PPYP target loci using KAPA HiFi HotStart ReadyMix® (2×) (KAPA BIOSYSTEMS) for 23 and 20 cycles, respectively. PCR amplicons were purified with AMPure XP® beads (BECKMAN COULTER) using a 1:1 bead ratio. Amplicon quality and size were verified on an Agilent 2100 Bioanalyzer® and DNA was quantified using the Qubit dsDNA HS Assay Kit® (THERMO FISHER SCIENTIFIC). In the second PCR round, Illumina Nextera XT Index® sequencing adapters were added to 15 ng of purified amplicons using 8 PCR cycles. The final libraries were purified with AMPure XP® beads (BECKMAN COULTER) using a 1:1.12 bead ratio. Library quality and size were verified using Fragment Analyzer (ADVANCED ANALYTICAL) and quantified using Qubit dsDNA HS Assay Kit® (THERMO FISHER SCIENTIFIC). Libraries were pooled at equimolar ratio, spiked with 25% PhiX and sequenced using 2×250 bp paired-end sequencing on an Illumina Miseq System® at the Genomic Technologies Facility of the University of Lausanne (Switzerland).

For all identified mutations, Illumina raw reads were clustered using the Jukes-Cantor genetic distance model under the UPGMA tree building method to test for ERV locus-specific genetic variations in the mutation flanking region.

Whole Genome Sequencing of ERV-Mutated CHO Clone

To identify mutated ERV loci in the whole CHO genome, high-molecular-weight DNA was extracted from the sgRNA PPYP6-treated E10 clone using the blood & cell culture DNA kit (QIAGEN). DNA quality and quantity were verified using Fragment Analyzer (ADVANCED ANALYTICAL) and Qubit® (THERMO FISHER SCIENTIFIC), respectively. Sample sequencing was performed on a PacBio Sequel System® (PACIFIC BIOSCIENCES) at the Genomic Technologies Facility of the University of Lausanne (Switzerland).

Analysis of Therapeutic Protein Expression

To assess the therapeutic protein production capacity of ERV-modified cells, polyclonal cell populations and cell clones previously treated with ERV-specific or empty sgRNA expression plasmids were electroporated with a trastuzumab immunoglobulin G1 (IgG1) heavy and light chain expression vector bearing a puromycin resistance gene (31). As control, wild-type CHO-K1 cells were transfected with the same expression vector in parallel. Two days after transfection, cells were transferred to culture medium containing 5 µg/ml puromycin and selected for three weeks.

Immunoglobulin titers from cultures of stable trastuzumab expressing cell populations were quantified during ten-days fed-batch cultures as previously described (31). Briefly, cells were seeded at $0.3*10^6$ cells/ml in 5 ml initial culture volume without Puromycin selection. Cell culture was fed with HyClone® Cell boost 5 supplement (GE HEALTHCARE) at 16% of the initial culture volume on days zero, two, three and six to eight of the cell cultivation. Cell density and viability was assessed at days three, six, eight and ten and immunoglobulin secretion in the cell culture supernatant was measured on days six, eight and ten by sandwich ELISA.

Characterization of ERV Elements in CHO-K1 Cells

To search for ERVs present in CHO cells, the CHO-K1 genome was assembled de novo using PacBio® long-read sequencing, and the previously reported IAP and ML2G murine retroviral sequences were searched in this assembly (12, 13). Furthermore, we used as well profiles to complement and validate the ERV elements identified by sequence similarity. Approximately 160 copies of IAP-like proviral elements were found within the CHO genome. In addition to approximately 200 IAPs, 173 gammaretrovirus type-C proviruses were identified that shared at least 80% sequence identity to the ML2G sequence in CHO cells (12) (TABLE 3).

TABLE 3

Number and frequency of distinct type-C ERV sequences detected in the genome, transcriptome and viral particles of CHO-K1 cells.

| Detection level | Type-C ERV sequence number | ERV group relative frequency |
|---|---|---|
| Genomic DNA | 173 | group 1 ≅ group 2 |
| Cellular mRNA | 3-32 | group 1 > group2 |
| Viral particles | 1-5 | group 1 only |

Although the identified number of type-C proviruses was in line with previous estimations (6), it was noticed that some ERV copies could not be successfully placed in the assembly suggesting that 173 copies is likely an underestimation of the total reservoir of type-C ERV elements in CHO cells. Among the identified 173 type-C ERV sequences, only 112 contained the gag, pol and env genes, as required to produce a functional ERV. Phylogenetic analysis of these full-length hamster type-C ERV sequences revealed their close similarity to other mammalian retroviral elements, such as the Feline leukemia virus (FeLV) and the Murine leukemia virus (MLV) (data not shown). Among these type-C ERV sequences, we identified two distinct groups: group 1 and group 2 which were composed of 101 and 36 members, respectively (FIG. 1A). Group 1 and group 2 type-C ERVs formed the predominant and functionally most conserved sequence clusters, with complete 5' LTR-gag-pol-env-3' LTR proviral structures, and they also shared most similarity to MLV elements, which are known to produce viral particles infecting primate cell lines (16). This implied the ERVs of group 1 and 2 as the most likely candidates for viral particle formation.

Figure 1B:
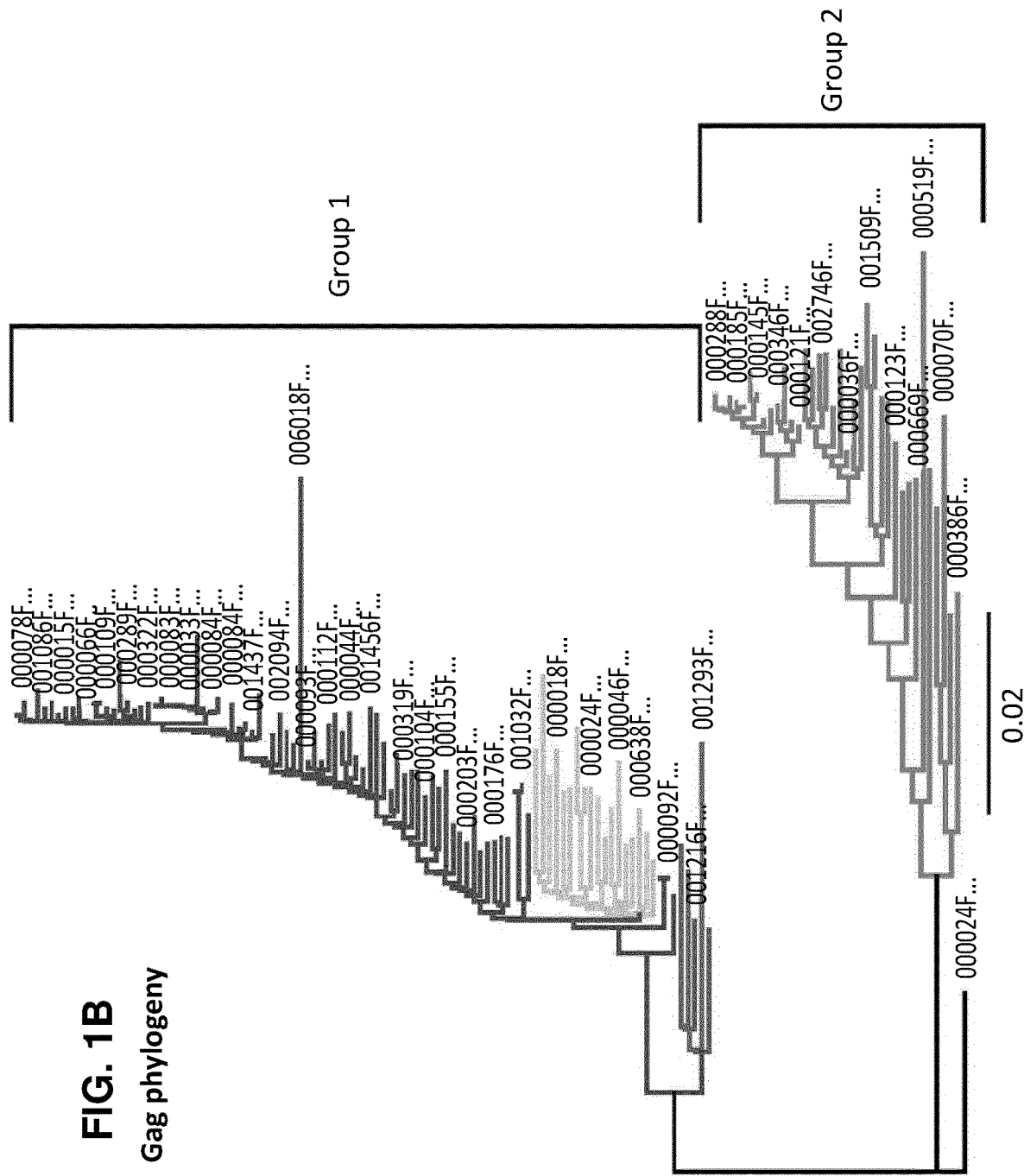
FIG. 1. Phylogenetic analysis of full-length type-C ERV DNA sequences within the CHO-K1 genome. Sequences alignments were realized with MAFFT aligner version 7 (64), with standard parameters, a scoring matrix of 200 PAM/k=2, a gap open penalty of 2.55 and an offer value of 0.123. Alignments were realized for the complete gag-pol-env sequence (A) or in the gag (B), pol (C) and env (D) sequences separately of 112 full-length type-C ERV. From these alignments, phylogenetic trees were made using GENEIOUS Tree Builder version 11.1.5 and using the genetic distance model HKY and the method of UPGMA based on sequence similarity. The scale under the tree show the substitution rate per nucleotide. Group 1 with its three subclusters and group 2 are indicated by brackets.

Further sequence analysis highlighted that the gag and pol genes were highly conserved among group 1 and group 2 ERV sequences but that ERVs belonging to group 1 showed overall less diversity than ERVs from group 2 (FIG. 1B-D), and revealed the presence of a possibly distinct and less conserved third group of ERVs, for instance from Env-based phylogeny (FIG. 1D). On average group 1 ERV sequences shared 99% sequence identity and likely form three subgroups (marked in different shades in FIG. 1B-D). However, the overall high conservation of these ERV sequences and the frequency of sequencing errors in genomes assembled using PacBio® reads hampered the direct identification of which of these group 1, 2 and group 3 ERVs may be functional and potentially active.

Figure 2:
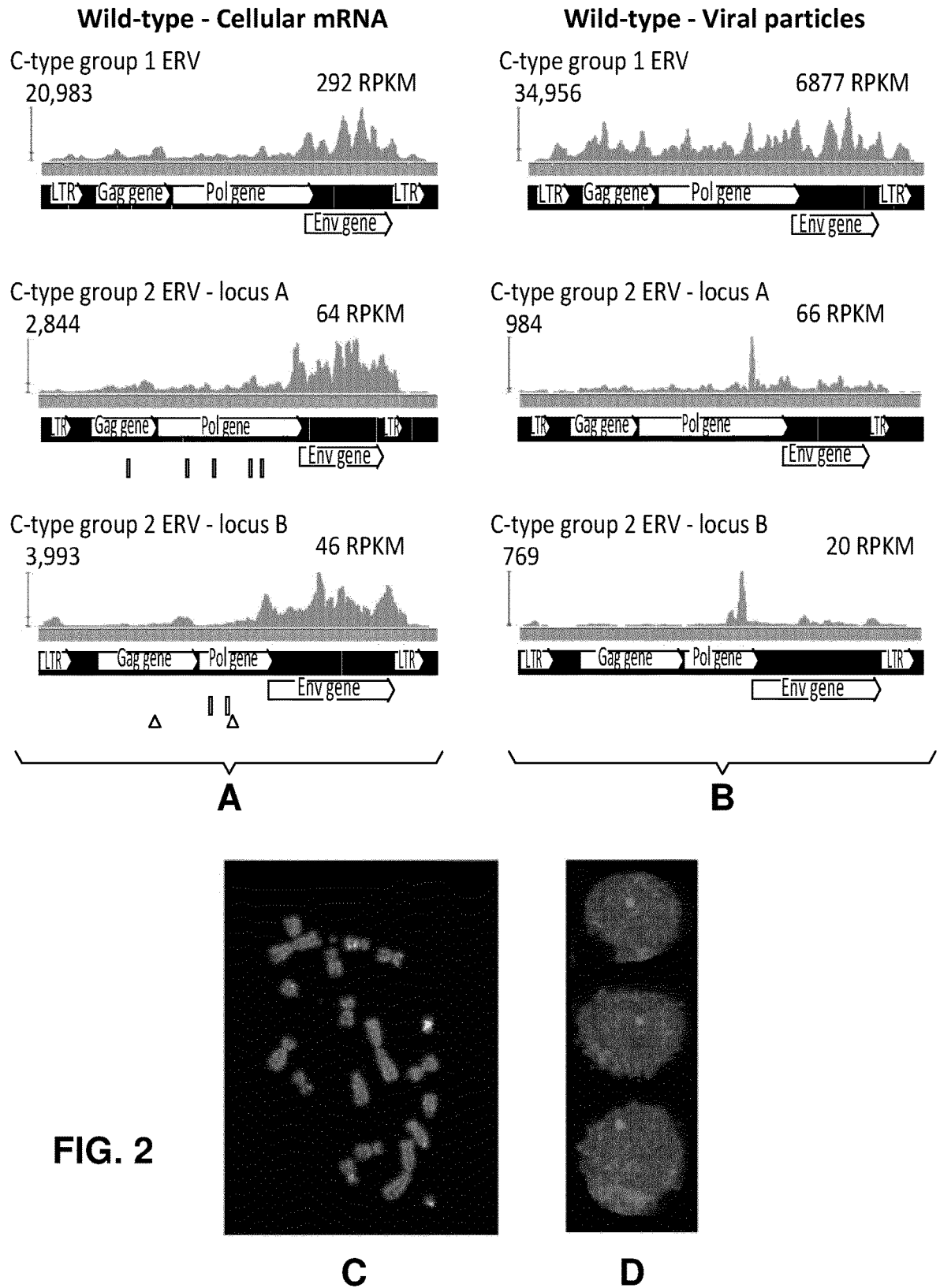
FIG. 2. Characterization of expressed type-C ERV sequences in wild-type CHO cells. Mapping of Illumina sequencing reads of total cellular RNA (A), or of viral particle RNA (B) obtained from CHO-K1 cells on group 1 and group 2 type-C ERV sequences. Reads were mapped to a consensus sequence for group 1 and on two distinct loci (locus A and locus B) for group 2 ERV. The maximal number of mapped reads is indicated on the left axis of each panel, and the Reads Per Kilobase Million (RPKM) are stated to the right. (C) Representative metaphase spread of CHO-K1 chromosomes FISH analysis using fluorescent probes specifically targeting group 1 type-C ERV. Chromosomal DNA is represented and the FISH signals of integrated retroviral sequences are shown as lighter dots (D) Three representative interphase CHO-K1 cells are shown, with mRNAs showing in the central region and group 1 type-C ERV RNA at the periphery. The bright light dot represents the nascent group 1 mRNA at the transcription site. Signs present on the schematic representation of group 2 ERV on locus A and B (A) show the mutation type occurring in these ERV sequences, 2 frameshift mutations N terminally and 3 stop codon mutations in the depiction (left) of C-type group 2 ERV-locus A and 2 deletions in the depiction (left) of C-type group 2 ERV-locus B, with the deletion size indicated as the number of bases.

To complement the genomic CHO ERV characterization, the total cellular mRNA was sequenced using Illumina Short-Read® technology to refine the transcribed ERV sequences. Type-C ERV mRNAs were among the top 10 most abundant transcripts in CHO cells (data not shown). Mapping of these Illumina® reads to type-C ERV representatives showed that 99.5% of all reads had sequences corresponding to group 1 and 2, indicating that these two groups contribute the vast majority of the transcribed ERVs of CHO cells. While the Illumina® reads mapped mainly on two easily distinguishable group 2 ERV sequences, they mapped on approximately 30 group 1 ERV sequences (FIG. 2A). As group 1 ERVs are most highly conserved, this did not allow unambiguous attribution of these reads to one or few unique group 1 loci. Interestingly, both transcribed group 2 ERV sequences contained interrupted ORFs and/or missing coding sequences, one containing a deletion of 2350 bp in the pol gene and the second having one frameshift in the gag and pol genes, as well as three stop codon mutations in pol. These mutations were confirmed by Sanger sequencing. In contrast, the transcribed group 1 ERV sequences seemed to encode full-length gag, pol and env transcripts. Overall, this suggested that between 3 to 32 ERV loci are transcribed, corresponding to approximately 2-20% of the total ERV elements in CHO cells (TABLE 3). Such an ERV expression frequency agrees with previous reports indicating that the majority of endogenized ERVs are epigenetically silenced in cell lines and organisms (32). Finally, among the total cellular mRNA, LTR-containing viral genomic RNA was also detected, indicating that CHO cells are capable of producing retroviral genomes that may be encapsulated and released as retroviral particles in the cell supernatant.

Retroviral-like particles released by cultured CHO cells were isolated, and the viral genomic RNA sequences were extracted and characterized by deep-sequencing using Illumina® technology. A twenty-fold enrichment in LTR-containing viral genomic RNA was observed when compared to the total cellular mRNA sequences (FIG. 2A). This indicated that CHO cells are able to shed retroviral particles containing genomic viral RNA into the cell supernatant. In-depth analysis of these viral RNA sequences indicated that group 1-derived reads were mostly present in the released viral particles (FIG. 2B). Moreover, these sequences could be mapped to just 1 to 5 different group 1 ERV sequences, suggesting that only few group 1 ERV loci are responsible for the production of viral particles (VPs) in CHO cells (TABLE 3).

To further characterize the functional group 1 type-C ERV sequences, group 1-specific probes for Fluorescent in-situ hybridization (FISH) experiments were designed. Using these probes, approximately 50-100 group 1 ERV integration sites in the CHO-K1 genome were detected, in line with the number of viral integration events detected in the newly assembled genome (FIG. 2C and TABLE 3). Retroviral integrations were dispersed throughout the CHO-K1 genome, with a possible integration hotspot in one of the smallest chromosomes. Additionally, when staining for group 1 nascent mRNAs, a unique highly transcribed site, suggesting that only a single group 1 ERV locus might be transcriptionally active, was observed (FIG. 2D).

Altogether, systematic ERV characterization at the genome, transcriptome and viral particle (VP) level identified several type-C group 1 ERVs as strong candidates for the expression and release of functional retroviral particles from CHO-K1 cells. Although the high sequence identity among the type-C ERV sequences concealed the exact number of expressed ERV loci, these data suggested that mutating few transcribed group 1 ERV loci by genome editing might suffice to prevent ERV particle formation.

Designing ERV-Specific Sg RNA Sequences for CRISPR-Cas9 Genome Editing

Figure 1C:
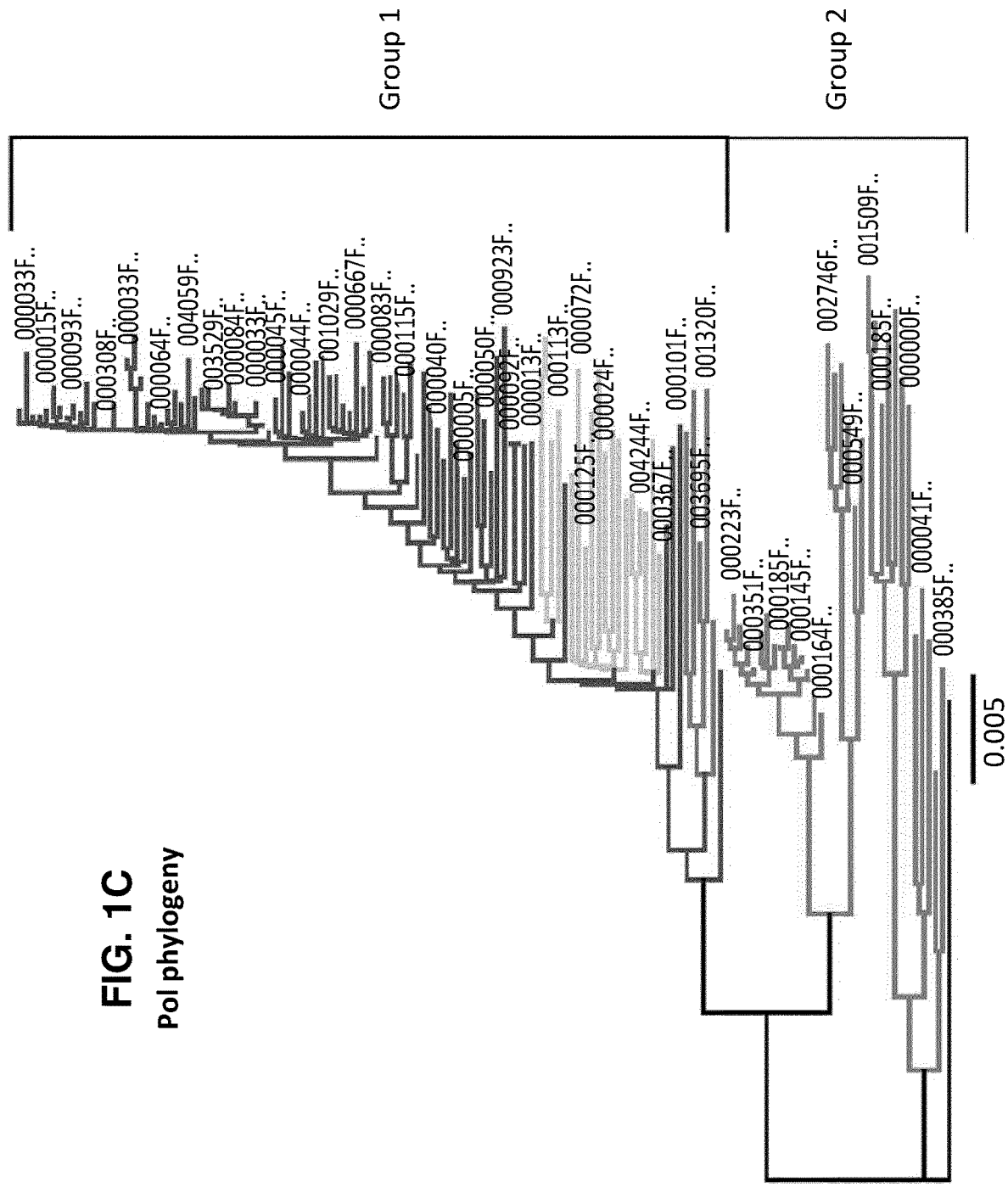
Figure 3:
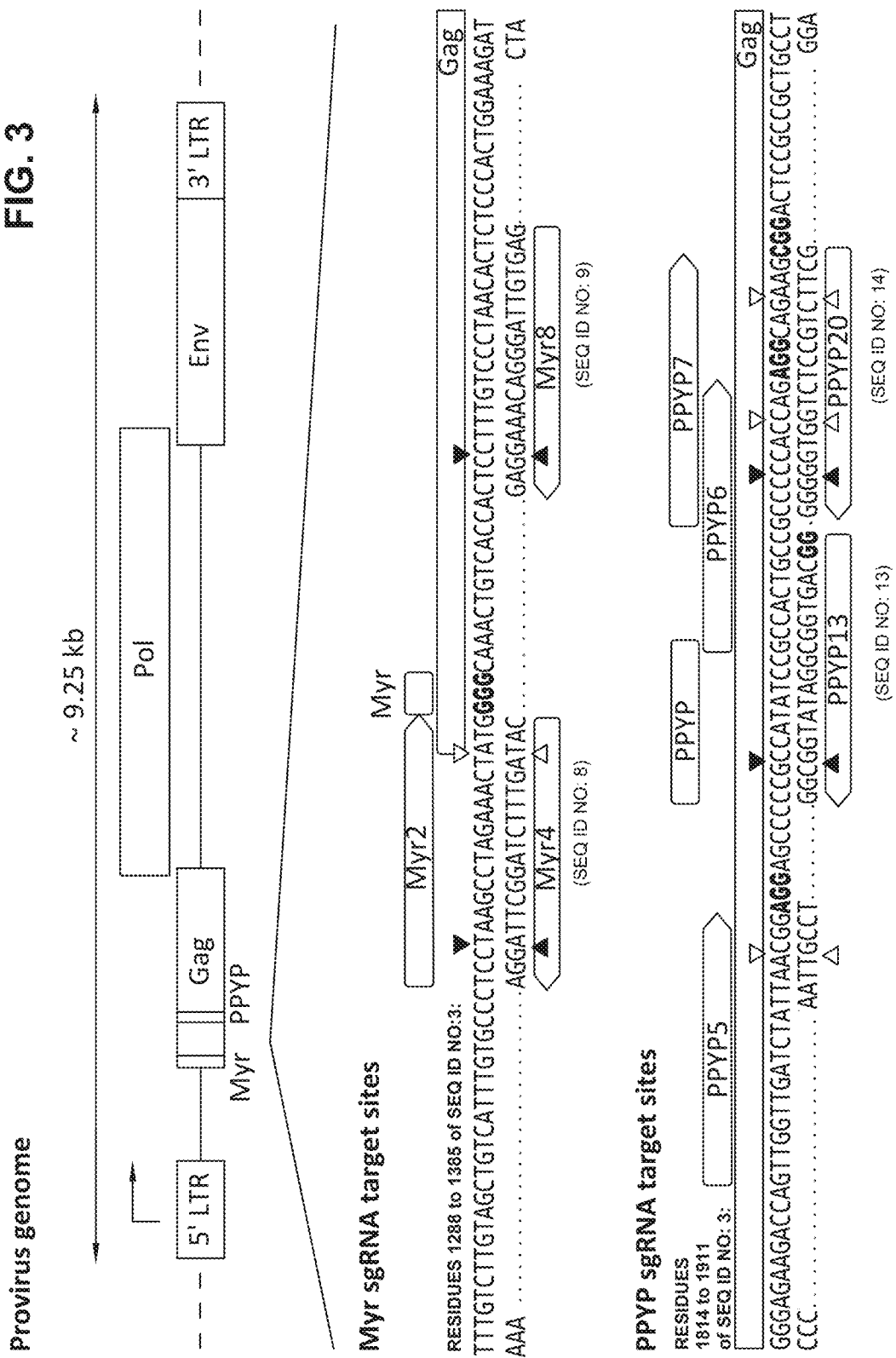
FIG. 3. CRISPR-Cas9 target sites for ERV mutagenesis. The orientation and position of the eight sgRNA sequences designed to target the Myristoylation (Myr) and PPYP motifs of the gag group 1 type-C ERVs are illustrated by grey arrows. The CRISPR-Cas9 DSB sites are shown by open triangles for sgRNAs targeting the forward strand (Myr2, PPYP5, PPYP6, PPYP7) and by filled triangles for sgRNA targeting the reverse strand (Myr4, Myr8, PPYP13, PPYP20). The Protospacer adjacent motif (PAM) sites are marked by bold letters.

To inhibit the release of potentially infective viral particles (VPs) from CHO cells, it was the aim to disrupt conserved ERV sequence motifs critical for VP release. The Gag protein plays a pivotal role during retrovirus budding, and, consistently, it was conserved among the type-C ERVs in CHO cells. However, in contrast to the pol gene for instance, the gag sequences were sufficiently different to distinguish group 1 from group 2 type-C ERV sequences, allowing to specifically target group 1 ERV particles (FIGS. 1B and 1C). Two conserved gag sequences involved in viral budding were selected—the myristoylation (Myr) and the PPxY motifs—as targets for CRISPR-Cas9-mediated mutagenesis. The N-terminal Myr motif locates at a glycine residue at position 2 downstream of the ATG translation initiation codon (FIG. 3). Myristoylation of Gag is generally considered essential for targeting the protein to the host plasma membrane (33). Mutations that directly interfere with Gag myristoylation, that block translation from the physiological start site or that create a loss-of-function gag transcript will perturb proper viral particle assembly at the plasma membrane, and hence block retroviral particle budding (33, 34). In addition to Myr, the conserved proline-rich PPxY motif also contributes to retrovirus budding, likely by interacting with the ESCRT machinery (35), and its mutation strongly inhibits viral particle release (36). The PPxY motif overlapped with a PPYP motif that is conserved in group 1 and group 2 CHO ERVs, which is termed PPYP hereafter to refer to this CHO-specific PPxY-related budding motif.

Eight sgRNAs against the group 1 gag consensus sequence were designed: three constructs targeting the Myr motif (Myr2, Myr4, Myr8) and five constructs targeting the PPYP motif (PPYP5, PPYP6, PPYP7, PPYP13, PPYP20) (FIG. 3). The selected sgRNA sequences located close to the corresponding target motifs and were predicted to perfectly match between 33 and 117 target ERV sequences, but to target up to 283 sites when allowing a maximum of three mismatches and non-canonical Protospacer adjacent motif (PAM) sites (TABLE 1). Importantly, all these potential cleavage sites map to ERV sequences, while other off-target sites in the CHO genome were not detected. Although these sgRNA sequences contain a multitude of predicted target sites, it was hypothesized that expressed ERVs might be preferentially cleaved by the CRISPR-Cas9 nuclease, due its preference for open chromatin (37).

Figure 7:
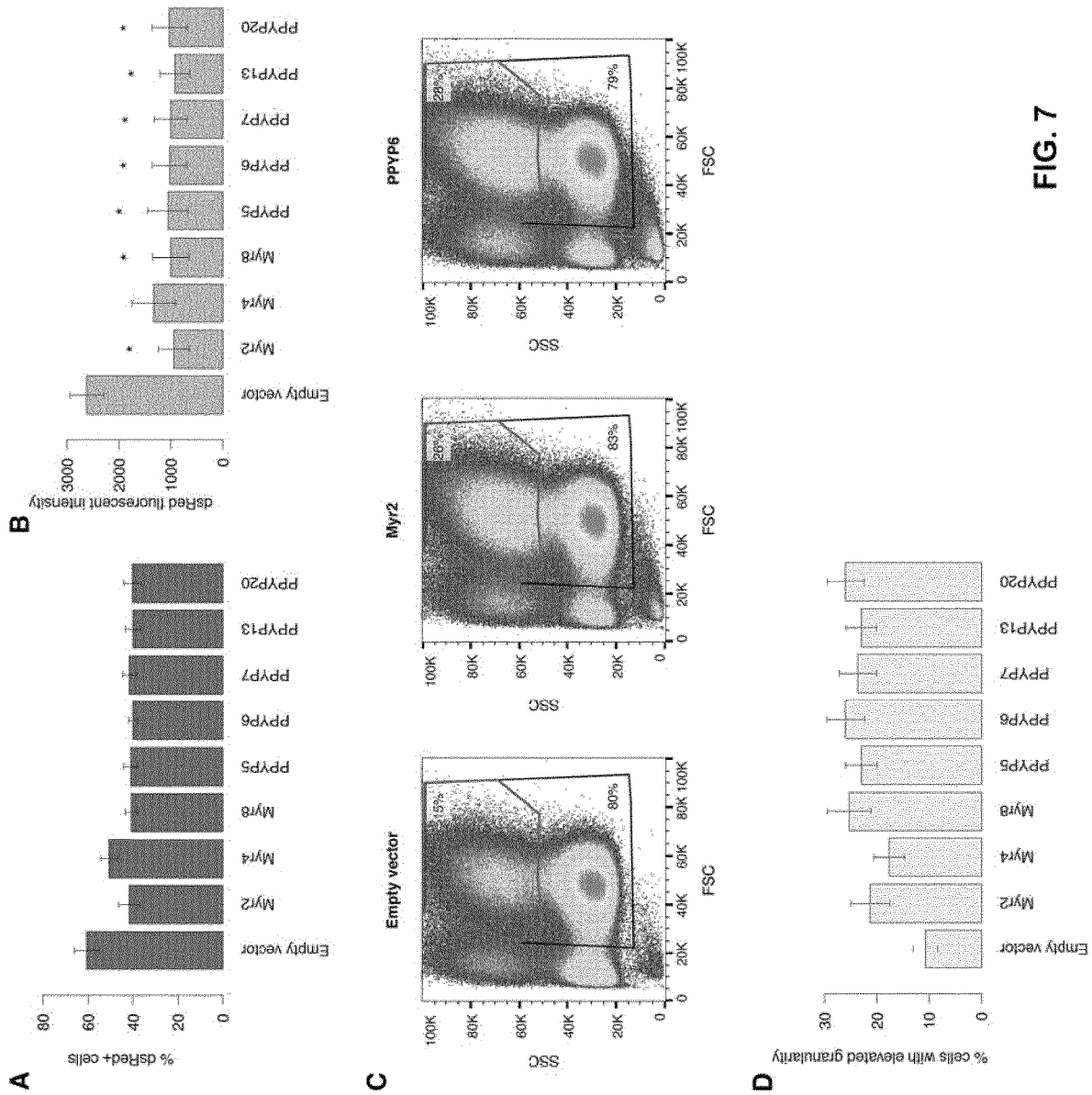
FIG. 7. Assessment of gag-specific sgRNA-mediated CRISPR-Cas9 cleavage by flow cytometry. Analysis of the of dsRed positive (dsRed+) cell frequency (A), the dsRed fluorescence intensity (B) and the frequency of high granularity cells (C and D) of CHO cells transfected with CRISPR-Cas9, Myr or PPYP motif-specific sgRNAs (Myr2, Myr4, Myr8, PPYP5, PPYP6, PPYP7, PPYP13, PPYP20 sgRNAs) or a non-targeting empty vector control and dsRed transfection control expression plasmids. Panel C shows size (FSC) vs granularity (SSC) flow cytometry density plots of the empty vector-, Myr2 sgRNA- and PPYP6-treated cells. The larger gate selects for intact non-debris cells while the smaller gate marks the CHO cell subpopulation with an elevated granularity level, as quantified in panel D. Statistical significance relative to the empty vector control was calculated using the two-tailed unpaired Student's t-test with Benjamini and Hochberg false discovery rate correction (n=3, error bars represent s.e.m, * $P<0.05$, ** $P<0.01$).

To mutate the Gag budding motifs, CHO-K1 parental cells were transiently transfected with CRISPR-Cas9 and Myr or PPYP sgRNA expression plasmids together with a dsRed transfection control plasmid. For CRISPR control samples, the gag-specific sgRNA expression plasmids were replaced with a non-targeting empty vector sgRNA control plasmid (empty vector) or left untreated (wild-type). Transfected dsRed positive (dsRed+) cells were bulk-sorted to enrich for cells containing mutations in the target motifs. Following treatments with ERV-specific sgRNAs, an overall reduced frequency of transfected dsRed+ cells as well as a significant drop in dsRed fluorescence intensity in dsRed+ cells compared to control samples were noted, suggesting that the most highly transfected cells may not survive because of a high frequency of genome cleavage (FIGS. 7A and B). Consistently, this effect was reduced for Myr4 sgRNA treated cells, which has the lowest number of predicted target sites. We also observed an elevated cell granularity following CRISPR treatment which inversely correlated with the frequency and expression intensity of dsRed+ cells (FIGS. 7C and D). Highly granular cells were previously reported to consist of pro-apoptotic and/or dying cell populations (38). Altogether, this provides evidence that CRISPR-mediated ERV cleavage impedes cell proliferation and survival, especially in highly transfected cells, implying that ERV-specific sgRNAs efficiently introduce DSBs at multiple target sites in the CHO genome.

Figure 8:
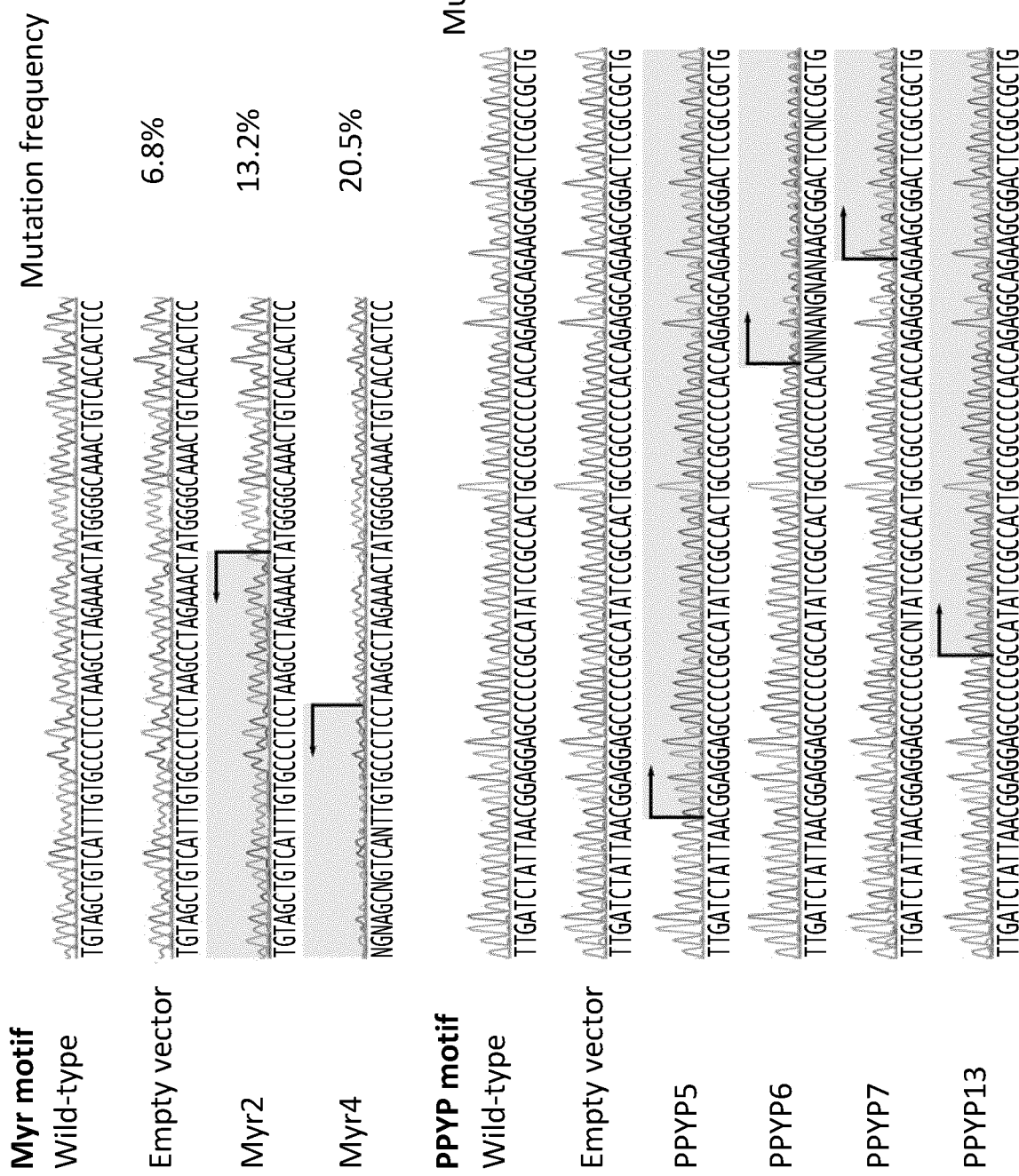
FIG. 8. Estimation of gag-specific sgRNA-mediated CRISPR-Cas9 cleavage efficiency by targeted mRNA sequencing of polyclonal CHO populations.

To estimate the CRISPR-mediated mutagenesis frequency within the expressed group 1 ERVs, the total cellular mRNA of bulk-sorted Myr- and PPYP-treated cells was reverse transcribed and PCR amplified, followed by the direct sequencing of the polyclonal PCR products or by their cloning into bacterial vectors prior to single colony sequence analysis. Based on these analyses, it was estimated that the designed gag-specific sgRNAs introduced mutations in roughly 9 to 35% of the ERV mRNAs, and that the Myr2 or PPYP6 sgRNAs were most efficient (FIG. 8, TABLE 4, TABLE 5). Interestingly, some of the recovered mutations were expected to block translation or introduce frameshifts, and thus should cause Gag loss-of-function phenotypes.

TABLE 4

Detection of CRISPR-mediated mutations in expressed type-C ERV sequences cloned into plasmid vectors.

| Sample | Analyzed sequence | Mutated sequences | Mutation frequency | Loss-of-function mutation frequency (1) |
|---|---|---|---|---|
| Myr2 sgRNA | 12 | 2 | 17% | 50% |
| PPYP6 sgRNA | 56 | 4 | 7% | 75% |
| PPYP13 sgRNA | 12 | 1 | 8% | 0% |
| Total | 80 | 7 | 9% | 42% |

(1) Includes translation inhibition and frameshift mutations and is expressed relative to the number of mutated sequences.

TABLE 5 shows mRNA Sanger sequencing data of the expressed ERV repair junctions of CHO-K1 cells treated with wild-type Cas9 nuclease and various sgRNAs (Myr2, PPYP6 and PPYP13). The sequences are derived from Sanger sequencing of cDNA PCR amplicons cloned into plasmid vectors.

TABLE 5

Sequence analysis of ERV-mutated CHO-K1 junction amplicons cloned into plasmid vectors.

| Sample (1) | | Sequence (2) | Features (3) | Mutation type (4) | Repair pathway (5) | Pattern score (6) | FORE CasT (7) |
|---|---|---|---|---|---|---|---|
| Myr2 sgRNA (n = 2) | | | | | | | |
| 4_5 | Genomic | 5'-CTGTCATTTG TGCCCTCCTAAGC CTAGAAACT-AT GGGGCAAACTGT CACCACTCCTTTG TCCC-3' (SEQ ID NO: 69) | 1 bp insertion, 1 bp MH | Outside ERV coding region | C-NHEJ (8) | — | 17.8% |
| | Junction | 5'-CTGTCATTTG TGCCCTCCTAAGC CTAGAAACTTATG GGGCAAACTGTC ACCACTCCTTTGT CCC-3' (SEQ ID NO: 70) | | | | | |

TABLE 5-continued

Sequence analysis of ERV-mutated CHO-K1 junction amplicons cloned into plasmid vectors.

| Sample (1) | | Sequence (2) | Features (3) | Mutation type (4) | Repair pathway (5) | Pattern score (6) | FORE CasT (7) |
|---|---|---|---|---|---|---|---|
| 4_9 | Genomic | 5'-CTGTCATTTG TGCCCTCCTAAGC CTAGAAACTATG GGGCAAACTGTC ACCACTCCTTTGT CCC-3' ((SEQ ID NO: 69) | 12 bp deletion, 5 bp MH | Translation inhibition | MMEJ | 329.4 | 13.4% |
| | Junction | 5'-CTGTCATTTG TGCCCTCCTAAGC CTAG--------- ---AAACTGTCAC CACTCCTTTGTCC C-3' (SEQ ID NO: 71) | | | | | |

PPYP6 sg RNA (n = 4)

| Sample (1) | | Sequence (2) | Features (3) | Mutation type (4) | Repair pathway (5) | Pattern score (6) | FORE CasT (7) |
|---|---|---|---|---|---|---|---|
| 1_6 | Genomic | 5'-CCTTTGATTC CTCCCAACCCCCC TTCCCATTCCAAC CTTTACCCTACCG TGATGAAAGACAC TAAGGCTAAAGAA AAGAAGACACCTA AGGTACTCCCTCC GGGAGAAGACCAG TTGGTTGATCTAT TAACGGAGGAGCC <u>CCCGCCATAT CCGCCATGCCGC CCCCACCAGAG GCAGAAGCGGAC TCCGCCGCTGCCT</u> TGGCGGAAGCGGC CCCTGACCCTT-3' (SEQ ID NO: 72) | 1: 27 bp deletion, 7 bp MH (89 bp upstream) 2: Deletion + Insertion (Replace-ment of 29 bp with 2 bp; net = 27 bp deletion), 15 bp MH | In-frame mutation | 1: SD-MMEJ (loop-out) 2: SD-MMEJ (loop-out) | — | — |
| | Junction | 5'-CCTTTGATTC CTCCCAACCCCCC TTCCCATTCCAAC CTTTACCCTACCG TGATGAAAGACAC TAAGGCTAAAGAA AAGAAGACACCTA AGGTACTCCCTCC GGGAGAAGACC-- ------------- ------------C <u>CCCGCCATAT CCGCCATA----</u> ------------ ----------<u>TCC</u> <u>GCC</u>GCTGCCTTGG CGGAAGCGGCCCC TGACCCTT-3' (SEQ ID NO: 73) | | | | | |
| 3_1 | Genomic | 5'-GCCCCCGC CATATCCGCC ACTGCCGCCCCCA *C-C*AGAGGCAG AAGCGGACTCCGC CGCTGCCTTG-3' (SEQ ID NO: 74) | 1 bp insertion, 1 bp MH | Frameshift mutation | C-NHEJ | — | 3.1% |
| | Junction | 5'-GCCCCCGC CATATCCGCC ACTGCCGCCCCCA CCCAGAGGCAGA AGCGGACTCCGCC GCTGCCTTG-3' (SEQ ID NO: 75) | | | | | |

TABLE 5-continued

Sequence analysis of ERV-mutated CHO-K1 junction amplicons cloned into plasmid vectors.

| Sample (1) | | Sequence (2) | Features (3) | Mutation type (4) | Repair pathway (5) | Pattern score (6) | FORE CasT (7) |
|---|---|---|---|---|---|---|---|
| 3_10 | Genomic | 5'-TCCGGGAGAA GACCAGTTGGTTG ATCTATTAACGGA GGA*GCCCCCGC* *CATATCCG*CC ACTGCCGCCCCCA *CC*AGAGGCAGA AGCGGACTCCGCC GCTGCCTTGGCGG AAGCGGCCCC-3' (SEQ ID NO: 76) | 4 bp deletion, 2 bp MH or 5 bp MH (22 bp upstream) | Frameshift mutation | MMEJ or SD-MMEJ (loop-out) | NA | 1.2% |
| | Junction | 5'-TCCGGGAGAA GACCAGTTGGTTG ATCTATTAACGGA GGA*GCCCCCGC* *CATATCCG*CC ACTGCC*GCC*---- *CC*AGAGGCAGAA GCGGACTCCGCCG CTGCCTTGGCGGA AGCGGCCCC-3' (SEQ ID NO: 77) | | | | | |
| 8_6 | Genomic | 5'-ATGGATCCTG GACCACACGGG<u>CA TCCCGATCAAGTG GCTTATATCGTCA CTTGGGAGGCTTT</u> GGTTCAGGACCCC CCTCCCTGGGTAC GTCCTTTCTTACA TCCCAAGGGCCCC TCTCTCCTTCCCC CCTCTAACCGCTC CAACCGACCCATT CCTTCGGCCCCTA CACCTCCCACTCC TTTGATTCCTCCC AACCCCCCTTCCC ATTCCAACCTTTA CCCTACCGTGATG AAAGACACTAAGG CTAAAGAAAAGAA GACACCTAAGGTA CTCCCTCCGGGAG AAGACCAGTTGGT TGATCTATTAACG GAGGAGCCC*CCG* *CC*ATATCCGC CACTGCCGCC<u>CCC</u> A*CC*AGAGGCA- ------------- ---<u>GAAGC</u>GGACT CCGCCGCTGCCTT GGCGG-3' (SEQ ID NO: 78) | Deletion + Insertion; (Replace-ment of 9 bp with 26 bp; net = 17 bp insertion); templated inversed insertion possibly from same or other ERV allele (9) | Frameshift mutation | HR | – | – |
| | Junction | 5'-ATGGATCCTG GACCACACGGG<u>CA TCCCGATCAAGTG GCTTATATCGTCA CTTGGGAGGCTTT</u> GGTTCAGGACCCC CCTCCCTGGGTAC GTCCTTTCTTACA TCCCAAGGGCCCC TCTCTCCTTCCCC CCTCTAACCGCTC CAACCGACCCATT CCTTCGGCCCCTA CACCTCCCACTCC TTTGATTCCTCCC AACCCCCCTTCCC ATTCCAACCTTTA CCCTACCGTGATG | | | | | |

TABLE 5-continued

Sequence analysis of ERV-mutated CHO-K1 junction amplicons cloned into plasmid vectors.

| Sample (1) | Sequence (2) | Features (3) | Mutation type (4) | Repair pathway (5) | Pattern score (6) | FORE CasT (7) |
|---|---|---|---|---|---|---|
| | AAAGACACTAAGG CTAAAGAAAAGAA GACACCTAAGGTA CTCCCTCCGGGAG AAGACCAGTTGGT TGATCTATTAACG GAGGAGCCCCCG CCATATCCGC CACTGCCGCC<u>CCC</u> <u>AAGTGACGATATA</u> <u>AGCCACTTGATCG</u> <u>GGATGC</u>GGACTCC GCCGCTGCCTTGG CGG-3' (SEQ ID NO: 79) | | | | | |
| | | PPYP13 sgRNA (n = 1) | | | | |
| (5_8) Genomic | 5'-TTAACGGAGG AGCCCCCGCC ATATCCGCCAC TGCCGCCCCACC AGAGGCAGAAGCG GACTCCGCCGCTG CCTTGGCGGAAGC GGCCCC------- -----TGACCCTT CACCAATGGCTTA-3' (SEQ ID NO: 80) | 12 bp insertion (10); likely from another ERV allele | In-frame mutation | HR | — | — |
| Junction | 5'-TTAACGGAGG AGCCCCCGCC ATATCCGCCAC TGCCGCCCCACC AGAGGCAGAAGCG GACTCCGCCGCTG CCTTGGCGGAAGC GGCCCCAGATCCA CCACCTGACCCTT CACCAATGGCTTA-3' (SEQ ID NO: 81) | | | | | |

TABLE 5 shows mRNA Sanger sequencing data of the expressed ERV repair junctions of CHO-K1 cells treated with wild-type Cas9 nuclease and various sgRNAs (Myr2, PPYP6 and PPYP13). In column 2, the predicted blunt-ended DSB sites induced by the various sgRNAs and the wild-type Cas9 nuclease are highlighted in italicized Arial Black font (e.g., A), PAM site are shown in bolded Arial front (e.g., A). Myr and PPYP target motifs are highlighted in regular Arial Black font (e.g., A). Pre-existing microhomologies (MH) of the microhomology-mediated end-joining (MMEJ) repair mechanism are shown in bold, while de novo MH of the synthesis-dependent microhomology-mediated end-joining (SD-MMEJ) mechanism being underlined with a double line. Inserted bases are represented in bold letters, deleted bases with a "-" sign, and replacements in bold black. (8) Frequent 1 bp insertions consisting of a duplication of the 4th nucleotide were also observed previously (Lemos 2018, Taheri 2018), (9) DNA template sequence for insertion located 290 bp upstream, (10) DNA template sequence for insertion located 71 bp downstream.

Table 5, column 2 shows the predicted blunt-ended DSB sites induced by the various sgRNAs and the wild-type Cas9 nuclease are highlighted (see table legend for further details). In column 3, the size of mutation and MH length (in bp) is provided. The distance between priming site and the break site for de novo MH are shown in parenthesis. Column 4 shows that ERV mutation types include in-frame mutations, out-of-frame mutations, translation inhibition (mutation of the ATG translation initiation codon) or mutations locating outside of the ERV coding region. Out-of-frame mutations and translation inhibition are likely, while in-frame mutations and mutations outside of the coding region are less likely to influence ERV expression and VLP formation. In column 5, the most probable DSB repair mechanism based on manual junction analysis is indicated. Possible repair mechanisms include C-NHEJ, MMEJ, SD-MMEJ (snap-back), SD-MMEJ (loop-out), single strand annealing (SSA), homologous recombination (HR), and unknown. For snap-back SD-MMEJ mechanism, de novo priming sites are inverted repeats, while loop-out SD-MMEJ mechanisms uses priming sites with direct repeats (Khodaveridan 2017). If the observed junction sequence is compatible with more than one mechanism and both appear equally likely, all potential pathways are listed. Junctions were verified for homologies at break site and templated insertions (SD-MMEJ) using program described in Schimmel et al. 2017 (Schimmel 2017). Colum 6 shows the score of each repair pattern according to the MH size and the deletion length. Pattern score was calculated using the RGenome "Microhomology-Predictor" tool (on the rgenome.net website under mich-calculator) described in Bae et al. 2014 (Bae 2014). The higher the score, the more likely the predicted mutation should be observed. The pattern score is only valid for repair junctions showing MHs at the break site (MMEJ-mediated repair). Column 7 shows the predicted frequencies of CRISPR-Cas9 editing outcomes using the online tool FORECasT1® (Favored Outcomes of Repair Events at Cas9 Targets; o the partslab.sanger.ac.uk website under FORECasT®) as described in Allan et al. 2018 (Allan 2018). The higher the frequency, the more junctions are expected to contain the predicted mutation pattern. Only the frequencies of the predicted ten most frequent mutations are listed.

Isolation and Characterization of ERV-Mutated CHO-K1 Clones

Given that roughly 10-15% of the expressed group 1 ERV sequences are predicted to be mutated, it was hypothesized that a potential reduction in viral particle release would be difficult to detect within a polyclonal population. Thus, single CHO cell clones were isolated from bulk-sorted Myr2- or PPYP6-edited cell pools, and screened for those having mutations in the expressed group 1 ERV sequences. 18 out of 95 (18%) and 14 out of 181 (8%) Myr2 and PPYP6 sgRNA-treated clones, respectively, contained group 1 ERV mutations at the mRNA level, in line with previous estimations (TABLE 6, also TABLE 4, 5).

TABLE 6

Detection of CRISPR-mediated mutations in the expressed type-C ERV sequences of edited CHO-K1 clones.

| Sample | # screened clones | # mutated clones | Mutation frequency | Loss-of-function mutation frequency* |
|---|---|---|---|---|
| Myr2 sgRNA | 95 | 18 | 19% | 11% |
| PPYP6 sgRNA | 181 | 14 | 8% | 79% |
| Total | 276 | 32 | 12% | 45% |

*Includes translation inhibition and frameshift mutations and is expressed relative to the number of mutated clones.

Among the Myr2-mutated clones, the majority possessed an identical 1 bp insertion upstream of the ATG start codon (TABLE 7), which likely resulted from staggered CRISPR-Cas9 cleavage (39). No clone treated with the PPYP6 sgRNA acquired a mutation spanning the PPYP motif. Nonetheless, two Myr2- and eleven PPYP6-derived clones contained mutations either blocking translation or frame-shifting the gag transcripts, hence making them promising candidates for reduced viral particle release. It was also observed that the Sanger sequencing chromatogram of the repair junctions of all clones showed a clear singly mutated sequence and lacked background noise in the CRISPR flanking sequences. This supported the hypothesis that only a single group 1 ERV locus might be prominently transcribed and leads to the production of viral particles by CHO cells.

TABLE 7

Sequence analysis of the expressed mRNA ERV sequences of mutated CHO-K1 clones.

| Clone (1) | | Sequence (2) | Features (3) | Mutation type (4) | Repair pathway (5) | Pattern score (6) | FORECasT (7) |
|---|---|---|---|---|---|---|---|
| Myr2 sgRNA (n = 18) | | | | | | | |
| C02 | Genomic | 5'-TGTCATTTGTGCCCTCCTAA GCCTAGAAACTATGGGGCAA ACTGTCACCACTCCTTTGTCC CTAACACTCTCCCACTGGAA-3' (SEQ ID NO: 82) | 2 bp deletion, 1 bp MH | Translation inhibition | C-NHEJ | — | 2.6% |
| | Junction | 5'-TGTCATTTGTGCCCTCCTAA GCCTAGAAAC--TGGGGCAAA CTGTCACCACTCCTTTGTCCC TAACACTCTCCCACTGGAA-3' (SEQ ID NO: 83) | | | | | |
| D12 | Genomic | 5'-CGACTCTCTCTCAATTCCT- 75bp-GAAACTATGGGGCAAAC TGTCACCACTCCTTTGT-3' (SEQ ID NO: 84) | 114 bp deletion, 3 bp MH | Translation inhibition | MMEJ | NA | — |
| | Junction | 5'-CGACTCTCTCTCAA------95b p-----------ACTGTCACCACT CCTTTGT-3' (SEQ ID NO: 85) | | | | | |
| G09 | Genomic | 5'-TCTTTGTCTTGTAGCTGTCA TTTGTGCCCTCCTAAGCCTAG AAACTATGGGGCAAACTGTCA CCACTCCTTTGTCCCTAACAC TCTCCCACTGGAAAGATGTAC AGGAATATGCTCATAACCAAT CT-3'(SEQ ID NO: 86) | 27 bp deletion, 2 bp MH | Outside ERV coding region | MMEJ | 51.8 | — |
| | Junction | 5'-TCTTTGTCTTGTAGCTGTC-- --------------ATGGGGCA AACTGTCACCACTCCTTTGTC CCTAACACTCTCCCACTGGAA AGATGTACAGGAATATGCTCA TAACCAATCT-3' (SEQ ID NO: 87) | | | | | |

TABLE 7-continued

Sequence analysis of the expressed mRNA ERV sequences of mutated CHO-K1 clones.

| Clone (1) | | Sequence (2) | Features (3) | Mutation type (4) | Repair pathway (5) | Pattern score (6) | FORE CasT (7) |
|---|---|---|---|---|---|---|---|
| H02 | Genomic | 5'-AGCTGTCATTTGTGCCCTC CTAAGCCTAGAAAAC*TATG*GGG CAAACTGTCACCACTCCTTTG TCCC-3'(SEQ ID NO: 88) | 3 bp deletion, no MH | Outside ERV coding region | C-NHEJ | — | — |
| | Junction | 5'-AGCTGTCATTTGTGCCCTC CTAAGCCTAGA---*TATG*GGGC AAACTGTCACCACTCCTTTGT CCC-3' (SEQ ID NO: 89) | | | | | |
| A04 (n = 14) | Genomic | 5'-CTCCTAAGCCTAGAAACT-A TGGGGGCAAACTGTCACCACT CC-3'(SEQ ID NO: 90) | 1 bp insertion, 1 bp MH | Outside ERV coding region | C-NHEJ (8) | — | 17.8% |
| | Junction | 5'-CTCCTAAGCCTAGAAACTT ATGGGGGCAAACTGTCACCACT CC-3' (SEQ ID NO: 91) | | | | | |

PPYP6 sgRNA (n = 14)

| Clone (1) | | Sequence (2) | Features (3) | Mutation type (4) | Repair pathway (5) | Pattern score (6) | FORE CasT (7) |
|---|---|---|---|---|---|---|---|
| A02 | Genomic | 5'-CCCCCGCCATATCCGCCAC TGCCGCCCC*CACCAGAGGCA GAAGCGGAC*TCCGCCGCTGC CTTGGCGGAAGC-3' (SEQ ID NO: 92) | Deletion + Insertion (Replace-ment of 20 bp with 10 bp; net = 10 bp deletion); inverted templated insertion from three possible ERV alleles | Frameshift mutation | HR | — | — |
| | Junction | 5'-CCCCCGCCATATCCGCCAC TGCCGCCCC*ACTGCTTCTG*---- ------TCCGCCGCTGCCTTGGC GGAAGC-3' (SEQ ID NO: 93) | | | | | |
| A07 | Genomic | 5'-CCCCCGCCATATCCGCCAC TGCCGCCCCCACCAGAGGCA GAAGCGGACTCCGCCGCTGC CTTGGC-3' (SEQ ID NO: 94) | 7 bp deletion, 2 bp MH flanking DSB | Frameshift mutation | Unknown (9) | — | 1.1% |
| | Junction | 5'-CCCCCGCCATATCCGCCAC TGCCGCCCCCA------CAGAAG CGGACTCCGCCGCTGCCTTG GC-3' (SEQ ID NO: 95) | | | | | |
| B11 (n = 3) | Genomic | 5'-CCCCCGCCATATCCGCCAC TGCCGCCCCCAC-CAGAGGC AGAAGCGGACTCCGCCGCTG CCTTGGC-3' (SEQ ID NO: 94) | 1 bp insertion, 1 bp MH | Frameshift mutation | C-NHEJ | — | 3.1% |
| | Junction | 5'-CCCCCGCCATATCCGCCAC TGCCGCCCCCACCCAGAGGC AGAAGCGGACTCCGCCGCTG CCTTGGC-3' (SEQ ID NO: 96) | | | | | |
| D08 | Genomic | 5'-GGAGAAGACCAGTTGGTTG ATCTATTAACGGAGGAGCCCC CCGCCATATCCGCCACTGCC GCCCCCACCAGAGGCAGAAG CGGACTCCGCC-3' (SEQ ID NO: 97) | 9 bp deletion, 2 bp MH | In-frame mutation | MMEJ | 191.4 | 2% |
| | Junction | 5'-GGAGAAGACCAGTTGGTTG ATCTATTAACGGAGGAGCCCC CCGCCATATCCGCCACTGCC GCCCC-----CAGAAGCGGAC TCCGCC-3' (SEQ ID NO: 98) | | | | | |
| E10 | Genomic | 5'-AGCCCCGCCATATCCGCC ACTGCCGCCCC*CACCA*AGG CAGAAGCGGACTCCGCCGCT GCCTTG-3' (SEQ ID NO: 99) | 37 bp deletion, 6 bp MH | Frameshift mutation | MMEJ | 172.7 | — |
| | Junction | 5'-AGCCCCGCCATATCCGCC --------------------GCT GCCTTG-3' (SEQ ID NO: 100) | | | | | |

TABLE 7-continued

Sequence analysis of the expressed mRNA ERV sequences of mutated CHO-K1 clones.

| Clone (1) | | Sequence (2) | Features (3) | Mutation type (4) | Repair pathway (5) | Pattern score (6) | FORE CasT (7) |
|---|---|---|---|---|---|---|---|
| G12 (n = 2) | Genomic | 5'-CCCCCGCCATATCCGCCAC TGCCGCCCCCACCAGAGGCA GAAGCGGACTCCGCCGCTGC CTTGGC-3'(SEQ ID NO: 101) | 3 bp deletion, 3 bp MH or 4 bp MH (4 bp downstream) | In-frame mutation | MMEJ or SD-MMEJ (loop-out) | 258.3 | 14.8% |
| | Junction | 5'-CCCCCGCCATATCCGCCAC TGCCGCCCCA---GAGG<u>C</u>AG <u>A</u>AGCGGACTCCGCCGCTGCC TTGGC-3' (SEQ ID NO: 102) | | | | | |
| K3 | Genomic | 5'-CCCCCGCCATATCCGCCAC TGCCGCCCCCACCAGAGGCA GAAGCGGACTCCGCCGCTGC CTTGGCGGAAGCGG-3' (SEQ ID NO: 103) | 22 bp deletion, 2 bp MH or 5 bp MH (6 bp upstream) | Frameshift mutation | MMEJ or SD-MMEJ (snap-back) | 133.1 | — |
| | Junction | 5'-CCCCCGCCATA<u>TCC</u>GCCAC TGC--------------GGA<u>CTCC</u> GCCGCTGCCTTGGCGGAAGC GG-3' (SEQ ID NO: 104) | | | | | |
| K9 (n = 2) | Genomic | 5'-CCCCCGCCATATCCGCCAC TGCCGCCCCCACCAGAGGCA GAAGCGGACTCCGCCGCTGC C-3'(SEQ ID NO: 105) | 1 bp deletion, 1 bp MH | Frameshift mutation | C-NHEJ | — | 19.5% |
| | Junction | 5'-CCCCCGCCATATCCGCCAC TGCCGCCCCAC-AGAGGCA GAAGCGGACTCCGCCGCTGC C-3' (SEQ ID NO: 106) | | | | | |
| K12 | Genomic | 5'-TTAACGGAGGAGCCCCCG CCATATCCGCCACTGCCGCC CCCACCAGAGGCAGAAGCGG ACTCCGC-3' (SEQ ID NO: 107) | Deletion + Insertion (Replace-ment of 3 bp with 1 bp; net = 2 bp deletion) | Frameshift mutation | Unknown | — | — |
| | Junction | 5'-TTAACGGAGGAGCCCCCG CCATATCCGCCACTGCCGCC CCCAC--AAGGCAGAAGCGGA CTCCGC-3' (SEQ ID NO: 108) | | | | | |
| K14 | Genomic | 5'-AGGAGCCCCCGCCATATCC GCCACTGCCGCCCCCACCAG AGGCAGAAGCGGACTCCCCC GCCATATCCGCGGAAGCGGC CCCTGACCCTT-3' (SEQ ID NO: 109) | 13 bp deletion, 2 bp MH or 5 bp MH (15 bp downstream) | Frameshift mutation | MMEJ or SD-MMEJ (loop-out) | 208.8 | — |
| | Junction | 5'-AGGAGCCCCCGCCATATCC GCCACT<u>GCC</u>-----------GCAGA AGCGGACTCC<u>GCCGC</u>TGCCT TGGCGGAAGCGGCCCCTGAC CCTT-3' (SEQ ID NO: 110) | | | | | |

Table 7 shows mRNA Sanger sequencing data of the expressed ERV repair junctions of CHO-K1 clones treated with wild-type Cas9 nuclease and the Myr2 or PPYP6 sgRNAs (Junctions), versus the unmutated sequence of the parental non-engineered Cho cell (Genomic). The sequences are derived from Sanger sequencing of cDNA PCR amplicons. If the same repair junction was detected more than once, the number is indicated below each sample name as (n=). In column 2, predicted blunt-ended DSB sites induced by the two sgRNAs and the wild-type Cas9 nuclease are highlighted in italicized Arial Black font (e.g., A), PAM sites and Myr and PPYP target motifs are highlighted in regular Arial Black font (e.g., A). Pre-existing microhomologies (MH) of the microhomology-mediated end-joining (MMEJ) repair mechanism are shown in bold grey letters (e.g. GC), while de novo MH of the synthesis-dependent microhomology-mediated end-joining (SD-MMEJ) mechanism are underlined with a double line. Inserted bases are represented in small bold Courier letters (e.g., c), deleted bases with a "-" sign, and replacements in italic underlined with a single bold line. (the dark highlighted boxes contain GGG). NA: not available. (8) Frequent 1 bp insertions consisting of a duplication of the 4th nucleotide were also observed previously (Lemos2018, Taheri2018). (9) Unknown mechanism but similar junction pattern was described in Shin et al. 2017 (Shin 2017).

To further investigate the CRISPR-derived mutations at the genome level, the Myr and PPYP flanking regions of type-C ERVs were deep sequenced in a subset of CHO clones bearing mutations in the expressed ERV sequences (TABLE 7). Two Myr2- and four PPYP6-edited clones with Gag loss-of-function mutations were selected in the expressed group 1 type-C ERV sequences (clones CO2 and D12 for Myr2; A02, E10, K03 and K14 for PPYP6) as well as one Myr2-derived clone with a large mutation outside of the group 1 ERV coding (G09) and genotyped them along with wild-type and empty vector control samples.

Table 7 shows mRNA Sanger sequencing data of the expressed ERV repair junctions of CHO-K1 clones treated with wild-type Cas9 nuclease and the Myr2 or PPYP6 sgRNAs. The sequences are derived from Sanger sequencing of cDNA PCR amplicons. In column 2 the predicted blunt-ended DSB sites induced by the two sgRNAs and the wild-type Cas9 nuclease are highlighted (see table legend for further details). In column 3, the size of mutation and MH length (in bp) is provided. The distance between priming site and the break site for de novo MH are shown in parenthesis.

Column 4 indicates that ERV mutation types include in-frame mutations, out-of-frame mutations, translation inhibition (mutation of the ATG translation initiation codon) or mutations locating outside of the ERV coding region. Out-of-frame mutations and translation inhibition are likely, while in-frame mutations and mutations outside of the coding region are less likely to influence ERV expression and VLP formation. In column 5, the most probable DSB repair mechanism based on manual junction analysis. Possible repair mechanisms include C-NHEJ, MMEJ, SD-MMEJ (snap-back), SD-MMEJ (loop-out), single strand annealing (SSA), homologous recombination (HR), and unknown. For snap-back SD-MMEJ mechanism, de novo priming sites are inverted repeats, while loop-out SD-MMEJ mechanisms uses priming sites with direct repeats (Khodaveridan 2017). If the observed junction sequence is compatible with more than one mechanism and both appear equally likely, all potential pathways are listed. Junctions were verified for homologies at break site and templated insertions (SD-MMEJ) using program described in Schimmel et al. 2017 (Schimmel 2017). Column 6 shows the score of each repair pattern according to the MH size and the deletion length. Pattern score was calculated using the RGenome "Microhomology-Predictor" tool (http://www.rgenome.net/mich-calculator/) described in Bae et al. 2014 (Bae2014). The higher the score, the more likely the predicted mutation should be observed. The pattern score is only valid for repair junctions having MHs at the break site (MMEJ-mediated repair). Column 7, shows the predicted frequencies of CRISPR-Cas9 editing outcomes using the online tool FORECasT (Favoured Outcomes of Repair Events at Cas9 Targets; https://partslab.sanger.ac.uk/FORECasT) as described in Allan et al. 2018 (Allan 2018). The higher the frequency, the more junctions are expected to contain the predicted mutation pattern. Only the frequencies of the predicted ten most frequent mutations are listed.

Figure 4:
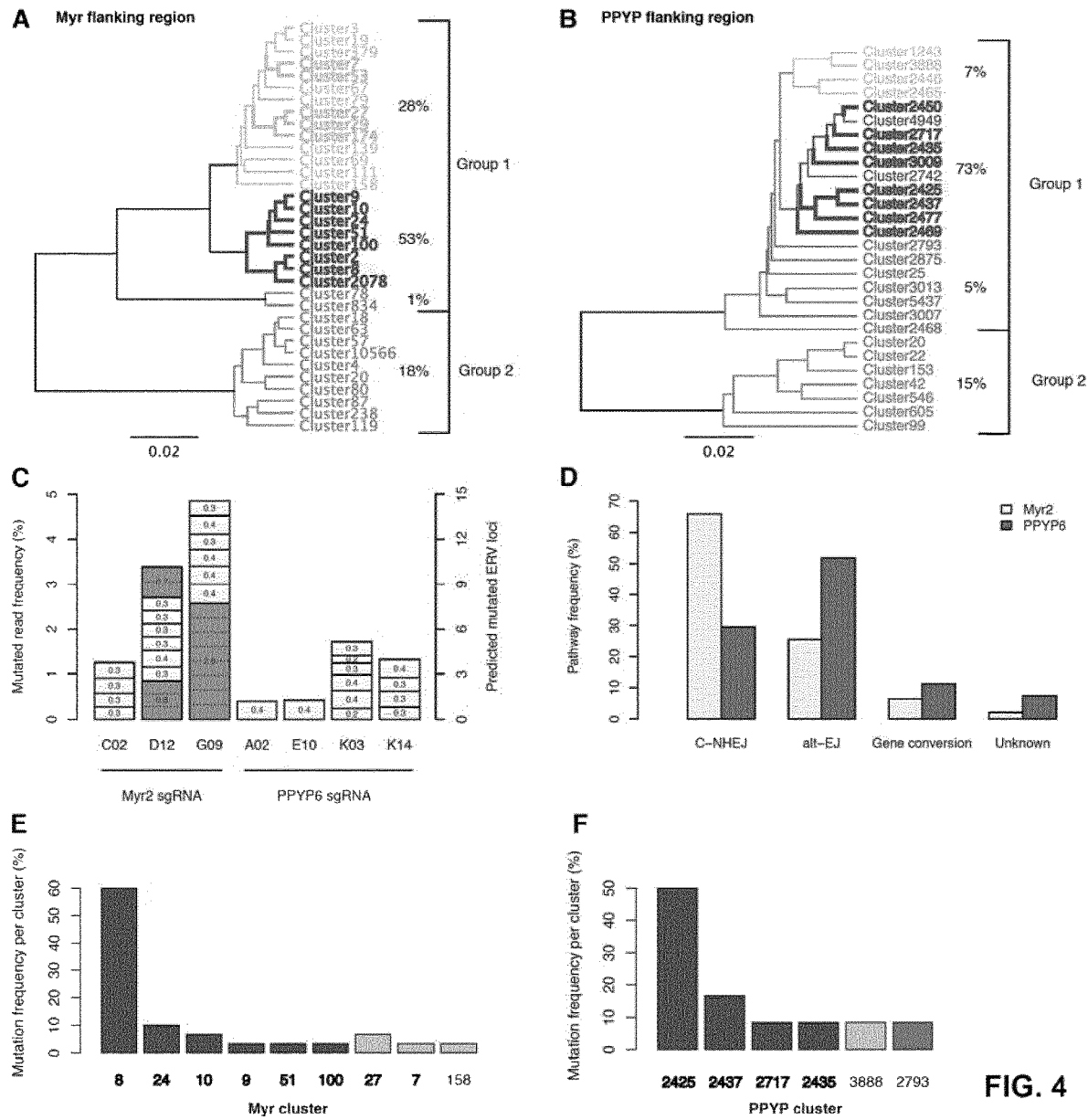
FIG. 4. Assessment of sequence diversity in the Myr and PPYP motif flanking regions and analysis of CRISPR-derived mutations by deep DNA sequencing. Targeted amplification of approximately 300 bp surrounding the Myr and PPYP CRISPR target sites was performed using type-C ERV specific primers and amplicons were analyzed by Illumina deep sequencing. Clustering analysis was based on 97% similarity of wild-type CHO-K1 deep sequencing reads from the Myr (A) and PPYP (B) flanking sequences. Clusters are indicated by brackets according to the phylogenetic groups identified in FIG. 1. Clusters containing the Myr2 sgRNA and PPYP6 sgRNA recognition sites and an adjacent PAM sequence are shown in bold, and the most abundant cluster per target site is Cluster 8 for the Myr (A)/(E) and cluster 2425 for PPYP (B)/(F). Values to the right represent the frequency of reads obtained for each subcluster relative to the total number of reads. (C) Number of distinct mutations and their corresponding read frequencies in seven clones (C02, D12, G09, A02, E10, K03, K14) isolated from Myr2 or PPYP6 sgRNA-treated polyclonal populations. All clones display mutations in the expressed group 1 type-C ERV locus. Grey shaded boxes represent mutations occurring at a higher than average read frequency (>0.4%, left-hand side axis) and the predicted number of ERV loci containing an identical mutation is indicated as dashed lines. The estimated total number of mutated ERV loci of each clone is indicated by the right-hand side axis. (D) Frequency of Myr2 or PPYP6 sgRNA-induced repair junctions compatible with C-NHEJ, alt-EJ or HR-mediated gene conversion DSB repair mechanisms. Repair junctions incompatible with these three main DSB repair mechanisms are grouped as Unknown. A total of 74 DNA repair junctions ($n_{Myr}$=47, $n_{PPYP}$=27) obtained from both Sanger mRNA and Illumina deep DNA sequencing were analyzed. (E and F) Frequency of the wild-type CHO clusters representing best the mutation-flanking sequence of 30 Myr2- and 12 PPYP6-derived mutation deep sequencing reads. Clusters containing the Myr2 or PPYP6 sgRNA recognition sites including an adjacent PAM site are shown in bold letters (on-targets), while clusters with sgRNA mismatches are shown in normal letters (off-targets). Off-target cluster possesses mismatches at position 13 or 15 in the sgRNA recognition site.
Figure 5:
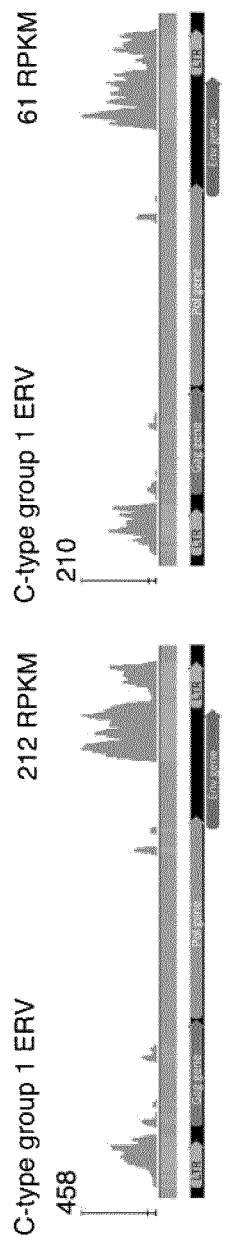
FIG. 5. Viral particle RNA sequencing of CHO clones mutated in the expressed group 1 type-C ERV sequence. Mapping of viral RNA particle deep sequencing reads from a Myr2 sgRNA clone (D12, left panels) and a PPYP6 sgRNA clone (E10, right panels) on group 1 consensus sequence and group 2 locus A and locus B, were performed as shown for the wild-type CHO viral particles (FIG. 2B). D12 and E10 mutants both contain Gag loss-of-function mutations in the functionally relevant group 1 type-C ERV locus. The number of reads mapping to each panel is indicated on the left axis and the Reads Per Kilobase Million (RPKM) are stated to the right.
Figure 5:
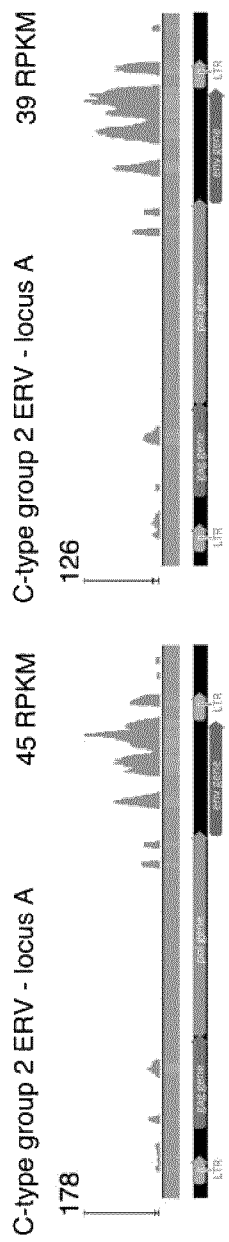
Figure 5:
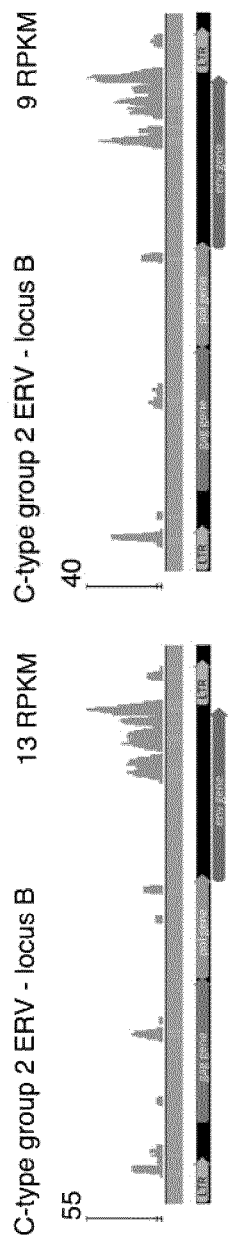

To detect CRISPR-derived mutations and distinguish them from sequence variations naturally occurring at each target, the reads from wild-type CHO cells were clustered and these cluster consensus sequences were used to create diversity profiles. When clustering by 97% sequence similarity, 34 Myr and 28 PPYP clusters were identified that represented the natural ERV sequence diversity present within the Myr and PPYP flanking regions (FIGS. 4A and 4B, FIG. 9). Despite the overall high sequence diversity, the Myr and PPYP motifs themselves were highly conserved, in agreement with their biological significance for viral budding. The identified clusters correlated well with the type-C ERV groups previously characterized from the CHO genome as well as with their predicted frequencies, corroborating the characterization of ERV sequences at the whole genome level (FIG. 1, FIGS. 4A and 4B).

For both targets, the largest cluster encompassed approximately 40% of all reads, and it was at least four-fold more abundant than the second largest cluster (highlight, FIGS. 4A and 4B). Interestingly, the consensus sequence of the largest clusters also conformed to the group 1 type-C ERV sequence determined from CHO viral particles. Among all clusters, 13 Myr and 8 PPYP clusters could be targeted by the Myr2 and PPYP6 sgRNAs, accommodating for 61% and 72% of the captured read diversity, respectively (bold letters, FIGS. 4A and 4B).

Using these wild-type CHO clusters and diversity profile, between 1 and 7 distinct CRISPR-derived mutations per clone were found, including the mutations already detected at the mRNA level (number of boxes, FIG. 4C). The detected mutation range spanned from a 114 bp deletion up to a 78 bp insertion. As expected, CHO cells treated with the empty vector expression plasmid lacked additional mutations in the CRISPR target sites. Some mutations, for instance a 1 bp insertion, occurred within all three genotyped Myr2-treated clones but were absent in the PPYP6 clones, as expected from sgRNA-specific repair outcomes (40).

Typically, a given mutation was detected at a read frequency of approximately 0.3%, which thus must represent a single ERV locus in the CHO genome (FIG. 4C). However, three Myr2-derived mutations were discovered at a read frequency well above 0.3%, with the same 1 bp insertion being present in 2.6% of all G09 clone reads. Consequently, this implies that the same mutation may occur more than once in the same clone. In support for this hypothesis, the reads of predicted single locus mutations (i.e. clones A02 or E10) were highly similar in the mutation flanking region, while the reads of abundant mutations (i.e. G09 1_1) contained variations in the mutation flanking regions, suggesting that the same mutations may have occurred repeatedly at distinct ERV loci (FIG. 10). In the case of G09 1_1, five ERV groups could be distinguished with one group having four-times more reads than the others, indicating that this mutation should have occurred at eight distinct ERV loci in the G09 clone. Therefore, it was concluded that each clone acquired between 1 and 14 ERV mutations following transient CRISPR transfection (FIG. 4C). The identification of clones having only one mutated ERV at the DNA level, together with the finding that this mutation was identical to the single mutation detected at the intracellular RNA level, further substantiated that a single group 1 type-C ERV locus is transcribed, and likely responsible for the release of type-C retroviral particles from CHO cells.

The repeated occurrence of identical mutations within one clone raised the question of whether they may result from gene conversion, an homologous recombination (HR)-related repair mechanism, in which a previous mutated ERV locus is used as template to repair other cleaved ERV sites. To find evidence for HR activity following Myr2- and PPYP6-mediated cleavage, the previously obtained mRNA and DNA data were combined and a total of 74 DNA repair junctions ($n_{Myr}$=47, $n_{PPYP}$=27) were analyzed. While Myr2 sgRNA-mediated cleavage led to an overall higher mutation frequency, with a preference for insertions, PPYP6 sgRNA mostly produced deletions. Notably, Gag loss-of-function mutations were observed in 70% of PPYP6 sgRNA-induced repaired junctions, but only in 30% of all Myr2 sgRNA-derived mutations (FIG. 11B). The majority of Myr2- and PPYP6-derived repair junctions were compatible with classical non-homologous end-joining (C-NHEJ) and alternative end-joining (alt-EJ) repair activities (FIG. 4D). C-NHEJ typically leads to small insertion and deletions, while alt-EJ utilizes microhomologies at the DSB site to anneal broken ends, which often results in larger and more complex mutations. Although alt-EJ repair is considered to be a backup pathway in most mammalian cells, between 25%-55% alt-EJ compatible junctions were detected when targeting the gag gene, supporting conclusions of intrinsically elevated alt-EJ activities in CHO cells (41, 42). Among the alt-EJ repair junctions, some could be uniquely attributed to the microhomology-mediated end-joining (MMEJ) or the synthesis-dependent microhomology-mediated end-joining (SD-MMEJ) alt-EJ subpathways, while others were consistent with both MMEJ and SD-MMEJ repair (43, 44) (FIG. 11D). Interestingly, approximately 10% of all analyzed repair junctions contained either insertions templated from other ERV loci or from the same ERV locus but using a distant sequence, while others manifested apparent duplications devoid of microhomologies, as mediated by alt-EJ mechanisms. All of these latter junctions are consistent with homology-directed repair activities at Myr2- and PPYP6 target sites following CRISPR cleavage (FIG. 4D). Thus, HR-mediated gene conversion might indeed have caused the multiple occurrences of certain mutations.

Next, it was assessed whether mutations occurred more frequently in some type-C ERV clusters, indicating a preferential cleavage of certain ERV loci. As expected, mutations associated uniquely with clusters of group 1, but not of group 2, confirming sgRNA specificity for group 1 only (FIGS. 4E and 4F). The majority of mutations located within the most abundant Myr or PPYP clusters, which represent the actively transcribed and hence expressed ERVs. The other mutations were seen in additional clusters, although at lower frequencies, all of which contained a Myr2 or PPYP6 sgRNA recognition sites adjacent to a PAM sequence (FIGS. 4E and 4F, bold font). Surprisingly, CRISPR cleavage in Myr and PPYP clusters containing a one base pair mismatch to the sgRNA target site were also observed, supporting previous reports indicating that CRISPR-Cas9 tolerates small mismatches during target recognition (45) (FIGS. 4E and 4F, normal font). Overall, it was concluded that the clusters associated with a high frequency of mutations most likely encompass expressed ERV loci.

Identification of a Unique Viral Particle (VP)-Producing ERV Locus in CHO-K1 Cells The Sanger chromatograms as well as the read frequencies of gag mutations observed during RNA and targeted DNA amplicon sequencing, respectively, corroborated the assumption that a single group 1 type-C ERV locus is transcribed, and may therefore mediate viral particle production by CHO cells. To further substantiate this assumption, the genome of the E10 clone was fully sequenced using the PacBio® approach, so as to obtain reads sufficiently long for the unambiguous determination of ERV-containing loci. This clone was selected as it appeared to contain only a single mutated ERV, so as to correlate its unique mutation at the RNA level with a potentially unique genomic locus (FIG. 4C). Analysis of the E10 clone genome sequence led to the identification of a single ERV locus bearing the mutation detected at the mRNA level (FIGS. 12A and 12B). The predicted ERV integration site was then validated by PCR amplification and DNA Sanger sequencing using locus-specific primers located outside of the ERV sequence in the parental CHO cell line as well as the deep-sequenced clones. All deep-sequenced clones, which contain CRISPR-derived mutations at the mRNA level, possessed the identical mutation also at this ERV locus, further supporting that this genomic region harbors the expressed type-C ERV element (FIG. 12C). Interestingly, this particular ERV integration was found to be hemizygous, as the other allele was devoid of a corresponding ERV integration, and to have occurred into open chromatin between two moderately expressed CHO cell genes.

Next, it was assessed whether Gag loss-of-function mutations in this expressed ERV locus may lead to the anticipated inhibition of viral particle budding. Besides the previously characterized mutated clones, we analyzed in parallel their corresponding bulk-sorted polyclonal populations, as well as a clone devoid of detectable mutations in the expressed group 1 ERV sequence (B01 for Myr2, B03 for PPYP6), as additional controls. First, viral particles were extracted from the supernatant of the CHO cell cultures and the amount of type-C viral genomes was quantified by RT-qPCR. Preliminary data suggested that viral particles shed by Gag loss-of-function mutants contain 80% less group 1 C-type genomic viral RNA than control samples, while the amount of group 2 genomic viral RNA remained close to detection limit (data not shown). To substantiate this finding, RNA extracted from the viral particles shed by the D12 (Myr2 sgRNA) and E10 (PPYP6 sgRNA) clones was Illumina deep-sequenced. Remarkably, a more than 250-fold reduction in reads mapping to the group 1 ERV sequence in both D12 and E10 were observed when compared to wild-type CHO cells, while the trace amounts of reads mapping to group 2 remained close to the detection level (compare FIG. 13). This indicated that mutations in the single expressed group 1 ERV sequence that block translation initiation (D12) or introduce a frameshift in the gag gene downstream of the PPYP motif (E10) are sufficient to severely reduce the budding of complete viral particles.

Characterization of Edited CHO Cell Lines Displaying Reduced Viral Budding

Figure 6:
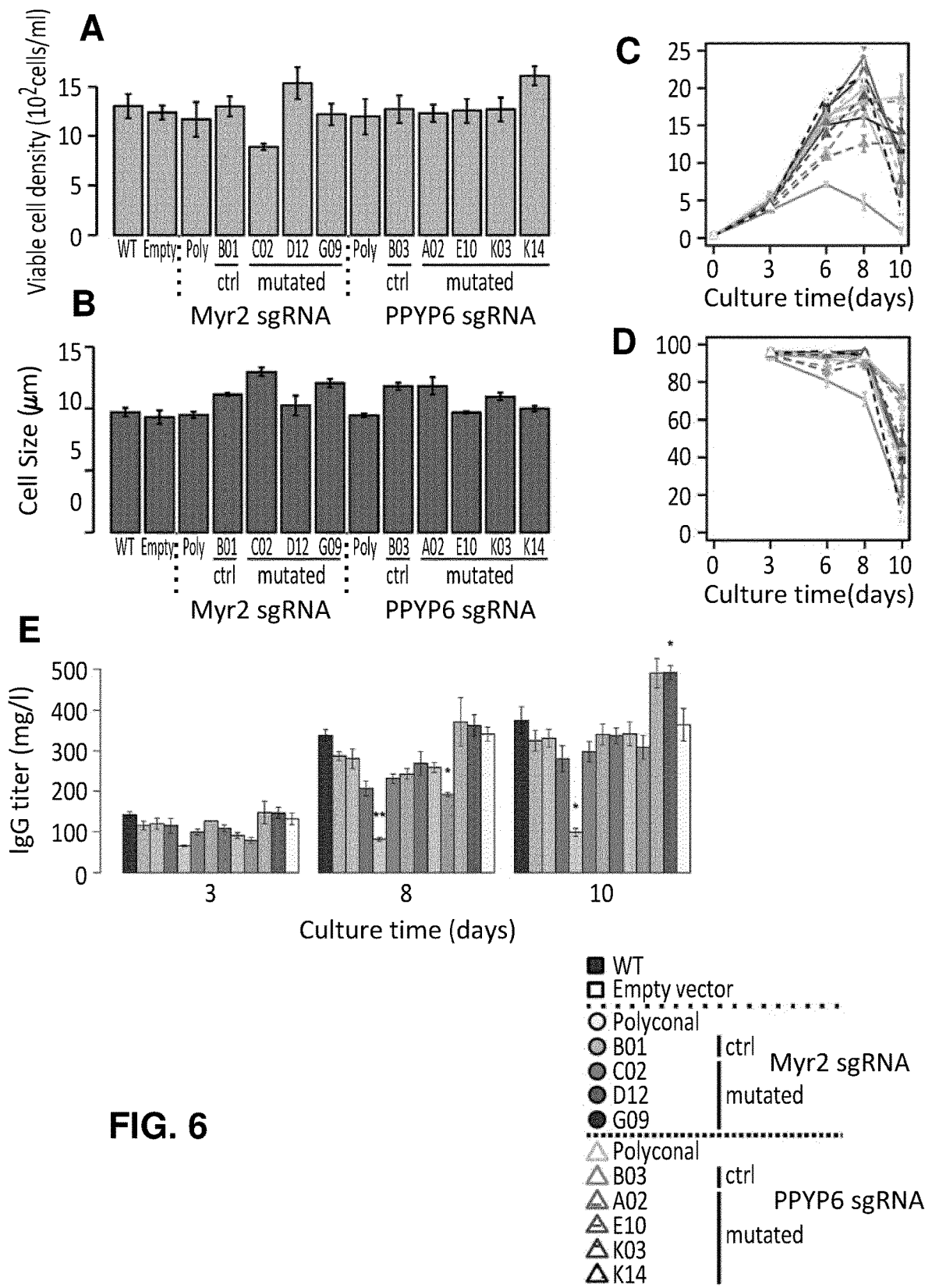
FIG. 6. Assessment of cell growth, cell size and therapeutic IgG Immunoglobulin production in ERV-mutated CHO cells. Viable cell density (A) and cell size (B) was measured in wild-type CHO cells (WT), empty sgRNA vector-treated cells (Empty), bulk-sorted polyclonal CRISPR-treated cells (Poly) as well as in clones containing mutations in the expressed ERV locus (C02, D12, G09, A02, E10, K03 and K14) or not (B01, B03) after five days of culture. The same samples were stably transfected to express an IgG Immunoglobulin antibody and assessed for cell density (C), cell viability (D) and IgG production (E) during ten-days fed-batch cultures. Statistical significance relative to the empty vector control was calculated using the two-tailed unpaired Student's t-test with Benjamini and Hochberg false discovery rate correction (n 2, error bars represent s.e.m, * $P<0.05$, ** $P<0.01$).

Having observed that CRISPR mutagenesis had efficiently inactivated viral particle release, it was next tested whether ERV inactivation would affect other CHO cell properties, such as cell growth, cell size and therapeutic protein production. ERV-edited clones were found to proliferate at similar rates as polyclonal populations, wild-type and empty vector-treated cell controls, with a density reaching approximately $12.5 \times 10^6$ cells/ml after five days in culture (FIG. 6A). Such a cell density concords with the expected CHO-K1 doubling time of roughly 20 h (46). Although two Myr2 sgRNA clones (C02, D12) and one PPYP6 sgRNA clones (K14) showed slightly modified cell cycle durations, the effect was not statistically significant. In addition, cell sizes tended to be elevated in ERV-edited cells, notably in the CO2 clone, but they did not differ significantly when compared to the empty vector control cells (FIG. 6B).

Finally, the capacity of ERV-edited CHO cells to produce therapeutic proteins was assessed, a pivotal property of CHO cells for biotechnological use. The previously characterized ERV-mutated cells were used to generate polyclonal populations stably expressing a humanized therapeutic IgG immunoglobulin and quantified IgG secretion during ten-days fed-batch cultures. ERV-edited clones and polyclonal populations expressing the IgG protein demonstrated cell growth and cell viability properties similar to those of wild-type and empty vector control cells, as observed without therapeutic protein expression (FIGS. 6C and 6D). IgG titers in the cell culture supernatants increased over the course of the fed-batch experiment, as expected from the accumulation of the secreted IgG protein, reaching around 300-400 mg/l at the end of the fed-batch for control cells and most ERV-edited cell clones (FIG. 6E). Thus, ERV mutagenesis did not globally affect the capability of CHO cells to produce IgG proteins, although clone CO2 (Myr2 sgRNA) secreted significantly less immunoglobulins, likely reflecting its reduced growth and increased cell size, while clones E10 and K03 (both PPYP6 sgRNA) produced 50% more IgG relative to the empty vector control. Overall, this indicated that CHO clones that were exposed to multi-loci ERV editing generally maintain normal CHO characteristics, while some clones, especially those with mutations in the PPYP region, appeared to have acquired a higher metabolic capacity to produce therapeutic proteins. However, this apparently augmented metabolism capacity could not be correlated to a specific ERV mutation type or to the total number of mutations, nor to cell growth or size, suggesting clone-specific effects.

As the person skilled in the art will appreciate, the above description is not limiting, but provides examples of certain embodiments of the present invention. With the guidance provided above, the person skilled in the art is able to devise a wide variety of alternatives not specifically set forth herein.

REFERENCES

1. Berting, A., Farcet, M. R. and Kreil, T. R. (2010) Virus susceptibility of Chinese hamster ovary (CHO) cells and detection of viral contaminations by adventitious agent testing. *Biotechnol. Bioeng.,* 106, 598-607.
2. Hartley, J. W. and Rowe, W. P. (1976) Naturally occurring murine leukemia viruses in wild mice: characterization of a new "amphotropic" class. *J. Virol.,* 19, 19-25.
3. Shepherd, A. J., Wilson, N. J. and Smith, K. T. (2003) Characterisation of endogenous retrovirus in rodent cell lines used for production of biologicals. *Biologicals,* 31, 251-260.
4. Hojman, F., Emanoil-Raivier, R., Lesser, J. and Périès, J. (1989) Biological and molecular characterization of an endogenous retrovirus present in CHO/HBs-A Chinese hamster cell line. *Dev. Biol. Stand.,* 70, 195-202.
5. Emanoil-Ravier, R., Hojman, F., Servenay, M., Lesser, J., Bernardi, A. and Peries, J. (1991) Biological and molecular studies of endogenous retrovirus-like genes in Chinese hamster cell lines. *Dev. Biol. Stand.,* 75, 113-122.
6. Dinowitz, M., Lie, Y. S., Low, M. A., Lazar, R., Fautz, C., Potts, B., Sernatinger, J. and Anderson, K. (1992) Recent studies on retrovirus-like particles in Chinese hamster ovary cells. *Dev. Biol. Stand.,* 76, 201-207.
7. Manly, K. F., Givens, J. F., Taber, R. L. and Zeigel, R. F. (1978) Characterization of Virus-like Particles Released from the Hamster Cell Line CHO-K1 After Treatment with 5-Bromodeoxyuridine. *J. Gen. Virol.,* 39, 505-517.
8. Gould, R. R. and Borisy, G. G. (1977) The pericentriolar material in Chinese hamster ovary cells nucleates microtubule formation. *J. Cell Biol.,* 73, 601-615.
9. Heine U, Kramarsky B, Wendel E, S. R. (1979) Enhanced Proliferation of Endogenous Virus in Chinese Hamster Cells Associated with Microtubules and the Mitotic Apparatus of the Host Cell. *J. Gen. Virol.,* 44, 45-55.
10. Anderson, K. P., Low, M.-A., Lie, Y. S., Keller, G.-A. and Dinowitz, M. (1991) Endogenous origin of defective retroviruslike particles from a recombinant Chinese hamster ovary cell line. *Virology,* 181, 305-311.
11. Reuss, F. U. (1992) Expression of intracisternal A-particle-related retroviral element-encoded envelope proteins detected in cell lines. *J. Virol.,* 66, 1915-1923.
12. Lie, Y. S., Penuel, E. M., Low, M. A., Nguyen, T. P., Mangahas, J. O., Anderson, K. P. and Petropoulos, C. J. (1994) Chinese hamster ovary cells contain transcriptionally active full-length type C proviruses. *J. Virol.,* 68, 7840-7849.
13. Anderson, K. P., Lie, Y. S., Low, M. A., Williams, S. R., Fennie, E. H., Nguyen, T. P. and Wurm, F. M. (1990) Presence and transcription of intracisternal A-particle-related sequences in CHO cells. *J. Virol.,* 64, 2021-2032.
14. Tihon, C. and Green, M. (1973) Cyclic AMP-amplified Replication of RNA Tumour Virus-like Particles in Chinese Hamster Ovary Cells. *Nat. New Biol.,* 244, 227.
15. Wurm, F. (2013) CHO Quasispecies—Implications for Manufacturing Processes. *Processes,* 1, 296-311.
16. Donahue, R. E., Kessler, S. W., Bodine, D., McDonagh, K., Dunbar, C., Goodman, S., Agricola, B., Byrne, E., Raffeld, M. and Moen, R. (1992) Helper virus induced T cell lymphoma in nonhuman primates after retroviral mediated gene transfer. *J. Exp. Med.,* 176, 1125-1135.
17. Urnovitz, H. B. and Murphy, W. H. (1996) Human endogenous retroviruses: nature, occurrence, and clinical implications in human disease. *Clin. Microbiol. Rev.,* 9, 72-99.
18. Kaminski, R., Chen, Y., Fischer, T., Tedaldi, E., Napoli, A., Zhang, Y., Karn, J., Hu, W. and Khalili, K. (2016) Elimination of HIV-1 Genomes from Human T-lymphoid Cells by CRISPR/Cas9 Gene Editing. *Sci. Rep.,* 6, 22555.
19. Yang, L., Güell, M., Niu, D., George, H., Lesha, E., Grishin, D., Aach, J., Shrock, E., Xu, W., Poci, J., et al. (2015) Genome-wide inactivation of porcine endogenous retroviruses (PERVs). *Science.,* 350, 1101-1104.
20. Niu, D., Wei, H.-J., Lin, L., George, H., Wang, T., Lee, I.-H., Zhao, H.-Y., Wang, Y., Kan, Y., Shrock, E., et al. (2017) Inactivation of porcine endogenous retrovirus in pigs using CRISPR-Cas9. *Science.,* 357, 1303-1307.
21. Fu, Y., Foden, J. A., Khayter, C., Maeder, M. L., Reyon, D., Joung, J. K. and Sander, J. D. (2013) High-frequency off-target mutagenesis induced by CRISPR-Cas nucleases in human cells. *Nat. Biotechnol.,* 31, 822-826.
22. Zhu, L. J., Holmes, B. R., Aronin, N. and Brodsky, M. H. (2014) CRISPRseek: A Bioconductor package to identify target-specific guide RNAs for CRISPR-Cas9 genome-editing systems. *PLoS One,* 9, e108424.
23. Xu, H., Xiao, T., Chen, C.-H., Li, W., Meyer, C. A., Wu, Q., Wu, D., Cong, L., Zhang, F., Liu, J. S., et al. (2015) Sequence determinants of improved CRISPR sgRNA design. *Genome Res.,* 25, 1147-1157.
24. Chari, R., Mali, P., Moosburner, M. and Church, G. M. (2015) Unraveling CRISPR-Cas9 genome engineering parameters via a library-on-library approach. *Nat. Methods,* 12, 823.
25. Sander, J. D., Zaback, P., Joung, J. K., Voytas, D. F. and Dobbs, D. (2007) Zinc Finger Targeter (ZiFiT): An engineered zinc finger/target site design tool. *Nucleic Acids Res.,* 35, 599-605.
26. Sander, J. D., Maeder, M. L., Reyon, D., Voytas, D. F., Joung, J. K. and Dobbs, D. (2010) ZiFiT (Zinc Finger Targeter): An updated zinc finger engineering tool. *Nucleic Acids Res.,* 38, 462-468.
27. Ran, F. A., Hsu, P. D., Wright, J., Agarwala, V., Scott, D. A. and Zhang, F. (2013) Genome engineering using the CRISPR-Cas9 system. *Nat. Protoc.,* 8, 2281-2308.
28. Brinkman, E. K., Chen, T., Amendola, M. and Van Steensel, B. (2014) Easy quantitative assessment of genome editing by sequence trace decomposition. *Nucleic Acids Res.,* 42, 1-8.
29. Yoon, H. and Leitner, T. (2015) PrimerDesign-M: A multiple-alignment based multiple-primer design tool for walking across variable genomes. *Bioinformatics,* 31, 1472-1474.
30. Fadrosh, D. W., Ma, B., Gajer, P., Sengamalay, N., Ott, S., Brotman, R. M. and Ravel, J.

30. (2014) An improved dual-indexing approach for multiplexed 16S rRNA gene sequencing on the Illumina MiSeq platform. *Microbiome*, 2, 6.
31. Le Fourn, V., Girod, P. A., Buceta, M., Regamey, A. and Mermod, N. (2014) CHO cell engineering to prevent polypeptide aggregation and improve therapeutic protein secretion. *Metab. Eng.*, 21, 91-102.
32. Feschotte, C. and Gilbert, C. (2012) Endogenous viruses: insights into viral evolution and impact on host biology. *Nat. Rev. Genet.*, 13, 283.
33. Morikawa, Y., Hinata, S., Tomoda, H., Goto, T., Nakai, M., Aizawa, C., Tanaka, H. and Mura, S. (1996) Complete Inhibition of Human Immunodeficiency Virus Gag Myristoylation Is Necessary for Inhibition of Particle Budding. *J. Biol. Chem.*, 271, 2868-2873.
34. Wapling, J., Srivastava, S., Shehu-Xhilaga, M. and Tachedjian, G. (2007) Targeting Human Immunodeficiency Virus Type 1 Assembly, Maturation and Budding. *Drug Target Insights*, 2, 159-182.
35. Henzy, J. E., Gifford, R. J., Johnson, W. E. and Coffin, J. M. (2014) A Novel Recombinant Retrovirus in the Genomes of Modern Birds Combines Features of Avian and Mammalian Retroviruses. *J. Virol.*, 88, 2398-2405.
36. Segura-Morales, C., Pescia, C., Chatellard-Causse, C., Sadoul, R., Bertrand, E. and Basyuk, E. (2005) Tsg101 and Alix Interact with Murine Leukemia Virus Gag and Cooperate with Nedd4 Ubiquitin Ligases during Budding. *J. Biol. Chem.*, 280, 27004-27012.
37. Daer, R. M., Cutts, J. P., Brafman, D. A. and Haynes, K. A. (2017) The Impact of Chromatin Dynamics on Cas9-Mediated Genome Editing in Human Cells. *ACS Synth. Biol.*, 6, 428-438.
38. Gosselin, K., Deruy, E., Martien, S., Vercamer, C., Bouali, F., Dujardin, T., Slomianny, C., Houel-Renault, L., Chelli, F., De Launoit, Y., et al. (2009) Senescent keratinocytes die by autophagic programmed cell death. *Am. J. Pathol.*, 174, 423-435.
39. Lemos, B. R., Kaplan, A. C., Bae, J. E., Ferrazzoli, A. E., Kuo, J., Anand, R. P., Waterman, D. P. and Haber, J. E. (2018) CRISPR/Cas9 cleavages in budding yeast reveal templated insertions and strand-specific insertion/deletion profiles. *Proc. Natl. Acad. Sci.*, 115, E2040 L P-E2047.
40. Bae, S., Kweon, J., Kim, H. S. and Kim, J. (2014) Microhomology-based choice of Cas9 nuclease target sites. *Nat. Methods*, 11, 705-706.
41. Kostyrko, K., Neuenschwander, S., Junier, T., Regamey, A., Iseli, C., Schmid-Siegert, E., Bosshard, S., Majocchi, S., Le Fourn, V., Girod, P.-A., et al. (2017) MAR-Mediated transgene integration into permissive chromatin and increased expression by recombination pathway engineering. *Biotechnol. Bioeng.*, 114, 384-396.
42. Kostyrko, K. and Mermod, N. (2015) Assays for DNA double-strand break repair by microhomology-based end-joining repair mechanisms. *Nucleic Acids Res.*, 44, e56.
43. Sfeir, A. and Symington, L. S. (2015) Microhomology-Mediated End Joining: A Back-up Survival Mechanism or Dedicated Pathway? *Trends Biochem. Sci.*, 40, 701-714.
44. Yu, A. M. and McVey, M. (2010) Synthesis-dependent microhomology-mediated end joining accounts for multiple types of repair junctions. *Nucleic Acids Res.*, 38, 5706-17.
45. Lin, Y., Cradick, T. J., Brown, M. T., Deshmukh, H., Ranjan, P., Sarode, N., Wile, B. M., Vertino, P. M., Stewart, F. J. and Bao, G. (2014) CRISPR/Cas9 systems have off-target activity with insertions or deletions between target DNA and guide RNA sequences. *Nucleic Acids Res.*, 42, 7473-7485.
46. Byrne, G., O'Rourke, S. M., Alexander, D. L., Yu, B., Doran, R. C., Wright, M., Chen, Q., Azadi, P. and Berman, P. W. (2018) CRISPR/Cas9 gene editing for the creation of an MGAT1-deficient CHO cell line to control HIV-1 vaccine glycosylation. *PLoS Biol.*, 16, 1-23.
47. Semaan, M., Ivanusic, D. and Denner, J. (2015) Cytotoxic effects during knock out of multiple Porcine Endogenous Retrovirus (PERV) sequences in the pig genome by Zinc Finger Nucleases (ZFN). *PLoS One*, 10, 1-18.
48. Wang, T., Birsoy, K., Hughes, N. W., Krupczak, K. M., Post, Y., Wei, J. J., Lander, E. S. and Sabatini, D. M. (2015) Identification and characterization of essential genes in the human genome. *Science.*, 350, 1096-1101.
49. Aguirre, A. J., Meyers, R. M., Weir, B. A., Vazquez, F., Zhang, C. Z., Ben-David, U., Cook, A., Ha, G., Harrington, W. F., Doshi, M. B., et al. (2016) Genomic copy number dictates a gene-independent cell response to CRISPR/Cas9 targeting. *Cancer Discov.*, 6, 914-929.
50. Ihry, R. J., Worringer, K. A., Salick, M. R., Frias, E., Ho, D., Theriault, K., Kommineni, S., Chen, J., Sondey, M., Ye, C., et al. (2018) P53 inhibits CRISPR-Cas9 engineering in human pluripotent stem cells. *Nat. Med.*, 24, 939-946.
51. O'Connor, M. J. (2015) Targeting the DNA Damage Response in Cancer. *Mol. Cell*, 60, 547-560.
52. Orlando, S. J., Santiago, Y., DeKelver, R. C., Freyvert, Y., Boydston, E. A., Moehle, E. A., Choi, V. M., Gopalan, S. M., Lou, J. F., Li, J., et al. (2010) Zinc-finger nuclease-driven targeted integration into mammalian genomes using donors with limited chromosomal homology. *Nucleic Acids Res.*, 38, 1-15.
53. Cristea, S., Freyvert, Y., Santiago, Y., Holmes, M. C., Urnov, F. D., Gregory, P. D. and Cost, G. J. (2013) In vivo cleavage of transgene donors promotes nuclease-mediated targeted integration. *Biotechnol. Bioeng.*, 110, 871-880.
54. Guirouilh-Barbat, Lambert, S., Bertrand, P. and Lopez, B. S. (2014) Is homologous recombination really an error-free process? *Front. Genet.*, 5, 175.
55. Benson, F. E., Stasiak, A. and West, S. C. (1994) Purification and characterization of the human Rad51 protein, an analogue of E. coli RecA. *EMBO J.*, 13, 5764-71.
56. Stark, J. M., Hu, P., Pierce, A. J., Moynahan, M. E., Ellis, N. and Jasin, M. (2002) ATP hydrolysis by mammalian RAD51 has a key role during homology-directed DNA repair. *J. Biol. Chem.*, 277, 20185-20194.
57. Lee, J. S., Park, J. H., Ha, T. K., Samoudi, M., Lewis, N. E., Palsson, B. O., Kildegaard, H. F. and Lee, G. M. (2018) Revealing Key Determinants of Clonal Variation in Transgene Expression in Recombinant CHO Cells Using Targeted Genome Editing. *ACS Synth. Biol.*, 10.1021/acssynbio.8b00290.
58. Pilbrough, W., Munro, T. P. and Gray, P. (2009) Intraclonal protein expression heterogeneity in recombinant CHO cells. *PLoS One*, 4, e8432.
59. Sigal, A., Milo, R., Cohen, A., Geva-Zatorsky, N., Klein, Y., Liron, Y., Rosenfeld, N., Danon, T., Perzov, N. and Alon, U. (2006) Variability and memory of protein levels in human cells. *Nature*, 444, 643-646.
60. Schmieder, V., Bydlinski, N., Strasser, R., Baumann, M., Kildegaard, H. F., Jadhav, V. and Borth, N. (2018) Enhanced Genome Editing Tools For Multi-Gene Deletion Knock-Out Approaches Using Paired CRISPR sgRNAs in CHO Cells. *Biotechnol. J.*, 13, 1700211.
61. Hu, W., Kaminski, R., Yang, F., Zhang, Y., Cosentino, L., Li, F., Luo, B., Alvarez-Carbonell, D., Garcia-Mesa, Y., Karn, J., et al. (2014) RNA-directed gene editing specifically eradicates latent and prevents new HIV-1 infection. *Proc. Natl. Acad. Sci.*, 111, 11461-11466.

62. Manrique, M. L., Celma, C. C. P., González, S. A. and Affranchino, J. L. (2001) Mutational analysis of the feline immunodeficiency virus matrix protein. *Virus Res.*, 76, 103-113.

63. Kawada, S., Goto, T., Haraguchi, H., Ono, A. and Morikawa, Y. (2008) Dominant Negative Inhibition of Human Immunodeficiency Virus Particle Production by the Nonmyristoylated Form of Gag. *J. ViroL*, 82, 4384-4399.

64. Nakamura, T., Yamada, K. D., Tomii, K. and Katoh, K. (2018) Parallelization of MAFFT for large-scale multiplesequence alignments. *Bioinformatics*, 34, 2490-2492.

65. Puri, V., Konda, S., Ranjit, S., Aouadi, M., Chawla, A., Chouinard, M., Chakladar, A. and Czech, M. P. (2007) Fat-specific Protein 27, a Novel Lipid Droplet Protein That Enhances Triglyceride Storage. *J. Biol. Chem.*, 282, 34213-34218.

66. Bortug, K., Järvinen, P. M., Salzer, E., Racek, T., Mönch, S., Garncarz, W., Gertz, E. M., Schaffer, A. A., Antonopoulos, A., Haslam, S. M., et al. (2014) JAGN1 deficiency causes aberrant myeloid cell homeostasis and congenital neutropenia. *Nat. Genet.*, 46, 1021-1027.

The invention claimed is:

1. An engineered cell comprising:
a genome of the cell, wherein the genome of the cell has been engineered to comprise alterations within ERV sequences integrated into the genome, wherein the ERV sequences include at least one full-length ERV sequence comprising SEQ ID NO: 3 or a sequence having 95% sequence identity with SEQ ID NO: 3 integrated into the genome, wherein one to twenty of the alternations are within one or more gag sequence of the ERV sequences, and wherein at least one of the alterations is within a gag gene of the at least one full-length ERV sequence resulting in at least one altered full-length ERV sequence.

2. The engineered cell of claim 1, wherein the genome comprises more than ERV sequences integrated into the genome.

3. The engineered cell of claim 2, wherein, of the more than ERV sequences, more than 10 are full-length ERV sequence(s) corresponding to SEQ ID NO: 3 or a sequence having more than 95% sequence identity with SEQ ID NO: 3.

4. The engineered cell of claim 1, wherein at least one of the at least one alteration within the gag gene is a loss-of-function mutation.

5. The engineered cell of claim 1, wherein the alteration(s) in the at least one full-length ERV sequence(s) introduces a frameshift in the gag gene downstream of a PPYP motif.

6. The engineered cell of claim 1, wherein the alteration(s) is/are within the Myr motif of SEQ ID NO: 90 and/or PPYP Gag budding motifs of SEQ ID NO:101, or a sequence up to 5, 10, 15, 20, 25, 30, 35, 40, 45 or 50 nucleotides, including consecutive nucleotides, 5' and/or 3' of the Myr motif of SEQ ID NO: 90 and/or PPYP Gag budding motifs of SEQ ID NO:101.

7. The engineered cell of claim 1, wherein the genome comprises one or more alteration(s) which comprise(s) a deletion equal to or more than 1%, 2%, 3%, 4%, 5%, 10%, 20%, 30%, 40%, 50%, 60%, 70%, 80%, 90% or 100% consecutive nucleotides of SEQ ID NO: 3 or a sequence having more than 95%, 96%, 97%, 98%, 99% sequence identity therewith from the genome and optionally alterations in, including deletions of, nucleotide 1 to 30020, and 39348 to 59558 of SEQ ID NO: 1.

8. The engineered cell according to claim 7, wherein the genome of the engineered cell comprising the deletion comprises:
(i) not more than 50% consecutive nucleotides of SEQ ID NO: 3, or
(ii) a sequence having more than 95% sequence identity with (i) and wherein the engineered cell is a CHO cell.

9. The engineered cell according to claim 7,
wherein at least consecutive nucleotides of SEQ ID NO: 3 are deleted from the genome.

10. The engineered cell of claim 9, wherein the genome of the cell comprises:
(i) at least 80% consecutive nucleotides of SEQ ID NO: 4 and/or sequences having at least 95% sequence identity with SEQ ID NO: 4 and, directly adjacent thereto,
(ii) at least 80% consecutive nucleotides of SEQ ID NO: 5 and/or sequences having at least 95% sequence identity with SEQ ID NO: 5.

11. The engineered cell of claim 7, wherein the alterations comprise a deletion equal to or more than 5% consecutive nucleotides of SEQ ID NO: 3 or of a sequence having more than 95% sequence identity with SEQ ID NO: 3 from the genome.

12. The engineered cell of claim 11, wherein the alterations comprise a deletion equal to or more than 10% consecutive nucleotides of SEQ ID NO: 3 or of a sequence having more than 95% sequence identity therewith from the genome.

13. The engineered cell of claim 7, wherein said cell further comprises a transgene, optionally integrated into the genome, and the deletion is within SEQ ID NO: 90 and/or SEQ ID NO: 101 or a sequence having at least 90% sequence identity SEQ ID NO: 90 and/or SEQ ID NO: 101.

14. The engineered cell of claim 1, wherein the alteration(s) in the at least one full-length ERV sequence(s) is in the gag gene, that comprises SEQ ID NO: 101 and wherein (i) sequences encoding the SEQ ID NO: 101 and/or a sequence up to 5, 10, 15, 20, 25, 30, 35, 40, 45 or 50 nucleotides, including consecutive nucleotides, 5' and/or 3' flanking the sequences in (i) comprise the alteration(s).

15. The engineered cell of claim 1, wherein the genome comprises not more than 15 alteration(s) in the ERV sequences.

16. The engineered cell of claim 1, wherein the alteration(s) is/are deletions, insertions, substitutions or combinations thereof and are alterations of the N-terminal Myr motif-encoding DNA sequence of SEQ ID NO: 90 or a PPYP mutation within SEQ ID NO: 101 that inhibits the release of viral particles from the host cell, or one or several frameshift mutations that infer with a translation of the gag mRNA into a full-length GAG protein.

17. The engineered cell of claim 1, wherein the alteration(s) is/are frameshift mutation(s) within SEQ ID NO: 90 or SEQ ID NO: 101.

18. The engineered cell of claim 1, wherein the alteration(s) are insertions of at least 5, 10, 15, 20, 25, 30, 50 or 100 nucleotides, deletions of at least 5, 10, 15, 20, 25, 30, 50 or 100 nucleotides, including consecutive nucleotides, or combinations thereof or combinations of insertions, substitution and/or deletions resulting together in an addition and/or removal of at least 5, 10, 15, 20, 25, 30, 50 or 100 nucleotides.

19. The engineered cell of claim 1, wherein the cell releases a number of viral particles (VP), viral like particles (VLP) or retroviral (like) particles (RV (L) Ps) per unit of time, the number being reduced more than 2-fold relative to the VPs, VLPs or RV (L) Ps per unit of time released by its non-engineered counterpart.

20. The engineered cell of claim 1, wherein said engineered cell releases no or substantially no RVP.

21. The engineered cell of claim 1, wherein said cell further comprises a transgene, optionally integrated into the genome.

22. The engineered cell of claim 21, wherein the transgene is a marker gene encoding a marker protein, a biotherapeutic and/or a non-coding RNA.

23. A method for producing a transgene product comprising:
providing the engineered cell of claim 1,
introducing at least one transgene encoding the transgene product into the engineered cell, and
expressing the at least one transgene in the cell, wherein said engineered cell releases no or substantially no VP or VLP.

* * * * *

UNITED STATES PATENT AND TRADEMARK OFFICE
CERTIFICATE OF CORRECTION

| | |
|---|---|
| PATENT NO. | : 12,404,527 B2 |
| APPLICATION NO. | : 17/417131 |
| DATED | : September 2, 2025 |
| INVENTOR(S) | : Duroy et al. |

Page 1 of 2

It is certified that error appears in the above-identified patent and that said Letters Patent is hereby corrected as shown below:

On the Title Page

Item (73), in Column 1, in "Assignee", Line 1, delete "Selexs" and insert -- Selexis --, therefor.

In the Specification

In Column 1, Line 18, delete ""P100579WO-segl-000001.txt"," and insert -- "P100579WO-seql-000001.txt", --, therefor.

In Column 14, Line 2, delete "Kit 6®." and insert -- Kit®. --, therefor.

In Column 21, Line 9, delete "CO2" and insert -- $CO_2$ --, therefor.

In Column 27, Line 61, delete "341" and insert -- 30µl --, therefor.

In Column 29, Line 58, delete "(2×)" and insert -- (2X) --, therefor.

In Column 31, Line 7, delete "≅" and insert -- ≃ --, therefor.

In Column 32, Line 51, delete "Sg RNA" and insert -- sgRNA --, therefor.

In Columns 35-36, Line 18, delete "sg RNA" and insert -- sgRNA --, therefor.

In Column 50, Line 44, delete "CO2" and insert -- C02 --, therefor.

In Column 50, Line 63, delete "CO2" and insert -- C02 --, therefor.

Signed and Sealed this
Tenth Day of February, 2026

John A. Squires
*Director of the United States Patent and Trademark Office*

CERTIFICATE OF CORRECTION (continued)
U.S. Pat. No. 12,404,527 B2

In Column 53, Line 42, delete "L P-E2047." and insert -- LP-E2047. --, therefor.

In Column 55, Line 12, delete "*ViroL,*" and insert -- *Virol.,* --, therefor.

In Column 56, Line 10, delete "Schaffer," and insert -- Schäffer, --, therefor.

In the Claims

In Column 253, in Claim 2, Line 16, delete "ERV" and insert -- 160 ERV --, therefor.

In Column 253, in Claim 3, Line 19, delete "ERV" and insert -- 160 ERV --, therefor.

In Column 253, in Claim 9, Line 53, before "consecutive" insert -- 80% --.

SEQUENCE LISTING

```
<160> NUMBER OF SEQ ID NOS: 110

<210> SEQ ID NO 1
<211> LENGTH: 59558
<212> TYPE: DNA
<213> ORGANISM: Cricetulus griseus
<220> FEATURE:
<221> NAME/KEY: misc_feature
<222> LOCATION: (1)..(30020)
<223> OTHER INFORMATION: CHO genome outside of ERV on 5' end
<220> FEATURE:
<221> NAME/KEY: misc_feature
<222> LOCATION: (30021)..(39247)
<223> OTHER INFORMATION: ERV type-C, LTR to LTR
<220> FEATURE:
<221> NAME/KEY: misc_feature
<222> LOCATION: (39248)..(59558)
<223> OTHER INFORMATION: CHO genome outside of ERV on 3' end

<400> SEQUENCE: 1
tggttctatc gagacagcta catccgcttc tccacacagc ccttctccct gaagaacctg      60
gacaagtgag ctttccctcc acctcccttg actgccagg ctagtgagga ggtcagcaga     120
caaacagaac agtgggctct gcgggcaggg aaggcaggct tttcgccgcc actcatcctc     180
tgccctgaag gagcttgcca agagggtgcc cttgggttac cgaaatgagc aaaacaagaa     240
ctcctgctaa tcaagggctt acatcctagc aatgagcttg agtaatcatg gctaacatgc     300
tagaaggtga tatgtgttag gaagaaaatg tagatctggg taatggcaga ttaagagaaa     360
cttgagaggg gaaaggcaac ttgcagtttg ctcttgggat gagaggaaac cttgaggaga     420
cctgggttca aattctatct ctgcagcatc cagattgtgt tcctctagag acatgaaaag     480
agacttaagc ctcagtttca gttagagccc agtggtccca tctgtaatcc cagcacttgg     540
gagtctgagt ctgaaggatt ttgaggtcat tctgggctat ataatgagac ccccactcaa     600
gacaaaacaa gccaggtgtg gtagctccta actgtaatcc tagaacttgg ctaaggcagg     660
agccaaaatc aagccaggta cggtattgga ggcccgtgat cccagtgctt agaaggtaga     720
ggcaggacaa tcagttcact gtcaccctca gctacatgcc aagttttatc taacctgggc     780
aacatgagac catttcatag aaaaagacca gcctccgttt ccacatctga agactggagc     840
agcaatacac tgtagctgct tatcatcaag tacttcacat gtgataagtt gttcctgctt     900
ggttatacca cagccacttc tcaatggctc acaatgaagt gagttattgc cattttaaaa     960
agagatgaga ggggcaaagg ttaaatgact tgcctgagat ctcatagttg atcatcggtg    1020
aagctgggat ttgaccatcc agggtcatcg tccccctgcc acacatagga atggtgaact    1080
gaaactaggc ccaaagcact tgatacttac tgtggcctgc aggcaacact ggagcattct    1140
gagaaatgac tagccctggc cgtgggtgaa tagggagtgg ggcagggagt gggggtgggg    1200
```

-continued

```
tggaggggtg cagcttctgt gcttctgtcc tgttgatctt ccagcagggg cccctctcag    1260
ttgagatccc ctagacggct gaccacaggg ttctgcctgc agccctgagg ttgggctcca    1320
gggctgagcc tgtgtctctg atccactcta gctctgtgca cctatgtaac aattccatcc    1380
agagatacct ggagacctcc tgtcaccggc accggatgct gccctcggac aacatgtggt    1440
ccagccagag gtttcaggcc cacctgcagg aaatgggtgc cccaaatgcc tggtctagtg    1500
tcattgtacc cggcatgaag gctgctgtga tccatgccct gcagacctcc caagacactg    1560
tgcagtgccg aaaggccagc tttgagctct atggggccga ctttgtgttt ggggaagact    1620
tccggccctg gttgattgag atcaatgcca gccccaccat ggccacttcc acagctgtaa    1680
ctgcccgcct gtgtgctggt gtgcaagcag ataccctccg tgtggtcatt gaccggcgac    1740
tggaccgtac ctgtgacacg ggagcctttg agctcatcta taagcaggtg agatgtccca    1800
gcacctccca caggcaaccc tacagcaaag ccctggctgg ggtctgctgt gagacagagt    1860
tcaagactga ctctacacac ggggcatctt aacacagaca cgtcccactg gcctgtctcc    1920
tcatctgtgg aagatactgt cctttgagag ccattaatgc catgagtttg tagtcatagg    1980
tagtattttc agaggccctg ggacctgctc agtttccatg gtaattccaa gcctctaggt    2040
agtaaccttta ttctctcatc tgtaaagtaa gactgtacct ggctcctcct ttgtgtgctg    2100
tgagaatggg tggtttgatc ttcacacaag ggtttgctaa agtaccaagc tggaggacat    2160
agaggatatg aggccatgaa cctcaaggcc tgcctatcaa gagttaatta ttagtgtcta    2220
tcattgttat aacgattatt atgttactca tcttcttcca aaaacagatt tgatcttgct    2280
tatttataat aagtatagaa ttgcttgggg ttttttgtttt tgttttttgtg ggttttgttg    2340
agatagggtt tttctgtata gctttggatc ctgttctgga acttgctctg tagaccaggc    2400
tggccttgaa ctcacctttg actgcctctg cctcccgagt gctgggacta aaggtgtgca    2460
ccaccattgc ccgacctaga attgtttttt attcagccaa aaacattac cttgccctcg    2520
tggtctaatt ctctctagaa acacccttag gagcacacca ggggcatgcc ctatagaaat    2580
cctaggtttt ctcagtccag tctagttgac aactgatatt agccaccaca gctggacatg    2640
gggctccacc ttccacctcc cagtatttgg aaggctgaga caggggatca cttttagttc    2700
aagggaagct tgggttacac agtgagttcc aggctagcct gggcttcaca gtgagaccct    2760
acttaaaaac atcatacaaa caaacaaaca aacaaacctt taaacgtatg tttttaaggg    2820
tttctgaatt ctgaggacag ttttttaagat ctttgagcta agattcacca aggtctaggt    2880
ttgctacagg aagggaaaac actgatcacc tgacctgggt ggcctcatgt ttcctacagg    2940
tcctgatcac cttagaataa tgtgctggca aagggttccg tctttgttag ggatgccatc    3000
actaggtgtc cagggtggaa tccaggcctg cgttttttagc atgtgcagtt ctactgagct    3060
acacctccag cctaaaaaat gtaaaggagg agatgcatgc aggtgtgcat acacctgtaa    3120
tcccctgggca acagaagcaa gaggactgtc acaggttcac caccacctgg ttacagggtt    3180
tataataagg tcctgtcaca aacaatgtag tcttggaaga gaggagagga aatggggaag    3240
aggaagtaat ttgcagttta aaatagagca aaattgccgg gcgttggtgg tgcacacctt    3300
taatcccagc actcgggagg cagaggcagg cgcatctctg tgaattcgag actagcatgg    3360
tctacaagag ctagtttcag gacagcctcc agagctacag agacaccctg tctcaaaaaa    3420
aaaaaaaaaa aaaaaaaaaa agcgaaattt gtatggacat ggcaacacgt gcctgtaatc    3480
ccaacactta gggggctgag gttggaggat caggagttca agttatcct tggctgtatg    3540
tgagcttgaa gccaacctgg gcctacagca ctgtctgttc cacaatctgt ctttatctgt    3600
```

```
ttgtctcctt atgttgttca gctcggtctg ttctctgaat gtttgtctca gaacaaacaa    3660
aattgaatag ggctgggcat acgcactttt caaatgtcct ttgtccccca ggtatctttc    3720
attgctgatt tggttttgag cttgagggtc agtgtacaac aaggtggtta caatggtggc    3780
tttgtctgtc tctgatctcc tttatctagg acagtgccac tgctgtatcc ctggcaccct    3840
ggtcctttgc aggccaggca ggccagcctg caccaccgcc ccacactgtt ttatctgttt    3900
ttctccttat gttgttcaga tcggtctgtt ctctgaatgc cctgtaaact agaagatagg    3960
ctaacaagct gatggggttc agggttgaga ttttggcaa aaaacactca tgtgatgcta     4020
ggtacctcat gtgactgtca caaggcacaa ccaggaatct ctagttccca atgccgaatt    4080
tgaccttaga ctaaggtggc tgccaccaga gccacatcct cccctttgta gctttttca     4140 tttttcttta cattatttat tgtgtttgag tttgtacatg tgtgtggtca cacatgccac    4200
agcacacatg tgggagtcag agggcaactt atgggagttg gttctctcct cccatcccat    4260
gggtcctggg gcttgaactc agcaagtacc ttataagcta tctcaatact gtttgcctcc    4320
aaaatgtatt actttgtgta gctgtccctt ttctgttgct aataacagaa tactacagac    4380
agtgtaagtt acaaagaaaa taggctcaat tgtatccatc ttttgctgcc catggcatga    4440
aaacacttgc atcccaacac aggccagagg tcgctttagt gtgaagcagg attgagtgca    4500
tgtctgcatg gctaagactc tctacttctc tggtttcctg atccctaggg ctctgggact    4560
ctagatcctc tggaccccctt gataatagag ggagcttcct gtttctcaga agtgccttt    4620 gaccatatat cccagaaact gattccatcc atctctgccg tgtgtcacta gtcactagat    4680
ggcgtcactg tcatctctca ctagtgtctg agatggcctt gtcttctctc ctgcccacag    4740
cctgctgtgg aggtgcccca gtacgtgggg atccggctca tggtggaggg ctctaccatc    4800
aagaagccca tagcagcttg tcatcggcgg acagcggtcc gctcatcact ccctcatctg    4860
ctggcccagc aaggctgtgg ggaaggcaag gactcaggac cccctatcca caggtcagct    4920
tctaggaaag atgctggggc caggagcctg ggacacactg agaagccaga ctctgcggcc    4980
accacctcag tcccccggaaa ggggaagaaa ggcaaggcaa aaagtgccac agccctggtc    5040
tgcatcaccc tgcagaaatg ggagtcccac aacaccaggg tgggcccac cttcaacagg     5100 ttaatgtgtc tgaaacagcc tgaggcctgg ggtagtacca tgtcccccaa accccgcagt    5160
gttcccaagg ccatttctgc ctgctctcca agccctcccc aagcatctgg gcttgccctc    5220
ctgccaaaag gccaccagtg atagcaagta tgaaccaaat atctttaaat acataaccaa    5280
atgagtatta caaagtagtc accctgccag gcagttagac caaaggctcg gtcctagagt    5340
gcgcgcccag agtccagacc catgctgctg ctctagccag cctttgccct cacctttctc    5400
tggagaaagg tgctgccacc atgcccttcc ccattcctaa ccagcccct cagccctcat     5460 aacgccctag tgaggtaggt gctattgtcc ccattttcca gccgaggtag cagcaagttt    5520
aaggacgttg cccgaggttg cacagctcag aaggggcaga gctgggatgc agacccaggt    5580
ctgttggtct cccaaccctg tgttcttccc actgcctctg gaggaggagc tgggaggggc    5640
tccatctgcc cttaccttgt atcccccacc tttacacatg tactgtggaa caattggtca    5700
ggctggggcc tcacccagat cctcacagct ccccttctcc cacagcccg tcctacctcc     5760 ctagtctcca ttccaaggcc tggctgcctt cttcccatgt gctccgaccc cagggccggg    5820
tcctcagact accgaatggc caactggtgg gctctaaggc tctgtcaacc acaggcaagg    5880
ccttgatgac tctacctact gccaaggttc tgatgtcctt cccacctcac cctgatctca    5940
```

-continued

```
agctggcacc cagcatgctg aagccaggaa aggtgggcct cgagctgtgc ctcacaccct    6000
ggcgggtagt gctgagcagt gggatcgggg ctgaagggca cgaacagagg gcagcgctcg    6060
gaccatacag cgccccaggg aagggcttgt cttctccaga accctgttcc aagacagagg    6120
cctgatcata tctctttccc tcccctcctt gcaccgaggc tgctattccc ctgcaccttc    6180
gaggccccca ctttggaagt gcctcgaggc ctctgccctt tgaagttgga cctcttccta    6240
gcacccacag gaaagtcacg gccaaaggca agttcaaggc catactctgc gacaaagcca    6300
gggctgaggc atacccccaag agaggctga gcctccccaa acccttgacc cttattctga    6360
catgccggac actgagaacc atgggggata ggaggctaga gaaaccctg ctctgatctc    6420
tactgcccca tcctggatcc agcatcaaat taaaaaagc aattaaagtt ctctggactt    6480
ggcttgaata atgtgcggct aggctcataa aagagttgac cagcagggcc tccatcagca    6540
agggccacag tccccacccca gcgacagaca ttggctttct ctgcagggag acggatgggt    6600
ggggaaagag ccttcactat acagatgatg acactgagac atggcttgcc tgagaccaca    6660
gcaggcggaa agtcagccat caggagtgcc ccttcccaaa gacaagctgg gctggcagaa    6720
gagcttctga tggtcacaga acattatgac aagagacggg cttccctaa acctcagcct    6780
ttctccggag agtatgtccc tcagtgaggg gtcggtcaag acacctcaaa ctgcaaaacc    6840
caagaaacag gtcaagtgtg gcatttccta cctgtagagc ctcagctgct ggtcctccaa    6900
aagcggtatc tagctgtagc gtgtgaatgc ttcctgagtg gggcagggtg gagaggagag    6960
tgcggtgttg aaatccaatg acctgtgtct cccaaagtca gaagagctca tgcctgcaca    7020
gtggtgtgtg tctgtcctcc caggacttgg gaggcagagg caggtgcatc tctgaattcc    7080
agtccagcca gggatatacc aagaggccca gcctcaaaag caaacaaacc tcctcgtgac    7140
caggagtaca gcagatgcca cctccagacc tggccactgt tcacttgagc agagagcaca    7200
gtccctggtc aacacttgct ttctcagcag atcctcaaaa gcagacttgt gaggtaggac    7260
tttattatt ttaagtccag agagcggtca cctgcccaac gccacacagt aagtgagtgg    7320
tttaactggg atttatctta ggttggtagg actaaggagt caaagacctt gaccgtactc    7380
agcaccaagc ccactgtcct tgagctgggt cacggcccctt ctttctattt tccaattggg    7440
ggttaagcac tgtctatcgg tgagagagcc gcaggcactg cagggtccga gagaagtacg    7500
agggtagggg tgccacaagt tcactagggg ggtccctgga tctggtgcct gggaggagga    7560
ggcggtgcaa gtgcaggtgc aagggcatct gggccacctg ggaaggacgc aggcgaaggc    7620
gtctgaggag agcttcgtcc agcacctgga gtgggaaaga cagcagccca cctgagttcc    7680
agccagagga gcccctggct ctgatggacc tctctggtct gcaactgcca tcatttctc    7740
aacaggcagg cagggatttc tctccacaca gagctaagtt acgtttcagc tccttttgtg    7800
tttagtgaag ccatgtgatt aagccactca ccaatgggat gtgaggaaaa cacagaccta    7860
gccctcaaag ccccgattca caaaaacatc cagtctcccc ttatggccag gaagcaatag    7920
cccttttctc caagtggcta cccagagtca ggtccactcc tactgtatgc ccatttgcca    7980
gacttaatcc aagaagaaac aatggacttc agggcctgtc agaggtcagc tccccactcc    8040
ttgagctaac agacagaagg aagcctgagg aagtcacagc accacagagg caagggtggc    8100
cccagaggcc aagcctgttc ccccaattcc ctaaatacag agcaggcatg tgggcctgaa    8160
gacctacctg tctctggagc ttggtggtct tggctggcca cagaaagcgc tgcccagaa    8220
cggtgcccac tcgaggagca taggtgtggt ccccaagcac tgggcagagc tgtagagcca    8280
tgtgcacctg aagctgactg gggaacactg aaagatgggg ggaggcagtt gctcttcttg    8340
```

```
atcatcaagg actgtcccca ttcccagagc ctgtgcatct atgaggtgac ctctgcctcc    8400
acagagggcc atgagcagat caggacaatg acagctggca accttcccag cctgggggca    8460
ttgaacccaa cagaactgaa gctcctggga ataagtatgt gggttgggtg ctaaactgtg    8520
ggtgtgcacc taaaactctg cctcctgctg agcccactct cagagtcccc agatgctctt    8580
ttttttttgt tttgttttt gttttttcag gcggggtttc tctgtggctt tggaggctgt    8640
cctggaacta gctcttgtag accaggctgg tctcgaactc agagagaggt gcctgcctct    8700
gcctccccag tgctgggatt aaaggcatgc ccaccaccg cccggccacc agatgctctt    8760
tggatgttgc aaaacaacat cttcctcata ggcttcattt cccctgcaga gtactgttca    8820
gccctacctg tcagtggctg cagctggacc agagcacagc cacagcctgt ggccatcaca    8880
tggaaatggc tgagggtcct cttgacacct tctaggatgt cctttcgaga tggggatgtc    8940
acggggatgg cctaggatac cagtcaagaa tgacttagca cacgtagg agcccaattg      9000 agccacccct gctgccggct gacttaggac agggcctcag aacaggcagc agcaacttgc    9060
ctgttagagg acaggggaat agccaccca tgcacatagt gcagactcct ctgtaaggca     9120
aaacctgaaa ggactcctag tggcttctga ctcacaagat caatgccatc catgcgttcc    9180
agcttcaggg ccacgtggat agtcccctca gaaggctcag ggatgccatc agtgatgcca    9240
ctgagaaaga gaaggaagt ctcagagcag ccagctggga ccttccttgg ccctgggagt     9300 cacccgcat ctctcaccag taggtggctg tgggcctctg tgttctcctt gagtgaacga     9360
agaacttctg caagcggctt gctgtctggg ggcagctgga gagaagcaca agcccagacg    9420
cctccctgaa agaagaggac aagtcacata agcctcttg gttggaaaaa atgagggcca    9480
gattggctgc tcctgcagag gactagcact cggcacccac atagtgggtc ccaactgtaa    9540
ttccacttcc aagagagctg atgccctctt ctggcctctg gggcaccggg catgcactgt    9600
ggtacacaga cacacatgca ggctggcctc cgggggcaca aggcatgtgt ggtgcacgga    9660
catacatgca ggctaaacac acatttaaaa acaaatcttt ggtcttttt aaaggagacc    9720 ctcccaccaa ggggctggag aaatgaatca gtggttaaga gcactagctg ctcttccaga    9780
gtacctgggt tcagcaccca catggcagct cacaactgta gctccagttc cagggatct     9840 gagaccctca cacagacaca catgcaggta aaacaccaat gcactatata tatatatata    9900
tatagataga tagatagata gatagataga gagagagaga gagagaccac cttcccacct    9960
ccccaaatga acaccaggac tacagtccag acctaagaaa caaatcctgg ccaggcagtg   10020
gtggtgcacg ccttaaatcc cagcacttgg gaggcagagg caggcgcatc tctgtgagtt   10080
cgagaccaac ttggtctaca agagctagtt ccagggcagc ctccaaagct acagagaaac   10140
cctgtctcaa aaaaaaaaa aaaaaaaaa aaaaaaaaa aaaaaaaaaa aaagggggg       10200 ggaaataaac aaatcccaag accttttttc tggcccccag agaactcaga caaatgccct   10260
aagagttact acacatgcca ggcacctgaa taggactctt atatacagtg ggtgtaaaat   10320
aaaggcccac cacactcctc acttactttc caggtgctcg cacaacctgg agctcccggt   10380
gtttgagccc cagggcctgg ctcagctgtg gcagcacaga aagcaaggtc agctccccag   10440
gtctccctga gaagtaagag ggagaaaaca agttgccaga gcaccatcca acgaactcct   10500
ccccaccagc cttccctcc ttgtccctgc ccatacctgt cacaggcaga ccctgtggct    10560
tgttcagtgt caccagaggt cctgaaatat tcggtagatg tcagcaaaag cagggcagcc   10620
tgtgtgcatg cagcctctgg ttataagctc ccaagcccac tccaaactga acttcctgct   10680
```

```
ccccgcaccc agggcctttg cacctgctgc cctgagcttt cattaatatt gggtccctta   10740
tcacacacct ccctataatg tgtgcccctc ctacagtcct tgactgtttg gtctgagacc   10800
agctcaaaca ggccggcctc aaactcaact ataggtaagt ctggtcttga actcttgatc   10860
ctccttgcct ctgtctccca agttctggga ttacaggtgt ggtcaccact cccagaaaca   10920
gcagagattc actattcctc acatcagaac gcttgctctc tcaaggcagg agccagccat   10980
atttatccca gtactgtgta gcctcctcat tgctacaatg cactgaagtt cagcaaagtt   11040
gtcattccta aaggcacaca gcatgctgct tacagacccc aggaaactaa cttctgctcc   11100
cgagggtctt agaatgcgag gcggtgtgaa ggtttcctat gcctggcgga gggaatgtga   11160
cggctacagg ggtccgactc cagggggtcg gaggctccct caccttgctg atccaccaca   11220
gctgccctca gcacctcagc cagctcctcc gggccgaggt tctctgttcg cagaagcccg   11280
gggaagggct ggtcctccac tgcgtccttg cacttgctgg aaccttgagg ttgaggccga   11340
cccctgagaa aaacgacaga agccggtacc tccaacgccc acgctgccca gtgcagcctt   11400
ttcgtacaca accctcagaa cccccggctc ggctgacagt tgtggtccac aggccccccaa   11460
gactacagaa ggggcatcag acgctcggag cgccaaccat ctcgtgtcgg gtcacacaac   11520
gcggctggga ttagaaccca tgtcctgatc tgagtgcccg acctgccctc cccttgtcct   11580
agcctccctc ctacacgaaa gtgttgagtt ataatcaccg ggcctcggtg ccgaagcctg   11640
catctctcgg ccgtgcgcca gccgccagcc ggggccgcca ggtgccagac acacaacgcc   11700
aaacgcggaa gacgcccatc gccgcagcaa gcacagacgc atgcgtgtcc acggactgcc   11760
ccaccgcgtg catcctccgt gcgccgattg gtcagcctgg ctgtcaatca gagcatcgag   11820
caggcggagc ttcgaggacg gaagagccaa actttccttt ggctgaggaa ggtaaagtac   11880
ggtctccggc tctgctttgg gggaaactga ggcaggaggc gcggttattt actcgcggta   11940
gaggacgtgt cttagaatag aaagaggcga gtttgcagat agattgtttc agttctcagg   12000
acccttaatc tgaaacccat ccttgtaaag cagagggaga aggtgaagcc ccacagcctt   12060
cgggccaggg cacctgcatg gaaatggtct gcgacattaa ccatcccatg actgtggctc   12120
aggtggtaga gagattttc taggatgcac gagttcctgg gttcgatccc cagcaccaca   12180
cgaagaccaa gatcacagat acagactgag ttggagacca gcctgggata tgtaaggccc   12240
ttctatcaca agaaaaacaa actaggccgg gtgtggtggt gctcttcttc aacagaggcc   12300
aacctggtct agacagtgag tttcaggaca gccggagcta cacagagaaa ccctgtcccc   12360
cccccccaaa aaaaaagaa aagaaaaaca agcttggtgc ggtccacata gtaagttcca   12420
cactggccag tatgttgtta attccaaaga tggaatgagt gtaaggaaaa aggccagcca   12480
aagaaacaca ctttggctct gcaaccagaa ccaaagaaat gcacccttgt cagaagccag   12540
ccttggtgac gcccccccc ccaatgccta gctagccgcc agctagccta gcatcccacc   12600
cctcaggttc caggacctgg cctgagaagc aactaacacc ttcccccatt tccttagtta   12660
gtgcttgaga taaacatagg agattccaga tacctggcct gagaagcaac taacacctat   12720
tctttctcca cacaggagat tccggatacc tgcctgagag caattaacat tcattcctcc   12780
cccacctcct ttttctctgc ttcctcctttt ctctataaaa accccttgta ataatcaata   12840
aatgggcctt gacaagaaaa cctgcttggt cccgctcttt ctttcccgcc catcattttc   12900
aggcgtgatc cacctcggac tcaggaatta ccggagcccc gagggccggg gtacaccctg   12960
accctgaaac cagtgccaga gaaacacact ttggccctgg aatcagagcc agtgaaagaa   13020
atacaccctg gctctaaaat cacagtcaaa aggctaaaaa ggaccagtga aggaacaca    13080
```

```
ctttggccct gaaaccagag ccaaatctaa ccctaaacct gtgcagaaaa ccaaccaatc    13140
cctgagcagg agatctagcc attctgagct cagggattga aatctgacca atccccaccc    13200
tggaaatctc cctgggaaaa ctctgccccc ccctaagaat ccctatataa accctgtgcc    13260
tgttcagctt caggctgcct ggctgccctc tgccactgga ttcttgaatg aggtttgggt    13320
aagaactttc gccggagcag agaccaccct acacactggc tctccagggg actggagttg    13380
aactgttaca atttaaccag ggaaaccctc tcctccccaa gcagagctga tacactgagg    13440
aaggcctttc cctgaagcag ggctgtaagc cgctatgctt actgtgacct gtggcattcc    13500
ttggctccta aacgccagaa taccttccca tcccagctgt aacactcagt attctgtgac    13560
tccggagtgc cagaatactt tgcatctgag ccataacaca gtattctttg ctcccgagt     13620 accagaatcc attccttccc atccaatccg ttgaaatgct tacaatgaga aaaaccacga    13680
acccaaatca ttgagaccaa attaattaaa gtttttttt cattcatgta cgagactgcc     13740
tcccccaagg cctgatttga gaggtcagca ttggatgtga ggaagacaag ggggttttgt    13800
tgttttggtt ttttgagaca gggtttctct gtgtagcttt ggagcctgtc ctggaacttg    13860
ccctgtagat taggttggcc tagaactctc agagatctgc ctgcctctgc cacttgagtg    13920
ctaggattaa aggcatgtgc caccaccgcc tggcctcacc tggatcacac agacacatat    13980
atacataatt aataaaatac agacctggcc tttaatccca gcactaatct acatagtgag    14040
ttgcaggaca accagagtta catgaccctg tctcaaaaaa aaaaaaaaa aaaaaaaaa      14100 acaacctaaa taaataaaat gcagaaagta acaatatgta cataataaaa ataatgaaat    14160
aataacataa ttgaggaaca gtggggcatg gtggcatgtg cctttaatcc catcacttac    14220
tgatctacat cccaagcctg aaggaccttg ctgaaagggc tccagcacta gactgttgct    14280
tctggcagag aaagtggctc tcaacctgct ggtcaacgac ccctttgggg gtagaagggc    14340
cctttcacag gggtagccta agaccatcag aaaatacaga tattcacatt acaattcata    14400
acagtagcaa aattacagtt ataaggtagc aacaaaaata attctatggt taggagtggg    14460
tctccataac atgaggaact gtattaaagg ttgcagcatt aggaaggttg agaaccacca    14520
atttaggggc agatgctgcc tccttcacag cactcagcca cagttgtgtt gtgtccttgt    14580
tgaggttcta tccggtcctc caaagttcag ctgtgggaaa ctaaatcttt aacttcataa    14640
taatggtaat tggaggctgg agtaattagt accagataaa atcatgaaga gtgtgcttcc    14700
atgatggcca ttaacagctt tctaaggaga gcagagaaaa aaacctttc ctcgttgtgg     14760 aatgacttcc tccgtgttgg tgtgcaccag aaaggccccc tgcttgtgct aagtggagct    14820
atgccatgct cttggactct gcagcctcta gaaccatgat ccagatcaac tgtgtgtctg    14880
tgtgatttgt tttatttta ttatgtgtgc atgcctgtgt gtctgcgtaa gtgtatacca     14940
tatgtgttgc aggtgcacgg agaggccata aaagggcat cagatcctcc gaagctagag     15000
ttttaggcag tcgagagcct ccacgtgggt gctgggaact gaactcagag cctctgcaag    15060
ctcagccagt gctcagccag tgctcctcag tttgtgtgct tgttttcagt actgcagatg    15120
gatccaggac cccacacgtg ccaggcaagc attctctcac tgagctgcac cctcagactg    15180
gtctcaggtg gtttgttata gcaacagaaa acagacatgt ggaaggagtg atggcgtatc    15240
ttgactgaga ggaggaataa cttggctact cgcacagcac atgtctgggc aggttcacaa    15300
ggaggcttcc agggacaatt ggcacctaag aaccctgacc taatgaatgg atgaaccatt    15360
cagaatttgg atgggttctt gggggggggt gagggaactg tggtgggtgg ggactgcttg    15420
```

```
gaggaagtag ggtgtttgtt gtgggtggct ctcggaggct atgtcttaca ttggctcctt    15480
tctgttttgg ttctttcaat ttcctgttgt gtgctattct gctacaaccg cctcacccag    15540
tagattgcag cctctgttaa tcaagacagg gtcttactgt gtagccctgg ctggcctgga    15600
actcatagag atctgtttct tctgcctctt gagtgctgga attaaagacg tgtgccacca    15660
ccaccacctg acctagagga caactttatt ttttttaatt ttttatttat tatgtacaca    15720
ttgttcctgc ctgcgcacca gaagagggca ccagatctca ttatacatgg ctgtgagcca    15780
ccatgtgggt gctggtactt gaactcagga cctctggaag agcagccggt gctcttaacc    15840
tctgagccat ctctccagcc ccctgggatga ttaattgtag aagtttcagt tctttctttt    15900 tgttttgtt ttttgagaca gagtcacact acgtatcttc aactgatctg gaacatgcta    15960
cgtagacaag gctggcttca aatgtgtgtc aatgttcctg cctctgcttc cagagtgctg    16020
ggattatagg catgtcccta aatctgttat ttttttaaac acttattttt gagggggagt    16080
cggtggtggt gctgttgtac gtacatatgt agagatcaaa gggcatcttg tgggagtctg    16140
ttctctcctt ccaccaatgg gttctaggga ctgaattcag gttctggagc ttgacagcaa    16200
gcaccttaat ctgctacaac atcttgttgg tactaaatcc atggagaatt gaaaggattg    16260
tttattgttg ggcccgggaa tatagctctg tggtagtaga atgcttgcct aatatgtgtg    16320
agattcttaa aaaatcattg attgtttttct taaaccaact ttttaatttg ttaaaaccaa    16380
cttttaaagg atatatctag gcatggtggc acacagcatt aaccctagca cttgagagat    16440
agaggcaggc agatctccta tgaatttgag gccatcctat tctacgagtt ccagtacagc    16500
caggactaca ggactgtgtg atatgcacaa cacaggaagg actgatgaca aatttggtaa    16560
aaaaaagaaa gaaaaacagc aagtggtttc acattgtccg gcttcacctg gagtgggtga    16620
ctgtgggtac tcctgaagcc tcccaggagt gggtgactat tctgtcagac tgtgggtatt    16680
cccgaagcct cctaggaggc ctcctgtgca tcacagaagt ggcttgagca agaacttggg    16740
acagactggg caagtgcaca gctataatcc cagcactgca gaggtgaggg ctgatgggtc    16800
aggagctcac agttatcctt gactacagga agtctgaggc cagtctgagc tatgtgagac    16860
tctaaaacat acatgagtca gtgagttggc tcagccagta agggtgcttg ataccaagtc    16920
tgaccacctg agtctgatcc ccagaatcca catggtagga gcagagaacc aactcccagg    16980
agctgtcctt tgacctctgg acttatgcta ttgcatatgc ataccaatac ataactccct    17040
aaaatacaaa atacatatgt ttgggctttt tgtttgtttt gttttgtttt ttcgagacag    17100
gtttctctgt gtagctttgg agcctatcct ggcactcgct ctggacacca ggctggcctc    17160
caactcacag agatctgcct gcctctgcct cccgagtgct gggattaaag gcgtgtgcca    17220
ccaacgcccg actgatgttt gggctttttt gatggttttt atgtgtgtgt gtgtgtgtgt    17280
gtgtgtgtgt gtgtgtaatt agaaggagaa agagagagag ggagagagag acagagagac    17340
agagacagag acagagacag agacagagac agagagagga gagagagcca aagtctggtt    17400
tgtggcccat tcaactaagc agacttctcc tccaccaatg gtgtccacca atggcccagg    17460
aaaggccatt tccccacttg aaccagcgcc tggccctctg gagggttagt tcctttactc    17520
tttggaggtc tccctccctg ccccatagca ggctgccctc tcttgctccc ttcccacagg    17580
cagctacctt catcccagtg ggctatgagc tcctggaaga aaaggaggag ccaaattttg    17640
cctaggctga gggctcagtg ccaggtggca gccacagtca actgctgaac ttgtgaaact    17700
ggaccccagg agaagaagcc tgggacaaac atcagcttgc atcagctccc tctggctcag    17760
ttacagcttt gcagcaggtg tggacaggct ggtgcttcag caatgggaaa caggactgat    17820
```

```
gcaaaccagg cctccaggag gccaagccct ggagccagcc tgcagtgaac cagcctccag    17880
ccacatctac aactgtgtga gggcctagaa tagaaagtgt acttgacctg tctgtccttg    17940
agtgctcttc tcttctcaca cttggctcca ggcatggggc agcttccagc gatggctttc    18000
cagacaagct tgagtaactt ggcccttttgt cttagtgttt tctaaatcca aataggcttt    18060
acagggagga ttgtgaaatt atgttagctt tggatctgag agccagactg aaacctggct    18120
tcctacaggc ctagtctttc ctgcttaggt cagttacctg tcactaataa atggggctc     18180 cttttcctac cagccaccaa gatggctgaa gtggaggaga agaaatgaac cttccacaaa    18240
ttcacatact acaatgtgga cctggatcag ctgttgacag gttctaggaa ctgctgatgc    18300
agttgtacag caccccagag gtggtgtctg aaccacggcc tgtggcagaa gcagtactcg    18360
ctactcaaac acctgagaaa gctcaagaag gaggcaccaa ccatggagta acccgaggtg    18420
ctgaagaccc acctgaggga cacgatcatc ctgcctgaga tggtgtgtgt gtacaatggc    18480
aaaaccttca gccaggtgga aatcaaacca gagctgatca actgctacct aggcgagctc    18540
ttcatcacct ccaagcccat gaagcatggc cagcctggta ttggtgccac ccactcctcc    18600
agctgcatcc ccctcaagta gctgtggcca acaaagactc atgtttaaaa agaaaattgg    18660
aagccaggca ttggtggcac acgcctttaa tcccagcact cgggagacag aggcaggtgg    18720
atctctgtga gttggaggcc agcctggtct ccagagcgag tgccaggata ggctccaaag    18780
ctacacagag aaaccctgtc tcgaaaaacc aaaaataaat aaataaataa ataaataaaa    18840
taaagaaaag aaaagaaaag aaaaatgggg gctcactctg agaagacctg actcctcctc    18900
ctcctcagaa ctctctggtt tgtttttgca gtgctggggt cactgtgcca ggctagagac    18960
tcactgcaat ctgagggtgg aagtgctgag caggaacagg gaactgtgta taagctggca    19020
taggcattga taaattcccc tgtagatgga ccaggacctt caacccgaa cacatggaaa     19080 gttattgtaa aatacaacag ttgggaatca aaagagtggt ttgatccacc ttacaggcaa    19140
atttcattcg gaaactgaca acacatatgg atcatgtggt ctgcctgaat atcaaatatg    19200
gcaggcctca aaaatcaact gcagatttta atataacatt taattattca tctattaatt    19260
aatttattct gtctcataat atcaaacctt atctattaaa agggagcagg gctggggatg    19320
tggctcagtt ggtagagaat ttgcctagca tgctggaaac cctgggttcc gggttcaatc    19380
cccagagcca cataaattgg atgtggtgtt tcacatctgt aatgctagca cttaggaagt    19440
ggaaacaaat ggatcataag ttcaaggtca tcctccacta cataataaat ttggagccag    19500
cctaggcttc tgtatctaga agaaaaaaca gggcaccact gatgcaactc attgcataaa    19560
agcaattgct gtgtgagcct gacaatccaa gctcaatcct tagaaccaag agtggaatga    19620
aagttgtctt ctgggccatg cacgcctttg atcccagcac tcgggaggca gaggcaagtg    19680
gatctctgtg agttcgaggc cagcctggtc tacagagtga gttccaggat aggctccaaa    19740
gctacacaga gaaaccctgt ctcaaaaaaa aaaaaaaaa aaaccaacaa aaaaagaag     19800 gttgtcctct gacctccaca cctgcaccat agtactggca taccaacaca cacacacaca    19860
cacacacaca cacacacacc agtaatgaca aatgctatct cctgtaattc tcggcaaata    19920
gtttcaaaca aagaacacag gcaaagatga ggtattggca taaataattt acttcaggct    19980
ctaataccat acattagtgg ggaatgagaa caaaggagg aattgtctga cttcccctgg     20040
ggatcacaaa ctctatccat tcggcccagc aagggcgcca atgaaaggtg aagaagccac    20100
gattccatcc aagtccagct tggtgaaccg gtgagtttac taggttactt acaggtgggg    20160
```

```
cctgggtgac tcaaaatcac aggtgactcc ctccaaatct gcatcagtga catcctggct    20220
ttagttaacc ttttacctct tatatactct agcaccgccc caagatcatg agcagctggg    20280
gcggggcagg agggaggaat ggctgggatt tcaggtgcta agacccctg  acactctcct    20340 cccttcctaa tacaggtgtt aactatttcc ataccctagc cataggcctc accgtcactg    20400
tggcatttgg ttcattttgt tgtcttgatt caggtcaaag tattctggag gccaccatag    20460
caatgtctgt tgcttgatga gcatggtcaa ggcaggaggg gactgcagag agggagtggc    20520
acatagggat ggcatgtgaa gaccgagtgg cagacttggt gccaaagcct gccagggaca    20580
agtgtttgtc ccctaaacta cctgtgacat gaaggaagga actgagccag gctaggaagt    20640
tctcccgtga ccagcccacc ccagagctcc agcccttcct gcagtttcct tggtgctgtg    20700
ctgtgagagg ggtgcaggtt ggtgagaagc tctccagctg ccaggcttgt gggtgcttct    20760
agcagagtgc aaggtctcca gtcacatcct ggctgggga  cggcatctga ggacttgggc    20820
cttcattgca gcatcttcag acaggcgggg aggaggagg  aggtcttggc cttggacggc    20880
tgttcttcct cagtggcatc caggaactgc tgcatataac tggaggagcc aagcagcatg    20940
tggcctgtgg cctgcatgct gaagagggcc cagcggagca tttccctggg agacagcaag    21000
gcactcaggt taaacactcc ccatgctatc tccccaaatg tcttctccat ttttctatgc    21060
tggcctaaag cagttggctt caagttagac ttctttcttt gtttctactt cttttatttt    21120
tgagatagaa tcttaacact ttatctcagg ttagctagaa attcatttat gtagctcagt    21180
ctggctttga actcacagaa atctcctgcc tcaatctcct gatgctgttg cagttatggg    21240
ccaccacacc taacttttt  tggtttggtt tggttttgat ttggctcttt ttgaaacaga    21300
atctggagat cctcctgtct tgtcctccca agtgctaggt atacagacat gtcccaccat    21360
actgggctca agctagcttt tctccttagg aagatttaag tgtcactaaa gtaaaatgac    21420
aaaaatgctt ccaagtacag acaggaactg ggaaccaggc tcatagctag ccatccctta    21480
cacatagttc tgcctctact cttgtgacaa cttttctgga  accccttgct ttttcccatg    21540
cttaacttga gttctcaaaa caaagctttt tattttcttg taatgatatt ttgtttcttt    21600
cttttctctt ctatggtgct ggggatggaa cccagggctt tatttgtgca taagcagctg    21660
acctgccatg gagctatgtc cccagcccca tatatttttt ttttcaagac agggtttctc    21720
tgtgtagctt tggagcctat cctggcactc actctggaga ctaggctggc ctcaaactca    21780
cagagatccg cctgcctctg cctcccgagt gctgggatta aaggcgtgtg ccaccaacgc    21840
tcggcatcca gccccatatt ttttaaacta ctctggacca gccagattaa tttacataac    21900
acatgtctac cctttgtaac actgcttctt agactttata gtcttcccag gccagttctc    21960
agaatgctgg ccacaaggct cccatgcctg atatcatatt ctaagcatag aacttggacc    22020
agacagggct gaacactgat ccagagtggt ttgtttatat ctaaaatatt taaaatatat    22080
tttaaaatat tataaagatg ggtgatgtaa ctaatttagt gcttgccttt catgaacaaa    22140
gccctgggtt tgatccccag caccgcaata acccagagtg gtaatatagg actgtaaacc    22200
taggatccag cactgtggag gtagaagcag gtggatccca agttcaaagt catccttggc    22260
tacatagcaa gtgtgagacc agcctgagat acatgagacc ctgccaaaaa aaaaaaaaaa    22320
aagctttaac tgttctggtt ctgagctcca gcagccagaa gctttgtgac ttgtaaaatg    22380
ggtaatgagt ttgaaactaa tgtgaagcac ttagcatttg gtctgatgga cagaaaatgg    22440
gacatgcagc caagagcagc tggctgaatg caacttctcc cacagctatt gacaagggct    22500 cggcagggt  cactaggagt tgctggtctt aagaacaata aggaagagaa aacacaagaa    22560
```

```
agagaaatac tgccaggccg cggtggcaca tgcctttaat cccagcactc aggaagtaga   22620
gacaggcaaa tctctgtgag ttcgaggcca gcctagtctt cagagcaagt tccaggacag   22680
ctacggttac atagtgatac cctgtctcaa aaaagcatat atatatatat atatatatat   22740
atatatatat atatattgaa tttagtggcc tgaggcaatg gctcagtggg taaagtgctt   22800
gccatatggc catgaggccc tgaaagccca tgtaaaactg gggatggctg cctgtatctg   22860 tgacccccagt actcctctca tggtgagaca gagagacaag agactcctct gaagctttca   22920
ggccagcaag cctggcccag acaacagaca aacagcaaag accctgcttg aaacacagtg   22980
gaagatgaga ccagcacctt aggctgtcct ctgacttcga aatgcacgct gtggtacatg   23040
ggtgcccaca ttcacacaca tatagagata aagactggct gggcagtggt gacacacgcc   23100
tttaatgcca gcacccttga ggcagaggca gttagatctc tgagtccaag gccagcctgg   23160
tctacagagt gagtttcaag acagccaggg caacacagag aaataagaaa agagaaaaaa   23220
aaaagatata aagactgaaa ctgaaaatat aatatattag ggctagaagt atagcttaat   23280
ggcatggtgc ttgtctagca tgtatgaagg tcctggttta atccccagct ttgaagcatg   23340
tgtgtgtgtt tgtttctttt tgtggtactg gggaactgga cacaaggcct taggcaagtg   23400
ctctgccatt gaactacagc ctcagctttc ttttcttttt taaaaatgtt tatttatttt   23460
atgtatatga gtactctatc tgcatgtatg actttatgct agaagagggc gtgagatccc   23520
actatagatg gttgtgagct accatgtggg tgctgggaat tgaactcagg acctcaggaa   23580
cagcagccag tgctcttaac cgttgagcca tctctccagc cccctcagct ttctttttac   23640
ccccccacac acaatatctc tctaagttgc ccagtttagc cttgaactta ctctgtagcc   23700
taggcaagct tctaatttgc catcctcctg tctcaatttc ctaggcacct gggagtacaa   23760
ggccatgtat agctttatat atatgtttcg tgcagtgcct tcaaagttat ttctcaaatt   23820
agagaactga gttttgactc tagccagcca gtcttaaaaa ggaatgaaaa taaggcctat   23880
tctacaaatg aatgaacctt gaaaacagaa ttcttgtggg gaaagaatca tgatcccatt   23940
tctatgaggt ctctaggata gatcaatgga gcaacagaaa gtagagtaaa ggtgagcagg   24000
gtctcgggag agggctgaga accattattt actgagtaca gcttctgctg cctggtgcaa   24060
aggttctgga aaccaaggca atgcttgcac aacatgatta gttacttcat gctagacact   24120
tcaagcggcc acagttgaaa aatgttgaat gtgcagattt tagcacgggt gttttttctt   24180
gaaggtctca ttgtgtagct ctagctagaa tttggaactt gaaatgtaga ccaggctagc   24240
ctaaaattct caggagatct acctgcctct gcctcctgaa tgctggctgg gattaaggga   24300
gtgagctacc acacctgacc ccttagtaca ttttttttt taaatcacag taacaccact   24360
aagtcactca gctaaccaca gtttgacatc agttttatt ttctctaagt ttttattttt   24420
gttgttgttt tattttgttt ttcaagacag ggtttctctg tgtaacagcc ctagctaccc   24480
tggaacttgg tctgtaaacc agactggcct tgaactcaca gagactcacc tgcctcagcc   24540
tcccgagtgc tgggaccaaa gatatgactc ctggcctttt tatttcttt ccatgtgtgg   24600 gaggtagggg ttatgcacct gagtgcagtg cccacagtgg tcagaagagg gcaacatatc   24660
tcctagagtt gcagttacat gtggttgtga gctggctgag gttggtgccg ggaactggac   24720
ctaggtcctc gggctgagtg gttccctttt tctgtttttg ttttcaatac agggtctgat   24780
ctggcccagg ctgtccttga actcctgatt ctacacctcc aaagtactgg aattatagtt   24840
acattttcac ttacaaaaat attagctgtg gaaatagctc aggatatgag tatgtgctta   24900
```

```
gcatgcgtgc tgccctgggt cctatcccca gcacacaaaa gaaagcacat gactgtcatt    24960
ctttgttagc ccccagtgcc aacccaggct ttgagagagt tcagctttgg gtagacacaa    25020
aggacctctg gttagctagt ctcccaccct gctgtcccaa tctactcact tcacgacgcg    25080
cttggcccgg tagcagtgca ggtcatagga aagtgtgtat gtgtcataga gggtcgcctt    25140
cacgttcagg cagccgatga agtcctgggg gttcagcttg tataggtcaa aggttacccg    25200
ggccacatca atcttctttg ttggcttctg ggaaagggat agctgtggtc tcgtcttgcg    25260
ctgcaagaca agtccatgtt agctcgcctc tgggactcct tccacgccct cgacactcac    25320
ccctgctgga ggagactgtc acctgttctg atgggggctt ccacttctgc cccttctgca    25380
ggaccatgaa cacagtatct cttgccaggg cttggaagta ttcttctgtc tcaacaatcg    25440
tgccgtcttc ctccagcacg agggagaagg gcttgtcttt aagtttcaag atatcctggg    25500
cctggaaaag aaggttggtg acatttctgc catccctatg gagccacaga gttgaggagc    25560
aaaggcccgc agtaaagcac ttcagctgcc agagagagag caagtgagct gccatccatc    25620
cgtgcgatgg actgactgtc actgtggggg cccactcaag ggctgtgtct cagtacttcc    25680
tactcccaag aaggagtgta gtctaataga atgggagtca tatgtgaggt ctttttatt    25740 gagaaataaa ttcatacca tgctgggcaa tattaggagt catatcgaag gccttgggca    25800
agctaggcaa actgcagcat tgaactatat ccccagcctt cttttgtactt tttgtttgga    25860 gacaggatct tactaagttg tttaggttgg cctggaactc actgtgtagt ataggtaggc    25920
ctcagccttc tatttagatc ttcttgactc agcctcctaa gtaacttgga ttacaggcct    25980
acactaccag gcccagctaa actttatttt gttggtggtg gttttttgtt tcttttgcta    26040
tgtagccgtg gctggccttg aactcacaga gatccacctg cctctgtctc ccaagtgctg    26100
gggttaaagg cacgttgtta tggaataatc ttttggtaca ctgtgaagtt gtgtctttgt    26160
caaggcgctt tctgactggt ttaataaaag aactgactgg ccagtagcta ggcaggaggt    26220
ataggcagga aagcaagaca cagaggactc tgtgaagaag ggcagagtct tgggagtcat    26280
gagcaaatgc agagggaagc aagatgaaag aaggtaccac tatgatgcag agggtagata    26340
gtaaaaggat taatttaagt catatgagct agctaaacac aactctaagc tatcagccaa    26400
gcatttataa ctaataatga gtctttgtgt agttatttga gaactggcta tcgggataga    26460
aaagtctgtc tatagtgtgc atcaccatac ctggccacta ttttaaattt ttattttaa    26520 ttatgcgtat atgtatgtat gtgggtcccc tggagcaagt gattgtgagc tgcccagtgt    26580
gagagctggg aactgaacct ctgtcctctg aaagtgcttt taacgactga gccaccactc    26640
tagccccaac aactcatttg taatcttgtt cctgccaaag ctacatggca tgaactgaag    26700
aaacaggtca ttcaaaactg agggacagga aataaaataa ctggcttgcc atctttaaaa    26760
gccagctaga agaatcagca ggtaagggta cttgcagtgc aaactttagc atttgagttc    26820
aatacctgga gcccacagta gaaggagaga atgactcccc aaatgttgcc ctgtgacctc    26880
catgtgtacc ctgtggcatg ggcatgccag tgctcacaca cacgcttcat agacttacag    26940
taataatttt aaatataaaa taaaactgtc tggatttgca ggacaatcag cagtgctcca    27000
acagagtctc aagataagct tgggggggtt cttgttatgt agccctagtt gggcaggaac    27060
ccctatatag agaccaggct gacctcaaac atgtggtcct cttgcttctt catgcatcac    27120
cacactcagc cttagtttta atttcttttg aggcataccc agcgtatcct ggaactcaat    27180
tatgtagccc aggctagcct caaacctgag atcttccata tctggtctcc cagatacgag    27240
ccaccatgcc tggctcattt ctccacgtgt aaatatgggg aaggggaatg aatggccctt    27300
```

```
tcagcaagaa aataaccacc cacccacggt tggtgtgaaa gacggtagtg cactgccctc    27360
cttctgtcac ttgaccatgt cacttatcac acacacagct ctccaggcgg aaatgccaac    27420
cctccagtgc caacaccttt ctccgcttaa gaccatgcca ctcatgcgca cagacttcag    27480
ggctctccag aaaccgaagc agccggcagg ctcaactctc agccaaggcc tggagagagc    27540
ctatgcaggg taccggcaga tcccttacct tgcccaggag gtcctccagg ctgtgagcca    27600
tgatgccttt gcgaaccttc cgatctgccg tgctaactcg acagggcctc gccctgggga    27660
cttcccggct gggcttagac accagctgtt gggtcaccac tgcagtgctc actgctacat    27720
gcctggggac aacagtttgt acagcagatg acctgcctgc ggctaccagg tctgcccatg    27780
cctgcctgct tgctgagttc aggtgtgacc tttccttcca accaatcatg gctgcttcag    27840
gcggctttca caaagtccat cagaagacac agctccgatt tggaggggca gggaaatcag    27900
cgggaatctt gcttaaatca gactcacttc agtgcctctg agtggagccc aaggactgct    27960
aacaagtccc caagctgtgt cagtgtggct ggttcttgga ccagccacat tctcctgtgg    28020
atggcttctg ctttttgtggc cttgttcacc ttgcctaaga ggcagggtga atggagctg    28080 gtgtgtgtat atatgtgggg tgtgtgtgtg tgtgtgtgtg tgtgtgtgtg tgtgtgtgtg    28140
tgtgtgtgtg tgtgtaaatc ggcctgtaga atatgtgggg actctgaggt acacagggta    28200
gaaagaaagg agcagagaga atttgggtct tggctggaat tccaagtttc tctctgttac    28260
ggatttgcta ggtgacagca tacccagcct gtgactcagt ttcctcatct gttgacttgg    28320
catagttgcc accacttccc agagaggagt gaggctcctg ggagatcagg aacaaaggca    28380
cctggtgccc agcctgaccc tttctactcc agatgtgatg ggaactgtgg cagtgacaga    28440
gagtaagatg gggactgtct agactgcaag atcttgggtg ctaccctagg cctcctgaat    28500
cagatctgtg ggggtttatt gtaagatttt gtctgttttg ttttaatggg ggtcttgctt    28560
atttgtttgt ttttttgggat agcatctcca tatatagccc tggtttactg gaactaattt    28620
cctcatctct gtctctgtct ctgtgtctgt gtctgtctct ctctctctct ctggacctgg    28680
acctatgcag accagactca aactcaccaa gatcctcatg ccactgctcc ccaagagcca    28740
ggattcaaaa catatgccac catgcctggc catatcagct agaccccaca tgactttttt    28800
tgtcttttaa aatgggatgc ctatgtagcc ctgactgacc tgggacttgc tgtgcccact    28860
acaggctggc tcaaactca gatctgcctg cgtctgcctc ctgagtgctg ggattgaaag    28920
cgtgtaccat cacatccagc ccctacatgg ttttatacc tattaaagtt ttcaaagttc    28980
taatagatgg ctccccagct ttcccctcc ttcccatacc cagctctcct tacctggaca    29040
gtgacttagg gtacaggagg ctgagagact tcatggcata gtccatcctt gtcagctgga    29100
ttgtgttgga cctggatcgg aggcagtaac ctatctggtt agagtgggaa gggagggagg    29160
ggtccctctc tttctttctt tgactcagtg gatcccagcc cccacacggc aaccctctgc    29220
cccagtctct cctcctaccc ccaatttccc tgaatccaca ccaactacac tgagtcagcg    29280
tctaccatcc ccacccattc cacagcccca gaacaactca ctccatgttt ctctgcccca    29340
agctctggtt acactgagct gaggaaccca agtcaaggct gaagaggccc tcactgattt    29400
gtccctgtcc ctggggggcag agtccacatt atgctggcag gaggtgagtc ataccacctc    29460
atgctgtgag agacttgaaa gtcacctatt gtccagaaac tccacaggca gtcagacctt    29520
ggagagcctg ctctaaccat gggccttga gcaataaagt cctcctgagg cttagaactg    29580
gctaagagaa cttctctgtga tcttaaagac tgtctaggct tgtgttcacc aataccttag    29640
```

```
ctgttaccac tgagcccttg gcaccataac taatgtgaca aaggagctga caccgaactt   29700
ctattgaggc ttaactaatt tagttaggta actactgtgg tttgtgacgc caggtacccc   29760
actggacatt acagttgtag tggagtaatc ctgggctcat gtgcccsctg cctttcctcc   29820
tatattgctg ttctctggtt cttgcctgct gagctgcaag tctctgcaca ggcagtctct   29880
tctacctgca atgcttgtct caaactcaga gctcaacata agtcacctag aagccccagc   29940
tcctggctgc caactcagga aagccttttc tggtgccctc ttgcctggta ccagattgat   30000
ccctgtgccc tgcccttcca tgtgaaagac ccctctccct tagccctttc tttctcaagt   30060
ttgtctcctc ttcctcctgt cggcggcttc cccgatcccc accccggtg gccttttccc    30120 gcccggcccg agaacaagca ccgggtgggg ccggcccgag aacaagcacc gggtggggcc   30180
ggcccgagaa tgagcaccag gtgggccagc ccgagaacga gcaccgggtg ggctggcacg   30240
agggcgagca ccaggtgggt cagcacgagg acaaacaccg agtgagccgg cctggagctc   30300 tgccctgag ccccgcccc gcccgaagag aaacactccg tcccaaggtc tccgccccca    30360
aggtcagcca tcaggaaaag ggggggaatt gagtctgctg taccagacac cagaccttga   30420
gaatatgctg atctggaatg gctctgtgtc tcatttgaac catccaatgg aaatgattct   30480
gtatttcgcc tcatttgaaa gactctgtgt ttcacctcat ttgaataact ctgtactttg   30540
cctcatttga taaccctgt atagcgcctc atatacattg accaatggga atagctctgt    30600
ataatgcctc attagaatta tccaatagaa tccttgctcc tagcttgcgc cttttttcct   30660
atataaggac cccttttccc ttggctcggg gcgcttagcc acacagaagc taagtcgccc   30720
caggtacctg cgtctccaat aaagcctctt gtttttacat ccagtcgtg gcctcgctga    30780 ttcctgggtg tgtgggtctc cctctacgaa agtgcctctt cggggtcttt catttggggg   30840
ctcgtccggg attgagaccc gcccaggac caccgaccca cgtctgggag gtaagtgttg     30900
tgcggatccg ctgttttgtc ttgtctggtc tgagtctgtc ttgtgaattg cgcttgcgtt   30960
tgtagtatac agctgtgtac atttgtaggc ggatccgagg agggactgac gggtccgaac   31020
tcccgaccgc ggctccagga gacgtcctgg tagcgtttga agccctcagg aagagggatt   31080
tgtattttga acttgggaag ccctcagggt gagagatttg tactttgaac ttagatctat   31140
gactggacat tttcccagtc tctttggaga aggccctcgg cttgagggat ttgcaatctt   31200
tactggggac gaggaaggag ggccccsttc ctcgactctc tctcaattcc ttctgtcgac   31260
tctctgtcga aaccgcgctg cgaaagtctg ttctgtgtta ttcggtcttt gtcttgtagc   31320
tgtcatttgt gccctcctaa gcctagaaac tatgggggcaa actgtcacca ctcctttgtc   31380
cctaacactc tcccactgga aagatgtaca ggaatatgct cataaccaat ctgttaatgt   31440
gcgtaaacgc aaatggatta ctctttgttc ttcagaatgg ccgaccttg atgtaggctg    31500 gccgcgagat ggtaccttta accccagac tatattccag ataaaagaga agattatgga    31560
tcctggacca cacgggcatc ccgatcaagt ggcttatatc gtcacttggg aggctttggt   31620
tcaggacccc cctccctggg tacgtccttt cttacatccc aagggcccct ctctccttcc   31680 ccctctaac cgctccaacc gacccattcc ttcggcccct acacctccca ctcctttgat    31740
tcctcccaac cccccttccc attccaacct ttacccctacc gtgatgaaag acactaaggc   31800
taaagaaaag aagacaccta aggtactccc tccgggagaa gaccagttgg ttgatctatt   31860
aacggaggag cccccgccat atccgccact gccgccccca ccagaggcag aagcggactc   31920
cgccgctgcc ttggcggaag cggccsctga cccttcacca atggcttatc gactaagagg   31980
tcgtagggag cagcccgttc cagattcaac cactctgccc ctccgaactg ggctgaacgg   32040
```

```
ccaacctcag tattggccat tctcagcatc ggacctctat aactggaaaa ataataatcc   32100
ttcttttcct gcagaccccg tgaggctgac atctctcata gagtcggtac tcacgactca   32160
ccaacccacc tgggatgatt gtcagcagct tttgcaggtc cttttaacct cggaagagaa   32220
acagcgcgtg ctactagaag cacgaaaaaa tgtcccagga gtaaacgggc agcccaccca   32280
gctacccaat gaaattgatg cggcttgccc tcttgaaaga cctgaatggg attttaccac   32340
cgaagcaggt aggacccacc tgcgtctcta tcgccagttg ctggtagcgg gactccgggg   32400
ggcaggacgc agacccacta atttggccca ggtgaagcag ataatacagg gtgcggagga   32460
atcacctgcc gcttttctag agagattgaa agaagcgtac aggatgtata ctccctataa   32520
tccggaagat ccaggtcagg ccaccaacgt ttctatgtcc tttatttggc aatcagcccc   32580
ggacataaga aacaagcttc aaaggctaga aaatctacag ggatatacac tccaagattt   32640
gttgaaggaa gcagaacgta ttttaataa gagggaaaca cagacagaaa gagaagaacg   32700
ttggaggaag gaaactcagg agagagagga aagactaaga caggaagctg aggaaaaaga   32760
ggttgcgaga gaccgtaagc ggaataaaga aatgagcagg ttattggcca cagtagtgac   32820
aggccagaga cagaatagac agagggatga cagaagggg ccccacctgg cagggaccca   32880
atgtgcttac tgtaaagaaa aaggacattg gcaagagaa tgccctaaga acccccgggc   32940
caagcttcca ccgccaaggg tttctgacct cctgaaccta aagattaga ggagtcgggg   33000 ccaggagccc ccccctgagc ccaggataac actgcaagtc gggggcatc cggtcacctt   33060 cctagtcgat acaggggcac aacattccgt tctgaatcgg tcacccggac ccctgagtca   33120
caggactgca tgggtacagg gagctacagg cggaaagcag taccattgga ctacaaatcg   33180
gcagctccag ctcgcgaccg ataaggttat gcattctttc ctccatgtgc cagactgccc   33240 ctaccccta ctaggacggg acctattgac caaattaaaa gctcaaatac actttgagag   33300
gtcagaagtc aaagtcacag ggccagaggg aattcccctt accatcttga caatgtccat   33360
agaagatgaa tatagactcc atgaaaagag gactaattcg aacaatcagg aaaccctga   33420 tcactggctt gcggaatttc cccaagcctg ggctgaaaca ggaggaatgg gccttgccat   33480
taaccaggcc ccaattatag taaccttaaa agctgccatc cttcctgcat ccgtcagaca   33540
gtatccaatg cctaaagaag cccgcgaagg aattcggcca catattaaaa ggttacttga   33600
acaagggatt ctggtgccct gtaaatctcc ttggaataca cccttgctac ccgttaggaa   33660
gccgggaact aatgactacc ggccagtaca ggacctgaga gaagtcaata aaaggataga   33720
ggacatacac cctactgtcc ccaaccctta caatttgctg agtggattgc cacctaacta   33780
tacctggtac acagtcttag atcttaaaga cgctttcttc tgcctccgcc tgcatcccac   33840
cagccagcct atatttgcct ttgaatggca ggacgcggcc cttggaatct ctgggcagct   33900
gacttggact aggctaccte aagggtttaa gaacagccct acccttttg atgaagcttt   33960 acatcaggac ctggcagaat tccgggttag gtaccccgct ctaatcctct tacaatatgt   34020
agatgacatt ctcctggcag ccaaaaccaa agggaaatgc aaggaaggca ctcaagccct   34080
cctccagact cttgggagcc tagggtaccg ggcatccgcc aagaaggccc agatatgtca   34140
gaaacaggtg acctatttag gatacaagat aaaggatgga cgtcgatggc taacggaagc   34200
ccgtatgcga gccatcttag acattcccac cccacaaaat ccccgccaac tgagagaatt   34260
cttgggaacg gcaggcttct gccgcctatg gatccctggg tttgccgaaa tggcggctcc   34320
cctctacccc ctcactcggc cagggggttgc ttttaaatgg gaagagcccc aaagaaaagc   34380
```

```
cttcaccgac atcaaaaagg ctctccttga atcaccagcc ctgggtctac cggacttagc   34440
taagccattt gaacttttta tagatgagaa ggagggctat gctaaggag  tcctcaccca   34500 aaatctgggg ccttggagaa ggcccactgc atacctctcc aagaaattgg atcctgtggc   34560
atcgggatgg ccaccctgcc ttcgaatgat tgctgctata gccctgctgg taaaagattc   34620
tcacaagcta accttggggc agcctttgac catacatgcc cctcatgcag tagaggcagt   34680
catcagacag cctccagata gatggcttac taatgcccga atgactcatt accagactat   34740
gctgttagac aaagaccggg tccacttcgg gcctttggtg actctgaacc cagccaccct   34800
gctccccctc cctggggagc ccgaggctca tgattgctta caggtattgg ccgaggccca   34860
tggagcgaga tccgacctga ctgaccagcc tctacctagc ccggaccaca tctggttcac   34920
ggatggaagc agcttttttgc atcaaggaga acgaaaggcg ggcgcggcag tcaccacaga   34980
gaatcaggtc gtctgggccc aggcactccc ccctggaact tccgcacaga gggcagaact   35040
catagcactc acgcaggctc taaaattggc agaaggtaag aggctcaccg tgtatacaga   35100
cagtcgttat gcctttgcca ctgcccatat acatggagaa atttacagac ggaggggggct   35160 gcttacctcc gaagggaaag acattaaaaa taaggaggaa atcctcgctc tcttaagggc   35220
tcttcatctg cccgctgcct taagtatcat acattgccct ggacaccaaa aaggggattc   35280
tttcgaagca aggggcaatc gaagggcaga cttggctgcc cgagaggcgg ccctgaccac   35340
agacaccact aacctcctgg ctctagagcc caccaacgac catcccttcc cctcatggga   35400
ctatgaacaa agagacatcc aaaccctaga gaaattggga gccgcaaagg aaccaaacgg   35460
ggattggact tatgaaggaa agactgtcat cccctaccgg gtaaccaagt acctagtgac   35520 attttacat aagatgacac atctgagctc caagaagatg cgggagctcc tcgaacgaga   35580
agaggaattc aatttccttt tggggaagaa cgatattcta aaacaggtaa ctgagcaatg   35640
tgatgcgtgc gcccgagtca acgcatccag actgaagctt cctcccggga accgggtcag   35700
aggctaccgg cccggaacac attgggagat agatttcact gagattaaac caggaaaata   35760
tggatacaag tatctattaa ttttgtaga cacctttca  ggatgggttg aagccttccc   35820
tactaaacat gaaacagcca agatcgttac taagaaattg cttgaagaaa tctttccccg   35880
ttatgggatg cctcaggtat tgggaacaga caatgggccc gccttcgtct cccaggtaag   35940
tcagtcagtg gccaccttat tggggattga ttggaaatta cattgtgctt atagacccca   36000
aagttcagga caggtagaaa ggatgaatag aacaatcaag gagactttaa caaaattgtc   36060
gcttgcaact ggcactagag actgggtcct cctactcccc ctagcactct accgcgctcg   36120
taatacccct ggaccacatg ggctcacacc ctttgagatc ctgtatggag tacctactcc   36180
tatcattaac tttcttgatc aagatgtctc agattttgct aactcccctt ctctccaagc   36240
tcatttacag gccctccaac tagtacaacg ggaggtctgg aaaccccttg ctcaagctta   36300
taaagaccag agggaccatc ccaccatccc ccattcctac cagatcgggg acactgtttg   36360
ggtccggcgt caccaggcca agaaccttga acccgctgg aagggaccct acatcgtttt   36420
gcttaccact cccaccgcac tcaaggtaga cggcattgca gcttggatac atgcttcaca   36480
tgtaaagcca gcccaaccca ccgattcagc cactgcatca gaatgaccg cacaccgcac   36540 tcaaaatcct ttaaagataa gactctctcg tacaccctcc tgttgattgg ttgtctgttt   36600
accccccatg tagcaactaa cccccacagg gtttataata tcacctggaa aatagccaat   36660
ctagggaccg gggaaatagc caacctcagc acttatatag ggactctaca tgatgggttc   36720
cctcctctct atgtcgacct atgtgactta gtagggtctg attgggatcc ctctgaccag   36780
```

```
gaaccattcc cagggtacgg atgccaccac cctgggggaa ggataggaac aagaagcaag   36840
gatttttatg tttgccccgg ccataaacca actcatggct gcgggggggcc gcaggaaggg   36900 tactgtgcaa gatggggatg tgaaaccaca ggggaggctt actggaaacc ctcttcctct   36960
tgggatttca tcactctcaa acggagggag atcccagggt acgcagggaa aggaccatgg   37020
agatgtgggc aaagagcctg cggaccttgt tatgatagtg ccggaggggg aggttttcaa   37080
ggcgccaccc ccggaggaaa atgcaaccct ctcatcctaa ggttcacaga tgctggaaaa   37140
agaactactt gggatagtcc taaggtctgg ggactcaggc tgcaccgagc agggaaagat   37200
ccggtgactt tattctccct gtacagacaa attactcccc taagccaaca atcagttggg   37260
ccaaacatag taatagcgga ccagagatcc ccaacccatt ttcaagtccc taaacccccct   37320 accgttccta aagctatcac tcctacacca ggtgctgtca ccttctcccc caccccagat   37380
gccctaaaca tcgagataac cagagaccct ccaggtacca gagatagatt attacaatta   37440
atccaaggag tttaccaagc cttaaatttt tcagacccca acaagactca ggaatgctgg   37500
ttatgcctag tttcccggcc cccatattat gaaggcgtgg caatactggg caactactcc   37560
aaccagacct cagcacctac cagttgcgga gctgctatgc agcacaagct cacaatatct   37620
gaggtctcag gaaaggggct atgcataggc aggattcctt cctcacatca agaattatgt   37680
aaccaagtag agccattatc tcaggacagc cgatacccttg ttgcccctta tggaacttat   37740
tgggcttgca gtactgggtt gactccctgt gtctctacca ctgttctcaa caccaccatt   37800
gacttttgta tattgataga actttggccc aaagtcacat accaccaacc tgaatatgtt   37860
tacagcgtac tagagaaatc aacccgatat aagagggagc caatatcctt taccgtggcc   37920
ctattattag gaggaataac aatgggggggc atagcagccg gcataggggac cggaaccgtt   37980 gccctacagg gaattaatca ttttaagctt ctacaacaag ccatgcacac ggatatccag   38040
gtcctagaag agtcagtcag tgcactcgag aaatccttaa catcactctc tgaggtggtc   38100
ctgcaaaaca gacggggatt agatttatta ttttttacagg aagggggggct atgtgctgcc   38160 ctcaaggaag aatgctgctt ttatgcagat catacaggaa tagttaggga tagcatggcc   38220
aaacttaggg agaggctaaa acagaggcaa cagctatttg agtctcaaca aggatggttc   38280
gagggatggt tcgctaartc cccctggttg actacccctta tatccacgct catgggacct   38340
ctggttattc tattttttgat cctcatattt ggtccctgca ttctgaacaa actgactcaa   38400
ttcatcagag aacgactatc tgttgtacag gctttagtct taactcaaca atatcatcag   38460
ctaaagcaaa tagatccaga gtatctagag acctctgaat gaaagattcc attcagttac   38520
aagagaaatg ggggaatgaa agacccctct cccttagccc tttctttctc aagtttgtct   38580
cctcttcctc ctgtcggcgg cttccccgat ccccacccccc ggtggccttt ccccgcccgg   38640
cccgagaaca agcaccgggt ggggccggcc cgagaacaag caccgggtgg ggccggcccg   38700
agaatgagca ccaggtgggc cagcccgaga acgagcaccg ggtgggctgg cacgagggcg   38760
agcaccaggt gggtcagcac gaggacaaac accgagtgag ccggcctgga gctctgcccc   38820
tgagcccccg ccccgcccga agagaaacac tccgtcccaa ggtctccgcc ccaaggtca   38880 gccatcagga aaagggggggg aattgagtct gctgtaccag acaccagacc ttgagaatat   38940
gctgatctgg aatggctctg tgtctcattt gaaccatcca atggaaatga ttctgtatttt   39000 cgcctcattt gaaagactct gtgtttcacc tcatttgaat aactctgtac tttgcctcat   39060
ttgaataacc ctgtatagcg cctcatatac attgaccaat gggaatagct ctgtataatg   39120
```

```
cctcattaga attatccaat agaatccttg ctcctagctt gcgcctttt tcctatataa    39180
ggacccctt tcccttggct cggggcgctt agccacacag aagctaagtc gccccaggta    39240
cctgcgtctc caataaagcc tcttgttttt acatccagtt cgtggcctcg ctgattcctg    39300
ggtgtgtggg tctccctcta cgaaagtgcc tcttcggggt cttcacatg ttcatttctg    39360
ctgcagctct cgggtcccca ctgtgcctgt tttcagcccg tagcacaggg acccagtgtg    39420
aacaccagga gtgggcaggc atggagaact gcctcctcag tgaaggaaaa ccattcttcc    39480
cttctgataa ctcgggttct ccccggtcaa ccttacagag ttagagaccc tcgtccccac    39540
ttaatgctac ccaagcactc ttgtttcacc ctgtttctaa tacccaccac tcacacagct    39600
ccacaaaacc caccacacct gctctgtggt agccaaatac cccagctctt ctcctcccct    39660
cacctcctag cctcctggca atactgcgtg gccaggcaca gcccaggcct cctccatttt    39720
atttctatct cctgtgaagc cactcccttg gccccagccc cagctgggga aaagagcaca    39780
ggagtgagtc tgaaactctc cctagggatt caagccaga ctgacttcca gaaagccccg    39840
aaaggggaag aaggcatgtt tcgaaagctc tagaaggaag aggtactgcc caggacttgg    39900
taccaggcaa gagggcacag aaagcaacag acggggcttg tggtctgcgt tccacccctc    39960
acaccagctg tttgcgctca cccgagttgc cttctttcag ccctggattt tctcctgtgc    40020
atgaggaata acgctcctgt tgaagccagg aatggtggct cagagctgta atctcagcac    40080
ttggtagact gaggcataaa aagggccatg agtttgaagc tagcctgggc tatagagtta    40140
ggtcctgtct caaaacaaa aatatagtca gacggtggtg gcacacactt ttgatcccag    40200
cactcggaag gcagaggcag gcggatctct gtgagttcaa ggccagcctg gtctccagag    40260
cgagtgccag gataggctcc aaagctacac agagaaaccc tgtctcgaaa aacaaaata    40320
aataaataaa taaaaagaa atatctttt tttttgagt caggcaagat acttgagttt    40380
tattatgtct gtctaaaagc aggtgttagg cctatttgta gtgaagcgtg gtgtgctggc    40440
gctgcaacac cggtgaggaa gcaggaacct gatctcagag cccaagaact gcttgacagc    40500
aggccttcgg cacttgccct ctgaaatctc ttccaccttc atcaggttaa tggagtgtgc    40560
acgggcacag tgcgggcacc cgtgtcttgg tagcactgtt tgacggctcc agcagcggtc    40620
aggtcccggt attcttggca catgttgtgt gtgtcatgtt gtgagttgta gtgcagccat    40680
accgcaaagt tcttcacccg cagtgggggcc tcaggtcgca ctgcacagtg tacgatctcc    40740
tcggatgact tcttcatctt gttcatctgt gcccaaaatc gggacttggc caccacatgg    40800
ttcgtcgcaa agatgtgcat gaggtatagg agtggtgtgt ggcacttccg ggtgggcaag    40860
cagcgcccca ccaccttgta ctcccgaagc gtgcctgagg ccttcgtggc tgatctgtcc    40920
ttgttggccg ccagccacaa aaataaaagg aaatatcttg cctataatgt tacaatccca    40980
tccagcactt gggaagccaa ggcaggaagg cctctgtgga tgagaccagc ctgggctaca    41040
gagtgacaac ctgccaagag aatgggtgg gtaatcccaa atcttgggta tagtgaagta    41100
caggactcaa gagacagagg caggaggatc atctccagtt caagcaagc ccgagctata    41160
aggcctcaaa acaaaaaaa gaatattaga tctatgattt attgctataa acactacaac    41220
ttaaaaaaaa ttaaaataag gacagcaaga tgactcagtg aatgagggtt tgaatttgat    41280
ccccagtacc cacatagtac aaagagagaa ctgactccca taggttgtct ttccgtgaaa    41340
actctccctc ccttcctccc tctctctttc tctctctcta aatgaaaatg tttacatcaa    41400
agcctctaca aagagcattc atgttacacc tagcgttgga gagatgtctc agtggtcaag    41460
agcgctgact tctcttccag aggatccagg ttctattaca agtacccatg tggcaattca    41520
```

```
caatcattta taactcagtt ccaggggatc tgactccctc ttcaggcctc tgtgggcctt   41580
catgtgtgtg gtgcaaagac ttgcacgaag gcaaaacact gtacacataa aataaaaata   41640
agagacagaa aagggaattt attcagtgtg gccataccag aaaagatgag aggaccagtc   41700
tcttcaaccc tgttttttgga gtgcagatgg tagctctagg aatttacagg agaagaacaa   41760
aaaatgggat gagctggtgg tgcaggcctc tcagtgcttg agaggcagag gcagaggcag   41820
gggaatctct gtgggtacaa ggacagcctg actgacctgg tggattccgg gctaaccgaa   41880
actacaaaat aagacactac ctctaaagtt aaaacaaaaa agggaggcaa taagtatgca   41940
tagctaagca ttctattcta ttctgcccaa accactctaa ttgacggcta cctccagtct   42000
gaagtaaggg tcctgcagta gctaggaaga ggactacctc ccaggctgac tgttcctggc   42060
tctggcaaca aactgaaaag gaaaactggt tcagaaggag atcagagcag aggggccaaa   42120
ttagaacgag gattgtgcct tccttcaggt ttagaacaac cactggagaa ttttaggtac   42180
tgctgtggta gtttggaaca agacgaggca aaaacttatt actggcaatc tgtaatgtcc   42240
ccataaatcc ttttatatc tatttttaaa aagatttcta tattatatgt acagcattct   42300
gtctgcatat atgcctgcag gccagaagag agctccagat tttattacag atcgttgtga   42360
gccaccatat ggttgctggg aattaaactc aggacctctg gaagagcagc cagtgctctt   42420
aacctctgag ccatctctcc agccctctat tttatttttt aaaagaatta ttttatgtgt   42480
atgaatattt gcatgtatgt atgtgcacca cattcatgca gtgcctatgg aagccagaag   42540
aggacgacag attccctgaa accagagtta caggggctgt gagttgcttt atggtgctga   42600
gaactgagct tccttcctgt acaagaaaag cacatgctgt taaccactga gctgtccctc   42660
cagccctccc caccccttg tgtgtgtgtg tacttgtatg tgtatgtatg tggacatgtg   42720
agcatgtgtg gaagtcagag gatggtttgc aggagttggt tctctccttc taccctgtgg   42780
gtcctaggga taaaactcag gctggtagca tgtccctcta cctgcaaagc catctcctgg   42840
gctttgtccc aataaatttc ttgctctccc ttggtatctt cattcttaaa gggaaggaca   42900
gagctacagg tacaatgggt gaaaattggc ctttagttac cagtcttgaa gatgagtact   42960
taaatttttt tcagaatcct ttttttttt ttaaatcttt ttatttatgt atacagtatt   43020
ttgtctgcat gtatgcctcc aggccagaag agggcaccag atctcataat ggatggttgt   43080
gagccaccat gtggttgttg ggaattgaac tcaggacctc tggaagagca gacagtgctc   43140
ttaacctctg agccatctct ccagctcaag aatccttttt tttttttttt tttttaagg   43200 cagggttcct ttgtgtagcc ttagttgttc tggaattagg tttgtagacc aggctggcct   43260
gaattcaaag acccacctga ctctgcctcc cagggtgctg ggactaaagg tgtgtgccac   43320
gacacctggc taagatgagt gcttttttaaa tgcctatcac atctacaggc acaactgatt   43380
gggaagctga ttcaaacctt gagatagcaa agggatagag gtgttgatgc aacataaaga   43440
cagagatgcc cagattttct ccttcctta gtcactgggc gggactctgc aggtccagtg   43500
aggactcact ggctctcttg ttaaagcctt atttagagtt aagccaatcc ttggaagagg   43560
catcattcat tcattgaaca cttgcagtgt gttaccctgt taattcagca gaaagcaaga   43620
cagctttagg ccacacctgg agcagctgga ccagagacca agtggaagca ggaatgctga   43680
tgtacacttc tcatcctgat cccctggagg ctgtcagcct gggccacaca gtgcgagatc   43740
ctgcctcaaa aacgttttg ctacccattg gtgattgtac atgtactttg ttctagcact   43800
caggaggtag ggccagcctg gtctacaaag gacagccaat gctacacaga gaaaccctgt   43860
```

```
ctagaaaaac aaaacaacaa cagaaacttt tttgtctgat gtttcatctt gtttcttttc   43920
taataatgta ctgggcagag aaaaacaaaa taatgcagtt gggcctggag cttagacct    43980 gggattccag cacttaagag atagaggcaa gctcattgct ttgagtttaa ggtccctctg   44040
ccctgcatag tgagttgcag gtcagtgtgg actatagagt aagaccttga ctttcaaaaa   44100
gcacaagggg ccaggcgttg gtggctcaca gctttaatcc cagcactcgg gaggcagagg   44160
caggaggatc tctgtgagtt tgaggccagc ctggtctaca gagggagttc caggacagcc   44220
tccaaaacaa tacagagaaa ccctgtctca aaacaaaac aaacaaaac aaacaaaaa      44280 tgtcaaaaag cacaagggcc atcaaaatgg ctcagtgggc aattacaaac ttgatgacct   44340
gagtccattc cttgagacct acataatgga aagaactgac tcccctaagt tgtcttctga   44400
ccttcacaca taccgtgtgt gtgtgtgtgt gtgtgtgtgt gtgtgtgtgt gtgtgtgtgt   44460
gtacatgcac gcgctctcgt gagcaagtac gctcctgata ctaaattaat aaaaaggatt   44520
aaaaaagtaa aaccacaaac atgaaccaaa ccaatgtggt gtaataacct atgtctggag   44580
aactaacagg tttctggacc cagagaggta gagaagataa tctaatgtct tcaggggaat   44640 taggggata aagcatcaga gcataaagaa agtttccctc acttgggaag tagtggaggc    44700
aggagcatca ggaattcaag gtcatctcat ctatatagta agtaagttca agactagcct   44760
gggttacatg agaccctgtc tcaaaaaaaa aaaaaaaaa aaaaaaaaa aaaaaaaaa      44820 ggaagcatgg tgcaacagat ttgagattga aacacaaaaa tagctcaact ctggggcaga   44880
cagcagagtc aggggaaagt ctaaggaagt tctggggaaa gggtcaggag gcccctccct   44940
gcttcattca cgccccaaac atctattaaa cattccatgt gtacttggtg tttctggcct   45000
gaggatgact cacagaggct gacacactaa gttaatcaca ggaagcacag aagaaaaaaa   45060 aaaaaaaag aaaaaacagg cctaatgcaa tggaatgcct gactgagggg gttcttcaca    45120
gtgctttgga gacgacccctt tgtgtctcat tgaaattcat ctctcaagaa acactcctca   45180
aatgtttaca cattgtcagg cactttgagc tgcaggaca cagaggactc agttctggtc     45240
cctgcctttg gaattcacaa ttgttgctct tccaaagaac tggggttcgg ctctcagcac   45300
ccacttaagg aggcccatga ccatttgtaa cttcagctca accgcttcca caagtaccca   45360
cacacatgtc tgtcccccaa acacacctat attcttcatg ctaaccttgt gacactatga   45420
gcaaaatcaa agacattaag aagccaggtt cagtgccctg tgccttagtc ctaacatttg   45480
agaggctaaa tcaaacagga attgaggcca cttggacagc atcaagagaa attatctttg   45540
aacatatgaa atgatattat cacagaaata gaattgcaat ttaaaccagg tatgtgatcc   45600
cctctccccc caccaaaaga aaaaaaaata gagggctgga gaaatggctc agtggtaaag   45660
agcacctgct gttcttgcaa aggatctaga ttgttttgtt ttgttgagac agagccacac   45720
tatgtaactc tggctgtcct ggaattcact atgtagatca ggctagctgg tatgtatgtc   45780
tgtccacaaa tgcatgcctg gtgttagagg cttccagaag tgtgtgtcag accctctgga   45840
actggagtta taggtggttg tgagctgcca tgtgggtgat gtaattgtac ttgggcccctt  45900 tgcaagagca accagtgccc ttaaccctg atacttgctt ttaaggaatt tgcatttttg    45960
ttttgaaatt acatgttgga aaagttttcc acatcagtaa gaaatgccat ccttactatt   46020
tcttcctgca gcttctcaga aatatttttt aatctttttt tttaagattt tatttattta   46080
tttattatgt acacaacatt ctgcttcatg tatatctgca caccagaaga gggcaccaga   46140
tctcattcaa ggtggttgtg agccactatg tggttgctgg gaattgaact caggacctct   46200
agaagagtag tcagtgctct taacctctga gctatctctc cagcccctca gaaatatttt   46260
```

```
aattcaaaaa tctttcttag ccagctctca agccactgga ttacttcttg cttctgctac   46320
tgacatagac ttcatcttga ttcactccat acagcaacta gatgtgtgta tataaatgac   46380
agatagatca tagatggatg gatggatgga tagatagata gatagatgat agatagatag   46440
ataatctcac ttgctaccta ggctgacctc aaactcatgc ctcagtttcc taagtgatgt   46500
gattacgggc atacactatt atgcctagca taaccatttg tttgccttaa aattttttaa   46560
gattaatttt ttattatgta tacagtattg tgcctgcagg ccagaagagg gaatcagatc   46620
tcattacaga tggttgtcag ccaccatgtg gttgctggaa cttgaactca ggacctctgg   46680
aagaacagcc agtgctttta gcctctgagc catctctcca gcccccagcc tttaaaattt   46740
ttaattaatt tttttttgt ttgtgtatgg gtgtttggcc tgcatgtagg cctatgcact   46800
atatgtgtgt agtactcacc tagaccagaa gagggtgcca gagactctgg aattggagtt   46860
tcagtgcatg atgagctgcc aagtgggcct taatccccaa accccagagg gttgaagagg   46920
gatcagtggc taagggtgct tgttcttgca gaggacccag ttttgattcc cagagcccac   46980
atggtagctc agaacaagaa ctccggcttc agaggattct gcaccctctc tgggcctcat   47040
ctggtaccag gcatacatct ggtatgcaga tatatacacg ccctgagtgg tgacaaaacac  47100 tctgtgagtt caaggctggt ctacatagag aattccagga catagtgaga ccctgtctca   47160
accaaacaac ctggatcctt tgcaagaaga gcaggtgctt ttaaacactg gccatctct   47220 ccagcaccac ctccccccctt taatgataca taggtcccac atagcctagt tcggcctctt   47280
aactcctgac ataacacctc atgaattcct catcctcctg cctctacctt ttgagtgagt   47340
gacgagatta caaacgttcg ccaccatctt tgttcccagt tggccctcaa ggccccaggg   47400
tctcagttca gatcctgcca ctatggatac atagcattga aatggggaag gctgcctctg   47460
tgctgcctca gcctttgggt gacgcctctt gcttggcact gcattttcag gagcatgaca   47520
tctttgctct ggaccctgac cccaaggttg tgtggagctg taagaagtgt aagggtgtct   47580
ggtattggtg gcgcgcgcct ttaatcccag cactcgggag gcagaggcag cagaggatct   47640
ctgtgagttc aaggccagac tagactacag agcgagttca ggacagccag ggctgttaac   47700
acagagaaac actgtcttga aaagcaaaac aaaataaaac caacaaaaca acaacaacaa   47760
caaagtgtta agcgcgcatg caaccagcca ctgggcaatt agtcaaagat gccaagtcta   47820
gatagacatg cagttaagaa cttagggtct agagagatgc ctcggtggtt aagagaccag   47880
aagagtttgc atcccagcgc tcgcacagta gctaacaaca gtctatctta caccctcttc   47940
cagcctctcc tggcacaagg aacacacgtg gtgctcatag ttacaaaaca gacacaacac   48000
gcatacacaa agaaataact aattttttaaa atgtcttgta atcaagtaaa agtgctaact   48060
ctagggacta aattaattcc tcagtcgccc tactccagga gcggtaaggc tggccagaaa   48120
gaccaagaac gcacgcgcgg aggagaaacc acagagtcgg tcctcccggg atagagaggc   48180
cggaagtgct cgcggagctg cacgccgggt gctggaagcc tactgagccc cgaggaaggg   48240
ctccgctcgg ggcttggcgt ggtgggtgag ccggagggtc ggcgtgagcg gcctgggctt   48300
tggttctgaa tgatggcgtc tcgggcaggc ccgcgagcgg ccggcaccga cggcagcgac   48360
tttcagcacc gggagcgcgt cgccatgcac taccagatga ggtatgaggt gagccaggag   48420
cactgaggcc ttccccggga ggagcctgcg ggtctcggga agcgacgcgg gcgagcctca   48480
cggtgccgct ccccccagcca gctgtcgcgt actaccgggt ccccggctcc ggcgagcgcc   48540
tcgggtctgt ttacaggccg ggaagcccag tggcctgccc tcgcccgcct cgtgctttga   48600
```

```
gggatctgg cctgcagagg ctcaggggtc gatgctcagc ccctctgaat gaccttggag    48660
acatcatttt tctttttca aatcgaggtc ccgcagtgtc tagagttcag gctggcctgg    48720
aactcacggc cttccctcct cagcctcccg agtatgcgcc tggtctgaaa actaacattc    48780
ttaaagaaaa ctgcgtgtgt gcgtgtgtgt gtgtgtgtgt gtgtgtgtgt gcgcgcgcgc    48840
gcgcgcgtgt gtgtgtttgt gtgtgtgtaa gtttgcccac acgagagcag gtgtgctggc    48900
agaatgcagt gccagtaaag ggtgtgtgtg tgtgtgtgtg tgtgtgtgtg tgtgtgtgtg    48960
tgtgtgtgtg tgtgtgtgtg tgtgtgtgtg cgcgcgcgcg tgtgtgtgtt              49020
tgtgtgtaag tttgcccaca ttcttaaaga aaactgcgtg tgtatgtgtg tgtgtgtgtg    49080
tgtgtgtgtg tgtgtgtgtg tgtttgtgtg tgtgtaagtt tgcccacacg agagcaggtg    49140
tgctggcaga atgcagtgcc agtaaagggt gttggatctc ttggagctat agttacagac    49200
gtgtttaaat ccacctgaga ctagtactga ggaccaaacc ccgaagtgat tttgtgagat    49260
agcggcttgg tatggggtcc atgctagcct ccaggagcgg caggtgctct taaccactga    49320
gccatctctc cagtccccag gctgtcttgg aacttgctct gtagaccaga ctagaaatca    49380
gagatctgcc tgcctctgct gccaagtgca aggattaaag gtgtacacta cagccgccct    49440
gttgaccctg tctttaggaa gatgtcatgt gtactttaca aagagttttg atgtagtcat    49500
gtcttaagct tgttgtcac acaagatgaa attaattacc accagggaat ttttcatcaa    49560
attgtgctgt acttaaatat gcctaaagta aaatacttgg ggtcagactc ttgaagttta    49620
aaccaacacc aggtactgag ttgtgttgaa cccacacaac taccttgcct cctgcagatt    49680
gttaactctg ctggctgtgg tggttgaaga gaccccaca ttggcttagc tgttaagagc     49740
acttgctgtt cttggagagg gtctaaactc agttcccagc accgacatca ggaggctcac    49800
aaccaaacac ctgcaactcc ggttccaggg gttccgatgc cctctggctt cccgacagca    49860
caggcgtgtg cgtggtgcac acacatacac atgagataaa tttttaaaaa gaaagaaaag    49920
ccaatctggg tcctgccttc aaggagcttg agtgccagaa gtgattcttt tctccttacc    49980
tcccacattt cctataacaa attaattttc cccttaaatc cactgaatta ttcaactggt    50040
tcttggcctt tttctttaca gaaggatgac aagcccttg gacccttctt tttcaacttt     50100
aggcccctgc ctaatggatg ctcttgtttt catgcgtacc tagagcagac accttgcttg    50160
tgacaatatg aaaaggatat aattgagacc ccgagaagat caggactaag agatgtgcct    50220
ccttctcatg gaaactatat ctggagaaat acagggagcc caaactgtgt tccttgttgc    50280
taggcctccc cctaatggcc tttgtttctg tgatacgaag ccatctttct aaccacagct    50340
cagaattctt gtcatggctt ggtgagataa tgtcttagta cgttgtccag gccaacctcc    50400
aatcagagat cctctgcctc agcctcccag gtgccattac tgttcttcag tcttgaagtc    50460
tacacatgca tggtctttgt aactgttact acctctctgt gccttggcag ttgatttcct    50520
gaaacacaaa tactaaaaag cttattcctt tgtgcctgca tgtttttgcc tctgcgtaga    50580
agcccacttc cactcgtctc attacctctg ctgaaatagc tctctcctct agatataacc    50640
ttctctggct ttccatctca tgctaattgg ttcttccctg ggatagcgga tatcttcggt    50700
ttatatgtat ttacttgagt tttatacttc atgtttccca gcctctatca gaggctgtgt    50760
cattcagatt gtatctatgt gtccagtacc ggtgcctggt ggtcggagca atttaaatga    50820
aaattgcttc tccctctgct ctgccttaca gtgtgacgct caagagtgaa atcaagaagc    50880
tgatctacgt acatctggtc atatggctgc tgttggttgc caagatgtgt gtgggacacc    50940
tgaggctctt gtcacatgac caagtggcta tgccctatca gtggaatatc catatttatt    51000
```

```
gagcattgtg ccctctctct tgggccttct ctccttcctc gaaacaacat tagctacctg   51060
gtgctctcca tgatcagcat ggggctcttc tccatcgctc ccctcattta tggcagcatg   51120
gagatgttcc ctgccgccca gcaactctac cgccatggca aggcctaccg cttcctgttt   51180
ggtttctccg ctgtctccgt catgtaccta gtgttgatac tggcagtcca agttcatgcc   51240
tggcaactgt actacagtaa gaaactctta gactcttggt tcaccagcac acaggagaag   51300
aaacgtaaat gaagcctgcc tgatggacac atgaagggag ctgttcagaa tctccatgga   51360
ctgtggcatc tgtgatgttg gcacctagtg cacactatcc tcagattttg gccttgagtt   51420
ctctgttacc atctgctgag atgacaaatc tgtagtgttt aatttattct tgactagcca   51480
caaaccggat gaccgatgtc tgtggaacac ttcaagttga ggccctccag actgagcctt   51540
atccttgcct tctcttggtc aaattcctta cttccattta tcacctcttc atcaccgata   51600
ctaaaagaga tctggaataa atcagtgcag aaattctact tcaatctgta ggtcatgggg   51660
caagcaacat ttgggaagtt gctcccctaa aggctactct gtttactgca aaccatttta   51720
attaaaaaag aacttcaata aagttaagac tgtcctgtgc tttgtgtttg agatttgatt   51780
gaatttcaaa gttgtattgc tctagaggac ttagacatta tgagaagaat agatgttttcc  51840 tgagaacatg ggactggcgc tggaggagag acagtgtgaa gagtcttaag tcagctgcag   51900
ccctctagct cttaggtgag aacaaccctg ggatgggggt tgctggagga atggctcagg   51960
ggttaagagc actgacagag gacacaggtt tagttctcag cacccaaatg gtgacttaaa   52020
accatttgta actactgtcc cagggcattt gacgccttct tgcctccgga tgcactaggc   52080
agacatgagg tacaaaaaca acatgcaag caaaacactc aaaaaattaa aaaaaaaaa     52140 catggtctct caatgtagct gtggatgtac tagaactcac taagtagagc aatctgggct   52200
caaactcaca gagatcctcc tgcctttgcc taccaagtac agggatttaa ggtatgtgcc   52260
accacactta gcaatatata tttggccaga catttaatct ccacccataa agcagcttat   52320
ttggcttgga ttatgagctc cccttttat gcttgtttga cagggcttt ctctatagct     52380 ctggctgtcc tggaacttgc ttcgtggacc agactggcat caaactcaaa tccacctgcc   52440
tctgcctccc acgtgctggc attaaaggtg tgtgcatcac tgcccagctg ggttacgagc   52500
tttctatttg gttatttatg tttattagac ttttatgtgt ctaaaactga gtaataatac   52560
ccaaaaagaa tctgcttgtt ggggctataa ttttccagta actgacaaat aaacctgagt   52620
caaaataaga agaaaggggt ttgagttctt tttccctttt agtttctgtc attgattatt   52680
ccttggcctg cttgtttggg gaatgtgcaa aggaagctgc taactctatg gaagccagaa   52740
aaagaaaaag gtgagattcc agtgtcgcca ctaggggcag actgccagtg acgtaacttc   52800
ttcactcagc ccctcccaaa gcttcctcca cctccaaaaa tgtcaaggac tggtaactag   52860
tacatgggcc tttgagaaaa gatagcaggg agcttccagt cttggggaa tgtgcagtga    52920 acataacatc taattgtgtg agagacccac agctgagata cagtttaaga gtcacaccta   52980
gaagtcttca cagtaaataa ggcagcaaag gtgtgcatcc ctttgcactg gactttatta   53040
tgcctagatg atgctcagat ctgtaactgc agagatctgg ccactacagt tgtaattctt   53100
ttgtcctgga aatgtgttgc ttgtacagtc tgcaaagcta attcctccag ctatcccact   53160
gatcatttct ttggagcagg ggcagtttcc agacagaatt tctctgtgta gtcctcgcta   53220
tcctggaact cagagatctg cctgctgtgt gctgggacta aaggcatgta ccaccatgcc   53280
cagctcctac tgatcatttc aaagataact tcttgtgcct caggcctatt gctgttcctg   53340
```

```
cttcctgtgt ttacgggaac acagctctgg atcatccacc ctgcaagttt aagtccgtcc    53400
ccactccata tacacactgc ctattcggtg aacctcctat agatacccctg ataagttccc    53460 tagcttctca gtttaacact tagaactctc cctacttaag ggaggcctct cagtggtgaa    53520
gtgctcctct agcatgcacc gaggcctggg tgtgactccc tcgtaacaac aaataaaaac    53580
aaaccttttc tgctcttaca ttcctttatt aatctttaag atgccacttg tatgaaaatt    53640
cctcaatttt caattcctca atttgaagaa caactttaat ttgtctggtt gctttcacct    53700 tattcctttta ttattatttt ctaacaagac agagcccaga atgaccttaa gctatgtggc    53760
tgaggatgac tttgaactcc tgatgctttg tctctacttc ctaagtgcta ggattacaag    53820
tatgcaccat cactcctggc ttatattact cgtccccccac cccaccccca tagaccaagc    53880
cttgaccttt attttttaaaa gctgcatatt tattctgctt tctgacttag tgtttgtgcc    53940
ttcaacactt tcacaaccct tttctctcct caataaggaa agcctgcttg atcctgtcac    54000
ggacacactt ggcacacaag gagccaccac agcccctgct gacgtgcttc tttgtctaga    54060
cagtctcata aggactttgg gtctcacagc atgaacccctt caagtctgcc tgggcacaca    54120
ccacatgggg attcaggtgc tttcccagtc ttcttggtat aaaggtaaac aatcctgttg    54180
ccagggttcg agacagccta gtttcgttag aggctgtatt gtaggaaagc ctacaatggt    54240
atgtcaaaca ctggaccatt cgagtgcctc taagcaccat ccctggaaga ggaagagctg    54300
tattatttgt tttatattga cagaattgct actttgtatg tcttctgtag ctcattagtg    54360
ttcactctga gcttattgaa tgaattaact tgccctttg aggacaaagg tctgtatttc    54420
acagaaaaca gaactggact gaagcagaaa gaagcccatg gacaagggag tttgtcatga    54480
gcttagctga ggcacacatt gctaacttca acaactgtg atgcaaacaa ttaaaactgc    54540
agtgcagacc ccctgctttt ctcccaataa attttccaca taagttctgt ccccccccca    54600
aaaaaaaaac ctgttagcac attattagtc aaagagctaa aacctgtttt tggtcatcag    54660
aatagtgttt tactgaaagt ctttgaatac cttgtagact aatttcactc attgtgaaat    54720
tagtcaacag tttaaaaca ctatcatgcc aacatcagtt tttgttagtt ttgtgcttgg    54780
aattctgctt ttctagcctt ttcctataac ttttttctgc ctcatggtta tggtgttcac    54840
aagtcctctt gatttagtgg gaagaatgct atttgggtta gaaagttcag ctgggtatgg    54900
gggtacatgt ctaatcccaa cctttggcag gttgaggcag caggaatact ctgagtttga    54960
ggccagcctg acatacatac atacatacat acatacatac atacatacat acatacaaac    55020
actatctcaa aaaacaaagt tggagttaaa gtatcaacca caggactaag atcaacctgc    55080
ctgttcacag gttgctttaa agctccaata gccggttgga gagatggctc agaggttaag    55140
agcactggct gctcttccag aggtcctgag ttcaattccc agcaaccaca tagtggctca    55200
cagccatcca ttatgaggtc aggtgccctc ttctggtgtg cagatgtaca tggaagcaga    55260
atgttgttac ataataaata cataaaatct taaaaaaaaa aaactccaat agccaaagta    55320
ttatgaaggc attctaaaat ttttaattta ttttcatttt attttggag acacagtttc    55380 tctgtgtaaa acccccaact gtcctggaac tcactctaga ccagactggc ctccaactca    55440
cagagataaa cctacctctg cctcccaagt actgggatta ggcgggcag tggtatcgcc    55500 cacctttaat cccaacactc gagaggcaga ggttggtgga tctctgtgag tttgagacca    55560
gcctggtctg caagagctag ttctaggaca gcctccaaag ccacagagaa accctgtctt    55620
gaaaaaaaca aaaaacaaac aaaaagcaag ttaatctgga attaaaagtg tatgccacca    55680
cacctgatgt aaatttaaaa tttttttttaa attaattttt ctatacacag gtgttttgcc    55740
```

```
agcatgtatg tttgtatagc acatgtgaac ctggtgccta aaaagccaaa agagtgcatc    55800
tgatcccctg ggactggagt tacaaatgga gtgctgccat gtgggtgctg agaattaaaa    55860
ccaaatcttc tagaagagca gccagtgagt gcccttaact gctgcagcat ctttctggct    55920
cttgtgaagg cattttatgg agtctgtaac accatatggg tatcaaaagc cgtgtggtca    55980
cctgatcttt gcagcaagac aggagagaga aggtgtttga gagacttgag ggatggtcta    56040
gacaccaaag aaaggtttgt gtgttgtgag caatgactga ttattaggtt gagattctag    56100
ccagggagtt tactatctct tgtttgattt attacatttt attgccatcc taggaattaa    56160
atagggtttt acatttgcta agcaagtgtt ctctcaacat ccttatatcc cctcccgat     56220 ttctgacact tactatagct cagcttgtcc ttgaactcag caatcctgcc tccatagtgc    56280
cgggattatg gatgtttcca ctcccagctg agcctgttct tcatgtgttg catgggcatt    56340
gcagatctct cccattgctg tgaggctgaa ataaatgtgg atgaactttg tagtacatag    56400
tcgtttacat atcaagatgc ctttccttgg taaacagtgt tatgcttgcc tctcaaattg    56460
ggagtgtctt cctgttttaa gaataatcct cttccctctt ttcttcctct ctcctccttt    56520
cccctccttc tgacagggtc tctttataga atattcctgc ctctctctgc cttccaaatg    56580
ttgtgtaggt gtacatcacc atgcctgcct agttagaatg acgtctcaga atgctggagg    56640
ttaatttcac attcttagtc cacattatcc tgactggtat gttcaaggtg ccctgacagt    56700
aggtacagac ccagcagacc tcaggaagtg accattacag caagatcctg tagctgctac    56760
tcatagcctg ttgggagccc gtgcatagga aagaatggca agaaaaaatg gctgccagag    56820
ggcgtcccca tagtatactc tgtcactaag catgcatgct tcagagcttg ccaaaacctc    56880
ctgagtccct ggcttggtcc ccaaataaag gtcattagag catgaagtct tggtcaactg    56940
attgagactc ctttggagag tgcaaggctt ctatgtagat gcccctgttg cctcctattc    57000
tgtctaattt cttactctcc ctgttgacag ctgccaatct cctttctcct aggactgtgc    57060
ccactcatca ctcactgtga taagacccct ttccttttct ttgttccttc ctggtctgcc    57120
tgcctgcccc cccccccacc tctccctttt catggtctca tgaaaactgc tctcagactc    57180
actatgtagc taaggatgac tggagctccc aatcctcctg cccctacttc cctaattctg    57240
ggattacaag tttatgccac cacattccac tttctgattt ccttccttac atcttaattc    57300
cactagcttt atcacactgc taaagctaaa actttctttg caaaatgaga tccagaaacc    57360
cacagactct ccatagtagg ttctgacagg gaaacagctg acattgtatg gtgttctgcc    57420
ttcccatttc tttgctgtgt gtgttttggg acaagtctcg gtcttcctgt atttccttcc    57480
ttccttcctt ccttccttcc ttcttttttcc attttttatt tgaattataa acacgattgt    57540
tttacatgtt aatcccagtt ccctctccct ccccctcctcc ctaccaccat ccccaactaa    57600
aaccctacct atcacatatc ctttctgctc cccagggagg gtgaggcctt ccatagggt     57660 cctcagggtc cgtcatatcc tttgggatag ggcctaggcc cacctccgtg tatcttggct    57720
cagggagtat ccctctatgt ggaatgggct cccaaagtcc acacctatgc taaggataag    57780
tactgctcta ctacaagagg ctccatggat ttctgaggtc tcctcactaa cacccacatt    57840
caggggtctg gatcagttcc atgctggttt cccagctatc agtctgggga ccaagagctc    57900
cctgttgttc aggtcagctg tttctgtggg tttcaccagc ctggtctgga ccccttgct     57960 cttcattcat ccttctctgc aactgtattc cagttcagtt tagtgtttag ctgtgggtgt    58020
ctgcttctac ttcttccagc tgctggatga aggctatagg atggcatata agtcagtcat    58080
```

```
caatgtcatt atcaggggag ggcatttaaa gcagcctctc ctctgttgct tagattgtta    58140
gttggtgtca tctttgtagc tctccaggca tttccctagt gcctgatttc tctgtaaacc    58200
taaaattttc cctctattat ggtatctctt atcttgtttt cttctattct tcccccaact    58260
caacctttct gctccctcat atactcatct tcccttctca ttctcctagc tccttcctcc    58320
ccttcccaat ttgctcagga gatctggtcc ctttccccct ctccagggga ccatgtatgt    58380
ctctcttaga gtcctccttg ttacctagct tctctggctt ttttttttt tttaagattt    58440 atttattatg tgtacagtgt tctgcctgca ggtcagaaga gggcaccaga tcccattaca    58500
gatggttgtg agccaccatg tggttgctgg gaattgaact ccggaccttt ggaagagcag    58560
tcagtgctct taaccgctga gccatctctc cagccctttc taaaactgga cattagccta    58620
gcctcaaggg ttgtgatgct aacaatacaa gctaaagaga gcaatgggca tgatccaaag    58680
ccagatagtt cagcaaatat tgatttcatc ccttcccttt tcggaacaga ctccagccac    58740
accaaatatg taaaccagca agacaaaaaa cagcaggcta tcttttccca cttttttgctt    58800 tgtctatgtt tgttggacaa tgtcaaacta tgtagcccag accccttctg taactttcca    58860
tgtagaccag gctggcctcc aactcaaatt cccagcaatc tacctgtctc tgcctctgga    58920
gttctgggaa taaaggtgtg catcaccatg cctggcctca ataagtcctt gtcttatggt    58980
cttctttcct cctccttac ttcttatcct cctccctctc tcttcccttt ccctttatct    59040
ttatttcttt attgtcaccg tttctttct gcttctctta ccatgcttta acaaccatca    59100
ggaagcaact aaccaaatgt tctcatcttg agagtcaggt cagaagatct aggagtcaag    59160
aaagacacgt gtaaaataga gctcacatac caagcattag aaaactcgca gtggcactaa    59220
aagatggctc aggggataag aacacttaca tggtgactca caaccatttg taattccagt    59280
tgcagacaat tcaatatctc cttctgatct ctaagggcac ccagaatgta catacataca    59340
ttcaggtaaa acgttcatat acattaaaaa taataagcct taagaattag aaaagagggc    59400
tggagagatg gctcagaggt taagagcacc gactgctctt ccagaggtcc tgagttcaat    59460
tcccagcaac cacatggtgg ctcacaacca tctgtaatga gatctggtgc cctcttctgg    59520
tgtgcagata tacatggaag ctgaatgttg tatacata                            59558
```

<210> SEQ ID NO 2
<211> LENGTH: 60000
<212> TYPE: DNA
<213> ORGANISM: Cricetulus griseus
<220> FEATURE:
<221> NAME/KEY: misc_feature
<222> LOCATION: (1)..(59559)
<223> OTHER INFORMATION: Locus of ERV integration, allele 2 (without the
ERV integrated in allele 1, at position 30020)

<400> SEQUENCE: 2

```
tggttctatc gagacagcta catccgcttc tccacacagc ccttctccct gaagaacctg      60
gacaagtgag ctttccctcc acctcccttg actgcccagg ctagtgagga ggtcagcaga     120
caaacagaac agtgggctct gcgggcaggg aaggcaggct tttcgccgcc actcatcctc     180
tgccctgaag gagcttgcca agagggtgcc cttgggttac cgaaatgagc aaaacaagaa     240
ctcctgctaa tcaagggctt acatcctagc aatgagcttg agtaatcatg gctaacatgc     300
tagaaggtga tatgtgttag gaagaaaatg tagatctggg taatggcaga ttaagagaaa     360
cttgagaggg gaaaggcaac ttgcagtttg ctcttgggat gagaggaaac cttgaggaga     420
cctgggttca aattctatct ctgcagcatc cagattgtgt tcctctagag acatgaaaag     480
```

-continued

```
agacttaagc ctcagtttca gttagagccc agtggtccca tctgtaatcc cagcacttgg    540
gagtctgagt ctgaaggatt ttgaggtcat tctgggctat ataatgagac ccccactcaa    600
gacaaaacaa gccaggtgtg gtagctccta actgtaatcc tagaacttgg ctaaggcagg    660
agccaaaatc aagccaggta cggtattgga ggcccgtgat cccagtgctt agaaggtaga    720
ggcaggacaa tcagttcact gtcaccctca gctacatgcc aagttttatc taacctgggc    780
aacatgagac catttcatag aaaaagacca gcctccgttt ccacatctga agactggagc    840
agcaatacac tgtagctgct tatcatcaag tacttcacat gtgataagtt gttcctgctt    900
ggttatacca cagccacttc tcaatggctc acaatgaagt gagttattgc cattttaaaa    960
agagatgaga ggggcaaagg ttaaatgact tgcctgagat ctcatagttg atcatcggtg   1020
aagctgggat ttgaccatcc agggtcatcg tcccccctgcc acacatagga atggtgaact   1080
gaaactaggc ccaaagcact tgatacttac tgtggcctgc aggcaacact ggagcattct   1140
gagaaatgac tagccctggc cgtggtgaat agggagtgg ggcagggagt ggggtgggg    1200 tggaggggtg cagcttctgt gcttctgtcc tgttgatctt ccagcagggg ccctctcag    1260 ttgagatccc ctagacggct gaccacaggg ttctgcctgc agccctgagg ttgggctcca   1320
gggctgagcc tgtgtctctg atccactcta gctctgtgca cctatgtaac aattccatcc   1380
agagatacct ggagacctcc tgtcaccggc accggatgct gccctcggac aacatgtggt   1440
ccagccagag gtttcaggcc cacctgcagg aaatgggtgc cccaaatgcc tggtctagtg   1500
tcattgtacc cggcatgaag gctgctgtga tccatgccct gcagacctcc caagacactg   1560
tgcagtgccg aaaggccagc tttgagctct atggggccga cttttgtgttt ggggaagact   1620 tccggccctg gttgattgag atcaatgcca gccccaccat ggcaccttcc acagctgtaa   1680
ctgcccgcct gtgtgctggt gtgcaagcag atacccctccg tgtggtcatt gaccggcgac   1740
tggaccgtac ctgtgacacg ggagccttg agctcatcta taagcaggtg agatgtccca   1800
gcacctccca caggcaaccc tacagcaaag ccctggctgg ggtctgctgt gagacagagt   1860
tcaagactga ctctacacac ggggcatctt aacacagaca cgtcccactg gcctgtctcc   1920
tcatctgtgg aagatactgt cctttgagag ccattaatgc catgagtttg tagtcatagg   1980
tagtattttc agaggccctg ggacctgctc agtttccatg gtaattccaa gcctctaggt   2040
agtaacctta ttctctcatc tgtaaagtaa gactgtacct ggctcctcct ttgtgtgctg   2100
tgagaatggg tggtttgatc ttcacacaag ggtttgctaa agtaccaagc tggaggacat   2160
agaggatatg aggccatgaa cctcaaggcc tgcctatcaa gagttaatta ttagtgtcta   2220
tcattgttat aacgattatt atgttactca tcttcttcca aaaacagatt tgatcttgct   2280
tatttataat aagtatagaa ttgcttgggg ttttttgtttt tgtttttgtg ggttttgttg   2340
agatagggtt tttctgtata gctttggatc ctgttctgga acttgctctg tagaccaggc   2400
tggccttgaa ctcacctttg actgcctctg cctcccgagt gctgggacta aaggtgtgca   2460
ccaccattgc ccgacctaga attgttttt attcagccaa aaacattac cttgccctcg    2520 tggtctaatt ctctctagaa acacccttag gagcacacca ggggcatgcc ctatagaaat   2580
cctaggtttt ctcagtccag tctagttgac aactgatatt agccaccaca gctgacatg    2640 gggctccacc ttccacctcc cagtatttgg aaggctgaga caggggatca cttttagttc   2700
aagggaagct tgggttacac agtgagttcc aggctagcct gggcttcaca gtgagaccct   2760
acttaaaaac atcatacaaa caaacaaaca aacaaacctt taaacgtatg ttttttaaggg   2820 tttctgaatt ctgaggacag ttttttaagat ctttgagcta agattccacca aggtctaggt   2880
```

```
ttgctacagg aagggaaaac actgatcacc tgacctgggt ggcctcatgt ttcctacagg    2940
tcctgatcac cttagaataa tgtgctggca aagggttccg tctttgttag ggatgccatc    3000
actaggtgtc cagggtggaa tccaggcctg cgttttagc atgtgcagtt ctactgagct     3060
acacctccag cctaaaaaat gtaaggagg agatgcatgc aggtgtgcat acacctgtaa     3120
tccctgggca acagaagcaa gaggactgtc acaggttcac caccacctgg ttacagggtt    3180
tataataagg tcctgtcaca acaatgtag tcttggaaga gaggagagga aatgggggaag    3240 aggaagtaat ttgcagttta aaatagagca aaattgccgg gcgttggtgg tgcacacctt    3300
taatcccagc actcgggagg cagaggcagg cgcatctctg tgaattcgag actagcatgg    3360
tctacaagag ctagtttcag gacagcctcc agagctacag agacaccctg tctcaaaaaa    3420
aaaaaaaaaa aaaaaaaaaa agcgaaattt gtatggacat ggcaacacgt gcctgtaatc    3480
ccaacactta gggggctgag gttggaggat caggagttca aagttatcct tggctgtatg    3540
tgagcttgaa gccaacctgg gcctacagca ctgtctgttc cacaatctgt ctttatctgt    3600
ttgtctcctt atgttgttca gctcggtctg ttctctgaat gtttgtctca gaacaaacaa    3660
aattgaatag ggctgggcat acgcactttt caaatgtcct ttgtccccca ggtatctttc    3720
attgctgatt tggttttgag cttgagggtc agtgtacaac aaggtggtta caatggtggc    3780
tttgtctgtc tctgatctcc tttatctagg acagtgccac tgctgtatcc ctggcaccct    3840
ggtcctttgc aggccaggca ggccagcctg caccaccgcc ccacactgtt ttatctgttt    3900
ttctccttat gttgttcaga tcggtctgtt ctctgaatgc cctgtaaact agaagatagg    3960
ctaacaagct gatggggttc agggttgaga ttttggcaa aaaacactca tgtgatgcta     4020
ggtacctcat gtgactgtca caaggcacaa ccaggaatct ctagttccca atgccgaatt    4080
tgaccttaga ctaaggtggc tgccaccaga gccacatcct cccctttgta gctttttttca   4140 tttttcttta cattatttat tgtgtttgag tttgtacatg tgtgtggtca cacatgccac    4200
agcacacatg tgggagtcag agggcaactt atgggagttg ttctctcct cccatcccat     4260 gggtcctggg gcttgaactc agcaagtacc ttataagcta tctcaatact gtttgcctcc    4320
aaaatgtatt actttgtgta gctgtcccc ttctgttgct aataacagaa tactacagac     4380
agtgtaagtt acaaagaaaa taggctcaat tgtatccatc ttttgctgcc catggcatga    4440
aaacacttgc atcccaacac aggccagagg tcgcttagt gtgaagcagg attgagtgca     4500
tgtctgcatg gctaagactc tctacttctc tggtttcctg atccctaggg ctctgggact    4560
ctagatcctc tggaccccctt gataatagag ggagcttcct gttttctcaga agtgcctttt   4620 gaccatatat cccagaaact gattccatcc atctctgccg tgtgtcacta gtcactagat    4680
ggcgtcactg tcatctctca ctagtgtctg agatggcctt gtcttctctc ctgcccacag    4740
cctgctgtgg aggtgcccca gtacgtgggg atccggctca tggtggaggg ctctaccatc    4800
aagaagccca tagcagcttg tcatcggcgg acagcggtcc gctcatcact ccctcatctg    4860
ctggcccagc aaggctgtgg ggaaggcaag gactcaggac cccctatcca caggtcagct    4920
tctaggaaag atgctggggc caggagcctg ggacacactg agaagccaga ctctgcggcc    4980
accacctcag tccccggaaa ggggaagaaa ggcaaggcaa aaagtgccac agccctggtc    5040
tgcatcaccc tgcagaaatg ggagtcccac aacaccaggg tgggccccac cttcaacagg    5100
ttaatgtgtc tgaaacagcc tgaggcctgg ggtagtacca tgtcccccaa accccgcagt    5160
gttcccaagg ccatttctgc ctgctctcca agccctcccc aagcatctgg gcttgccctc    5220
```

```
ctgccaaaag gccaccagtg atagcaagta tgaaccaaat atctttaaat acataaccaa    5280
atgagtatta caaagtagtc accctgccag gcagttagac caaaggctcg gtcctagagt    5340
gcgcgcccag agtccagacc catgctgctg ctctagccag cctttgccct cacctttctc    5400
tggagaaagg tgctgccacc atgcccttcc ccattcctaa ccagcccccct cagccctcat    5460 aacgccctag tgaggtaggt gctattgtcc ccattttcca gccgaggtag cagcaagttt    5520
aaggacgttg cccgaggttg cacagctcag aaggggcaga gctgggatgc agacccaggt    5580
ctgttggtct cccaaccctg tgttcttccc actgcctctg gaggaggagc tgggaggggc    5640
tccatctgcc cttaccttgt atcccccacc tttacacatg tactgtgaa caattggtca    5700 ggctggggcc tcacccagat cctcacagct tcccttctcc cacagccccg tcctacctcc    5760
ctagtctcca ttccaaggcc tggctgcctt cttcccatgt gctccgaccc cagggccggg    5820
tcctcagact accgaatggc caactggtgg gctctaaggc tctgtcaacc acaggcaagg    5880
ccttgatgac tctacctact gccaaggttc tgatgtcctt cccacctcac cctgatctca    5940
agctggcacc cagcatgctg aagccaggaa aggtgggcct cgagctgtgc ctcacaccct    6000
ggcgggtagt gctgagcagt gggatcgggg ctgaagggca cgaacagagg gcagcgctcg    6060
gaccatacag cgccccaggg aagggcttgt cttctccaga accctgttcc aagacagagg    6120
cctgatcata tctctttccc tcccctcctt gcaccgaggc tgctattccc ctgcaccttc    6180
gaggccccca ctttggaagt gcctcgaggc ctctgccctt tgaagttgga cctcttccta    6240
gcacccacag gaaagtcacg gccaaaggca agttcaaggc catactctgc gacaaagcca    6300
gggctgaggc atacccccaag aagaggctga gcctccccaa accttgacc cttattctga    6360 catgccggac actgagaacc atgggggata ggaggctaga gaaacccctg ctctgatctc    6420
tactgcccca tcctggatcc agcatcaaat taaaaaaagc aattaaagtt ctctggactt    6480
ggcttgaata atgtgcggct aggctcataa aagagttgac cagcagggcc tccatcagca    6540
agggccacag tcccccaccca gcgacagaca ttggctttct ctgcagggag acggatgggt    6600
ggggaaagag ccttcactat acagatgatg acactgagac atggcttgcc tgagaccaca    6660
gcaggcggaa agtcagccat caggagtgcc ccttcccaaa gacaagctgg gctggcagaa    6720
gagcttctga tggtcacaga acattatgac aagagacggg ctttccctaa acctcagcct    6780
ttctccggag agtatgtccc tcagtgaggg gtcggtcaag acacctcaaa ctgcaaaacc    6840
caagaaacag gtcaagtgtg gcatttccta cctgtagagc ctcagctgct ggtcctccaa    6900
aagcggtatc tagctgtagc gtgtgaatgc ttcctgagtg gggcagggtg gagaggagag    6960
tgcggtgttg aaatccaatg acctgtgtct cccaaagtca gaagagctca tgcctgcaca    7020
gtggtgtgtg tctgtcctcc caggacttgg gaggcagagg caggtgcatc tctgaattcc    7080
agtccagcca gggatatacc aagaggccca gcctcaaaag caaacaaacc tcctcgtgac    7140
caggagtaca gcagatgcca cctccagacc tggccactgt tcacttgagc agagagcaca    7200
gtccctggtc aacacttgct ttctcagcag atcctcaaaa gcagacttgt gaggtaggac    7260
ttttattatt ttaagtccag agagcggtca cctgcccaac gccacacagt aagtgagtgg    7320
tttaactggg atttatctta ggttggtagg actaaggagt caaagacctt gaccgtactc    7380
agcaccaagc ccactgtcct tgagctgggt cacggcccctt ctttctattt tccaattggg    7440
ggttaagcac tgtctatcgg tgagagagcc gcaggcactg cagggtccga gagaagtacg    7500
agggtagggg tgccacaagt tcactagggg ggtccctgga tctggtgcct gggaggagga    7560
ggcggtgcaa gtgcaggtgc aagggcatct gggccacctg ggaaggacgc aggcgaaggc    7620
```

```
gtctgaggag agcttcgtcc agcacctgga gtgggaaaga cagcagccca cctgagttcc   7680
agccagagga gccccctggct ctgatggacc tctctggtct gcaactgcca tcatttctc    7740 aacaggcagg cagggatttc tctccacaca gagctaagtt acgtttcagc tccttttgtg   7800
tttagtgaag ccatgtgatt aagccactca ccaatgggat gtgaggaaaa cacagaccta   7860
gccctcaaag ccccgattca caaaaacatc cagtctcccc ttatggccag gaagcaatag   7920
cccttttctc caagtggcta cccagagtca ggtccactcc tactgtatgc ccatttgcca   7980
gacttaatcc aagaagaaac aatggacttc agggcctgtc agaggtcagc tccccactcc   8040
ttgagctaac agacagaagg aagcctgagg aagtcacagc accacagagg caagggtggc   8100
cccagaggcc aagcctgttc ccccaattcc ctaaatacag agcaggcatg tgggcctgaa   8160
gacctacctg tctctggagc ttggtggtct tggctggcca cagaaagcgc tggcccagaa   8220
cggtgcccac tcgaggagca taggtgtggt ccccaagcac tgggcagagc tgtagagcca   8280
tgtgcacctg aagctgactg ggaacactg aaagatgggg ggaggcagtt gctcttcttg    8340
atcatcaagg actgtcccca ttcccagagc ctgtgcatct atgaggtgac ctctgcctcc   8400
acagagggcc atgagcagat caggacaatg acagctggca accttcccag cctgggggca   8460
ttgaacccaa cagaactgaa gctcctggga ataagtatgt gggttgggtg ctaaactgtg   8520
ggtgtgcacc taaaactctg cctcctgctg agccactct cagagtcccc agatgctctt    8580
ttttttttgt tttgttttt gttttttcag gcggggtttc tctgtggctt tggaggctgt    8640
cctggaacta gctcttgtag accaggctgg tctcgaactc agagagaggt gcctgcctct   8700
gcctccccag tgctgggatt aaaggcatgc ccaccaccg cccggccacc agatgctctt    8760
tggatgttgc aaaacaacat cttcctcata ggcttcattt cccctgcaga gtactgttca   8820
gccctacctg tcagtggctg cagctggacc agagcacagc cacagcctgt ggccatcaca   8880
tggaaatggc tgagggtcct cttgacacct tctaggatgt cctttcgaga tggggatgtc   8940
acggggatgg cctaggatac cagtcaagaa tgacttagca cacgtagg agcccaattg     9000 agccacccct gctgccggct gacttaggac agggcctcag aacaggcagc agcaacttgc   9060
ctgttagagg acagggaat agccaccca tgcacatagt gcagactcct ctgtaaggca     9120
aaacctgaaa ggactcctag tggcttctga ctcacaagat caatgccatc catgcgttcc   9180
agcttcaggg ccacgtggat agtcccctca gaaggctcag ggatgccatc agtgatgcca   9240
ctgagaaaga gaaggaagt ctcagagcag ccagctggga ccttccttgg ccctgggagt    9300 cacccccgcat ctctcaccag taggtggctg tgggcctctg tgttctcctt gagtgaacga  9360
agaacttctg caagcggctt gctgtctggg ggcagctgga gagaagcaca agcccagacg   9420
cctccctgaa agaagaggac aagtcacata agcctcttg gttggaaaaa atgagggcca    9480
gattggctgc tcctgcagag gactagcact cggcacccac atagtgggtc ccaactgtaa   9540
ttccacttcc aagagagctg atgccctctt ctggcctctg ggcaccggg catgcactgt    9600 ggtacacaga cacacatgca ggctggcctc cgggggcaca aggcatgtgt ggtgcacgga   9660
catacatgca ggctaaacac acatttaaaa acaaatcttt ggtctttttt aaaggagacc   9720
ctcccaccaa ggggctggag aaatgaatca gtggttaaga gcactagctg ctcttccaga   9780
gtacctgggt tcagcaccca catggcagct cacaactgta gctccagttc caggggatct   9840
gagaccctca cacagacaca catgcaggta aaacaccaat gcactatata tatatatata   9900
tatagataga tagatagata gatagataga gagagagaga gagagaccac cttcccacct   9960
```

```
ccccaaatga acaccaggac tacagtccag acctaagaaa caaatcctgg ccaggcagtg      10020
gtggtgcacg cctttaatcc cagcacttgg gaggcagagg caggcgcatc tctgtgagtt      10080
cgagaccaac ttggtctaca agagctagtt ccagggcagc tccaaagct acagagaaac       10140 cctgtctcaa aaaaaaaaaa aaaaaaaaaa aaaaaaaaaa aaaaaaaaaa aaaaggggg       10200 ggaaataaac aaatcccaag acctttttc tggcccccag agaactcaga caaatgccct       10260
aagagttact acacatgcca ggcacctgaa taggactctt atatacagtg ggtgtaaaat      10320
aaaggcccac cacactcctc acttactttc caggtgctcg cacaacctgg agctcccggt      10380
gtttgagccc cagggcctgg ctcagctgtg gcagcacaga aagcaaggtc agctccccag      10440
gtctccctga gaagtaagag ggagaaaaca agttgccaga gcaccatcca acgaactcct      10500
ccccaccagc cttccctcc ttgtccctgc ccatacctgt cacaggcaga ccctgtggct       10560
tgttcagtgt caccagaggt cctgaaatat tcggtagatg tcagcaaaag cagggcagcc      10620
tgtgtgcatg cagcctctgg ttataagctc ccaagcccac tccaaactga acttcctgct      10680
ccccgcaccc agggcctttg cacctgctgc cctgagcttt cattaatatt gggtccctta      10740
tcacacacct ccctataatg tgtgcccctc ctacagtcct tgactgtttg gtctgagacc      10800
agctcaaaca ggccggcctc aaactcaact ataggtaagt ctggtcttga actcttgatc      10860
ctccttgcct ctgtctccca agttctggga ttacaggtgt ggtcaccact cccagaaaca     10920
gcagagattc actattcctc acatcagaac gcttgctctc tcaaggcagg agccagccat      10980
atttatccca gtactgtgta gcctcctcat tgctacaatg cactgaagtt cagcaaagtt      11040
gtcattccta aaggcacaca gcatgctgct tacagacccc aggaaactaa cttctgctcc      11100
cgagggtctt agaatgcgag gcggtgtgaa ggtttcctat gcctggcgga gggaatgtga      11160
cggctacagg ggtccgactc caggggtcg gaggctccct caccttgctg atccaccaca      11220
gctgccctca gcacctcagc cagctcctcc gggccgaggt tctctgttcg cagaagcccg      11280
gggaagggct ggtcctccac tgcgtccttg cacttgctgg aaccttgagg ttgaggccga     11340
cccctgagaa aaacgacaga agccggtacc tccaacgccc acgctgccca gtgcagcctt      11400
ttcgtacaca accctcagaa cccccggctc ggctgacagt tgtggtccac aggcccccaa      11460
gactacagaa ggggcatcag acgctcggag cgccaaccat ctcgtgtcgg gtcacacaac      11520
gcggctggga ttagaaccca tgtcctgatc tgagtgcccg acctgccctc cccttgtcct      11580
agcctccctc ctacacggaa gtgttgagtt ataatcaccg ggcctcggtg ccgaagcctg      11640
catctctcgg ccgtgcgcca gccgccagcc ggggccgcca ggtgccagac acacaacgcc      11700
aaacgcggaa gacgcccatc gccgcagcaa gcacagacgc atgcgtgtcc acggactgcc      11760
ccaccgcgtg catcctccgt gcgccgattg gtcagcctgg ctgtcaatca gagcatcgag      11820
caggcggagc ttcgaggacg gaagagccaa actttccttt ggctgaggaa ggtaaagtac     11880
ggtctccggc tctgctttgg gggaaactga ggcaggaggc gcggttattt actcgcggta      11940
gaggacgtgt cttagaatag aaagaggcga gtttgcagat agattgtttc agttctcagg      12000
acccttaatc tgaaacccat ccttgtaaag cagagggaga aggtgaagcc ccacagcctt      12060
cgggccaggg cacctgcatg gaaatggtct gcgacattaa ccatcccatg actgtggctc      12120
aggtggtaga gagattttc taggatgcac gagttcctgg gttcgatccc cagcaccaca      12180
cgaagaccaa gatcacagat acagactgag ttggagacca gcctgggata tgtaaggccc      12240
ttctatcaca agaaaacaa actaggccgg gtgtggtggt gctcttcttc aacagaggcc       12300
aacctggtct agacagtgag tttcaggaca gccggagcta cacagagaaa ccctgtcccc      12360
```

```
cccccccaaa aaaaaaagaa agaaaaaaca agcttggtgc ggtccacata gtaagttcca   12420
cactggccag tatgttgtta attccaaaga tggaatgagt gtaaggaaaa aggccagcca   12480
aagaaacaca ctttggctct gcaaccagaa ccaaagaaat gcacccttgt cagaagccag   12540
ccttggtgac gccccccccc ccaatgccta gctagccgcc agctagccta gcatcccacc   12600
cctcaggttc caggacctgg cctgagaagc aactaacacc ttcccccatt tccttagtta   12660
gtgcttgaga taaacatagg agattccaga tacctggcct gagaagcaac taacacctat   12720
tctttctcca cacaggagat tccggatacc tgcctgagag caattaacat tcattcctcc   12780
cccacctcct ttttctctgc ttcctccttt ctctataaaa accccttgta ataatcaata   12840
aatgggcctt gacaagaaaa cctgcttggt cccgctcttt cttttcccgcc catcattttc   12900
aggcgtgatc cacctcggac tcaggaatta ccggagcccc gagggccggg gtacaccctg   12960
accctgaaac cagtgccaga gaaacacact ttggccctgg aatcagagcc agtgaaagaa   13020
atacaccctg gctctaaaat cacagtcaaa aggctaaaaa ggaccagtga aaggaacaca   13080
ctttggccct gaaaccagag ccaaatctaa ccctaaacct gtgcagaaaa ccaaccaatc   13140
cctgagcagg agatctagcc attctgagct cagggattga aatctgacca atccccaccc   13200
tggaaatctc cctgggaaaa ctctgccccc ccctaagaat ccctatataa accctgtgcc   13260
tgttcagctt caggctgcct ggctgccctc tgccactgga ttcttgaatg aggtttgggt   13320
aagaactttc gccggagcag agaccaccct acacactggc tctccagggg actggagttg   13380
aactgttaca atttaaccag ggaaaccctc tcctcccaa gcagagctga tacactgagg    13440
aaggcctttc cctgaagcag ggctgtaagc cgctatgctt actgtgacct gtggcattcc   13500
ttggctccta aacgccagaa tacctttcca tcccagctgt aacactcagt attctgtgac   13560
tccggagtgc cagaatactt tgcatctgag ccataacaca gtattctttg gctcccgagt   13620
accagaatcc attccttccc atccaatccg ttgaaatgct acaatgagaa aaaaccacga   13680
acccaaatca ttgagaccaa attaattaaa gttttttttt cattcatgta cgagactgcc   13740
tcccccaagg cctgatttga gaggtcagca ttggatgtga ggaagacaag ggggttttgt   13800
tgttttggtt ttttgagaca gggtttctct gtgtagcttt ggagcctgtc ctggaacttg   13860
ccctgtagat taggttggcc tagaactctc agagatctgc ctgcctctgc cacttgagtg   13920
ctaggattaa aggcatgtgc caccaccgcc tggcctcacc tggatcacac agacacatat   13980
atacataatt aataaaatac agacctggcc tttaatccca gcactaatct acatagtgag   14040
ttgcaggaca accagagtta catgaccctg tctcaaaaaa aaaaaaaaa aaaaaaaaa     14100
acaacctaaa taaataaaat gcagaaagta acaatatgta cataataaaa ataatgaaat   14160
aataacataa ttgaggaaca gtggggcatg gtggcatgtg cctttaatcc catcacttac   14220
tgatctacat cccaagcctg aaggaccttg ctgaaagggc tccagcacta gactgttgct   14280
tctggcagag aaagtggctc tcaacctgct ggtcaacgac cccttgggg gtagaagggc    14340
cctttcacag gggtagccta agaccatcag aaaatacaga tattcacatt acaattcata   14400
acagtagcaa aattacagtt ataaggtagc aacaaaaata attctatggt taggagtggg   14460
tctccataac atgaggaact gtattaaagg ttgcagcatt aggaaggttg agaaccacca   14520
atttaggggc agatgctgcc tccttcacag cactcagcca cagttgtgtt gtgtccttgt   14580
tgaggttcta tccggtcctc caaagttcag ctgtgggaaa ctaaatcttt aacttcataa   14640
taatggtaat tggaggctgg agtaattagt accagataaa atcatgaaga gtgtgcttcc   14700
```

```
atgatggcca ttaacagctt tctaaggaga gcagagaaaa aaaccttttc ctcgttgtgg    14760
aatgacttcc tccgtgttgg tgtgcaccag aaaggccccc tgcttgtgct aagtggagct    14820
atgccatgct cttggactct gcagcctcta gaaccatgat ccagatcaac tgtgtgtctg    14880
tgtgatttgt tttatttta ttatgtgtgc atgcctgtgt gtctgcgtaa gtgtatacca    14940
tatgtgttgc aggtgcacgg agaggccata aaagggcat cagatcctcc gaagctagag    15000
ttttaggcag tcgagagcct ccacgtgggt gctgggaact gaactcagag cctctgcaag    15060
ctcagccagt gctcagccag tgctcctcag tttgtgtgct tgttttcagt actgcagatg    15120
gatccaggac cccacacgtg ccaggcaagc attctctcac tgagctgcac cctcagactg    15180
gtctcaggtg gtttgttata gcaacagaaa acagacatgt ggaaggagtg atggcgtatc    15240
ttgactgaga ggaggaataa cttggctact cgcacagcac atgtctgggc aggttcacaa    15300
ggaggcttcc agggacaatt ggcacctaag aaccctgacc taatgaatgg atgaaccatt    15360
cagaatttgg atgggttctt gggggggggt gagggaactg tggtgggtgg ggactgcttg    15420
gaggaagtag ggtgtttgtt gtgggtggct ctcggaggct atgtcttaca ttggctcctt    15480
tctgttttgg ttcttcaat ttcctgttgt gtgctattct gctacaaccg cctcacccag    15540
tagattgcag cctctgttaa tcaagacagg gtcttactgt gtagccctgg ctggcctgga    15600
actcatagag atctgtttct tctgcctctt gagtgctgga attaaagacg tgtgccacca    15660
ccaccacctg acctagagga caactttatt ttttttaatt ttttatttat tatgtacaca    15720
ttgttcctgc ctgcgcacca gaagagggca ccagatctca ttatacatgg ctgtgagcca    15780
ccatgtgggt gctggtactt gaactcagga cctctggaag agcagccggt gctcttaacc    15840
tctgagccat ctctccagcc ccctggatga ttaattgtag aagtttcagt tcttctttt     15900 tgttttgtt ttttgagaca gagtcacact acgtatcttc aactgatctg gaacatgcta    15960
cgtagacaag gctggcttca aatgtgtgtc aatgttcctg cctctgcttc cagagtgctg    16020
ggattatagg catgtcccta aatctgttat tttttaaac acttattttt gaggggagt      16080 cggtggtggt gctgttgtac gtacatatgt agagatcaaa gggcatcttg tgggagtctg    16140
ttctctcctt ccaccaatgg gttctaggga ctgaattcag gttctggagc ttgacagcaa    16200
gcaccttaat ctgctacaac atcttgttgg tactaaatcc atggagaatt gaaaggattg    16260
tttattgttg ggcccgggaa tatagctctg tggtagtaga atgcttgcct aatatgtgtg    16320
agattcttaa aaaatcattg attgttttct taaaccaact ttaatttg ttaaaaccaa      16380 cttttaaagg atatatctag gcatggtggc acacagcatt aaccctagca cttgagagat    16440
agaggcaggc agatctccta tgaatttgag gccatcctat tctacgagtt ccagtacagc    16500
caggactaca ggactgtgtg atatgcacaa cacaggaagg actgatgaca aatttggtaa    16560 aaaaagaaa gaaaaacagc aagtggtttc acattgtccg gcttcacctg gagtgggtga    16620
ctgtgggtac tcctgaagcc tcccaggagt gggtgactat tctgtcagac tgtgggtatt    16680
cccgaagcct cctaggaggc ctcctgtgca tcacagaagt ggcttgagca agaacttggg    16740
acagactggg caagtgcaca gctataatcc cagcactgca gaggtgaggg ctgatgggtc    16800
aggagctcac agttatcctt gactacagga agtctgaggc cagtctgagc tatgtgagac    16860
tctaaaacat acatgagtca gtgagttggc tcagccagta agggtgcttg ataccaagtc    16920
tgaccacctg agtctgatcc ccagaatcca catggtagga gcagagaacc aactcccagg    16980
agctgtcctt tgacctctgg acttatgcta ttgcatatgc ataccaatac ataactccct    17040
aaaatacaaa atacatatgt ttgggctttt tgtttgtttt gttttgtttt ttcgagacag    17100
```

```
gtttctctgt gtagctttgg agcctatcct ggcactcgct ctggacacca ggctggcctc   17160
caactcacag agatctgcct gcctctgcct cccgagtgct gggattaaag gcgtgtgcca   17220
ccaacgcccg actgatgttt gggctttttt gatggttttt atgtgtgtgt gtgtgtgtgt   17280
gtgtgtgtgt gtgtgtaatt agaaggagaa agagagagag ggagagagag acagagagac   17340
agagacagag acagagacag acagagagac agagagagga gagagagcca aagtctggtt   17400
tgtggcccat tcaactaagc agacttctcc tccaccaatg gtgtccacca atggcccagg   17460
aaaggccatt tccccacttg aaccagcgcc tggccctctg gagggttagt tcctttactc   17520
tttggaggtc tccctccctg ccccatagca ggctgccctc tcttgctccc ttcccacagg   17580
cagctacctt catcccagtg ggctatgagc tcctggaaga aaggaggag ccaaattttg   17640 cctaggctga gggctcagtg ccaggtggca gccacagtca actgctgaac ttgtgaaact   17700 ggacccagg agaagaagcc tgggacaaac atcagcttgc atcagctccc tctggctcag   17760
ttacagcttt gcagcaggtg tggacaggct ggtgcttcag caatgggaaa caggactgat   17820
gcaaaccagg cctccaggag gccaagccct ggagccagcc tgcagtgaac cagcctccag   17880
ccacatctac aactgtgtga gggcctagaa tagaaagtgt acttgacctg tctgtccttg   17940
agtgctcttc tcttctcaca cttggctcca ggcatggggc agcttccagc gatggctttc   18000
cagacaagct tgagtaactt ggccctttgt cttagtgttt tctaaatcca ataggctttt   18060
acagggagga ttgtgaaatt atgttagctt tggatctgag agccagactg aaacctggct   18120
tcctacaggc ctagtctttc ctgcttaggt cagttacctg tcactaataa atggggctc   18180 cttttcctac cagccaccaa gatggctgaa gtggaggaga agaaatgaac cttccacaaa   18240
ttcacatact acaatgtgga cctggatcag ctgttgacag gttctaggaa ctgctgatgc   18300
agttgtacag caccccagag gtggtgtctg aaccacggcc tgtggcagaa gcagtactcg   18360
ctactcaaac acctgagaaa gctcaagaag gaggcaccaa ccatggagta acccgaggtg   18420
ctgaagaccc acctgaggga cacgatcatc ctgcctgaga tggtgtgtgt gtacaatggc   18480
aaaaccttca gccaggtgga aatcaaacca gagctgatca actgctacct aggcgagctc   18540
ttcatcacct ccaagcccat gaagcatggc cagcctggta ttggtgccac ccactcctcc   18600
agctgcatcc ccctcaagta gctgtggcca acaaagactc atgtttaaaa agaaaattgg   18660
aagccaggca ttggtggcac acgcctttaa tcccagcact cggagacag aggcaggtgg   18720 atctctgtga gttggaggcc agcctggtct ccagagcgag tgccaggata ggctccaaag   18780
ctacacagag aaaccctgtc tcgaaaaacc aaaataaat aaataaataa ataaataaaa   18840
taaagaaaag aaaagaaaag aaaaatgggg gctcactctg agaagacctg actcctcctc   18900
ctcctcagaa ctctctggtt tgttttgca gtgctgggt cactgtgcca ggctagagac   18960
tcactgcaat ctgagggtgg aagtgctgag caggaacagg gaactgtgta aagctggca   19020 taggcattga taaattcccc tgtagatgga ccaggacctt tcaacccgaa cacatggaaa   19080
gttattgtaa aatacaacag ttgggaatca aaagagtggt ttgatccacc ttacaggcaa   19140
atttcattcg gaaactgaca acacatatgg atcatgtggt ctgcctgaat atcaaatatg   19200
gcaggcctca aaaatcaact gcagatttta atataacatt taattattca tctattaatt   19260
aatttattct gtctcataat atcaaacctt atctattaaa agggagcagg gctggggatg   19320
tggctcagtt ggtagagaat ttgcctagca tgctggaaac cctgggttcc gggttcaatc   19380
cccagagcca cataaattgg atgtggtgtt tcacatctgt aatgctagca cttaggaagt   19440
```

```
ggaaacaaat ggatcataag ttcaaggtca tcctccacta cataataaat ttggagccag    19500
cctaggcttc tgtatctaga agaaaaaaca gggcaccact gatgcaactc attgcataaa    19560
agcaattgct gtgtgagcct gacaatccaa gctcaatcct tagaaccaag agtggaatga    19620
aagttgtctt ctgggccatg cacgcctttg atcccagcac tcgggaggca gaggcaagtg    19680
gatctctgtg agttcgaggc cagcctggtc tacagagtga gttccaggat aggctccaaa    19740
gctacacaga gaaaccctgt ctcaaaaaaa aaaaaaaaa aaaccaacaa aaaaagaag     19800 gttgtcctct gacctccaca cctgcaccat agtactggca taccaacaca cacacacaca    19860
cacacacaca cacacacacc agtaatgaca aatgctatct cctgtaattc tcggcaaata    19920
gtttcaaaca aagaacacag gcaaagatga ggtattggca taaataattt acttcaggct    19980
ctaataccat acattagtgg ggaatgagaa caaaaggagg aattgtctga cttcccctgg    20040
ggatcacaaa ctctatccat tcggcccagc aagggcgcca atgaaaggtg aagaagccac    20100
gattccatcc aagtccagct tggtgaaccg gtgagtttac taggttactt acaggtgggg    20160
cctgggtgac tcaaaatcac aggtgactcc ctccaaatct gcatcagtga catcctggct    20220
ttagttaacc ttttacctct tatatactct agcaccgccc caagatcatg agcagctggg    20280
gcggggcagg agggaggaat ggctgggatt tcaggtgcta agacccctg acactctcct    20340 cccttctaa tacaggtgtt aactatttcc atacccctagc cataggcctc accgtcactg    20400
tggcatttgg ttcattttgt tgtcttgatt caggtcaaag tattctggag ccaccatag    20460 caatgtctgt tgcttgatga gcatggtcaa ggcaggaggg gactgcagag agggagtggc    20520
acatagggat ggcatgtgaa gaccgagtgg cagacttggt gccaaagcct gccagggaca    20580
agtgtttgtc ccctaaaacta cctgtgacat gaaggaagga actgagccag gctaggaagt    20640
tctcccgtga ccagcccacc ccagagctcc agcccttcct gcagtttcct tggtgctgtg    20700
ctgtgagagg ggtgcaggtt ggtgagaagc tctccagctg ccaggcttgt gggtgcttct    20760
agcagagtgc aaggtctcca gtcacatcct tggctgggga cggcatctga ggacttgggc    20820
cttcattgca gcatcttcag acaggcgggg aggagggagg aggtcttggc cttggacggc    20880
tgttcttcct cagtggcatc caggaactgc tgcatataac tggaggagcc aagcagcatg    20940
tggcctgtgg cctgcatgct gaagagggcc cagcggagca tttccctggg agacagcaag    21000
gcactcaggt taaacactcc ccatgctatc tccccaaatg tcttctccat ttttctatgc    21060
tggcctaaag cagttggctt caagttagac ttctttcttt gtttctactt cttttatttt    21120
tgagatagaa tcttaacact ttatctcagg ttagctagaa attcatttat gtagctcagt    21180
ctggctttga actcacagaa atctcctgcc tcaatctcct gatgctgttg cagttatggg    21240
ccaccacacc taactttttt tggtttggtt tggttttgat ttggctcttt ttgaaacaga    21300
atctggagat cctcctgtct tgtcctccca agtgctaggt atacagacat gtcccaccat    21360
actgggctca agctagcttt tctccttagg aagatttaag tgtcactaaa gtaaaatgac    21420
aaaaatgctt ccaagtacag acaggaactg ggaaccaggc tcatagctag ccatcccta    21480 cacatagttc tgcctctact cttgtgacaa ctttttctgga accccttgct ttttcccatg    21540
cttaacttga gttctcaaaa caaagctttt tatttttcttg taatgatatt ttgttcttt     21600 cttttctctt ctatggtgct ggggatggaa cccagggctt tatttgtgca taagcagctg    21660
acctgccatg gagctatgtc cccagcccca tatatttttt ttttcaagac agggtttctc    21720
tgtgtagctt tggagcctat cctggcactc actctggaga ctaggctggc ctcaaactca    21780
cagagatccg cctgcctctg cctcccgagt gctgggatta aaggcgtgtg ccaccaacgc    21840
```

```
tcggcatcca gccccatatt ttttaaacta ctctggacca gccagattaa tttacataac   21900
acatgtctac cctttgtaac actgcttctt agactttata gtcttcccag gccagttctc   21960
agaatgctgg ccacaaggct cccatgcctg atatcatatt ctaagcatag aacttggacc   22020
agacagggct gaacactgat ccagagtggt ttgtttatat ctaaaatatt taaaatatat   22080
tttaaaatat tataaagatg ggtgatgtaa ctaatttagt gcttgccttt catgaacaaa   22140
gccctgggtt tgatccccag caccgcaata acccagagtg gtaatatagg actgtaaacc   22200
taggatccag cactgtggag gtagaagcag gtggatccca agttcaaagt catccttggc   22260
tacatagcaa gtgtgagacc agcctgagat acatgagacc ctgccaaaaa aaaaaaaaaa   22320
aagctttaac tgttctggtt ctgagctcca gcagccagaa gctttgtgac ttgtaaaatg   22380
ggtaatgagt ttgaaactaa tgtgaagcac ttagcatttg gtctgatgga cagaaaatgg   22440
gacatgcagc caagagcagc tggctgaatg caacttctcc cacagctatt gacaagggct   22500
cggcaggggt cactaggagt tgctggtctt aagaacaata aggaagagaa acacaagaa    22560 agagaaatac tgccaggccg cggtggcaca tgcctttaat cccagcactc aggaagtaga   22620
gacaggcaaa tctctgtgag ttcgaggcca gcctagtctt cagagcaagt tccaggacag   22680
ctacggttac atagtgatac cctgtctcaa aaaagcatat atatatatat atatatatat   22740
atatatatat atatattgaa tttagtggcc tgaggcaatg gctcagtggg taaagtgctt   22800
gccatatggc catgaggccc tgaaagccca tgtaaaactg gggatggctg cctgtatctg   22860 tgacccagt actcctctca tggtgagaca gagagacaag agactcctct gaagctttca    22920
ggccagcaag cctggcccag acaacagaca aacagcaaag accctgcttg aaacacagtg   22980
gaagatgaga ccagcacctt aggctgtcct ctgacttcga aatgcacgct gtggtacatg   23040
ggtgcccaca ttcacacaca tatagagata aagactggct gggcagtggt gacacacgcc   23100
tttaatgcca gcacccttga ggcagaggca gttagatctc tgagtccaag gccagcctgg   23160
tctacagagt gagtttcaag acagccaggg caacacagag aaataagaaa agagaaaaaa   23220
aaaagatata aagactgaaa ctgaaaatat aatatattag ggctagaagt atagcttaat   23280
ggcatggtgc ttgtctagca tgtatgaagg tcctggttta atccccagct ttgaagcatg   23340
tgtgtgtgtt tgtttctttt tgtggtactg gggaactgga cacaaggcct taggcaagtg   23400
ctctgccatt gaactacagc ctcagctttc ttttctttt taaaaatgtt tatttatttt    23460
atgtatatga gtactctatc tgcatgtatg actttatgct agaagagggc gtgagatccc   23520
actatagatg gttgtgagct accatgtggg tgctgggaat tgaactcagg acctcaggaa   23580
cagcagccag tgctcttaac cgttgagcca tctctccagc cccctcagct ttcttttttac   23640 cccccacac acaatatctc tctaagttgc ccagtttagc cttgaactta ctctgtagcc   23700
taggcaagct tctaatttgc catcctcctg tctcaatttc ctaggcacct gggagtacaa   23760
ggccatgtat agctttatat atatgtttcg tgcagtgcct tcaaagttat ttctcaaatt   23820
agagaactga gttttgactc tagccagcca gtcttaaaaa ggaatgaaaa taaggcctat   23880
tctacaaatg aatgaaccctt gaaaacagaa ttcttgtggg gaaagaatca tgatcccatt   23940
tctatgaggt ctctaggata gatcaatgga gcaacagaaa gtagagtaaa ggtgagcagg   24000
gtctcgggag agggctgaga accattattt actgagtaca gcttctgctg cctggtgcaa   24060
aggttctgga aaccaaggca atgccttgcac aacatgatta gttacttcat gctagacact   24120
tcaagcggcc acagttgaaa aatgttgaat gtgcagattt tagcacgggt gtttttctt    24180
```

```
gaaggtctca ttgtgtagct ctagctagaa tttggaactt gaaatgtaga ccaggctagc    24240
ctaaaattct caggagatct acctgcctct gcctcctgaa tgctggctgg gattaaggga    24300
gtgagctacc acacctgacc ccttagtaca ttttttttt  taaatcacag taacaccact    24360
aagtcactca gctaaccaca gtttgacatc agttttatt  ttctctaagt ttttatttt     24420 gttgttgttt tattttgttt ttcaagacag ggtttctctg tgtaacagcc ctagctaccc    24480
tggaacttgg tctgtaaacc agactggcct tgaactcaca gagactcacc tgcctcagcc    24540
tcccgagtgc tgggaccaaa gatatgactc ctggcctttt tattttcttt ccatgtgtgg    24600
gaggtagggg ttatgcacct gagtgcagtg cccacagtgg tcagaagagg gcaacatatc    24660
tcctagagtt gcagttacat gtggttgtga gctggctgag gttggtgccg ggaactggac    24720
ctaggtcctc gggctgagtg gttcccttt  tctgttttg  ttttcaatac agggtctgat    24780
ctggcccagg ctgtccttga actcctgatt ctacacctcc aaagtactgg aattatagtt    24840
acattttcac ttacaaaaat attagctgtg gaaatagctc aggatatgag tatgtgctta    24900
gcatgcgtgc tgccctgggt cctatcccca gcacacaaaa gaaagcacat gactgtcatt    24960
ctttgttagc ccccagtgcc aacccaggct ttgagagagt tcagctttgg gtagacacaa    25020
aggacctctg gttagctagt ctcccaccct gctgtcccaa tctactcact tcacgacgcg    25080
cttggcccgg tagcagtgca ggtcatagga aagtgtgtat gtgtcataga gggtcgcctt    25140
cacgttcagg cagccgatga agtcctgggg gttcagcttg tataggtcaa aggttacccg    25200
ggccacatca atcttctttg ttggcttctg ggaaagggat agctgtggtc tcgtcttgcg    25260
ctgcaagaca agtccatgtt agctcgcctc tgggactcct tccacgccct cgacactcac    25320
ccctgctgga ggagactgtc acctgttctg atgggggctt ccacttctgc cccttctgca    25380
ggaccatgaa cacagtatct cttgccaggg cttggaagta ttcttctgtc tcaacaatcg    25440
tgccgtcttc ctccagcacg agggagaagg gcttgtcttt aagtttcaag atatcctggg    25500
cctggaaaag aaggttggtg acatttctgc catccctatg gagccacaga gttgaggagc    25560
aaaggcccgc agtaaagcac ttcagctgcc agagagagag caagtgagct gccatccatc    25620
cgtgcgatgg actgactgtc actgtggggg cccactcaag ggctgtgtct cagtacttcc    25680
tactcccaag aaggagtgta gtctaataga atgggagtca tatgtgaggt cttttttatt    25740
gagaaataaa ttcatacca  tgctgggcaa tattaggagt catatcgaag gcttgggca    25800 agctaggcaa actgcagcat tgaactatat ccccagcctt ctttgtactt tttgtttgga    25860
gacaggatct tactaagttg tttaggttgg cctggaactc actgtgtagt ataggtaggc    25920
ctcagccttc tatttagatc ttcttgactc agcctcctaa gtaacttgga ttacaggcct    25980
acactaccag gcccagctaa actttatttt gttggtggtg gttttttgtt tcttttgcta    26040
tgtagccgtg gctggccttg aactcacaga gatccacctg cctctgtctc ccaagtgctg    26100
gggttaaagg cacgttgtta tggaataatc ttttggtaca ctgtgaagtt gtgtctttgt    26160
caaggcgctt tctgactggt ttaataaaag aactgactgg ccagtagcta ggcaggaggt    26220
ataggcagga aagcaagaca cagaggactc tgtgaagaag ggcagagtct tgggagtcat    26280
gagcaaatgc agagggaagc aagatgaaag aaggtaccac tatgatgcag agggtagata    26340
gtaaaaggat taatttaagt catatgagct agctaaacac aactctaagc tatcagccaa    26400
gcatttataa ctaataatga gtcttttgtgt agttatttga gaactggcta tcgggataga    26460
aaagtctgtc tatagtgtgc atcaccatac ctggccacta ttttaaattt ttattttaa     26520 ttatgcgtat atgtatgtat gtgggtcccc tggagcaagt gattgtgagc tgcccagtgt    26580
```

```
gagagctggg aactgaacct ctgtcctctg aaagtgcttt taacgactga gccaccactc   26640
tagccccaac aactcatttg taatcttgtt cctgccaaag ctacatggca tgaactgaag   26700
aaacaggtca ttcaaaactg agggacagga aataaaataa ctggcttgcc atctttaaaa   26760
gccagctaga agaatcagca ggtaagggta cttgcagtgc aaactttagc atttgagttc   26820
aatacctgga gcccacagta gaaggagaga aatgactccc aaatgttgcc ctgtgacctc   26880
catgtgtacc ctgtggcatg ggcatgccag tgctcacaca cacgcttcat agacttacag   26940
taataatttt aaatataaaa taaaactgtc tggatttgca ggacaatcag cagtgctcca   27000
acagagtctc aagataagct tggggggggtt cttgttatgt agccctagtt gggcaggaac   27060
ccctatatag agaccaggct gacctcaaac atgtggtcct cttgcttctt catgcatcac   27120
cacactcagc cttagtttta atttcttttg aggcatacec agcgtatcct ggaactcaat   27180
tatgtagccc aggctagcct caaacctgag atcttccata tctggtctcc cagatacgag   27240
ccaccatgcc tggctcattt ctccacgtgt aaatatgggg aagggaatg aatggccctt    27300 tcagcaagaa aataaccacc cacccacggt tggtgtgaaa gacggtagtg cactgccctc   27360
cttctgtcac ttgaccatgt cacttatcac acacacagct ctccaggcgg aaatgccaac   27420
cctccagtgc caacaccttt ctccgcttaa gaccatgcca ctcatgcgca cagacttcag   27480
ggctctccag aaaccgaagc agccggcagg ctcaactctc agccaaggcc tggagagagc   27540
ctatgcaggg taccggcaga tcccttacct tgcccaggag gtcctccagg ctgtgagcca   27600
tgatgccttt gcgaaccttc cgatctgccg tgctaactcg acagggcctc gccctgggga   27660
cttcccggct gggcttagac accagctgtt gggtcaccac tgcagtgctc actgctacat   27720
gcctggggac aacagtttgt acagcagatg acctgcctgc ggctaccagg tctgcccatg   27780
cctgcctgct tgctgagttc aggtgtgacc tttccttcca accaatcatg gctgcttcag   27840
gcggctttca caaagtccat cagaagacac agctccgatt tggagggggca gggaaatcag   27900 cgggaatctt gcttaaatca gactcacttc agtgcctctg agtggagccc aaggactgct   27960
aacaagtccc caagctgtgt cagtgtggct ggttcttgga ccagccacat tctcctgtgg   28020
atggcttctg cttttgtggc cttgttcacc ttgcctaaga ggcagggtga aatggagctg   28080
gtgtgtgtat atatgtgggg tgtgtgtgtg tgtgtgtgtg tgtgtgtgtg tgtgtgtgtg   28140
tgtgtgtgtg tgtgtaaatc ggcctgtaga atatgtgggg actctgaggt acacaggta    28200 gaaagaaagg agcagagaga atttgggtct tggctggaat tccaagtttc tctctgttac   28260
ggatttgcta ggtgacagca tacccagcct gtgactcagt ttcctcatct gttgacttgg   28320
catagttgcc accacttccc agagaggagt gaggctcctg ggagatcagg aacaaaggca   28380
cctggtgccc agcctgaccc tttctactcc agatgtgatg ggaactgtgg cagtgacaga   28440
gagtaagatg gggactgtct agactgcaag atcttgggtg ctaccctagg cctcctgaat   28500
cagatctgtg ggggtttatt gtaagatttt gtctgttttg ttttaatggg ggtcttgctt   28560
atttgtttgt tttttgggat agcatctcca tatatagccc tggtttactg gaactaattt   28620
cctcatctct gtctctgtct ctgtgtctgt gtctgtctct ctctctctct ctggacctgg   28680
acctatgcag accagactca aactcaccaa gatcctcatg ccactgctcc caagagcca    28740 ggattcaaaa catatgccac catgcctggc catatcagct agaccccaca tgactttttt   28800
tgtcttttaa aatgggatgc ctatgtagcc ctgactgacc tgggacttgc tgtgcccact   28860
acaggctggc ctcaaactca gatctgcctg cgtctgcctc ctgagtgctg ggattgaaag   28920
```

| | |
|---|---|
| cgtgtaccat cacatccagc ccctacatgg tttttatacc tattaaagtt ttcaaagttc | 28980 |
| taatagatgg ctccccagct ttccccttcc ttcccatacc cagctctcct tacctggaca | 29040 |
| gtgacttagg gtacaggagg ctgagagact tcatggcata gtccatcctt gtcagctgga | 29100 |
| ttgtgttgga cctggatcgg aggcagtaac ctatctggtt agagtgggaa gggagggagg | 29160 |
| ggtccctctc tttctttctt tgactcagtg gatcccagcc cccacacggc aaccctctgc | 29220 |
| cccagtctct cctcctaccc ccaatttccc tgaatccaca ccaactacac tgagtcagcg | 29280 |
| tctaccatcc ccacccattc cacagcccca gaacaactca ctccatgttt ctctgcccca | 29340 |
| agctctggtt acactgagct gaggaaccca agtcaaggct gaagaggccc tcactgattt | 29400 |
| gtccctgtcc ctgggggcag agtccacatt atgctggcag gaggtgagtc ataccacctc | 29460 |
| atgctgtgag agacttgaaa gtcacctatt gtccagaaac tccacaggca gtcgaccttt | 29520 |
| ggagagcctg ctctaaccat gggcccttga gcaataaagt cctcctgagg cttagaactg | 29580 |
| gctaagagaa cttictgtga tcttaaagac tgtctaggct tgtgttcacc aataccttag | 29640 |
| ctgttaccac tgagcccttg gcaccataac taatgtgaca aaggagctga caccgaactt | 29700 |
| ctattgaggc ttaactaatt tagttaggta actactgtgg tttgtgacgc caggtacccc | 29760 |
| actggacatt acagttgtag tggagtaatc ctgggctcat gtgccccctg cctttcctcc | 29820 |
| tatattgctg ttctctggtt cttgcctgct gagctgcaag tctctgcaca ggcagtctct | 29880 |
| tctacctgca atgcttgtct caaactcaga gctcaacata agtcacctag aagccccagc | 29940 |
| tcctggctgc caactcagga aagccttttc tggtgccctc ttgcctggta ccagattgat | 30000 |
| ccctgtgccc tgcccttcca tgttcatttc tgctgcagct ctcgggtccc cactgtgcct | 30060 |
| gttttcagcc cgtagcacag ggacccagtg tgaacaccag gagtgggcag gcatggagaa | 30120 |
| ctgcctcctc agtgaaggaa aaccattctt cccttctgat aactcgggtt ctccccggtc | 30180 |
| aaccttacag agttagagac cctcgtcccc acttaatgct acccaagcac tcttgtttca | 30240 |
| ccctgtttct aatacccacc actcacacag ctccacaaaa cccaccacac ctgctctgtg | 30300 |
| gtagccaaat accccagctc ttctcctccc cctcacctcc tagcctcctg gcaatactgc | 30360 |
| gtggccaggc acagcccagg cctcctccat tttatttcta tctcctgtga agccactccc | 30420 |
| ttggccccag ccccagctgg ggaaaagagc acagggagtg agtctgaaac tctccctagg | 30480 |
| gatttcaagc cagactgact tccagaaagc cccgaaaggg ggaagaaggc atgtttcgaa | 30540 |
| agctctagaa ggaagaggta ctgcccagga cttggtacca ggcaagaggg cacagaaagc | 30600 |
| aacagacggg gcttgtggtc tgcgttccac ccctcacacc agctgtttgc gctcacccga | 30660 |
| gttgccttct ttcagccctg gattttctcc tgtgcatgag aataacgct cctgttgaag | 30720 |
| ccaggaatgg tggctcagag ctgtaatctc agcacttggt agactgaggc ataaaagggg | 30780 |
| ccatgagttt gaagctagcc tgggctatag agttaggtcc tgtctcaaaa acaaaaatat | 30840 |
| agtcagacgg tggtggcaca cactttttgat cccagcactc ggaaggcaga ggcaggcgga | 30900 |
| tctctgtgag ttcaaggcca gcctggtctc cagagcgagt gccaggatag gctccaaagc | 30960 |
| tacacagaga aaccctgtct cgaaaaaaca aaataaataa ataaataaaa aagaaatatc | 31020 |
| ttttttttt tgagtcaggc aagatacttg agttttatta tgtctgtcta aaagcaggtg | 31080 |
| ttaggcctat ttgtagtgaa gcgtggtgtg ctggcgctgc aacacccggt gaggaagcag | 31140 |
| gaacctgatc tcagagccca agaactgctt gacagcaggc cttcggcact tgccctctga | 31200 |
| aatctcttcc accttcatca ggttaatgga gtgtgcacgg gcacagtgcg ggcacccgtg | 31260 |
| tcttggtagc actgtttgac ggctccagca gcggtcaggt cccggtattc ttggcacatg | 31320 |

```
ttgtgtgtgt catgttgtga gttgtagtgc agccataccg caaagttctt cacccgcagt   31380
ggggcctcag gtcgcactgc acagtgtacg atctcctcgg atgacttctt catcttgttc   31440
atctgtgccc aaaatcggga cttggccacc acatggttcg tcgcaaagat gtgcatgagg   31500
tataggagtg gtgtgtggca cttccgggtg ggcaagcagc gccccaccac cttgtactcc   31560
cgaagcgtgc ctgaggcctt cgtggctgat ctgtccttgt tggccgccag ccacaaaaat   31620
aaaaggaaat atcttgccta taatgttaca atcccatcca gcacttggga agccaaggca   31680
ggaaggcctc tgtggatgag accagcctgg gctacagagt gacaacctgc aagagaatg    31740 gggtgggtaa tcccaaatct tgggtatagt gaagtacagg actcaagaga cagaggcagg   31800
aggatcatct ccagttcaag acaagcccga gctataaggc ctcaaaaaca aaaaagaat    31860 attagatcta tgatttattg ctataaacac tacaacttaa aaaaaattaa aataaggaca   31920
gcaagatgac tcagtgaatg agggtttgaa tttgatcccc agtacccaca tagtacaaag   31980
agagaactga ctcccatagg ttgtctttcc gtgaaaactc tccctccctt cctccctctc   32040
tctttctctc tctctaaatg aaaatgttta catcaaagcc tctacaaaga gcattcatgt   32100
tacacctagc gttggagaga tgtctcagtg gtcaagagcg ctgacttctc ttccagagga   32160
tccaggttct attacaagta cccatgtggc aattcacaat catttataac tcagttccag   32220
gggatctgac tccctcttca ggcctctgtg ggccttcatg tgtgtggtgc aaagacttgc   32280
acgaaggcaa aacactgtac acataaaata aaaataagag acagaaaagg gaatttattc   32340
agtgtggcca taccagaaaa gatgagagga ccagtctctt caaccctgtt tttggagtgc   32400
agatggtagc tctaggaatt tacaggagaa gaacaaaaaa tgggatgagc tggtggtgca   32460
ggcctctcag tgcttgagag gcagaggcag aggcaggga atctctgtgg gtacaaggac    32520
agcctgactg acctggtgga ttccgggcta accgaaacta caaaataaga cactacctct   32580
aaagttaaaa caaaaagggg aggcaataag tatgcatagc taagcattct attctattct   32640
gcccaaacca ctctaattga cggctacctc cagtctgaag taagggtcct gcagtagcta   32700
ggaagaggac tacctcccag gctgactgtt cctggctctg gcaacaaact gaaaaggaaa   32760
actggttcag aaggagatca gagcagaggg gccaaattag aacgaggatt gtgccttcct   32820
tcaggtttag aacaaccact ggagaatttt aggtactgct gtggtagttt ggaacaagac   32880
gaggcaaaaa cttattactg gcaatctgta atgtccccat aaatcctttt tatatctatt   32940
tttaaaaaga tttctatatt atatgtacag cattctgtct gcatatatgc ctgcaggcca   33000
gaagagagct ccagattta ttacagatcg ttgtgagcca ccatatggtt gctgggaatt    33060
aaactcagga cctctggaag agcagccagt gctcttaacc tctgagccat ctctccagcc   33120 ctctattta tttttaaaa gaattatttt atgtgtatga atatttgcat gtatgtatgt    33180
gcaccacatt catgcagtgc ctatggaagc cagaagagga cgacagattc cctgaaacca   33240
gagttacagg gggctgtgag ttgctttatg gtgctgagaa ctgagcttcc ttcctgtaca   33300
agaaaagcac atgctgttaa ccactgagct gtccctccag ccctccccac cctttgtgt    33360 gtgtgtgtac ttgtatgtgt atgtatgtgg acatgtgagc atgtgtggaa gtcagaggat   33420
ggtttgcagg agttggttct ctccttctac cctgtgggtc ctagggataa aactcaggct   33480
ggtagcatgt ccctctacct gcaaagccat ctcctgggct ttgtcccaat aaatttcttg   33540
ctctcccttg gtatcttcat tcttaaaggg aaggacagag ctacaggtac aatgggtgaa   33600
aattggcctt tagttaccag tcttgaagat gagtacttaa atttttttca gaatcctttt   33660
```

```
tttttttttta aatcttttta tttatgtata cagtattttg tctgcatgta tgcctccagg    33720
ccagaagagg gcaccagatc tcataatgga tggttgtgag ccaccatgtg gttgttggga    33780
attgaactca ggacctctgg aagagcagac agtgctctta acctctgagc catctctcca    33840
gctcaagaat cctttttttt ttttttttt tttaaggcag ggtttctttg tgtagcctta    33900
gttgttctgg aattaggttt gtagaccagg ctggcctgaa ttcaaagacc cacctgactc    33960
tgcctcccag ggtgctggga ctaaaggtgt gtgccacgac acctggctaa gatgagtgct    34020
ttttaaatgc ctatcacatc tacaggcaca actgattggg aagctgattc aaaccttgag    34080
atagcaaagg gatagaggtg ttgatgcaac ataaagacag agatgcccag attttctcct    34140
tcctttagtc actgggcggg actctgcagg tccagtgagg actcactggc tctcttgtta    34200
aagccttatt tagagttaag ccaatccttg gaagaggcat cattcattca ttgaacactt    34260
gcagtgtgtt accctgttaa ttcagcagaa agcaagacag ctttaggcca cacctggagc    34320
agctggacca gagaccaagt ggaagcagga atgctgatgt acacttctca tcctgatccc    34380
ctggaggctg tcagcctggg ccacacagtg cgagatcctg cctcaaaaac gttttgcta    34440 cccattggtg attgtacatg tactttgttc tagcactcag gaggtagggc cagcctggtc    34500
tacaaaggac agccaatgct acacagagaa accctgtcta gaaaaacaaa acaacaacag    34560 aaacttttttt gtctgatgtt tcatcttgtt tcttttctaa taatgtactg ggcagagaaa    34620
aacaaaataa tgcagttggg cctggaggct tagacctggg attccagcac ttaagagata    34680
gaggcaagct cattgctttg agtttaaggt ccctctgccc tgcatagtga gttgcaggtc    34740
agtgtggact atagagtaag accttgactt tcaaaaagca caaggggcca ggcgttggtg    34800
gctcacagct ttaatcccag cactcgggag gcagaggcag gaggatctct gtgagtttga    34860
ggccagcctg gtctacagag ggagttccag gacagcctcc aaaacaatac agagaaaccc    34920
tgtctcaaaa acaaaacaaa acaaaacaaa acaaaaatgt caaaaagcac aagggccatc    34980
aaaatggctc agtgggcaat tacaaacttg atgacctgag tccattcctt gagacctaca    35040
taatggaaag aactgactcc cctaagttgt cttctgacct tcacacatac cgtgtgtgtg    35100
tgtgtgtgtg tgtgtgtgtg tgtgtgtgtg tgtgtgtgtg tacatgcacg cgctctcgtg    35160
agcaagtacg ctcctgatac taaattaata aaaaggatta aaaagtaaa accacaaaca    35220 tgaaccaaac caatgtggtg taataaccta tgtctggaga actaacaggt ttctggaccc    35280
agagaggtag agaagataat ctaatgtctt caggggaatt aggggataa agcatcagag    35340 cataaagaaa gtttccctca cttgggaagt agtggaggca ggagcatcag gaattcaagg    35400
tcatctcatc tatatagtaa gtaagttcaa gactagcctg ggttacatga gaccctgtct    35460
caaaaaaaaa aaaaaaaaaa aaaaaaaaa aaaaaaaag gaagcatggt gcaacagatt    35520
tgagattgaa acacaaaaat agctcaactc tggggcagac agcagagtca ggggaaagtc    35580
taaggaagtt ctgggaaagg gtcaggaggc ccctccctgc ttcattcacg ccccaaacat    35640
ctattaaaca ttccatgtgt acttggtgtt tctggcctga ggatgactca cagaggctga    35700
cacactaagt taatcacagg aagcacagaa gaaaaaaaaa aaaaagaaa aaacaggcct    35760 aatgcaatgg aatgcctgac tgaggggggtt cttcacagtg cttggagac gacccttgt    35820 gtctcattga aattcatctc tcaagaaaca ctcctcaaat gtttacacat tgtcaggcac    35880
tttgagctgc agggacacag aggactcagt tctggtccct gcctttggaa ttcacaattg    35940
ttgctcttcc aaagaactgg ggttcggctc tcagcaccca cttaaggagg cccatgacca    36000
tttgtaactt cagctcaacc gcttccacaa gtacccacac acatgtctgt cccccaaaca    36060
```

```
cacctatatt cttcatgcta accttgtgac actatgagca aaatcaaaga cattaagaag    36120
ccaggttcag tgccctgtgc cttagtccta acatttgaga ggctaaatca aacaggaatt    36180
gaggccactt ggacagcatc aagagaaatt atctttgaac atatgaaatg atattatcac    36240
agaaatagaa ttgcaattta aaccaggtat gtgatcccct ctccccccac caaaagaaaa    36300
aaaaatagag ggctggagaa atggctcagt ggtaaagagc acctgctgtt cttgcaaagg    36360
atctagattg ttttgttttg ttgagacaga gccacactat gtaactctgg ctgtcctgga    36420
attcactatg tagatcaggc tagctggtat gtatgtctgt ccacaaatgc atgcctggtg    36480
ttagaggctt ccagaagtgt gtgtcagacc ctctggaact ggagttatag gtggttgtga    36540
gctgccatgt gggtgatgta attgtacttg ggccctttgc aagagcaacc agtgccctta    36600
acccctgata cttgctttta aggaatttgc atttttgttt tgaaattaca tgttggaaaa    36660
gttttccaca tcagtaagaa atgccatcct tactatttct tcctgcagct tctcagaaat    36720 atttttaat cttttttttt aagattttat ttatttattt attatgtaca caacattctg    36780
cttcatgtat atctgcacac cagaagaggg caccagatct cattcaaggt ggttgtgagc    36840
cactatgtgg ttgctgggaa ttgaactcag gacсctctaga agagtagtca gtgctcttaa    36900
cctctgagct atctctccag cccctcagaa atattttaat tcaaaaatct ttcttagcca    36960
gctctcaagc cactggatta cttcttgctt ctgctactga catagacttc atcttgattc    37020
actccataca gcaactagat gtgtgtatat aaatgacaga tagatcatag atggatggat    37080
ggatggatag atagatagat agatgataga tagatagata atctcacttg ctacctaggc    37140
tgacctcaaa ctcatgcctc agtttcctaa gtgatgtgat tacgggcata cactattatg    37200
cctagcataa ccatttgttt gccttaaaat ttttttaagat taatttttta ttatgtatac    37260
agtattgtgc ctgcaggcca aagagggaa tcagatctca ttacagatgg ttgtcagcca    37320
ccatgtggtt gctggaactt gaactcagga ccctctggaag aacagccagt gcttttagcc    37380
tctgagccat ctctccagcc cccagccttt aaaattttta attaatttttt tttttgtttg    37440 tgtatgggtg tttggcctgc atgtaggcct atgcactata tgtgtgtagt actcacctag    37500
accagaagag ggtgccagag actctggaat tggagtttca gtgcatgatg agctgccaag    37560
tgggccttaa tccccaaacc ccagaggggtt gaagagggat cagtggctaa gggtgcttgt    37620
tcttgcagag gacccagttt tgattccag agcccacatg gtagctcaga caagaactc    37680 cggcttcaga ggattctgca ccсctctctgg gcctcatctg gtaccaggca tacatctggt    37740
atgcagatat atacacgccc tgagtggtga caaacactct gtgagttcaa ggctggtcta    37800
catagagaat tccaggacat agtgagaccc tgtctcaacc aaacaacctg gatccttгtc    37860 aagaagagca ggtgctttta aacactgggc catctctcca gcaccacctc ccccctttaa    37920
tgatacatag gtcccacata gcctagttcg gcctcttaac tcctgacata accctcatg    37980 aattcctcat cctcctgcct ctacctttгg agtgagtgac gagattacaa acgttcgcca    38040
ccatctttgt tcccagttgg ccctcaaggc cccagggtct cagttcagat cctgccacta    38100
tggatacata gcattgaaat ggggaaggct gcctctgtgc tgcctcagcc tttgggtgac    38160
gcctcttgct tggcactgca ttttcaggag catgacatct ttgctctgga ccctgacccc    38220
aaggttgtgt ggagctgtaa gaagtgtaag ggtgtctggt attggtggcg cgcgccttta    38280
atcccagcac tcgggaggca gaggcagcag aggatctctg tgagttcaag gccagactag    38340
actacagagc gagttcagga cagccagggc tgttaacaca gagaaacact gtcttgaaaa    38400
```

```
gcaaaacaaa ataaaaccaa caaaacaaca acaacaacaa agtgttaagc gcgcatgcaa   38460
ccagccactg ggcaattagt caaagatgcc aagtctagat agacatgcag ttaagaactt   38520
agggtctaga gagatggctc ggtggttaag agaccagaag agtttgcatc ccagcgctcg   38580
cacagtagct aacaacagtc tatcttacac cctcttccag cctctcctgg cacaaggaac   38640
acacgtggtg ctcatagtta caaaacagac acaacacgca tacacaaaga aataactaat   38700
ttttaaaatg tcttgtaatc aagtaaaagt gctaactcta gggactaaat taattcctca   38760
gtcgccctac tccaggagcg gtaaggctgg ccagaaagac caagaacgca cgcgcggagg   38820
agaaaccaca gagtcggtcc tcccgggata gagaggccgg aagtgctcgc ggagctgcac   38880
gccgggtgct ggaagcctac tgagccccga ggaagggctc cgctcggggc ttggcgtggt   38940
gggtgagccg gagggtcggc gtgagcggcc tgggctttgg ttctgaatga tggcgtctcg   39000
ggcaggcccg cgagcggccg gcaccgacgg cagcgacttt cagcaccggg agcgcgtcgc   39060
catgcactac cagatgaggt atgaggtgag ccaggagcac tgaggccttc cccgggagga   39120
gcctgcgggt ctcgggaagc gacgcgggcg agcctcacgg tgccgctccc ccagccagct   39180
gtcgcgtact accgggtccc cggctccggc gagcgcctcg ggtctgttta caggccggga   39240
agcccagtgg cctgccctcg cccgcctcgt gctttgaggg gatctggcct gcagaggctc   39300
aggggtcgat gctcagcccc tctgaatgac cttggagaca tcattttct  ttttcaaat   39360 cgaggtcccg cagtgtctag agttcaggct ggcctgaac  tcacgccctt ccctcctcag   39420
cctcccgagt atgcgcctgg tctgaaaact aacattctta agaaaactg  cgtgtgtgcg   39480 tgtgtgtgtg tgtgtgtgtg tgtgtgtgcg cgcgcgcgcg cgcgtgtgtg tgtttgtgtg   39540
tgtgtaagtt tgcccacacg agagcaggtg tgctggcaga atgcagtgcc agtaaagggt   39600
gtgtgtgtgt gtgtgtgtgt gtgtgtgtgt gtgtgtgtgt gtgtgtgtgt gtgtgtgtgt   39660
gtgtgtgtgt gtgtgtgtgt gcgcgcgcgc gtgtgtgtgt ttgtgtgtaa gtttgcccac   39720
attcttaaag aaaactgcgt gtgtatgtgt gtgtgtgtgt gtgtgtgtgt gtgtgtgtgt   39780
gtgtttgtgt gtgtgtaagt ttgcccacac gagagcaggt gtgctggcag aatgcagtgc   39840
cagtaaaggg tgttggatct cttggagcta tagttacaga cgtgtttaaa tccacctgag   39900
actagtactg aggaccaaac cccgaagtga ttttgtgaga tagcggcttg gtatggggtc   39960
catgctagcc tccaggagcg gcaggtgctc ttaaccactg agccatctct ccagtcccca   40020
ggctgtcttg gaacttgctc tgtagaccag actagaaatc agagatctgc ctgcctctgc   40080
tgccaagtgc aaggattaaa ggtgtacact acagccgccc tgttgaccct gtctttagga   40140
agatgtcatg tgtactttac aaagagtttt gatgtagtca tgtcttaagc tttgttgtca   40200
cacaagatga aattaattac caccagggaa ttttcatca  aattgtgctg tacttaaata   40260
tgcctaaagt aaaatacttg gggtcagact cttgaagttt aaaccaacac caggtactga   40320
gttgtgttga acccacacaa ctaccttgcc tcctgcagat tgttaactct gctggctgtg   40380
gtggttgaag agacccccac attggcttag ctgttaagag cacttgctgt tcttggagag   40440
ggtctaaact cagttcccag caccgacatc aggaggctca caaccaaaca cctgcaactc   40500
cggttccagg ggttccgatg ccctctggct tcccgacagc acaggcgtgt gcgtggtgca   40560
cacacataca catgagataa attttaaaa  agaaagaaaa gccaatctgg gtcctgcctt   40620
caaggagctt gagtgccaga agtgattctt ttctccttac ctcccacatt tcctataaca   40680
aattaatttt ccccttaaat ccactgaatt attcaactgg ttcttggcct cttctcttac   40740
agaaggatga caagcccttt ggacccttct tttcaacttt taggcccctg cctaatggat   40800
```

```
gctcttgttt tcatgcgtac ctagagcaga caccttgctt gtgacaatat gaaaaggata   40860
taattgagac cccgagaaga tcaggactaa gagatgtgcc tccttctcat ggaaactata   40920
tctggagaaa tacagggagc ccaaactgtg ttccttgttg ctaggcctcc ccctaatggc   40980
ctttgtttct gtgatacgaa gccatctttc taaccacagc tcagaattct tgtcatggct   41040
tggtgagata atgtcttagt acgttgtcca ggccaacctc caatcagaga tcctctgcct   41100
cagcctccca ggtgccatta ctgttcttca gtcttgaagt ctacacatgc atggtctttg   41160
taactgttac tacctctctg tgccttggca gttgatttcc tgaaacacaa atactaaaaa   41220
gcttattcct ttgtgcctgc atgttttttgc ctctgcgtag aagcccactt ccactcgtct   41280
cattacctct gctgaaatag ctctctcctc tagatataac cttctctggc tttccatctc   41340
atgctaattg gttcttccct gggatagcgg atatcttcgg tttatatgta tttacttgag   41400
ttttatactt catgtttccc agcctctatc agaggctgtg tcattcagat tgtatctatg   41460
tgtccagtac cggtgcctgg tggtcggagc aatttaaatg aaaattgctt ctccctctgc   41520
tctgccttac agtgtgacgc tcaagagtga atcaagaag ctgatctacg tacatctggt   41580
catatggctg ctgttggttg ccaagatgtg tgtgggacac ctgaggctct tgtcacatga   41640
ccaagtggct atgccctatc agtgggaata tccatattta ttgagcattg tgccctctct   41700
cttgggcctt ctctccttcc ctcgaaacaa cattagctac ctggtgctct ccatgatcag   41760 catgggctc ttctccatcg ctcccctcat ttatggcagc atggagatgt tccctgccgc   41820
ccagcaactc taccgccatg gcaaggccta ccgcttcctg tttggtttct ccgctgtctc   41880
cgtcatgtac ctagtgttga tactggcagt ccaagttcat gcctggcaac tgtactacag   41940
taagaaactc ttagactctt ggttcaccag cacacaggag aagaaacgta aatgaagcct   42000
gcctgatgga cacatgaagg gagctgttca gaatctccat ggactgtggc atctgtgatg   42060
ttggcaccta gtgcacacta tcctcagatt ttggccttga gttctctgtt accatctgct   42120
gagatgacaa atctgtagtg tttaatttat tcttgactag ccacaaaccg gatgaccgat   42180
gtctgtggaa cacttcaagt tgaggccctc cagactgagc cttatccttg ccttctcttg   42240
gtcaaattcc ttacttccat ttatcacctc ttcatcaccg atactaaaag agatctggaa   42300
taaatcagtg cagaaattct acttcaatct gtaggtcatg gggcaagcaa catttgggaa   42360
gttgctcccc taaaggctac tctgtttact gcaaaccatt ttaattaaaa aagaacttca   42420
ataaagttaa gactgtcctg tgctttgtgt ttgagatttg attgaatttc aaagttgtat   42480
tgctctagag gacttagaca ttatgagaag aatagatgtt tcctgagaac atgggactgg   42540
cgctggagga gagacagtgt gaagagtctt aagtcagctg cagccctcta gctcttaggt   42600
gagaacaacc ctgggatggg ggttgctgga ggaatggctc aggggttaag agcactgaca   42660
gaggacacag gtttagttct cagcacccaa atggtgactt aaaaccattt gtaactactg   42720
tcccagggca tttgacgcct tcttgcctcc ggatgcacta gcagacatg aggtacaaaa   42780 acaaacatgc aagcaaaaca ctcaaaaaat taaaaaaaa aaacatggtc tctcaatgta   42840
gctgtggatg tactagaact cactaagtag agcaatctgg gctcaaactc acagagatcc   42900
tcctgccttt gcctaccaag tacagggatt taaggtatgt gccaccacac ttagcaatat   42960
atatttggcc agacatttaa tctccaccca taaagcagct tatttggctt ggattatgag   43020 ctccccttt tatgcttgtt tgagacaggg cttctctata gctctggctg tcctggaact   43080
tgcttcgtgg accagactgg catcaaactc aaatccacct gcctctgcct cccacgtgct   43140
```

```
ggcattaaag gtgtgtgcat cactgcccag ctgggttacg agctttctat ttggttattt   43200
atgtttatta gacttttatg tgtctaaaac tgagtaataa tacccaaaaa gaatctgctt   43260
gttgggcta  taattttcca gtaactgaca aataaacctg agtcaaaata agaagaaagg   43320
ggtttgagtt cttttccct  tttagtttct gtcattgatt attccttggc ctgcttgttt   43380
ggggaatgtg caaaggaagc tgctaactct atggaagcca gaaaagaaa  aaggtgagat   43440
tccagtgtcg ccactagggg cagactgcca gtgacgtaac ttcttcactc agcccctccc   43500
aaagcttcct ccacctccaa aaatgtcaag gactggtaac tagtacatgg gcctttgaga   43560
aaagatagca gggagcttcc agtcttgggg gaatgtgcag tgaacataac atctaattgt   43620
gtgagagacc cacagctgag atacagttta agagtcacac ctagaagtct tcacagtaaa   43680
taaggcagca aaggtgtgca tcccttttgca ctggactttta ttatgcctag atgatgctca   43740
gatctgtaac tgcagagatc tggccactac agttgtaatt cttttgtcct ggaaatgtgt   43800
tgcttgtaca gtctgcaaag ctaattcctc cagctatccc actgatcatt tctttggagc   43860
aggggcagtt tccagacaga atttctctgt gtagtcctcg ctatcctgga actcagagat   43920
ctgcctgctg tgtgctggga ctaaaggcat gtaccaccat gcccagctcc tactgatcat   43980
ttcaaagata acttcttgtg cctcaggcct attgctgttc ctgcttcctg tgtttacggg   44040
aacacagctc tggatcatcc accctgcaag tttaagtccg tccccactcc atatacacac   44100
tgcctattcg gtgaacctcc tatagatacc ctgataagtt ccctagcttc tcagtttaac   44160
acttagaact ctccctactt aaggggaggc ctctcagtgg tgaagtgctc ctctagcatg   44220
caccgaggcc tgggtgtgac tccctcgtaa caacaaataa aaacaaacct tttctgctct   44280
tacattcctt tattaatctt taagatgcca cttgtatgaa aattcctcaa ttttcaattc   44340
ctcaatttga agaacaactt taatttgtct ggttgctttc accttattcc tttattatta   44400
ttttctaaca agacagagcc cagaatgacc ttaagctatg tggctgagga tgactttgaa   44460
ctcctgatgc tttgtctcta cttcctaagt gctaggatta caagtatgca ccatcactcc   44520
tggcttatat tactcgtccc ccaccccac  cccatagacc aagccttgac ctttattttt   44580
aaaagctgca tatttattct gctttctgac ttagtgtttg tgccttcaac actttcacaa   44640
cccttttctc ttcctcaata aggaaagcct gcttgatcct gtcacggaca cacttggcac   44700
acaaggagcc accacagccc ctgctgacgt gcttctttgt ctagacagtc tcataaggac   44760
tttgggtctc acagcatgaa cccttcaag  tctgcctggg cacacaccac atggggattc   44820
aggtgctttc ccagtcttct tggtataaag gtaaacaatc ctgttgccag gggttcgaga   44880
cagcctagtt tcgttagagg ctgtattgta ggaaagccta caatggtatg tcaaacactg   44940
gaccattcga gtgcctctaa gcaccatccc tggaagagga agagctgtat tatttgtttt   45000
atattgacag aattgctact ttgtatgtct tctgtagctc attagtgttc actctgagct   45060
tattgaatga attaacttgc cctttttgagg acaaaggtct gtatttcaca gaaaacagaa   45120
ctggactgaa gcagaaagaa gcccatggac aagggagttt gtcatgagct tagctgaggc   45180
acacattgct aacttcaaac aactgtgatg caaacaatta aaactgcagt gcagacccc   45240
ctgctttctc ccaataaatt ttccacataa gttctgtccc ccccccaaaa aaaaaacctg   45300
ttagcacatt attagtcaaa gagctaaaac ctgtttttgg tcatcagaat agtgttttac   45360
tgaaagtctt tgaatacctt gtagactaat ttcactcatt gtgaaattag tcaacagttt   45420
taaaacacta tcatgccaac atcagttttt gttagttttg tgcttggaat tctgcttttc   45480
tagccttttc ctataacttt tttctgcctc atggttatgg tgttcacaag tcctcttgat   45540
```

```
ttagtgggaa gaatgctatt tgggttagaa agttcagctg ggtatggggg tacatgtcta   45600
atcccaacct ttggcaggtt gaggcagcag gaatactctg agtttgaggc cagcctgaca   45660
tacatacata catacataca tacatacata catacataca tacaaacact atctcaaaaa   45720
acaaagttgg agttaaagta tcaaccacag gactaagatc aacctgcctg ttcacaggtt   45780
gctttaaagc tccaatagcc ggttggagag atggctcaga ggttaagagc actggctgct   45840
cttccagagg tcctgagttc aattcccagc aaccacatag tggctcacag ccatccatta   45900
tgaggtcagg tgccctcttc tggtgtgcag atgtacatgg aagcagaatg ttgttacata   45960
ataaatacat aaaatcttaa aaaaaaaaaa ctccaatagc caaagtatta tgaaggcatt   46020
ctaaaatttt taatttattt tcattttatt tttggagaca cagtttctct gtgtaaaaac   46080
cccaactgtc ctggaactca ctctagacca gactggcctc caactcacag agataaacct   46140
acctctgcct cccaagtact gggattaggc cgggcagtgg tatcgcccac ctttaatccc   46200
aacactcgag aggcagaggt tggtggatct ctgtgagttt gagaccagcc tggtctgcaa   46260
gagctagttc taggacagcc tccaaagcca cagagaaacc ctgtcttgaa aaaaacaaaa   46320
aacaaacaaa aagcaagtta atctggaatt aaaagtgtat gccaccacac ctgatgtaaa   46380
tttaaatttt tttttaaatt aattttcta tacacaggtg ttttgccagc atgtatgttt   46440
gtatagcaca tgtgaacctg gtgcctaaaa agccaaaaga gtgcatctga tcccctggga   46500
ctggagttac aaatggagtg ctgccatgtg ggtgctgaga attaaaacca aatcttctag   46560
aagagcagcc agtgagtgcc cttaactgct gcagcatctt tctggctctt gtgaaggcat   46620
tttatggagt ctgtaacacc atatgggtat caaaagccgt gtggtcacct gatctttgca   46680
gcaagacagg agagagaagg tgtttgagag acttgaggga tggtctagac accaaagaaa   46740
ggtttgtgtg ttgtgagcaa tgactgatta ttaggttgag attctagcca gggagtttac   46800
tatctcttgt ttgatttatt acattttatt gccatcctag gaattaaata gggttttaca   46860
tttgctaagc aagtgttctc tcaacatcct tatatcccct ccccgatttc tgacacttac   46920
tatagctcag cttgtccttg aactcagcaa tcctgcctcc atagtgccgg gattatggat   46980
gtttccactc ccagctgagc ctgttcttca tgtgttgcat gggcattgca gatctctccc   47040
attgctgtga ggctgaaata aatgtggatg aactttgtag tacatagtcg tttacatatc   47100
aagatgcctt tccttggtaa acagtgttat gcttgcctct caaattggga gtgtcttcct   47160
gttttaagaa taatcctctt ccctctttc ttcctctctc ctcctttccc ctccttctga   47220
cagggtctct ttatagaata ttcctgcctc tctctgcctt ccaaatgttg tgtaggtgta   47280
catcaccatg cctgcctagt tagaatgacg tctcagaatg ctggaggtta atttcacatt   47340
cttagtccac attatcctga ctggtatgtt caaggtgccc tgacagtagg tacagaccca   47400
gcagacctca ggaagtgacc attacagcaa gatcctgtag ctgctactca tagcctgttg   47460
ggagcccgtg cataggaaag aatggcaaga aaaatggct gccagagggc gtccccatag   47520
tatactctgt cactaagcat gcatgcttca gagcttgcca aaacctcctg agtccctggc   47580
ttggtcccca aataaaggtc attagagcat gaagtcttgg tcaactgatt gagactcctt   47640
tggagagtgc aaggcttcta tgtagatgcc cctgttgcct cctattctgt ctaatttctt   47700 actctcctg ttgacagctg ccaatctcct ttctcctagg actgtgccca ctcatcactc   47760
actgtgataa gaccccttt ctttctttg ttccttcctg gtctgcctgc ctgctccccc   47820
ccccacctct ccctttcat ggtctcatga aaactgctct cagactcact atgtagctaa   47880
```

```
ggatgactgg agctcccaat cctcctgccc ctacttccct aattctggga ttacaagttt    47940
atgccaccac attccacttt ctgatttcct tccttacatc ttaattccac tagctttatc    48000
acactgctaa agctaaaact ttctttgcaa aatgagatcc agaaaccac agactctcca     48060 tagtaggttc tgacagggaa acagctgaca ttgtatggtg ttctgccttc ccatttcttt    48120
gctgtgtgtg ttttttggaca agtctcggtc ttcctgtatt tccttccttc cttccttcct  48180
tccttccttc ttttccatt ttttatttga attataaaca cgattgtttt acatgttaat    48240
cccagttccc tctccctccc ctcctcccct accaccatcc ccaactaaaa ccctacctat    48300
cacatatcct ttctgctccc cagggagggt gaggccttcc ataggggtcc tcagggtccg    48360
tcatatcctt tgggataggg cctaggccca cctccgtgta tcttggctca gggagtatcc    48420
ctctatgtgg aatgggctcc caaagtccac acctatgcta aggataagta ctgctctact    48480
acaagaggct ccatggattt ctgaggtctc ctcactaaca cccacattca ggggtctgga    48540
tcagttccat gctggtttcc cagctatcag tctggggacc aagagctccc tgttgttcag    48600
gtcagctgtt tctgtgggtt tcaccagcct ggtctgacc cctttgctct tcattcatcc     48660
ttctctgcaa ctgtattcca gttcagttta gtgtttagct gtgggtgtct gcttctactt    48720
cttccagctg ctggatgaag gctataggat ggcatataag tcagtcatca atgtcattat    48780
caggggaggg catttaaagc agcctctcct ctgttgctta gattgttagt tggtgtcatc    48840
tttgtagctc tccaggcatt tccctagtgc ctgatttctc tgtaaaccta aaattttccc    48900
tctattatgg tatctcttat cttgttttct tctattcttc ccccaactca acctttctgc    48960
tccctcatat actcatcttc ccttctcatt tcctagctc cttcctcccc ttcccaattt     49020
gctcaggaga tctggtccct ttccccttct ccaggggacc atgtatgtct ctcttagagt    49080
cctccttgtt acctagcttc tctggctttt ttttttttt taagatttat ttattatgtg    49140
tacagtgttc tgcctgcagg tcagaagagg gcaccagatc ccattacaga tggttgtgag    49200
ccaccatgtg gttgctggga attgaactcc ggacctttgg aagagcagtc agtgctctta    49260
accgctgagc catctctcca gcccttcta aaactggaca ttagcctagc ctcaagggtt     49320
gtgatgctaa caatacaagc taaagagagc aatgggcatg atccaaagcc agatagttca    49380
gcaaatattg atttcatccc ttccttttc ggaacagact ccagccacac caaatatgta     49440
aaccagcaag acaaaaaaca gcaggctatc ttttcccact ttttgctttg tctatgtttg    49500
ttggacaatg tcaaactatg tagcccagac cccttctgta actttccatg tagaccaggc    49560
tggcctccaa ctcaaattcc cagcaatcta cctgtctctg cctctggagt tctgggaata    49620
aaggtgtgca tcaccatgcc tggcctcaat aagtccttgt cttatggtct tctttctcc     49680 tcctttactt cttatcctcc tccctctctc ttcccttcc ctttatcttt atttcttat     49740 tgtcaccgtt tcttttctgc ttctcttacc atgctttaac aaccatcagg aagcaactaa    49800
ccaaatgttc tcatcttgag agtcaggtca gaagatctag gagtcaagaa agacacgtgt    49860
aaaatagagc tcacatacca agcattagaa aactcgcagt ggcactaaaa gatggctcag    49920
gggataagaa cacttacatg gtgactcaca accatttgta attccagttg cagacaattc    49980
aatatctcct tctgatctct aagggcaccc agaatgtaca tacatacatt caggtaaaac    50040
gttcatatac attaaaaata ataagcctta agaattagaa aagagggctg gagagatggc    50100
tcagaggtta agagcaccga ctgctcttcc agaggtcctg agttcaattc ccagcaacca    50160
catggtggct cacaaccatc tgtaatgaga tctggtgccc tcttctggtg tgcagatata    50220
catggaagct gaatgttgta tacatattaa ataaataaaa tcttaaaaaa agagaattag    50280
```

```
aaaagaaaaa aaagcttcat gtgtgtgtgg aaacctccat gaggtagaat gggataaaag    50340
ctcttgattc tatgcttagt ctggctagat cacctctcct gttctctgga tctctctgac    50400
ttgactgtag aggttggctc tgtacaaggc agcactgtca gcagatcctg ttggttcaaa    50460
gaggtaggtg aagccaagag actacaggtg acagcagatt gggagggccc agcacaggtg    50520
cagctcactg gaagggtcca gcacaggtgc agctcactgg aagggcccag cacaagcgca    50580
gcaccttggg ctatagactt tgaccttgac caaatcactt tcctctctgc ttccttattt    50640
ctctccttac gaaattaaac aaataatcct catttacctg cctcacaagt tgtttagagg    50700
gatcaaatat tgctgttgct ttgtgaactg taagtagata agctatttag atgagatata    50760
tcatgattga cattcactca gccatgaagc acaggcttcc tgacaggcac tgctaggtga    50820
tggagaagaa caaatgagtc tctccatctc tcttttctca gcactaggat tgaacccagg    50880
gccttgcata cactaagcaa gtgcactgcc gccgagctta tctgttttta cctcctttta    50940
aaaatattgt ttatgagctg ggtggtggtg gcacacttct ttaatcccag cacttgagag    51000
gcagaggcag ggggagctct gtgacttcga ggccagcctg gtctgtagag tgagttccaa    51060
gacagccagg gctacaaaat aaaaccctgt ctcaaaaaac aaaaacaaaa acaaaaacaa    51120
aatcaacaaa atgtatgaat gcaaaaacaa aaggatactt tagggtcgca ggtagattgg    51180
gaacttcaaa tgtgggccaa agaaggctg tggccctgct tctgaaggat ggtccagacc    51240
gaatctcaga aggacaaagt gtcggggcta agatgtagct tcgttgatag agttcatgca    51300
tgcctagcac gaaatcctgg gttcagtctc cagccctgaa gaaactggat atggtggttc    51360
acgcccgtaa cctcagcact tgggaggtag aggtagaagg accaggagtt taaggaccgg    51420
gcccagccta cgatacgtga gaacctgtct tgatgatgat gataatggga ctggagagat    51480
ggctcctgtg taaagtgctg cataaacacg aggacctgag ttctggtccc cagcaccagc    51540
atgataccag gccatggcag aatataccte tagctccagt atcgagtaga ggagacaggt    51600
ggaccctggg gcttgcctcc ccaccagctt agctgagaca gcaaggtcta ggttcaatga    51660
gagatcctgt ctcaaaacaa aatagagata aatcaggaag acaccctggt gtcagctctg    51720
gcctccacac gagcctgcaa gcacacctgc ccatacaaca cacacacaca cacacacaca    51780
cacacacaca cacacacaca cacacacaca cacacacaca ccctggtgtc agctctggcc    51840
tccacacgag cctgcaagca cacctgccca tacaacacac acacacac acacacacac    51900 aaacacacac acacacacac acacacacac acacacctaa attttttaa ttaatttaaa    51960 aagaagagac aatagcaata ccaagatgca atgacccagt ggacatgccc taactgtcc    52020 tcccatcgtg gagattgcca aggtgaggct gaagcagcta aagtctccat gaatgagagg    52080
aagctgtgag atgatgggga gggtccccac aaagcctgga gccttgtcag cctttttccc    52140
tgcaccggaa accacaggaa accaggtcag tgtgtgtggc tgctccctct gctccagagc    52200
tcagctgtca gttttggggc ttcctgagca agctgtatta tttagtttgt ccttgaagct    52260
agagaccact ttgacctgga gtcgagaaga gttggaaagc cagctagctg gggagccaga    52320
gtgtacatgg ataacacaag aagtttattt gtgttatatg ttggcctatt tttttgccta    52380
actttaaatg atgtaccaat tgcttcttta tcttcagcat tcagtataga caagtgccga    52440
atagctgtta attctcaaaa tggaagatgt gtaactgtct atgacagatc caagttctag    52500
aacatgctaa taggcgtgcc agatctgcag tgtttgagga gggttaagaa atgggtgcat    52560
ttccacaaca gggtgctggt ccctttcctg ttacctctcc gccacaccaa gagccccctg    52620
```

```
tgacgtgaga gcagtaaggc tttctaccaa acaggtggac aagtgaatta gtgttcacca    52680
gtgccctggc tcaggagaag gaatgtgacc cagcctgctg gttaggatag aggaggagct    52740
tcagggcagg gtggatccag ggcagggctt ggtgagagcg cctgctggta ctgtgtgctc    52800
ctcacagctc cagggccagg ccctgctgcc ctgctgccct cctgcaaaca acaaagccat    52860
ggtctctgtg ccctgatcct gcagaagctt atggggagcc ccagactgac aacctggttc    52920
ctgcctctcc tcttactgct cttcagcctg tctatgtctg ctgaggttgg ctgtccctac    52980
ctgccacgct ggaccagcca ctgtctactg gcttcccatg tggtaaggtc ctgctgctag    53040 gtggggggaca cttgcttggc acagagtaga aactccccag tctcctgtct gccctttcct    53100
acctctgaaa tccctgtgat ctagtggcag cctctctgtg tccaccatgt ggtcctgaag    53160
gttctgttgg gctgaggtcc ttggaaggat gagaagaaaa cagctggggt ggatggacag    53220
tgggctgtgg gtctcagaac cggatgatcg gcacaaagag ttcagggagc atgcacctcc    53280
tgcagttccc ttctaaccac acctctctca tttcttttcc gcactgggct ctgtacctcc    53340
aggataagaa ttctgccggt gagtcctgtt tcttgttctg cttcactccc catgctcccc    53400
tgagttccag gtcccagtga gccatccatg gccattttgg ttcccagcct ggggagtagt    53460
ctagtatcaa tgggaaagtg cgggactagt gaagatttgc attgtaattc tgcctcagac    53520
gctatgactg cttttcactc tcccatctga ccctcggtct ctgagcacag gagaagagga    53580
gaaatgatta tgcgatgagg acagtgttgc tctctaccaa tggggaggat aaaatgagca    53640
ccatggctaa tctccaggca ctctggacaa gctggctctt cttatcaccg gtacctcact    53700
tgaccaggaa caataatcat cttccatact ttattgtgca ttctgcttta ccaagctttc    53760
ccccatgcct tatgtcactt ggtccttatg acaaacccac tttgagcagt ctggcacctg    53820
cccaataact taaccaagat tgtacctgta agctatatca gagcccagcc cgaaatccag    53880
tttggagaag gtaggtggga cccccttaggc cctaccattt ttcttgttcc tcttttttgtt    53940 tttgttttga gatagggcct cactatgtaa taacaaagcc tccataatta tttatttact    54000
tattttggtt cttcaagata gtgtttctct gtgtagtcct ggctgacctg gaactcactt    54060
tgtagactag gctggccatg aactcacaga gatccacctg cccctgcctc ctgagtgcta    54120
ggatcaaagg catacgccat caccacccag ctgcctccat cttttaatcc ttccatctca    54180
gcctcccaag gaatagctta cagccatgtg ttattgtgcc gactttctat catacacagg    54240
aagttctgtt caaactccct gccctaccct cctagccacg aagccttggc actggctctg    54300
ctgtttgtgc ctgcgtctga tgtcacggcc ttcaggtaag aaaagcagcc tttgagccat    54360
tcttagtgaa ggcatgaatc agggacagtt gaaaataact agctaggctg acacaagtgt    54420
caattgtcat atttgggacat atatttgtct tgttaacctc aagagggact tagagcatcc    54480
tagaataaca catcatgaca gacattcatg ggaccactat atctttgtgg aggtgccatc    54540
tttcatctgg cactaattcc taaaagccat gtgttctgta gacttgctat tgttaccttc    54600
cctctgtaaa atgggactgc cactctgctg cttcattgcc tcacttggta catacggaac    54660
acacacttta aaaccagcag tcataggcgg atggaaagat agcttagcca tcaagagtac    54720
tagatgctct tgcagaggac ctaagttcaa ttcccagcac ccatatcagg cagcatacaa    54780
ctgtaggtaa ctccaactct aaggaatctg atgtttctga tctcttaagc ctcatttata    54840
tgtgccaata catagatata catacacatg caagtaatta aacataaaat aaaatcacaa    54900
aaagttagtt taaaattgtt caccattagc tgagtgctag tggcgcacgc ctttaatccc    54960
agcactcggg aggcagcggc aggaggatct ctgtgatttt gaggcccgcc tgttctatag    55020
```

```
aatgagttct aggacaggct ccaaaacaat acagagaaac cctgtctcaa ataaataaat   55080
aaataaataa ataaataaat aaataaacaa acaaactaag aaagaaatca tgctacaatt   55140
aacactgctt ttgtgggagg tgtgtgtgtt tgtgtgtgtg tgcgtgtctg tcttttttct   55200
ttgttttatt ttatttttta aatatcttat gttagaggtg gagagatggc tcagttgttg   55260
agacagttgc tgcccttcca gaggatctgt attagattcc cagtaccctc atagtggctg   55320
tatacacaat tgtctgtaac tgtagttcag ggaatccagt gccttctttt gacctcagca   55380
ggcaccaggc atgcgcatgg tgtacattca tatgtgcagg taaaaccttc atacacataa   55440
aataaaataa ataaacctaa atatttaaaa aagaaatgaa atatctttta tttattgttt   55500
gacagtctca tacatgcaga caatctatct tggtcaaaac cacccacaat tcctccctcc   55560
catgcacttg gataactccc aatacatcac tgctccacat tcatgtctct tttaagatct   55620
tgtgtgtatg agtgctttgc ctgcatgtat atatgtgtat tacattcatg tagtactcat   55680
ggaagcatca aatccctgta gcactggagt tatagatggt tgggagccgc catgtgggtg   55740
ctgggaacca atcctgaatc taagaacatc aagtaggctg aactgctgat ccatcttcac   55800
acacacacac acacacacac acacacacac acacacgcac gcacgcacgc acgcacgcac   55860
gcacgcacgc acacagagag ccatcaaatt ttgagacaga ggcttactgt gtagtcctgg   55920
ctcacctgga acttgcagag tagaccaggc aggtgtcaaa atcaagagat cagcctgcct   55980
ctgcttctca atacaagtat aaaaccacgc cttgctctgt ttgttttgta aattcacgga   56040
gtccagctat gagtctgcct gctggaatgt tgactgatct ggttggcttg accttgtgca   56100
gttcctgtgc aggtaaccac agctgcagtg ggttcatgaa cacgacagtc atgccatgtc   56160
tagaagactt caaaacactc ttccacatct tctggctctc acattctttc tgccctgtct   56220
tctgcatttg ctgaaccttg aaggggctta attctgtttt ttactgaatc ataatttttg   56280
ccaccaaaga agctcaatat cattgctacc cttgatttct ataaacattc tacccaacat   56340
tgggccacat ctccagatag gacaggggcc aagaatgccc aggtaagaag tgtgtttccc   56400
tcccacaggc cttcagtgga actggttttcc tctcttggtg aagaaatcta aaagtcctcc   56460
taagtctgaa ttctactgga ggcgtagaag gccagcatcg tcccaggtac cctatcattt   56520
acaacactat ggccctcagc ccctttcttt cttgcccctt attttgttct tcagcaacaa   56580
gagggagttt gaaaatgtgg agattacgca ctaagggaaa ctgaggccaa aggaatttga   56640
acaacttgcc tgttaaatta atttgtctct cagggttcag aggcagagtt agaaagcaca   56700
cttcctggat cctggcagac ttcctggatc ctggctcaca tccactttgt tctctgcttg   56760
cagaggaagc tgctaagcag cctttccctg tctcaggaag accatagcat ttccaacccc   56820
ttcccagcca tctcccatgg agggccacac tgcaaaagga cccagccttt ggacaccgga   56880
ggagtagaac atttttcctag agcaggttca cagaagcgtg gaggtaggtg cgaggagcaa   56940
caagctggtg gtctcagcct tgcctgagcc agtctctgag tcgtccttct ccctaggacc   57000
tgaattctcc tttgatttgc tgcctgaggc acaggctatt cgggtgacta ttcctccagg   57060
cccagaggct agtgtgcgtc tttgttacca gtgggcactg gaatgtgaag acatgagcag   57120
tccttttgat acccaggtat ggagttccat gccttgcaaa gagacagatt acacaatttc   57180
tcagcaaatg ggatggggtg gggggttgg ggcccagaca aggaaagtaa ttgtccaaaa   57240
cttccttaca aaatgagata agtagcatta aaaacttgtt gggggcgggg gaggactaga   57300
tagaaaagat ggtgggctat gttacttgag aagagagacc agaaagaaat gagaatggta   57360
```

```
tgtattgcca gggagaggac tcttggtgtg attcgggtca aattaagaga ctttgctaag    57420
ggctggggac atacccgttg gtagaatgtt tacctagcat gcttgatctc tggcactgca    57480
cagatggagt gggaggtgga agcaggagaa tcagaagttc aaagtcttcc ttagatatat    57540
aatgagtctg aggtctgttt ggagtacgtg agtcttaaga gaaaaaaaaa aaaaaagctt    57600
tgttatttcc tcaggaggtt gttccctgaa aatttgacaa aactgtcata tgtgtcttgg    57660
tacttttccc tttcatacct tttgtctagc cctcagaaat gatattcccc agtctcacaa    57720
tccaggtctt gacagcctac tttaactgcc actcctcaca gatgccattg tatgtagctg    57780
ggcatcacat gcagagactg gagtccttca gcttgcttca tgtctacaat ggctatacct    57840
tctaacaata ccagccttta gtagaattga tgcttctaat actgcatggc atacagctgg    57900
aactcaagaa atgtatcgcc tcttccctaa ccctactgct tgtagagtac ctcaagaaaa    57960
tggccaggat atagaaccta tgagagggag aaataagttc catggagtag gaaagtaagg    58020
tatattgtcc aaggtcccgg cttcatcctg ccttgtccat agtgtccatg cttttcctta    58080
ggtgtctctt tttcttccc tttgtggttt tatcaacaga aaattgtgtc cgggggccac     58140
actgtagacc tgccttatga attcctcctg ccctgcatgt gtatagaggt gagcacaggg    58200
aaatgtggat tagccatggc tccttgtcca accgcatctc cagtaagtca acttagaaag    58260
gactcgggaa ggatggagat gacttggtga tagagcaggc cgtacacact aaggagagac    58320
tccaaaaaaa ccgggctact gggatgctta ggaagctggt gctggctagg ctatgagcca    58380
caccagaggt ggaagggtcc taggcaattc cacctcagcc ctgcctggat gctgtcttct    58440
ctggtccaga tttggcttca gctcacagac acagagtaga cagccatcat cgctgtgttc    58500
ttgagagcca aggttgcata tccctctcaa agtcatgttc tttccaaccc tccatttctc    58560
cttgtaagtc tgaagataaa gatgttttgg acattttttag ggggaagaca ggtactaaaa    58620
gaagggtatg gacagagacc tgggaaacaa gaagctgaca gaggagacaa ccagtggact    58680
ggactcgtag ggagtccaga gtgaggagtc aacacagggt actgggtact tgagaaagtc    58740
aacaatggag ctcagagagc ctaaaattga gtgatgcaac ctcgggaatt ctctgctgct    58800
gggaacagtt ctttggagac aggaggggtc atcccctctc atttgccact ccctcctatg    58860
ctctggaacc ccaacactta cacacactcc acagtgctgc ccattattgt ctgacagctc    58920
aagctgtttg atgacagtaa gccagagcca gaatgaagat gttaggaaag ccatttctaa    58980
caaacactct ctatgctccc caggcctcct acctgcaaga ggacaccgtg agatgcaaaa    59040
agtgtccctt ccagagctgg cctgaagcct gtgagtgttg tttgtattaa tcccgatgca    59100
cattcatact ccccctgctg tgtgtgtgtg tgtgtgtgtg tgtgtgtgtg tgtgtgtgtg    59160
tgtgtgtgtg atggaggaag accccagatg gcaggaggac atttcttca ggagccaggg    59220 gaagatgcca cagctgtcag ccaacagatg agctcctgag tgctgaacat tatgaatgga    59280 aaggatcgc ccagcgagtg tgtgagaggg ccaactgtag acctaggctc acttctcagt    59340
tctgccatag gttatcccca tagcccctcc cctttccctc atctgtaaaa tcccaaactg    59400
tttttgaggc ttgaatgaaa tattttaggg gaaagtggct ggtgttgtct ggagtgctgt    59460
atgtagaatg gtgaccttga ggagagagga cacttagaca caagtaacaa agtctaacgt    59520
acataggcag ggttatcatc aagggtatca gcccaggaca ggagaagccc agagacactg    59580
ttgtgagcag agagggtgtc acaggatggc acttgactga gctcaggaac tggacaggaa    59640
ttagaaagaa gaagcagggg gaagacagac tctgtgagga gcctacacag attctggata    59700
caggcgacag taagggctgt tcagtgtgga ggcctggatg gaaaggtaaa gccaaggaag    59760
```

```
ctgggtagaa agggagggag cgtggagtgc ttgcctgttg aggacctgtg aagcctggaa    59820
ttgtgctgga acattggtat tttctcctgg tgtcctgggg tggggtgggg agatggagtt    59880
acagctgggc tatggcctca ctcttgcacc tgccacctgc ccagatggct cggacttctg    59940
gaagtcagta cacttcactg actacagcca gaacaaccag atggtcatgg ctgtgacact    60000

<210> SEQ ID NO 3
<211> LENGTH: 9227
<212> TYPE: DNA
<213> ORGANISM: Cricetulus griseus
<220> FEATURE:
<221> NAME/KEY: misc_feature
<222> LOCATION: (1)..(9227)
<223> OTHER INFORMATION: expressed and VP-generating type-C group 1 ERV
<220> FEATURE:
<221> NAME/KEY: misc_feature
<222> LOCATION: (1334)..(1336)
<223> OTHER INFORMATION: Myr motif
<220> FEATURE:
<221> NAME/KEY: misc_feature
<222> LOCATION: (1851)..(1868)
<223> OTHER INFORMATION: PPYP motif

<400> SEQUENCE: 3
tgtgaaagac ccctctccct tagccctttc tttctcaagt ttgtctcctc ttcctcctgt       60
cggcggcttc cccgatcccc accccggtg gcctttcccc gcccggcccg agaacaagca      120
ccgggtgggg ccggcccgag aacaagcacc gggtggggcc ggcccgagaa tgagcaccag      180
gtgggccagc ccgagaacga gcaccgggtg ggctggcacg agggcgagca ccaggtgggt      240
cagcacgagg acaaacaccg agtgagccgg cctggagctc tgcccctgag cccccgcccc      300
gcccgaagag aaacactccg tcccaaggtc tccgccccca aggtcagcca tcaggaaaag      360 gggggggaatt gagtctgctg taccagacac cagaccttga gaatatgctg atctggaatg      420
gctctgtgtc tcatttgaac catccaatgg aaatgattct gtatttcgcc tcatttgaaa      480
gactctgtgt ttcacctcat ttgaataact ctgtactttg cctcatttga ataaccctgt      540
atagcgcctc atatacattg accaatggga atagctctgt ataatgcctc attagaatta      600
tccaatagaa tccttgctcc tagcttgcgc ctttttttcct atataaggac ccccttttccc      660 ttggctcggg gcgcttagcc acacagaagc taagtcgccc caggtacctg cgtctccaat      720
aaagcctctt gttttttacat ccagttcgtg gcctcgctga ttcctgggtg tgtgggtctc      780
cctctacgaa agtgcctctt cggggtcttt catttggggg ctcgtccggg attgagaccc      840
gcccagggac caccgaccca cgtctgggag gtaagtgttg tgcggatccg ctgtttttgtc      900 ttgtctggtc tgagtctgtc ttgtgaattg cgcttgcgtt tgtagtatac agctgtgtac      960
atttgtaggc ggatccgagg agggactgac gggtccgaac tcccgaccgc ggctccagga     1020
gacgtcctgg tagcgtttga agccctcagg aagagggatt tgtatttttga acttgggaag     1080 ccctcagggt gagagattttg tactttgaac ttagatctat gactgacat ttcccagtc      1140 tctttggaga aggccctcgg cttgagggat ttgcaatctt tactggggac gaggaaggag     1200 ggccccccttc ctcgactctc tctcaattcc ttctgtcgac tctctgtcga aaccgcgctg     1260
cgaaagtctg ttctgtgtta ttcggtctttt gtcttgtagc tgtcatttgt gccctcctaa     1320
gcctagaaac tatggggcaa actgtcacca ctcctttgtc cctaacactc tcccactgga     1380
aagatgtaca ggaatatgct cataaccaat ctgttaatgt gcgtaaacgc aaatggatta     1440
ctctttgttc ttcagaatgg ccgacctttg atgtaggctg gccgcgagat ggtaccttta     1500
```

```
accccccagac tatattccag ataaaagaga agattatgga tcctggacca cacgggcatc    1560
ccgatcaagt ggcttatatc gtcacttggg aggctttggt tcaggacccc cctccctggg    1620
tacgtccttt cttacatccc aagggcccct ctctccttcc cccctctaac cgctccaacc    1680
gacccattcc ttcggcccct cacctcccca ctcctttgat tcctcccaac ccccttccc     1740 attccaacct ttaccctacc gtgatgaaag acactaaggc taaagaaaag aagacaccta    1800
aggtactccc tccgggagaa gaccagttgg ttgatctatt aacgaggag ccccgccat      1860 atccgccact gccgccccca ccagaggcag aagcggactc cgccgctgcc ttggcggaag    1920
cggcccctga cccttcacca atggcttatc gactaagagg tcgtagggag cagcccgttc    1980
cagattcaac cactctgccc ctccgaactg ggctgaacgg ccaacctcag tattggccat    2040
tctcagcatc ggacctctat aactggaaaa ataataatcc ttcttttct gcagaccccg     2100 tgaggctgac atctctcata gagtcggtac tcacgactca ccaacccacc tgggatgatt    2160
gtcagcagct tttgcaggtc cttttaacct cggaagagaa acagcgcgtg ctactagaag    2220
cacgaaaaaa tgtcccagga gtaaacgggc agcccaccca gctacccaat gaaattgatg    2280
cggcttgccc tcttgaaaga cctgaatggg attttaccac cgaagcaggt aggacccacc    2340
tgcgtctcta tcgccagttg ctggtagcgg gactccgggg ggcaggacgc agacccacta    2400
atttggccca ggtgaagcag ataatacagg gtgcggagga atcacctgcc gcttttctag    2460
agagattgaa agaagcgtac aggatgtata ctccctataa tccggaagat ccaggtcagg    2520
ccaccaacgt ttctatgtcc tttatttggc aatcagcccc ggacataaga aacaagcttc    2580
aaaggctaga aaatctacag ggatatacac tccaagattt gttgaaggaa gcagaacgta    2640
tttttaataa gagggaaaca cagacagaaa gagaagaacg ttggaggaag gaaactcagg    2700
agagagagga aagactaaga caggaagctg aggaaaaaga ggttgcgaga gaccgtaagc    2760
ggaataaaga aatgagcagg ttattggcca cagtagtgac aggccagaga cagaatagac    2820
agagggatga cagaaggggg ccccacctgg acagggacca atgtgcttac tgtaaagaaa    2880
aaggacattg ggcaagagaa tgccctaaga accccgggc caagcttcca ccgccaaggg    2940
tttctgacct cctgaaccta gaagattaga ggagtcgggg ccaggagccc ccccctgagc    3000
ccaggataac actgcaagtc ggggggcatc cggtcacctt cctagtcgat acaggggcac    3060
aacattccgt tctgaatcgg tcacccggac ccctgagtca caggactgca tgggtacagg    3120
gagctacagg cggaaagcag taccattgga ctacaaatcg gcagctccag ctcgcgaccg    3180
ataaggttat gcattctttc ctccatgtgc cagactgccc ctaccccta ctaggacggg     3240 acctattgac caaattaaaa gctcaaatac actttgagag gtcagaagtc aaagtcacag    3300
ggccagaggg aattccccttt accatcttga caatgtccat agaagatgaa tatagactcc     3360
atgaaaagag gactaattcg aacaatcagg aaacccttga tcactggctt gcggaatttc    3420
cccaagcctg ggctgaaaca ggaggaatgg gccttgccat taaccaggcc ccaattatag    3480
taaccttaaa agctgccatc cttcctgcat ccgtcagaca gtatccaatg cctaaagaag    3540
cccgcgaagg aattcggcca catattaaaa ggttacttga acaagggatt ctggtgccct    3600
gtaaatctcc ttggaataca cccttgctac ccgttaggaa gccgggaact aatgactacc    3660
ggccagtaca ggacctgaga gaagtcaata aaaggataga ggacatacac cctactgtcc    3720 ccaacccctta caatttgctg agtggattgc cacctaacta tacctggtac acagtcttag    3780
atcttaaaga cgctttcttc tgcctccgcc tgcatcccac cagccagcct atatttgcct    3840
ttgaatggca ggacgcggcc cttggaatct ctgggcagct gacttggact aggctaccct    3900
```

```
aagggtttaa gaacagccct acccttttg atgaagcttt acatcaggac ctggcagaat    3960
tccgggttag gtacccgct ctaatcctct tacaatatgt agatgacatt ctcctggcag    4020
ccaaaaccaa agggaaatgc aaggaaggca ctcaagccct cctccagact cttgggagcc    4080
tagggtaccg ggcatccgcc aagaaggccc agatatgtca gaaacaggtg acctatttag    4140
gatacaagat aaaggatgga cgtcgatggc taacggaagc ccgtatgcga gccatcttag    4200
acattcccac cccacaaaat ccccgccaac tgagagaatt cttgggaacg gcaggcttct    4260
gccgcctatg gatccctggg tttgccgaaa tggcggctcc cctctacccc ctcactcggc    4320
caggggttgc ttttaaatgg gaagagcccc aaaagaaagc cttcaccgac atcaaaaagg    4380
ctctccttga atcaccagcc ctgggtctac cggacttagc taagccattt gaactttta    4440 tagatgagaa ggagggctat gctaagggag tcctcaccca aaatctgggg ccttggagaa    4500
ggcccactgc atacctctcc aagaaattgg atcctgtggc atcgggatgg ccaccctgcc    4560
ttcgaatgat tgctgctata gccctgctgg taaaagattc tcacaagcta accttggggc    4620
agcctttgac catacatgcc cctcatgcag tagaggcagt catcagacag cctccagata    4680
gatggcttac taatgcccga atgactcatt accagactat gctgttagac aaagaccggg    4740
tccacttcgg gcctttggtg actctgaacc cagccaccct gctccccctc cctggggagc    4800
ccgaggctca tgattgctta caggtattgg ccgaggccca tggagcgaga tccgacctga    4860
ctgaccagcc tctacctagc ccggaccaca tctggttcac ggatggaagc agcttttgc    4920 atcaaggaga acgaaaggcg ggcgcggcag tcaccacaga gaatcaggtc gtctgggccc    4980
aggcactccc ccctggaact tccgcacaga gggcagaact catagcactc acgcaggctc    5040
taaaattggc agaaggtaag aggctcaccg tgtatacaga cagtcgttat gcctttgcca    5100
ctgcccatat acatggagaa atttacagac ggagggggct gcttacctcc gaagggaaag    5160
acattaaaaa taaggaggaa atcctcgctc tcttaagggc tcttcatctg cccgctgcct    5220
taagtatcat acattgccct ggacaccaaa aagggggattc tttcgaagca aggggcaatc    5280
gaagggcaga cttggctgcc cgagaggcgg ccctgaccac agacaccact aacctcctgg    5340
ctctagagcc caccaacgac catcccttcc cctcatggga ctatgaacaa agagacatcc    5400 aaacccctaga gaaattggga gccgcaaagg aaccaaacgg ggattggact tatgaaggaa    5460
agactgtcat cccctaccgg gtaaccaagt acctagtgac attttttacat aagatgacac    5520 atctgagctc caagaagatg cgggagctcc tcgaacgaga agaggaattc aatttccttt    5580
tggggaagaa cgatattcta aaacaggtaa ctgagcaatg tgatgcgtgc gcccgagtca    5640
acgcatccag actgaagctt cctcccggga accgggtcag aggctaccgg cccggaacac    5700
attgggagat agatttcact gagattaaac caggaaaata tggatacaag tatctattaa    5760
tttttgtaga caccttttca ggatgggttg aagccttccc tactaaacat gaaacagcca    5820
agatcgttac taagaaattg cttgaagaaa tctttcccg ttatgggatg cctcaggtat    5880
tgggaacaga caatgggccc gccttcgtct cccaggtaag tcagtcagtg gccacccttat    5940 tggggattga ttggaaatta cattgtgctt atagacccca aagttcagga caggtagaaa    6000
ggatgaatag aacaatcaag gagactttaa caaaattgtc gcttgcaact ggcactagag    6060
actgggtcct cctactcccc ctagcactct accgcgctcg taatacccct ggaccacatg    6120
ggctcacacc ctttgagatc ctgtatgag tacctactcc tatcattaac tttcttgatc    6180
aagatgtctc agattttgct aactcccctt ctctccaagc tcatttacag gccctccaac    6240
```

```
tagtacaacg ggaggtctgg aaacccettg ctcaagctta taaagaccag agggaccatc    6300
ccaccatccc ccattcctac cagatcgggg acactgtttg ggtccggcgt caccaggcca    6360
agaaccttga accccgctgg aagggaccct acatcgtttt gcttaccact cccaccgcac    6420
tcaaggtaga cggcattgca gcttggatac atgcttcaca tgtaaagcca gcccaaccca    6480
ccgattcagc cactgcatca gaatggaccg cacaccgcac tcaaaatcct ttaaagataa    6540
gactctctcg tacaccctcc tgttgattgg ttgtctgttt accccccatg tagcaactaa    6600
cccccacagg gtttataata tcacctggaa aatagccaat ctagggaccg gggaaatagc    6660
caacctcagc acttatatag ggactctaca tgatgggttc cctcctctct atgtcgacct    6720
atgtgactta gtagggtctg attgggatcc ctctgaccag gaaccattcc cagggtacgg    6780
atgccaccac cctgggggaa ggataggaac aagaagcaag gatttttatg tttgccccgg    6840
ccataaacca actcatggct gcgggggggcc gcaggaaggg tactgtgcaa gatggggatg    6900
tgaaaccaca ggggaggctt actggaaacc ctcttcctct tgggatttca tcactctcaa    6960
acggagggag atcccagggt acgcaggaa aggaccatgg agatgtgggc aaagagcctg    7020
cggaccttgt tatgatagtg ccggaggggg aggttttcaa ggcgccaccc ccggaggaaa    7080
atgcaaccct ctcatcctaa ggttcacaga tgctggaaaa agaactactt gggatagtcc    7140
taaggtctgg ggactcaggc tgcaccgagc agggaaagat ccggtgactt tattctccct    7200
gtacagacaa attactcccc taagccaaca atcagttggg ccaaacatag taatagcgga    7260
ccagagatcc ccaacccatt ttcaagtccc taaaccccct accgttccta aagctatcac    7320
tcctacacca ggtgctgtca ccttctcccc caccccagat gccctaaaca tcgagataac    7380
cagagaccct ccaggtacca gagatagatt attacaatta atccaaggag tttaccaagc    7440
cttaaatttt tcagacccca acaagactca ggaatgctgg ttatgcctag tttcccggcc    7500
cccatattat gaaggcgtgg caatactggg caactactcc aaccagacct cagcacctac    7560
cagttgcgga gctgctatgc agcacaagct cacaatatct gaggtctcag gaaaggggct    7620
atgcataggc aggattcctt cctcacatca agaattatgt aaccaagtag agccattatc    7680
tcaggacagc cgataccttg ttgccccta tggaacttat tgggcttgca gtactgggtt    7740
gactccctgt gtctctacca ctgttctcaa caccaccatt gactttgta tattgataga    7800
actttggccc aaagtcacat accaccaacc tgaatatgtt tacagcgtac tagagaaatc    7860
aacccgatat aagagggagc caatatcctt taccgtggcc ctattattag gaggaataac    7920
aatgggggc atagcagccg gcataggac cggaaccgtt gccctacagg gaattaatca    7980
ttttaagctt ctacaacaag ccatgcacac ggatatccag gtcctagaag agtcagtcag    8040
tgcactcgag aaatccttaa catcactctc tgaggtggtc ctgcaaaaca gacggggatt    8100
agatttatta tttttacagg aaggggggct atgtgctgcc ctcaaggaag aatgctgctt    8160
ttatgcagat catacaggaa tagttaggga tagcatggcc aaacttaggg agaggctaaa    8220
acagaggcaa cagctatttg agtctcaaca aggatggttc gagggatggt tcgctaartc    8280
cccctggttg actaccctta tatccacgct catgggacct ctggttattc tattttttgat    8340
cctcatattt ggtccctgca ttctgaacaa actgactcaa ttcatcagag aacgactatc    8400
tgttgtacag gctttagtct taactcaaca atatcatcag ctaaagcaaa tagatccaga    8460
gtatctagag acctctgaat gaaagattcc attcagttac aagagaaatg ggggaatgaa    8520
agacccctct cccttagccc tttctttctc aagtttgtct cctcttcctc ctgtcggcgg    8580
cttccccgat ccccacccce ggtggccttt ccccgcccgg cccgagaaca agcaccgggt    8640
```

-continued

```
ggggccggcc cgagaacaag caccgggtgg ggccggcccg agaatgagca ccaggtgggc    8700
cagcccgaga acgagcaccg ggtgggctgg cacgagggcg agcaccaggt gggtcagcac    8760
gaggacaaac accgagtgag ccggcctgga gctctgcccc tgagccccccg ccccgcccga   8820 agagaaacac tccgtcccaa ggtctccgcc cccaaggtca gccatcagga aaaggggggg    8880
aattgagtct gctgtaccag acaccagacc ttgagaatat gctgatctgg aatggctctg    8940
tgtctcattt gaaccatcca atggaaatga ttctgtattt cgcctcattt gaaagactct    9000
gtgtttcacc tcatttgaat aactctgtac tttgcctcat ttgaataacc ctgtatagcg    9060
cctcatatac attgaccaat gggaatagct ctgtataatg cctcattaga attatccaat    9120
agaatccttg ctcctagctt gcgccttttt tcctatataa ggaccccttt tcccttggct    9180
cggggcgctt agccacacag aagctaagtc gccccaggta cctgcgt                  9227
```

<210> SEQ ID NO 4
<211> LENGTH: 30019
<212> TYPE: DNA
<213> ORGANISM: Cricetulus griseus
<220> FEATURE:
<221> NAME/KEY: misc_feature
<222> LOCATION: (1)..(30020)
<223> OTHER INFORMATION: 5' of SEQ ID NO: 1

<400> SEQUENCE: 4

```
tggttctatc gagacagcta catccgcttc tccacacagc ccttctccct gaagaacctg      60
gacaagtgag ctttccctcc acctcccttg actgcccagg ctagtgagga ggtcagcaga     120
caaacagaac agtgggctct gcgggcaggg aaggcaggct tttcgccgcc actcatcctc     180
tgccctgaag gagcttgcca agagggtgcc cttgggttac cgaaatgagc aaaacaagaa     240
ctcctgctaa tcaagggctt acatcctagc aatgagcttg agtaatcatg gctaacatgc     300
tagaaggtga tatgtgttag gaagaaaatg tagatctggg taatggcaga ttaagagaaa     360
cttgagaggg gaaaggcaac ttgcagtttg ctcttgggat gagaggaaac cttgaggaga     420
cctgggttca aattctatct ctgcagcatc cagattgtgt tcctctagag acatgaaaag     480
agacttaagc ctcagtttca gttagagccc agtggtccca tctgtaatcc cagcacttgg     540
gagtctgagt ctgaaggatt ttgaggtcat tctgggctat ataatgagac ccccactcaa     600
gacaaaacaa gccaggtgtg gtagctccta actgtaatcc tagaacttgg ctaaggcagg     660
agccaaaatc aagccaggta cggtattgga ggcccgtgat cccagtgctt agaaggtaga     720
ggcaggacaa tcagttcact gtcaccctca gctacatgcc aagttttatc taacctgggc     780
aacatgagac catttcatag aaaaagacca gcctccgttt ccacatctga agactggagc     840
agcaatacac tgtagctgct tatcatcaag tacttcacat gtgataagtt gttcctgctt     900
ggttatacca cagccacttc tcaatggctc acaatgaagt gagttattgc cattttaaaa    960
agagatgaga ggggcaaagg ttaaatgact tgcctgagat ctcatagttg atcatcggtg    1020
aagctgggat ttgaccatcc agggtcatcg tccccctgcc acacatagga atggtgaact    1080
gaaactaggc ccaaagcact tgatacttac tgtggcctgc aggcaacact ggagcattct    1140
gagaaatgac tagccctggc cgtgggtgaa tagggagtgg ggcagggagt gggggtgggg    1200
tggaggggtg cagcttctgt gcttctgtcc tgttgatctt ccagcagggg cccctctcag    1260
ttgagatccc ctagacggct gaccacaggg ttctgcctgc agccctgagg ttgggctcca    1320
gggctgagcc tgtgtctctg atccactcta gctctgtgca cctatgtaac aattccatcc    1380
```

```
agagatacct ggagacctcc tgtcaccggc accggatgct gccctcggac aacatgtggt    1440
ccagccagag gtttcaggcc cacctgcagg aaatgggtgc cccaaatgcc tggtctagtg    1500
tcattgtacc cggcatgaag gctgctgtga tccatgccct gcagacctcc caagacactg    1560
tgcagtgccg aaaggccagc tttgagctct atggggccga ctttgtgttt ggggaagact    1620
tccggccctg gttgattgag atcaatgcca gccccaccat ggcaccttcc acagctgtaa    1680
ctgcccgcct gtgtgctggt gtgcaagcag ataccctccg tgtggtcatt gaccggcgac    1740
tggaccgtac ctgtgacacg ggagcctttg agctcatcta taagcaggtg agatgtccca    1800
gcacctccca caggcaaccc tacagcaaag ccctggctgg ggtctgctgt gagacagagt    1860
tcaagactga ctctacacac ggggcatctt aacacagaca cgtcccactg gcctgtctcc    1920
tcatctgtgg aagatactgt cctttgagag ccattaatgc catgagtttg tagtcatagg    1980
tagtattttc agaggccctg ggacctgctc agtttccatg gtaattccaa gcctctaggt    2040
agtaaccttt ttctctcatc tgtaaagtaa gactgtacct ggctcctcct ttgtgtgctg    2100
tgagaatggg tggtttgatc ttcacacaag ggtttgctaa agtaccaagc tggaggacat    2160
agaggatatg aggccatgaa cctcaaggcc tgcctatcaa gagttaatta ttagtgtcta    2220
tcattgttat aacgattatt atgttactca tcttcttcca aaaacagatt tgatcttgct    2280
tatttataat aagtatagaa ttgcttgggg ttttttgtttt tgttttttgtg ggttttgttg    2340
agatagggtt tttctgtata gctttggatc ctgttctgga acttgctctg tagaccaggc    2400
tggccttgaa ctcacctttg actgcctctg cctcccgagt gctgggacta aaggtgtgca    2460
ccaccattgc ccgacctaga attgtttttt attcagccaa aaacattac cttgccctcg    2520
tggtctaatt ctctctagaa acacccttag gagcacacca ggggcatgcc ctatagaaat    2580
cctaggtttt ctcagtccag tctagttgac aactgatatt agccaccaca gctggacatg    2640
gggctccacc ttccacctcc cagtatttgg aaggctgaga cagggatca cttttagttc    2700
aagggaagct tgggttacac agtgagttcc aggctagcct gggcttcaca gtgagaccct    2760
acttaaaaac atcatacaaa caaacaaaca aacaaacctt taaacgtatg ttttttaaggg    2820
tttctgaatt ctgaggacag ttttttaagat ctttgagcta agattcacca aggtctaggt    2880
ttgctacagg aagggaaaac actgatcacc tgacctgggt ggcctcatgt ttcctacagg    2940
tcctgatcac cttagaataa tgtgctggca aagggttccg tctttgttag ggatgccatc    3000
actaggtgtc cagggtggaa tccaggcctg cgttttttagc atgtgcagtt ctactgagct    3060
acacctccag cctaaaaaat gtaaaggagg agatgcatgc aggtgtgcat acacctgtaa    3120
tccctgggca acagaagcaa gaggactgtc acaggttcac caccacctgg ttacagggtt    3180
tataataagg tcctgtcaca aacaatgtag tcttggaaga gaggagagga aatgggggaag    3240
aggaagtaat ttgcagtttta aaatagagca aaattgccgg gcgttggtgg tgcacacctt    3300
taatcccagc actcgggagg cagaggcagg cgcatctctg tgaattcgag actagcatgg    3360
tctacaagag ctagtttcag gacagcctcc agagctacag agacaccctg tctcaaaaaa    3420
aaaaaaaaaa aaaaaaaaaa agcgaaattt gtatggacat ggcaacacgt gcctgtaatc    3480
ccaacactta gggggctgag gttggaggat caggagttca aagttatcct tggctgtatg    3540
tgagcttgaa gccaacctgg gcctacagca ctgtctgttc cacaatctgt ctttatctgt    3600
ttgtctcctt atgttgttca gctcggtctg ttctctgaat gtttgtctca gaacaaacaa    3660
aattgaatag ggctgggcat acgcactttt caaatgtcct ttgtccccca ggtatctttc    3720
attgctgatt tggttttgag cttgagggtc agtgtacaac aaggtggtta caatggtggc    3780
```

```
tttgtctgtc tctgatctcc tttatctagg acagtgccac tgctgtatcc ctggcaccct    3840
ggtcctttgc aggccaggca ggccagcctg caccaccgcc ccacactgtt ttatctgttt    3900
ttctccttat gttgttcaga tcggtctgtt ctctgaatgc cctgtaaact agaagatagg    3960
ctaacaagct gatggggttc agggttgaga tttttggcaa aaaacactca tgtgatgcta    4020
ggtacctcat gtgactgtca caaggcacaa ccaggaatct ctagttccca atgccgaatt    4080
tgaccttaga ctaaggtggc tgccaccaga gccacatcct cccctttgta gcttttttca    4140
tttttcttta cattatttat tgtgtttgag tttgtacatg tgtgtggtca cacatgccac    4200
agcacacatg tgggagtcag agggcaactt atgggagttg gttctctcct cccatcccat    4260
gggtcctggg gcttgaactc agcaagtacc ttataagcta tctcaatact gtttgcctcc    4320
aaaatgtatt actttgtgta gctgtcccct ttctgttgct aataacagaa tactacagac    4380
agtgtaagtt acaaagaaaa taggctcaat tgtatccatc ttttgctgcc catggcatga    4440
aaacacttgc atcccaacac aggccagagg tcgctttagt gtgaagcagg attgagtgca    4500
tgtctgcatg gctaagactc tctacttctc tggtttcctg atccctaggg ctctgggact    4560
ctagatcctc tggaccccctt gataatagag ggagcttcct gtttctcaga agtgcctttt    4620
gaccatatat cccagaaact gattccatcc atctctgccg tgtgtcacta gtcactagat    4680
ggcgtcactg tcatctctca ctagtgtctg agatggcctt gtcttctctc ctgcccacag    4740
cctgctgtgg aggtgcccca gtacgtgggg atccggctca tggtggaggg ctctaccatc    4800
aagaagccca tagcagcttg tcatcggcgg acagcggtcc gctcatcact ccctcatctg    4860
ctggcccagc aaggctgtgg ggaaggcaag gactcaggac ccctatcca caggtcagct    4920
tctaggaaag atgctggggc caggagcctg ggacacactg agaagccaga ctctgcggcc    4980
accacctcag tcccccggaaa ggggaagaaa ggcaaggcaa aaagtgccac agccctggtc    5040
tgcatcaccc tgcagaaatg ggagtcccac aacaccaggg tgggcccac cttcaacagg    5100
ttaatgtgtc tgaaacagcc tgaggcctgg ggtagtacca tgtcccccaa accccgcagt    5160
gttcccaagg ccatttctgc ctgctctcca agccctcccc aagcatctgg gcttgccctc    5220
ctgccaaaag gccaccagtg atagcaagta tgaaccaaat atctttaaat acataaccaa    5280
atgagtatta caaagtagtc accctgccag gcagttagac caaaggctcg gtcctagagt    5340
gcgcgcccag agtccagacc catgctgctg ctctagccag cctttgccct caccttttctc    5400
tggagaaagg tgctgccacc atgcccttcc ccattcctaa ccagcccct cagccctcat    5460
aacgccctag tgaggtaggt gctattgtcc ccatttttcca gccgaggtag cagcaagttt    5520
aaggacgttg cccgaggttg cacagctcag aaggggcaga gctgggatgc agacccaggt    5580
ctgttggtct cccaaccctg tgttcttccc actgcctctg gaggaggagc tgggaggggc    5640
tccatctgcc cttaccttgt atccccccacc tttacacatg tactgtggaa caattggtca    5700
ggctggggcc tcacccagat cctcacagct tcccttctcc cacagcccg tcctacctcc    5760
ctagtctcca ttccaaggcc tggctgcctt cttcccatgt gctccgaccc cagggccggg    5820
tcctcagact accgaatggc caactggtgg gctctaaggc tctgtcaacc acaggcaagg    5880
ccttgatgac tctacctact gccaaggttc tgatgtcctt cccacctcac cctgatctca    5940
agctggcacc cagcatgctg aagccaggaa aggtgggcct cgagctgtgc ctcacaccct    6000
ggcgggtagt gctgagcagt gggatcgggg ctgaagggca cgaacagagg gcagcgctcg    6060
gaccatacag cgccccaggg aagggcttgt cttctccaga accctgttcc aagacagagg    6120
```

```
cctgatcata tctctttccc tccctcctt gcaccgaggc tgctattccc ctgcaccttc    6180
gaggcccca ctttggaagt gcctcgaggc ctctgccctt tgaagttgga cctcttccta    6240
gcacccacag gaaagtcacg gccaaaggca agttcaaggc catactctgc gacaaagcca    6300
gggctgaggc atacccaag aagaggctga gccttcccaa acccttgacc cttattctga    6360
catgccggac actgagaacc atgggggata ggaggctaga gaaaccctg ctctgatctc    6420
tactgcccca tcctggatcc agcatcaaat taaaaaagc aattaaagtt ctctggactt    6480
ggcttgaata atgtgcggct aggctcataa aagagttgac cagcagggcc tccatcagca    6540
agggccacag tccccaccca gcgacagaca ttggctttct ctgcagggag acggatgggt    6600
ggggaaagag ccttcactat acagatgatg acactgagac atggcttgcc tgagaccaca    6660
gcaggcggaa agtcagccat caggagtgcc ccttcccaaa gacaagctgg gctggcagaa    6720
gagcttctga tggtcacaga acattatgac aagagacggg ctttccctaa acctcagcct    6780
ttctccggag agtatgtccc tcagtgaggg gtcggtcaag acacctcaaa ctgcaaaacc    6840
caagaaacag gtcaagtgtg gcatttccta cctgtagagc ctcagctgct ggtcctccaa    6900
aagcggtatc tagctgtagc gtgtgaatgc ttcctgagtg gggcagggtg gagaggagag    6960
tgcggtgttg aaatccaatg acctgtgtct cccaaagtca gaagagctca tgcctgcaca    7020
gtggtgtgtg tctgtcctcc caggacttgg gaggcagagg caggtgcatc tctgaattcc    7080
agtccagcca gggatatacc aagaggccca gcctcaaaag caaacaaacc tcctcgtgac    7140
caggagtaca gcagatgcca cctccagacc tggccactgt tcacttgagc agagagcaca    7200
gtccctggtc aacacttgct ttctcagcag atcctcaaaa gcagacttgt gaggtaggac    7260
ttttattatt ttaagtccag agagcggtca cctgcccaac gccacacagt aagtgagtgg    7320
tttaactggg atttatctta ggttggtagg actaaggagt caaagacctt gaccgtactc    7380
agcaccaagc ccactgtcct tgagctgggt cacggccctt cttttctattt tccaattggg    7440
ggttaagcac tgtctatcgg tgagagagcc gcaggcactg cagggtccga gagaagtacg    7500
agggtagggg tgccacaagt tcactagggg ggtccctgga tctggtgcct gggaggagga    7560
ggcggtgcaa gtgcaggtgc aagggcatct gggccacctg gaaggacgc aggcgaaggc    7620
gtctgaggag agcttcgtcc agcacctgga gtgggaaaga cagcagccca cctgagttcc    7680
agccagagga gcccctggct ctgatggacc tctctggtct gcaactgcca tcattttctc    7740
aacaggcagg cagggatttc tctccacaca gagctaagtt acgtttcagc tccttttgtg    7800
tttagtgaag ccatgtgatt aagccactca ccaatgggat gtgaggaaaa cacagaccta    7860
gccctcaaag ccccgattca caaaaacatc cagtctcccc ttatggccag gaagcaatag    7920
cccttttctc caagtggcta cccagagtca ggtccactcc tactgtatgc ccatttgcca    7980
gacttaatcc aagaagaaac aatggacttc agggcctgtc agaggtcagc tccccactcc    8040
ttgagctaac agacagaagg aagcctgagg aagtcacagc accacagagg caagggtggc    8100
cccagaggcc aagcctgttc ccccaattcc ctaaatacag agcaggcatg tgggcctgaa    8160
gacctacctg tctctggagc ttggtggtct tggctggcca cagaaagcgc tggcccagaa    8220
cggtgcccac tcgaggagca taggtgtggt cccaagcac tgggcagagc tgtagagcca    8280
tgtgcacctg aagctgactg gggaacactg aaagatgggg ggaggcagtt gctcttcttg    8340
atcatcaagg actgtcccca ttcccagagc ctgtgcatct atgaggtgac ctctgcctcc    8400
acagagggcc atgagcagat caggacaatg acagctggca accttcccag cctggggca    8460
ttgaacccaa cagaactgaa gctcctggga ataagtatgt gggttgggtg ctaaactgtg    8520
```

```
ggtgtgcacc taaaactctg cctcctgctg agcccactct cagagtcccc agatgctctt   8580
ttttttttgt tttgttttt gttttttcag gcggggtttc tctgtggctt tggaggctgt    8640
cctggaacta gctcttgtag accaggctgg tctcgaactc agagagaggt gcctgcctct   8700
gcctccccag tgctgggatt aaaggcatgc cccaccaccg cccggccacc agatgctctt   8760
tggatgttgc aaaacaacat cttcctcata ggcttcattt ccctgcaga gtactgttca    8820
gccctacctg tcagtggctg cagctggacc agagcacagc cacagcctgt ggccatcaca   8880
tggaaatggc tgagggtcct cttgacacct tctaggatgt cctttcgaga tggggatgtc   8940
acggggatgg cctaggatac cagtcaagaa tgacttagca cacacgtagg agcccaattg   9000
agccacccct gctgccggct gacttaggac agggcctcag aacaggcagc agcaacttgc   9060
ctgttagagg acaggggaat agccaccca tgcacatagt gcagactcct ctgtaaggca    9120
aaacctgaaa ggactcctag tggcttctga ctcacaagat caatgccatc catgcgttcc   9180
agcttcaggg ccacgtggat agtcccctca gaaggctcag ggatgccatc agtgatgcca   9240
ctgagaaaga gaaggaagt ctcagagcag ccagctggga ccttccttgg ccctgggagt    9300
caccccgcat ctctcaccag taggtggctg tgggcctctg tgttctcctt gagtgaacga   9360
agaacttctg caagcggctt gctgtctggg ggcagctgga gagaagcaca agcccagacg   9420
cctcccctgaa agaagaggac aagtcacata aagcctcttg gttggaaaaa atgagggcca  9480
gattggctgc tcctgcagag gactagcact cggcacccac atagtgggtc ccaactgtaa   9540
ttccacttcc aagagagctg atgccctctt ctggcctctg gggcaccggg catgcactgt   9600
ggtacacaga cacacatgca ggctggcctc cgggggcaca aggcatgtgt ggtgcacgga   9660
catacatgca ggctaaacac acatttaaaa acaaatcttt ggtctttttt aaaggagacc   9720
ctcccaccaa ggggctggag aaatgaatca gtggttaaga gcactagctg ctcttccaga   9780
gtacctgggt tcagcaccca catggcagct cacaactgta gctccagttc caggggatct   9840
gagaccctca cacagacaca catgcaggta aaacaccaat gcactatata tatatatata   9900
tatagataga tagatagata gatagataga gagagagaga gagagaccac cttcccacct   9960
ccccaaatga acaccaggac tacagtccag acctaagaaa caaatcctgg ccaggcagtg  10020
gtggtgcacg cctttaatcc cagcacttgg gaggcagagg caggcgcatc tctgtgagtt  10080
cgagaccaac ttggtctaca agagctagtt ccagggcagc tccaaagct acagagaaac   10140
cctgtctcaa aaaaaaaaa aaaaaaaaa aaaaaaaaa aaaaaaaaa aaaagggggg      10200
ggaaataaac aaatcccaag acctttttc tggccccag agaactcaga caaatgccct    10260
aagagttact acacatgcca ggcacctgaa taggactctt atatacagtg ggtgtaaaat  10320
aaaggcccac cacactcctc acttactttc caggtgctcg cacaacctgg agctcccggt  10380
gtttgagccc cagggcctgg ctcagctgtg gcagcacaga aagcaaggtc agctccccag  10440
gtctccctga gaagtaagag ggagaaaaca agttgccaga gcaccatcca acgaactcct  10500
ccccaccagc ctttccctcc ttgtccctgc ccataccgt cacaggcaga ccctgtggct   10560
tgttcagtgt caccagaggt cctgaaatat tcggtagatg tcagcaaaag cagggcagcc  10620
tgtgtgcatg cagcctctgg ttataagctc ccaagcccac tccaaactga acttcctgct  10680
ccccgcaccc agggcctttg cacctgctgc cctgagcttt cattaatatt gggtccctta  10740
tcacacacct ccctataatg tgtgcccctc ctacagtcct tgactgtttg gtctgagacc  10800
agctcaaaca ggccggcctc aaactcaact ataggtaagt ctggtcttga actcttgatc  10860
```

```
ctccttgcct ctgtctccca agttctggga ttacaggtgt ggtcaccact cccagaaaca    10920
gcagagattc actattcctc acatcagaac gcttgctctc tcaaggcagg agccagccat    10980
atttatccca gtactgtgta gcctcctcat tgctacaatg cactgaagtt cagcaaagtt    11040
gtcattccta aaggcacaca gcatgctgct tacagacccc aggaaactaa cttctgctcc    11100
cgagggtctt agaatgcgag gcggtgtgaa ggtttcctat gcctggcgga gggaatgtga    11160
cggctacagg ggtccgactc caggggggtcg gaggctccct caccttgctg atccaccaca    11220
gctgccctca gcacctcagc cagctcctcc gggccgaggt tctctgttcg cagaagcccg    11280
gggaagggct ggtcctccac tgcgtccttg cacttgctgg aaccttgagg ttgaggccga    11340
cccctgagaa aaacgacaga agccggtacc tccaacgccc acgctgccca gtgcagcctt    11400
ttcgtacaca accctcagaa cccccggctc ggctgacagt tgtggtccac aggcccccaa    11460
gactacagaa ggggcatcag acgctcggag cgccaaccat ctcgtgtcgg gtcacacaac    11520
gcggctggga ttagaaccca tgtcctgatc tgagtgcccg acctgccctc cccttgtcct    11580
agcctccctc ctacacggaa gtgttgagtt ataatcaccg ggcctcggtg ccgaagcctg    11640
catctctcgg ccgtgcgcca gccgccagcc ggggccgcca ggtgccagac acacaacgcc    11700
aaacgcggaa gacgcccatc gccgcagcaa gcacagacga tgcgtgtcc acggactgcc    11760
ccaccgcgtg catcctccgt gcgccgattg gtcagcctgg ctgtcaatca gagcatcgag    11820
caggcggagc ttcgaggacg gaagagccaa actttccttt ggctgaggaa ggtaaagtac    11880
ggtctccggc tctgctttgg gggaaactga ggcaggaggc gcggttattt actcgcggta    11940
gaggacgtgt cttagaatag aaagaggcga gtttgcagat agattgtttc agttctcagg    12000
acccttaatc tgaaacccat ccttgtaaag cagagggaga aggtgaagcc ccacagcctt    12060
cgggccaggg cacctgcatg gaaatggtct gcgacattaa ccatcccatg actgtggctc    12120
aggtggtaga gagattttc taggatgcac gagttcctgg gttcgatccc cagcaccaca    12180
cgaagaccaa gatcacagat acagactgag ttggagacca gctgggata tgtaaggccc    12240
ttctatcaca agaaaaacaa actaggccgg gtgtggtggt gctcttcttc aacagaggcc    12300
aacctggtct agacagtgag tttcaggaca gccggagcta cacagagaaa ccctgtcccc    12360
cccccccaaa aaaaaagaa aagaaaaaca agcttggtgc ggtccacata gtaagttcca    12420
cactggccag tatgttgtta attccaaaga tggaatgagt gtaaggaaaa aggccagcca    12480
aagaaacaca ctttggctct gcaaccagaa ccaaagaaat gcacccttgt cagaagccag    12540
ccttggtgac gccccccccc ccaatgccta gctagccgcc agctagccta gcatcccacc    12600
cctcaggttc caggacctgg cctgagaagc aactaacacc ttcccccatt tccttagtta    12660
gtgcttgaga taaacatagg agattccaga tacctggcct gagaagcaac taacacctat    12720
tctttctcca cacaggagat tccggatacc tgcctgagag caattaacat tcattcctcc    12780
cccacctcct ttttctctgc ttcctccttt ctctataaaa accccttgta ataatcaata    12840
aatgggcctt gacaagaaaa cctgcttggt cccgctcttt ctttcccgcc catcattttc    12900
aggcgtgatc cacctcggac tcaggaatta ccggagcccc gagggccggg gtacaccctg    12960
accctgaaac cagtgccaga gaaacacact ttggccctgg aatcagagcc agtgaaagaa    13020
atacaccctg gctctaaaat cacagtcaaa aggctaaaaa ggaccagtga aggaacaca    13080
ctttggccct gaaaccagag ccaaatctaa ccctaaacct gtgcagaaaa ccaaccaatc    13140
cctgagcagg agatctagcc attctgagct cagggattga aatctgacca atccccaccc    13200
tggaaatctc cctgggaaaa ctctgccccc ccctaagaat ccctatataa accctgtgcc    13260
```

```
tgttcagctt caggctgcct ggctgccctc tgccactgga ttcttgaatg aggtttgggt    13320
aagaactttc gccggagcag agaccaccct acacactggc tctccagggg actggagttg    13380
aactgttaca atttaaccag ggaaaccctc tcctccccaa gcagagctga tacactgagg    13440
aaggcctttc cctgaagcag ggctgtaagc cgctatgctt actgtgacct gtggcattcc    13500
ttggctccta aacgccagaa tacctttcca tcccagctgt aacactcagt attctgtgac    13560
tccggagtgc cagaatactt tgcatctgag ccataacaca gtattctttg ctcccgagt    13620 accagaatcc attccttccc atccaatccg ttgaaatgct tacaatgaga aaaaccacga    13680
acccaaatca ttgagaccaa attaattaaa gttttttttt cattcatgta cgagactgcc    13740
tcccccaagg cctgatttga gaggtcagca ttggatgtga ggaagacaag ggggttttgt    13800
tgttttggtt ttttgagaca gggtttctct gtgtagcttt ggagcctgtc ctggaacttg    13860
ccctgtagat taggttggcc tagaactctc agagatctgc ctgcctctgc cacttgagtg    13920
ctaggattaa aggcatgtgc caccaccgcc tggcctcacc tggatcacac agacacatat    13980
atacataatt aataaaatac agacctggcc tttaatccca gcactaatct acatagtgag    14040
ttgcaggaca accagagtta catgaccctg tctcaaaaaa aaaaaaaaa aaaaaaaaa    14100 acaacctaaa taaataaaat gcagaaagta acaatatgta cataataaaa ataatgaaat    14160
aataacataa ttgaggaaca gtggggcatg gtggcatgtg cctttaatcc catcacttac    14220
tgatctacat cccaagcctg aaggaccttg ctgaaagggc tccagcacta gactgttgct    14280
tctggcagag aaagtggctc tcaacctgct ggtcaacgac ccctttgggg gtagaagggc    14340
cctttcacag gggtagccta agaccatcag aaaatacaga tattcacatt acaattcata    14400
acagtagcaa aattacagtt ataaggtagc aacaaaaata attctatggt taggagtggg    14460
tctccataac atgaggaact gtattaaagg ttgcagcatt aggaaggttg agaaccacca    14520 atttagggc agatgctgcc tccttcacag cactcagcca cagttgtgtt gtgtccttgt    14580
tgaggttcta tccggtcctc caaagttcag ctgtgggaaa ctaaatcttt aacttcataa    14640
taatggtaat tggaggctgg agtaattagt accagataaa atcatgaaga gtgtgcttcc    14700
atgatggcca ttaacagctt tctaaggaga gcagagaaaa aaaccttttc ctcgttgtgg    14760
aatgacttcc tccgtgttgg tgtgcaccag aaaggccccc tgcttgtgct aagtggagct    14820
atgccatgct cttggactct gcagcctcta gaaccatgat ccagatcaac tgtgtgtctg    14880
tgtgatttgt tttatttta ttatgtgtgc atgcctgtgt gtctgcgtaa gtgtatacca    14940
tatgtgttgc aggtgcacgg agaggccata aaaggggcat cagatcctcc gaagctagag    15000
ttttaggcag tcgagagcct ccacgtgggt gctgggaact gaactcagag cctctgcaag    15060
ctcagccagt gctcagccag tgctcctcag tttgtgtgct tgttttcagt actgcagatg    15120
gatccaggac cccacacgtg ccaggcaagc attctctcac tgagctgcac cctcagactg    15180
gtctcaggtg gtttgttata gcaacagaaa acagacatgt ggaaggagtg atggcgtatc    15240
ttgactgaga ggaggaataa cttggctact cgcacagcac atgtctgggc aggttcacaa    15300
ggaggcttcc agggacaatt ggcacctaag aaccctgacc taatgaatgg atgaaccatt    15360
cagaatttgg atgggttctt ggggggggt gagggaactg tggtgggtgg ggactgcttg    15420
gaggaagtag ggtgtttgtt gtgggtggct ctcggaggct atgtcttaca ttggctcctt    15480
tctgttttgt ttctttcaat ttcctgttgt gtgctattct gctacaaccg cctcacccag    15540
tagattgcag cctctgttaa tcaagacagg gtcttactgt gtagccctgg ctggcctgga    15600
```

```
actcatagag atctgtttct tctgcctctt gagtgctgga attaaagacg tgtgccacca    15660
ccaccacctg acctagagga caactttatt ttttttaatt ttttatttat tatgtacaca    15720
ttgttcctgc ctgcgcacca gaagagggca ccagatctca ttatacatgg ctgtgagcca    15780
ccatgtgggt gctggtactt gaactcagga cctctggaag agcagccggt gctcttaacc    15840
tctgagccat ctctccagcc ccctggatga ttaattgtag aagtttcagt tctttctttt    15900 tgttttttgtt ttttgagaca gagtcacact acgtatcttc aactgatctg gaacatgcta    15960
cgtagacaag gctggcttca aatgtgtgtc aatgttcctg cctctgcttc cagagtgctg    16020
ggattatagg catgtcccta aatctgttat tttttaaac acttattttt gagggggagt    16080
cggtggtggt gctgttgtac gtacatatgt agagatcaaa gggcatcttg tgggagtctg    16140
ttctctcctt ccaccaatgg gttctaggga ctgaattcag gttctggagc ttgacagcaa    16200
gcaccttaat ctgctacaac atcttgttgg tactaaatcc atggagaatt gaaaggattg    16260
tttattgttg ggcccgggaa tatagctctg tggtagtaga atgcttgcct aatatgtgtg    16320
agattcttaa aaaatcattg attgttttct taaaccaact ttttaatttg ttaaaaccaa    16380
cttttaaagg atatatctag gcatggtggc acacagcatt aaccctagca cttgagagat    16440
agaggcaggc agatctccta tgaatttgag gccatcctat tctacgagtt ccagtacagc    16500
caggactaca ggactgtgtg atatgcacaa cacaggaagg actgatgaca aatttggtaa    16560 aaaaagaaa gaaaaacagc aagtggtttc acattgtccg gcttcacctg gagtgggtga    16620
ctgtgggtac tcctgaagcc tcccaggagt gggtgactat tctgtcagac tgtgggtatt    16680
cccgaagcct cctaggaggc ctcctgtgca tcacagaagt ggcttgagca agaacttggg    16740
acagactggg caagtgcaca gctataatcc cagcactgca gaggtgaggg ctgatgggtc    16800
aggagctcac agttatcctt gactacagga agtctgaggc cagtctgagc tatgtgagac    16860
tctaaaacat acatgagtca gtgagttggc tcagccagta agggtgcttg ataccaagtc    16920
tgaccacctg agtctgatcc ccagaatcca catggtagga gcagagaacc aactcccagg    16980
agctgtcctt tgacctctgg acttatgcta ttgcatatgc ataccaatac ataactccct    17040
aaaatacaaa atacatatgt ttgggctttt tgtttgtttt gttttgtttt ttcgagacag    17100
gtttctctgt gtagctttgg agcctatcct ggcactcgct ctggacacca ggctggcctc    17160
caactcacag agatctgcct gcctctgcct cccgagtgct gggattaaag gcgtgtgcca    17220
ccaacgcccg actgatgttt gggcttttttt gatggttttt atgtgtgtgt gtgtgtgtgt    17280
gtgtgtgtgt gtgtgtaatt agaaggagaa agagagagag ggagagagag acagagagac    17340
agagacagag acagagacag agacagagac agagaggga gagagagcca aagtctggtt    17400
tgtggcccat tcaactaagc agacttctcc tccaccaatg gtgtccacca atggcccagg    17460
aaaggccatt tccccacttg aaccagcgcc tggccctctg gagggttagt tcctttactc    17520
tttggaggtc tccctcctg ccccatagca ggctgccctc tcttgctccc ttcccacagg    17580
cagctacctt catcccagtg ggctatgagc tcctggaaga aaaggaggag ccaaattttg    17640
cctaggctga gggctcagtg ccaggtggca gccacagtca actgctgaac ttgtgaaact    17700 ggacccccagg agaagaagcc tgggacaaac atcagcttgc atcagctccc tctggctcag    17760
ttacagcttt gcagcaggtg tggacaggct ggtgcttcag caatgggaaa caggactgat    17820
gcaaaccagg cctccaggag gccaagccct ggagccagcc tgcagtgaac cagcctccag    17880
ccacatctac aactgtgtga gggcctagaa tagaaagtgt acttgacctg tctgtccttg    17940
agtgctcttc tcttctcaca cttggctcca ggcatggggc agcttccagc gatggctttc    18000
```

```
cagacaagct tgagtaactt ggcccctttgt cttagtgttt tctaaatcca aataggcttt    18060
acagggagga ttgtgaaatt atgttagctt tggatctgag agccagactg aaacctggct    18120
tcctacaggc ctagtctttc ctgcttaggt cagttacctg tcactaataa atgggggctc    18180
cttttcctac cagccaccaa gatggctgaa gtggaggaga agaaatgaac cttccacaaa    18240
ttcacatact acaatgtgga cctggatcag ctgttgacag gttctaggaa ctgctgatgc    18300
agttgtacag caccccagag gtggtgtctg aaccacggcc tgtggcagaa gcagtactcg    18360
ctactcaaac acctgagaaa gctcaagaag gaggcaccaa ccatggagta acccgaggtg    18420
ctgaagaccc acctgaggga cacgatcatc ctgcctgaga tggtgtgtgt gtacaatggc    18480
aaaaccttca gccaggtgga aatcaaacca gagctgatca actgctacct aggcgagctc    18540
ttcatcacct ccaagcccat gaagcatggc cagcctggta ttggtgccac ccactcctcc    18600
agctgcatcc ccctcaagta gctgtggcca acaaagactc atgtttaaaa agaaaattgg    18660
aagccaggca ttggtggcac acgcctttaa tcccagcact cgggagacag aggcaggtgg    18720
atctctgtga gttggaggcc agcctggtct ccagagcgag tgccaggata ggctccaaag    18780
ctacacagag aaaccctgtc tcgaaaaacc aaaaataaat aaataaataa ataaataaaa    18840
taaagaaaag aaaagaaaag aaaaatgggg gctcactctg agaagacctg actcctcctc    18900
ctcctcagaa ctctctggtt tgtttttgca gtgctgggt cactgtgcca ggctagagac      18960
tcactgcaat ctgagggtgg aagtgctgag caggaacagg gaactgtgta taagctggca   19020
taggcattga taaattcccc tgtagatgga ccaggacctt tcaacccgaa cacatggaaa    19080
gttattgtaa aatacaacag ttgggaatca aaagagtggt ttgatccacc ttacaggcaa    19140
atttcattcg gaaactgaca acacatatgg atcatgtggt ctgcctgaat atcaaatatg    19200
gcaggcctca aaaatcaact gcagattta atataacatt taattattca tctattaatt      19260
aatttattct gtctcataat atcaaacctt atctattaaa agggagcagg gctgggatg     19320 tggctcagtt ggtagagaat ttgcctagca tgctggaaac cctgggttcc gggttcaatc    19380
cccagagcca cataaattgg atgtggtgtt tcacatctgt aatgctagca cttaggaagt    19440
ggaaacaaat ggatcataag ttcaaggtca tcctccacta cataataaat ttggagccag    19500
cctaggcttc tgtatctaga agaaaaaaca gggcaccact gatgcaactc attgcataaa    19560
agcaattgct gtgtgagcct gacaatccaa gctcaatcct tagaaccaag agtggaatga    19620
aagttgtctt ctgggccatg cacgcctttg atcccagcac tcgggaggca gaggcaagtg    19680
gatctctgtg agttcgaggc cagcctggtc tacagagtga gttccaggat aggctccaaa    19740
gctacacaga gaaaccctgt ctcaaaaaaa aaaaaaaaa aaaccaacaa aaaaagaag    19800 gttgtcctct gacctccaca cctgcaccat agtactggca taccaacaca cacacacaca    19860
cacacacaca cacacacacc agtaatgaca aatgctatct cctgtaattc tcggcaaata    19920
gtttcaaaca aagaacacag gcaaagatga ggtattggca taaataattt acttcaggct    19980
ctaataccat acattagtgg ggaatgagaa caaaaggagg aattgtctga cttcccctgg    20040
ggatcacaaa ctctatccat tcggcccagc aagggcgcca atgaaaggtg aagaagccac    20100
gattccatcc aagtccagct tggtgaaccg gtgagtttac taggttactt acaggtgggg    20160
cctgggtgac tcaaaatcac aggtgactcc ctccaaatct gcatcagtga catcctggct    20220
ttagttaacc ttttacctct tatatactct agcaccgccc caagatcatg agcagctggg    20280
gcggggcagg agggaggaat ggctgggatt tcaggtgcta agaccccctg acactctcct    20340
```

| | |
|---|---|
| ccctttctaa tacaggtgtt aactatttcc atacoctagc cataggcctc accgtcactg | 20400 |
| tggcatttgg ttcattttgt tgtcttgatt caggtcaaag tattctggag gccaccatag | 20460 |
| caatgtctgt tgcttgatga gcatggtcaa ggcaggaggg gactgcagag agggagtggc | 20520 |
| acatagggat ggcatgtgaa gaccgagtgg cagacttggt gccaaagcct gccagggaca | 20580 |
| agtgtttgtc ccctaaacta cctgtgacat gaaggaagga actgagccag gctaggaagt | 20640 |
| tctcccgtga ccagcccacc ccagagctcc agcccttcct gcagtttcct tggtgctgtg | 20700 |
| ctgtgagagg ggtgcaggtt ggtgagaagc tctccagctg ccaggcttgt gggtgcttct | 20760 |
| agcagagtgc aaggtctcca gtcacatcct tggctgggga cggcatctga ggacttgggc | 20820 |
| cttcattgca gcatcttcag acaggcgggg aggagggagg aggtcttggc cttggacggc | 20880 |
| tgttcttcct cagtggcatc caggaactgc tgcatataac tggaggagcc aagcagcatg | 20940 |
| tggcctgtgg cctgcatgct gaagagggcc cagcggagca tttccctggg agacagcaag | 21000 |
| gcactcaggt taaacactcc ccatgctatc tccccaaatg tcttctccat ttttctatgc | 21060 |
| tggcctaaag cagttggctt caagttagac ttctttcttt gttctactt cttttatttt | 21120 |
| tgagatagaa tcttaacact ttatctcagg ttagctagaa attcatttat gtagctcagt | 21180 |
| ctggctttga actcacagaa atctcctgcc tcaatctcct gatgctgttg cagttatggg | 21240 |
| ccaccacacc taactttttt tggtttggtt tggttttgat ttggctcttt ttgaaacaga | 21300 |
| atctggagat cctcctgtct tgtcctccca agtgctaggt atacagacat gtcccaccat | 21360 |
| actgggctca agctagcttt tctccttagg aagatttaag tgtcactaaa gtaaaatgac | 21420 |
| aaaaatgctt ccaagtacag acaggaactg ggaaccaggc tcatagctag ccatccctta | 21480 |
| cacatagttc tgcctctact cttgtgacaa cttttctgga accccttgct ttttcccatg | 21540 |
| cttaacttga gttctcaaaa caaagctttt tattttcttg taatgatatt ttgtttcttt | 21600 |
| cttttctctt ctatggtgct ggggatggaa cccagggctt tatttgtgca taagcagctg | 21660 |
| acctgccatg gagctatgtc cccagcccca tatattttt ttttcaagac agggtttctc | 21720 |
| tgtgtagctt tggagcctat cctggcactc actctggaga ctaggctggc ctcaaactca | 21780 |
| cagagatccg cctgcctctg cctcccgagt gctgggatta aaggcgtgtg ccaccaacgc | 21840 |
| tcggcatcca gccccatatt ttttaaacta ctctggacca gccagattaa tttacataac | 21900 |
| acatgtctac cctttgtaac actgcttctt agactttata gtcttcccag gccagttctc | 21960 |
| agaatgctgg ccacaaggct cccatgcctg atatcatatt ctaagcatag aacttggacc | 22020 |
| agacagggct gaacactgat ccagagtggt tgtttatat ctaaaatatt taaaatatat | 22080 |
| tttaaaatat tataaagatg ggtgatgtaa ctaatttagt gcttgccttt catgaacaaa | 22140 |
| gccctgggtt tgatccccag caccgcaata acccagagtg gtaatatagg actgtaaacc | 22200 |
| taggatccag cactgtggag gtagaagcag gtggatccca agttcaaagt catccttggc | 22260 |
| tacatagcaa gtgtgagacc agcctgagat acatgagacc ctgccaaaaa aaaaaaaaa | 22320 |
| aagctttaac tgttctggtt ctgagctcca gcagccagaa gctttgtgac ttgtaaaatg | 22380 |
| ggtaatgagt ttgaaactaa tgtgaagcac ttagcatttg gtctgatgga cagaaaatgg | 22440 |
| gacatgcagc caagagcagc tggctgaatg caacttctcc cacagctatt gacaagggct | 22500 |
| cggcaggggt cactaggagt tgctggtctt aagaacaata aggaagagaa aacacaagaa | 22560 |
| agagaaatac tgccaggccg cggtggcaca tgcctttaat cccagcactc aggaagtaga | 22620 |
| gacaggcaaa tctctgtgag ttcgaggcca gcctagtctt cagagcaagt tccaggacag | 22680 |
| ctacggttac atagtgatac cctgtctcaa aaaagcatat atatatat atatatatat | 22740 |

```
atatatatat atatattgaa tttagtggcc tgaggcaatg gctcagtggg taaagtgctt   22800
gccatatggc catgaggccc tgaaagccca tgtaaaactg gggatggctg cctgtatctg   22860
tgacccagt  actcctctca tggtgagaca gagagacaag agactcctct gaagctttca   22920
ggccagcaag cctggcccag acaacagaca aacagcaaag accctgcttg aaacacagtg   22980
gaagatgaga ccagcacctt aggctgtcct ctgacttcga aatgcacgct gtggtacatg   23040
ggtgcccaca ttcacacaca tatagagata aagactggct gggcagtggt gacacacgcc   23100
tttaatgcca gcacccttga ggcagaggca gttagatctc tgagtccaag gccagcctgg   23160
tctacagagt gagtttcaag acagccaggg caacacagag aaataagaaa agagaaaaaa   23220
aaaagatata aagactgaaa ctgaaaatat aatatattag ggctagaagt atagcttaat   23280
ggcatggtgc ttgtctagca tgtatgaagg tcctggttta atccccagct ttgaagcatg   23340
tgtgtgtgtt tgtttctttt tgtggtactg gggaactgga cacaaggcct taggcaagtg   23400
ctctgccatt gaactacagc ctcagctttc ttttcttttt taaaaatgtt tatttatttt   23460
atgtatatga gtactctatc tgcatgtatg actttatgct agaagagggc gtgagatccc   23520
actatagatg gttgtgagct accatgtggg tgctgggaat tgaactcagg acctcaggaa   23580
cagcagccag tgctcttaac cgttgagcca tctctccagc cccctcagct ttcttttttac  23640
ccccccacac acaatatctc tctaagttgc ccagtttagc cttgaactta ctctgtagcc   23700
taggcaagct tctaatttgc catcctcctg tctcaatttc ctaggcacct gggagtacaa   23760
ggccatgtat agctttatat atatgtttcg tgcagtgcct tcaaagttat ttctcaaatt   23820
agagaactga gttttgactc tagccagcca gtcttaaaaa ggaatgaaaa taaggcctat   23880
tctacaaatg aatgaacctt gaaaacagaa ttcttgtggg gaaagaatca tgatcccatt   23940
tctatgaggt ctctaggata gatcaatgga gcaacagaaa gtagagtaaa ggtgagcagg   24000
gtctcgggag agggctgaga accattattt actgagtaca gcttctgctg cctggtgcaa   24060
aggttctgga aaccaaggca atgcttgcac aacatgatta gttacttcat gctagacact   24120
tcaagcggcc acagttgaaa aatgttgaat gtgcagattt tagcacgggt gttttttctt   24180
gaaggtctca ttgtgtagct ctagctagaa tttggaactt gaaatgtaga ccaggctagc   24240
ctaaaattct caggagatct acctgcctct gcctcctgaa tgctggctgg gattaaggga   24300
gtgagctacc acacctgacc ccttagtaca ttttttttt  taaatcacag taacaccact   24360
aagtcactca gctaaccaca gtttgacatc agttttatt  ttctctaagt tttattttt   24420
gttgttgttt tattttgttt ttcaagacag ggtttctctg tgtaacagcc ctagctaccc   24480
tggaacttgg tctgtaaacc agactggcct tgaactcaca gagactcacc tgcctcagcc   24540
tcccgagtgc tgggaccaaa gatatgactc ctggcctttt tatttctttt ccatgtgtgg   24600
gaggtagggg ttatgcacct gagtgcagtg cccacagtgg tcagaagagg gcaacatatc   24660
tcctagagtt gcagttacat gtggttgtga gctggctgag gttggtgccg ggaactggac   24720
ctaggtcctc gggctgagtg gttcccttt  tctgtttttg ttttcaatac agggtctgat   24780
ctggcccagg ctgtccttga actcctgatt ctacacctcc aaagtactgg aattatagtt   24840
acattttcac ttacaaaaat attagctgtg gaaatagctc aggatatgag tatgtgctta   24900
gcatgcgtgc tgccctgggt cctatcccca gcacacaaaa gaaagcacat gactgtcatt   24960
ctttgttagc ccccagtgcc aacccaggct ttgagagagt tcagctttgg gtagacacaa   25020
aggacctctg gttagctagt ctcccaccct gctgtcccaa tctactcact tcacgacgcg   25080
```

```
cttggcccgg tagcagtgca ggtcatagga aagtgtgtat gtgtcataga gggtcgcctt    25140
cacgttcagg cagccgatga agtcctgggg gttcagcttg tataggtcaa aggttacccg    25200
ggccacatca atcttctttg ttggcttctg ggaaagggat agctgtggtc tcgtcttgcg    25260
ctgcaagaca agtccatgtt agctcgcctc tgggactcct tccacgccct cgacactcac    25320
ccctgctgga ggagactgtc acctgttctg atgggggctt ccacttctgc cccttctgca    25380
ggaccatgaa cacagtatct cttgccaggg cttggaagta ttcttctgtc tcaacaatcg    25440
tgccgtcttc ctccagcacg agggagaagg gcttgtcttt aagtttcaag atatcctggg    25500
cctggaaaag aaggttggtg acatttctgc catccctatg gagccacaga gttgaggagc    25560
aaaggcccgc agtaaagcac ttcagctgcc agagagagag caagtgagct gccatccatc    25620
cgtgcgatgg actgactgtc actgtggggg cccactcaag ggctgtgtct cagtacttcc    25680
tactcccaag aaggagtgta gtctaataga atgggagtca tatgtgaggt ctttttttatt    25740
gagaaataaa ttacatacca tgctgggcaa tattaggagt catatcgaag gccttgggca    25800
agctaggcaa actgcagcat tgaactatat ccccagcctt ctttgtactt tttgtttgga    25860
gacaggatct tactaagttg tttaggttgg cctggaactc actgtgtagt ataggtaggc    25920
ctcagccttc tatttagatc ttcttgactc agcctcctaa gtaacttgga ttacaggcct    25980
acactaccag gcccagctaa actttatttt gttggtggtg gttttttgtt tcttttgcta    26040
tgtagccgtg gctggccttg aactcacaga gatccacctg cctctgtctc ccaagtgctg    26100
gggttaaagg cacgttgtta tggaataatc ttttggtaca ctgtgaagtt gtgtctttgt    26160
caaggcgctt tctgactggt ttaataaaag aactgactgg ccagtagcta ggcaggaggt    26220
ataggcagga aagcaagaca cagaggactc tgtgaagaag ggcagagtct tgggagtcat    26280
gagcaaatgc agagggaagc aagatgaaag aaggtaccac tatgatgcag agggtagata    26340
gtaaaaggat taatttaagt catatgagct agctaaacac aactctaagc tatcagccaa    26400
gcatttataa ctaataatga gtcttttgtgt agttatttga gaactggcta tcgggataga    26460
aaagtctgtc tatagtgtgc atcaccatac ctggccacta ttttaaattt ttattttttaa    26520
ttatgcgtat atgtatgtat gtgggtcccc tggagcaagt gattgtgagc tgcccagtgt    26580
gagagctggg aactgaacct ctgtcctctg aaagtgcttt taacgactga gccaccactc    26640
tagccccaac aactcatttg taatcttgtt cctgccaaag ctacatggca tgaactgaag    26700
aaacaggtca ttcaaaactg agggacagga aataaaataa ctggcttgcc atctttaaaa    26760
gccagctaga agaatcagca ggtaagggta cttgcagtgc aaactttagc atttgagttc    26820
aatacctgga gcccacagta gaaggagaga aatgactccc aaatgttgcc ctgtgacctc    26880
catgtgtacc ctgtggcatg ggcatgccag tgctcacaca cacgcttcat agacttacag    26940
taataatttt aaatataaaa taaaactgtc tggatttgca ggacaatcag cagtgctcca    27000
acagagtctc aagataagct tggggggggtt cttgttatgt agcccctagtt gggcaggaac    27060
ccctatatag agaccaggct gacctcaaac atgtggtcct cttgcttctt catgcatcac    27120
cacactcagc cttagtttta atttcttttg aggcatacccc agcgtatcct ggaactcaat    27180
tatgtagccc aggctagcct caaacctgag atcttccata tctggtctcc cagatacgag    27240
ccaccatgcc tggctcattt ctccacgtgt aaatatgggg aaggggaatg aatggccctt    27300
tcagcaagaa aataaccacc cacccacggt tggtgtgaaa gacggtagtg cactgccctc    27360
cttctgtcac ttgaccatgt cacttatcac acacacagct ctccaggcgg aaatgccaac    27420
cctccagtgc caacaccttt ctccgcttaa gaccatgcca ctcatgcgca cagacttcag    27480
```

```
ggctctccag aaaccgaagc agccggcagg ctcaactctc agccaaggcc tggagagagc   27540
ctatgcaggg taccggcaga tcccttacct tgcccaggag gtcctccagg ctgtgagcca   27600
tgatgccttt gcgaaccttc cgatctgccg tgctaactcg acagggcctc gccctgggga   27660
cttcccggct gggcttagac accagctgtt gggtcaccac tgcagtgctc actgctacat   27720
gcctggggac aacagtttgt acagcagatg acctgcctgc ggctaccagg tctgcccatg   27780
cctgcctgct tgctgagttc aggtgtgacc tttccttcca accaatcatg gctgcttcag   27840
gcggctttca caaagtccat cagaagacac agctccgatt tggaggggca gggaaatcag   27900
cgggaatctt gcttaaatca gactcacttc agtgcctctg agtggagccc aaggactgct   27960
aacaagtccc caagctgtgt cagtgtggct ggttcttgga ccagccacat tctcctgtgg   28020
atggcttctg cttttgtggc cttgttcacc ttgcctaaga ggcagggtga atggagctg    28080 gtgtgtgtat atatgtgggg tgtgtgtgtg tgtgtgtgtg tgtgtgtgtg tgtgtgtgtg   28140
tgtgtgtgtg tgtgtaaatc ggcctgtaga atatgtgggg actctgaggt acacagggta   28200
gaaagaaagg agcagagaga atttgggtct tggctggaat tccaagtttc tctctgttac   28260
ggatttgcta ggtgacagca tacccagcct gtgactcagt ttcctcatct gttgacttgg   28320
catagttgcc accacttccc agagaggagt gaggctcctg ggagatcagg aacaaaggca   28380
cctggtgccc agcctgaccc tttctactcc agatgtgatg ggaactgtgg cagtgacaga   28440
gagtaagatg gggactgtct agactgcaag atcttgggtg ctaccctagg cctcctgaat   28500
cagatctgtg ggggtttatt gtaagatttt gtctgttttg ttttaatggg ggtcttgctt   28560
atttgtttgt tttttgggat agcatctcca tatatagccc tggtttactg gaactaattt   28620
cctcatctct gtctctgtct ctgtgtctgt gtctgtctct ctctctctct ctggacctgg   28680
acctatgcag accagactca aactcaccaa gatcctcatg ccactgctcc caagagcca    28740 ggattcaaaa catatgccac catgcctggc catatcagct agaccccaca tgactttttt   28800 tgtctttaa aatgggatgc ctatgtagcc ctgactgacc tgggacttgc tgtgcccact   28860
acaggctggc ctcaaaactca gatctgcctg cgtctgcctc ctgagtgctg ggattgaaag   28920
cgtgtaccat cacatccagc ccctacatgg tttttatacc tattaaagtt ttcaaagttc   28980
taatagatgg ctccccagct ttccccttcc ttcccatacc cagctctcct tacctggaca   29040
gtgacttagg gtacaggagg ctgagagact tcatggcata gtccatcctt gtcagctgga   29100
ttgtgttgga cctggatcgg aggcagtaac ctatctggtt agagtgggaa gggagggagg   29160
ggtccctctc tttctttctt tgactcagtg gatcccagcc cccacacggc aaccctctgc   29220
cccagtctct cctcctaccc ccaatttccc tgaatccaca ccaactacac tgagtcagcg   29280
tctaccatcc ccacccattc cacagcccca gaacaactca ctccatgttt ctctgcccca   29340
agctctggtt acactgagct gaggaaccca agtcaaggct gaagaggccc tcactgattt   29400
gtccctgtcc ctgggggcag agtccacatt atgctggcag gaggtgagtc ataccacctc   29460
atgctgtgag agacttgaaa gtcacctatt gtccagaaac tccacaggca gtcagacctt   29520
ggagagcctg ctctaaccat gggcccttga gcaataaagt cctcctgagg cttagaactg   29580
gctaagagaa ctttctgtga tcttaaagac tgtctaggct tgtgttcacc aataccttag   29640
ctgttaccac tgagcccttg gcaccataac taatgtgaca aaggagctga caccgaactt   29700
ctattgagcc ttaactaatt tagttaggta actactgtgg tttgtgacgc caggtacccc   29760
actggacatt acagttgtag tggagtaatc ctgggctcat gtgccccctg cctttcctcc   29820
```

```
tatattgctg ttctctggtt cttgcctgct gagctgcaag tctctgcaca ggcagtctct      29880
tctacctgca atgcttgtct caaactcaga gctcaacata agtcacctag aagccccagc      29940
tcctggctgc caactcagga aagccttttc tggtgccctc ttgcctggta ccagattgat      30000
ccctgtgccc tgcccttcc                                                   30019

<210> SEQ ID NO 5
<211> LENGTH: 29980
<212> TYPE: DNA
<213> ORGANISM: Cricetulus griseus
<220> FEATURE:
<221> NAME/KEY: misc_feature
<222> LOCATION: (1)..(29980)
<223> OTHER INFORMATION: 3' of SEQ ID NO:1

<400> SEQUENCE: 5
tgttcatttc tgctgcagct ctcgggtccc cactgtgcct gttttcagcc cgtagcacag        60
ggacccagtg tgaacaccag gagtgggcag gcatggagaa ctgcctcctc agtgaaggaa       120
aaccattctt cccttctgat aactcggqtt ctccccggtc aaccttacag agttagagac       180
cctcgtcccc acttaatgct acccaagcac tcttgtttca ccctgtttct aatacccacc       240
actcacacag ctccacaaaa cccaccacac ctgctctgtg gtagccaaat accccagctc       300
ttctcctccc cctcacctcc tagcctcctg gcaatactgc gtggccaggc acagcccagg       360
cctcctccat tttatttcta tctcctgtga agccactccc ttggcccag ccccagctgg       420 ggaaaagagc acagggagtg agtctgaaac tctccctagg gatttcaagc cagactgact       480
tccagaaagc cccgaaaggg ggaagaaggc atgtttcgaa agctctagaa ggaagaggta       540
ctgcccagga cttggtacca ggcaagaggg cacagaaagc aacagacggg gcttgtggtc       600
tgcgttccac ccctcacacc agctgtttgc gctcacccga gttgccttct ttcagccctg       660
gattttctcc tgtgcatgag gaataacgct cctgttgaag ccaggaatgg tggctcagag       720
ctgtaatctc agcacttggt agactgaggc ataaaagggg ccatgagttt gaagctagcc       780
tgggctatag agttaggtcc tgtctcaaaa acaaaaatat agtcagacgg tggtggcaca       840
cacttttgat cccagcactc ggaaggcaga ggcaggcgga tctctgtgag ttcaaggcca       900
gcctggtctc cagagcgagt gccaggatag gctccaaagc tacacagaga aaccctgtct       960
cgaaaaaaca aaataaataa ataaataaaa aagaaatatc ttttttttt tgagtcaggc      1020 aagatacttg agttttatta tgtctgtcta aaagcaggtg ttaggcctat ttgtagtgaa      1080
gcgtggtgtg ctggcgctgc aacacccggt gaggaagcag gaacctgatc tcagagccca      1140
agaactgctt gacagcaggc cttcggcact tgccctctga aatctcttcc accttcatca      1200
ggttaatgga gtgtgcacgg gcacagtgcg ggcacccgtg tcttggtagc actgtttgac      1260
ggctccagca gcggtcaggt cccggtattc ttggcacatg ttgtgtgtgt catgttgtga      1320
gttgtagtgc agccataccg caaagttctt cacccgcagt ggggcctcag gtcgcactgc      1380
acagtgtacg atctcctcgg atgacttctt catcttgttc atctgtgccc aaaatcggga      1440
cttggccacc acatggttcg tcgcaaagat gtgcatgagg tataggagtg gtgtgtggca      1500
cttccgggtg ggcaagcagc gccccaccac cttgtactcc cgaagcgtgc ctgaggcctt      1560
cgtggctgat ctgtccttgt tggccgccag ccacaaaaat aaaaggaaat atcttgccta      1620
taatgttaca atcccatcca gcacttggga agccaaggca ggaaggcctc tgtggatgag      1680
accagcctgg gctacagagt gacaacctgc caagagaatg gggtgggtaa tcccaaatct      1740
tgggtatagt gaagtacagg actcaagaga cagaggcagg aggatcatct ccagttcaag      1800
```

```
acaagcccga gctataaggc ctcaaaaaca aaaaagaat attagatcta tgatttattg    1860
ctataaacac tacaacttaa aaaaaattaa ataaggaca gcaagatgac tcagtgaatg    1920
agggtttgaa tttgatcccc agtacccaca tagtacaaag agagaactga ctcccatagg   1980
ttgtctttcc gtgaaaactc tccctcccctt cctccctctc tctttctctc tctctaaatg  2040
aaaatgttta catcaaagcc tctacaaaga gcattcatgt tacacctagc gttggagaga   2100
tgtctcagtg gtcaagagcg ctgacttctc ttccagagga tccaggttct attacaagta   2160
cccatgtggc aattcacaat catttataac tcagttccag gggatctgac tccctcttca   2220
ggcctctgtg ggccttcatg tgtgtggtgc aaagacttgc acgaaggcaa aacactgtac   2280
acataaaata aaaataagag acagaaaagg gaatttattc agtgtggcca taccagaaaa   2340
gatgagagga ccagtctctt caaccctgtt tttggagtgc agatggtagc tctaggaatt   2400
tacaggagaa gaacaaaaaa tgggatgagc tggtggtgca ggcctctcag tgcttgagag   2460
gcagaggcag aggcagggga atctctgtgg gtacaaggac agcctgactg acctggtgga   2520
ttccgggcta accgaaacta caaaataaga cactacctct aaagttaaaa caaaaaaggg   2580
aggcaataag tatgcatagc taagcattct attctattct gcccaaacca ctctaattga   2640
cggctacctc cagtctgaag taagggtcct gcagtagcta ggaagaggac tacctcccag   2700
gctgactgtt cctggctctg caacaaact gaaaaggaaa actggttcag aaggagatca    2760
gagcagaggg gccaaattag aacgaggatt gtgccttcct tcaggtttag aacaaccact   2820
ggagaatttt aggtactgct gtggtagttt ggaacaagac gaggcaaaaa cttattactg   2880
gcaatctgta atgtccccat aaatcctttt tatatctatt tttaaaaga tttctatatt    2940 atatgtacag cattctgtct gcatatatgc ctgcaggcca gaagagagct ccagatttta   3000
ttacagatcg ttgtgagcca ccatatggtt gctgggaatt aaactcagga cctctggaag   3060
agcagccagt gctcttaacc tctgagccat ctctccagcc ctctatttta ttttttaaaa   3120
gaattatttt atgtgtatga atatttgcat gtatgtatgt gcaccacatt catgcagtgc   3180
ctatggaagc cagaagagga cgacagattc cctgaaacca gagttacagg gggctgtgag   3240
ttgctttatg gtgctgagaa ctgagcttcc ttcctgtaca agaaaagcac atgctgttaa   3300
ccactgagct gtccctccag ccctccccac ccctttgtgt gtgtgtgtac ttgtatgtgt   3360
atgtatgtgg acatgtgagc atgtgtggaa gtcagaggat ggtttgcagg agttggttct   3420
ctccttctac cctgtgggtc ctagggataa aactcaggct ggtagcatgt ccctctacct   3480
gcaaagccat ctcctgggct ttgtcccaat aaatttcttg ctctcccttg gtatcttcat   3540
tcttaagggg aaggacagag ctacaggtac aatgggtgaa aattggcctt tagttaccag   3600
tcttgaagat gagtacttaa attttttttca gaatcctttt tttttttta aatcttttta   3660 tttatgtata cagtattttg tctgcatgta tgcctccagg ccagaagagg gcaccagatc   3720
tcataatgga tggttgtgag ccaccatgtg gttgttggga attgaactca ggacctctgg   3780
aagagcagac agtgctctta acctctgagc catctctcca gctcaagaat cctttttttt   3840
tttttttttt tttaaggcag ggtttctttg tgtagcctta gttgttctgg aattaggttt   3900
gtagaccagg ctggcctgaa ttcaaagacc cacctgactc tgcctcccag ggtgctggga   3960
ctaaaggtgt gtgccacgac acctggctaa gatgagtgct ttttaaatgc ctatcacatc   4020
tacaggcaca actgattggg aagctgattc aaaccttgag atagcaaagg gatagaggtg   4080
ttgatgcaac ataaagacag agatgcccag attttctcct tcctttagtc actgggcggg   4140
```

```
actctgcagg tccagtgagg actcactggc tctcttgtta aagccttatt tagagttaag    4200
ccaatccttg gaagaggcat cattcattca ttgaacactt gcagtgtgtt accctgttaa    4260
ttcagcagaa agcaagacag cttaggcca cacctggagc agctggacca gagaccaagt    4320
ggaagcagga atgctgatgt acacttctca tcctgatccc ctggaggctg tcagcctggg    4380
ccacacagtg cgagatcctg cctcaaaaac gttttgcta cccattggtg attgtacatg    4440
tactttgttc tagcactcag gaggtagggc cagcctggtc tacaaaggac agccaatgct    4500
acacagagaa accctgtcta gaaaaacaaa acaacaacag aaacttttt gtctgatgtt    4560 tcatcttgtt tcttttctaa taatgtactg ggcagagaaa aacaaaataa tgcagttggg    4620
cctggaggct tagacctggg attccagcac ttaagagata gaggcaagct cattgctttg    4680
agtttaaggt ccctctgccc tgcatagtga gttgcaggtc agtgtggact atagagtaag    4740
accttgactt tcaaaaagca caggggcca ggcgttggtg gctcacagct ttaatcccag    4800
cactcgggag gcagaggcag gaggatctct gtgagtttga ggccagcctg gtctacagag    4860
ggagttccag gacagcctcc aaaacaatac agagaaaccc tgtctcaaaa acaaaacaaa    4920
acaaaacaaa acaaaaatgt caaaaagcac aagggccatc aaaatggctc agtgggcaat    4980
tacaaacttg atgacctgag tccattcctt gagacctaca taatgaaag aactgactcc    5040 cctaagttgt cttctgacct tcacacatac cgtgtgtgtg tgtgtgtgtg tgtgtgtgtg    5100
tgtgtgtgtg tgtgtgtgtg tacatgcacg cgctctcgtg agcaagtacg ctcctgatac    5160
taaattaata aaaaggatta aaaagtaaa accacaaaca tgaaccaaac caatgtggtg    5220
taataaccta tgtctggaga actaacaggt ttctggaccc agagaggtag agaagataat    5280
ctaatgtctt cagggaatt aggggataa agcatcagag cataaagaaa gtttccctca    5340
cttgggaagt agtggaggca ggagcatcag gaattcaagg tcatctcatc tatatagtaa    5400
gtaagttcaa gactagcctg ggttacatga gaccctgtct caaaaaaaa aaaaaaaaa    5460 aaaaaaaaa aaaaaaaag gaagcatggt gcaacagatt tgagattgaa acacaaaaat    5520
agctcaactc tggggcagac agcagagtca gggaaagtc taaggaagtt ctgggaaagg    5580
gtcaggaggc ccctccctgc ttcattcacg ccccaaacat ctattaaaca ttccatgtgt    5640
acttggtgtt tctggcctga ggatgactca cagaggctga cactaagt taatcacagg    5700 aagcacagaa gaaaaaaaa aaaaagaaa aaacaggcct aatgcaatgg aatgcctgac    5760 tgaggggtt cttcacagtg ctttggagac gaccctttgt gtctcattga aattcatctc    5820
tcaagaaaca ctcctcaaat gtttacacat tgtcaggcac tttgagctgc agggacacag    5880
aggactcagt tctggtccct gcctttggaa ttcacaattg ttgctcttcc aaagaactgg    5940
ggttcggctc tcagcaccca cttaaggagg cccatgacca tttgtaactt cagctcaacc    6000
gcttccacaa gtacccacac acatgtctgt cccccaaaca cacctatatt cttcatgcta    6060
accttgtgac actatgagca aaatcaaaga cattaagaag ccaggttcag tgccctgtgc    6120
cttagtccta acatttgaga ggctaaatca acaggaatt gaggccactt ggacagcatc    6180
aagagaaatt atctttgaac atatgaaatg atattatcac agaaatagaa ttgcaattta    6240
aaccaggtat gtgatcccct ctccccccac caaaagaaaa aaaatagag gctggagaa    6300 atggctcagt ggtaaagagc acctgctgtt cttgcaaagg atctagattg ttttgttttg    6360
ttgagacaga gccacactat gtaactctgg ctgtcctgga attcactatg tagatcaggc    6420
tagctggtat gtatgtctgt ccacaaatgc atgcctggtg ttagaggctt ccagaagtgt    6480
gtgtcagacc ctctggaact ggagttatag gtggttgtga gctgccatgt gggtgatgta    6540
```

```
attgtacttg ggccctttgc aagagcaacc agtgccctta acccctgata cttgctttta   6600
aggaatttgc attttttgttt tgaaattaca tgttggaaaa gttttccaca tcagtaagaa   6660
atgccatcct tactatttct tcctgcagct tctcagaaat attttttaat ctttttttt   6720
aagattttat ttatttattt attatgtaca caacattctg cttcatgtat atctgcacac   6780
cagaagaggg caccagatct cattcaaggt ggttgtgagc cactatgtgg ttgctgggaa   6840
ttgaactcag gacctctaga agagtagtca gtgctcttaa cctctgagct atctctccag   6900
cccctcagaa atattttaat tcaaaaatct ttcttagcca gctctcaagc cactggatta   6960
cttcttgctt ctgctactga catagacttc atcttgattc actccataca gcaactagat   7020
gtgtgtatat aaatgacaga tagatcatag atggatggat ggatggatag atagatagat   7080
agatgataga tagatagata atctcacttg ctacctaggc tgacctcaaa ctcatgcctc   7140
agtttcctaa gtgatgtgat tacgggcata cactattatg cctagcataa ccatttgttt   7200
gccttaaaat tttttaagat taattttta ttatgtatac agtattgtgc ctgcaggcca   7260
gaagagggaa tcagatctca ttacagatgg ttgtcagcca ccatgtggtt gctggaactt   7320
gaactcagga cctctggaag aacagccagt gcttttagcc tctgagccat ctctccagcc   7380
cccagccttt aaaattttta attaattttt tttttgtttg tgtatgggtg tttggcctgc   7440
atgtaggcct atgcactata tgtgtgtagt actcacctag accagaagag ggtgccagag   7500
actctggaat tggagtttca gtgcatgatg agctgccaag tgggccttaa tccccaaacc   7560
ccagagggtt gaagagggat cagtggctaa gggtgcttgt tcttgcagag acccagttt   7620
tgattcccag agcccacatg gtagctcaga acaagaactc cggcttcaga ggattctgca   7680
ccctctctgg gcctcatctg gtaccaggca tacatctggt atgcagatat atacacgccc   7740
tgagtggtga caaacactct gtgagttcaa ggctggtcta catagagaat tccaggacat   7800
agtgagaccc tgtctcaacc aaacaacctg gatcctttgc aagaagagca ggtgcttta   7860
aacactgggc catctctcca gcaccacctc cccccttaaa tgatacatag gtcccacata   7920
gcctagttcg gcctcttaac tcctgacata acacctcatg aattcctcat cctcctgcct   7980
ctacctttg agtgagtgac gagattacaa acgttcgcca ccatctttgt tcccagttgg   8040
ccctcaaggc cccagggtct cagttcagat cctgccacta tggatacata gcattgaaat   8100
ggggaaggct gcctctgtgc tgcctcagcc tttgggtgac gcctcttgct tggcactgca   8160
ttttcaggag catgacatct ttgctctgga ccctgacccc aaggttgtgt ggagctgtaa   8220
gaagtgtaag ggtgtctggt attggtggcg cgcgccttta atcccagcac tcgggaggca   8280
gaggcagcag aggatctctg tgagttcaag gccagactag actacagagc gagttcagga   8340
cagccagggc tgttaacaca gagaaacact gtcttgaaaa gcaaacaaa ataaaaccaa   8400
caaaacaaca acaacaacaa agtgttaagc gcgcatgcaa ccagccactg ggcaattagt   8460
caaagatgcc aagtctagat agacatgcag ttaagaactt agggtctaga gagatggctc   8520
ggtggttaag agaccagaag agtttgcatc ccagcgctcg cacagtagct aacaacagtc   8580
tatcttacac cctcttccag cctctcctgg cacaaggaac acacgtggtg ctcatagtta   8640
caaaacagac acaacacgca tacacaaaga aataactaat ttttaaaatg tcttgtaatc   8700
aagtaaaagt gctaactcta gggactaaat taattcctca gtcgccctac tccaggagcg   8760
gtaaggctgg ccagaaagac caagaacgca cgcgcgagg agaaaccaca gagtcggtcc   8820
tcccgggata gagaggccgg aagtgctcgc ggagctgcac gccgggtgct ggaagcctac   8880
```

```
tgagccccga ggaagggctc cgctcgggc ttggcgtggt gggtgagccg gagggtcggc    8940
gtgagcggcc tgggctttgg ttctgaatga tggcgtctcg ggcaggcccg cgagcggccg    9000
gcaccgacgg cagcgacttt cagcaccggg agcgcgtcgc catgcactac cagatgaggt    9060
atgaggtgag ccaggagcac tgaggccttc cccgggagga gcctgcggt ctcgggaagc    9120
gacgcgggcg agcctcacgg tgccgctccc ccagccagct gtcgcgtact accgggtccc    9180
cggctccggc gagcgcctcg ggtctgttta caggccggga agcccagtgg cctgccctcg    9240
cccgcctcgt gctttgaggg gatctggcct gcagaggctc aggggtcgat gctcagcccc    9300
tctgaatgac cttggagaca tcattttct tttttcaaat cgaggtcccg cagtgtctag    9360
agttcaggct ggcctggaac tcacggcctt ccctcctcag cctcccgagt atgcgcctgg    9420
tctgaaaact aacattctta agaaaactg cgtgtgtgcg tgtgtgtgtg tgtgtgtgtg    9480
tgtgtgtgcg cgcgcgcgcg cgcgtgtgtg tgtttgtgtg tgtgtaagtt tgcccacacg    9540
agagcaggtg tgctggcaga atgcagtgcc agtaaagggt gtgtgtgtgt gtgtgtgtgt    9600
gtgtgtgtgt gtgtgtgtgt gtgtgtgtgt gtgtgtgtgt gtgtgtgtgt gtgtgtgtgt    9660
gcgcgcgcgc gtgtgtgtgt ttgtgtgtaa gtttgcccac attcttaaag aaaactgcgt    9720
gtgtatgtgt gtgtgtgtgt gtgtgtgtgt gtgtgtgtgt gtgtttgtgt gtgtgtaagt    9780
ttgcccacac gagagcaggt gtgctggcag aatgcagtgc cagtaaaggg tgttggatct    9840
cttggagcta tagttacaga cgtgtttaaa tccacctgag actagtactg aggaccaaac    9900
cccgaagtga ttttgtgaga tagcggcttg gtatggggtc catgctagcc tccaggagcg    9960
gcaggtgctc ttaaccactg agccatctct ccagtcccca ggctgtcttg gaacttgctc   10020
tgtagaccag actagaaatc agagatctgc ctgcctctgc tgccaagtgc aaggattaaa   10080
ggtgtacact acagccgccc tgttgaccct gtctttagga agatgtcatg tgtactttac   10140
aaagagtttt gatgtagtca tgtcttaagc tttgttgtca cacaagatga aattaattac   10200
caccagggaa ttttttcatca aattgtgctg tacttaaata tgcctaaagt aaaatacttg   10260
gggtcagact cttgaagttt aaaccaacac caggtactga gttgtgttga acccacacaa   10320
ctaccttgcc tcctgcagat tgttaactct gctggctgtg gtggttgaag agaccccac    10380
attggcttag ctgttaagag cacttgctgt tcttggagag ggtctaaact cagttcccag   10440
caccgacatc aggaggctca caaccaaaca cctgcaactc cggttccagg ggttccgatg   10500
ccctctggct tcccgacagc acaggcgtgt gcgtggtgca cacacataca catgagataa   10560
attttttaaaa agaaagaaaa gccaatctgg gtcctgcctt caaggagctt gagtgccaga   10620
agtgattctt ttctccttac ctcccacatt tcctataaca aattaatttt ccccttaaat   10680
ccactgaatt attcaactgg ttcttggcct ctttctttac agaaggatga caagcccttt   10740
ggacccttct ttttcaactt taggcccctg cctaatggat gctcttgttt tcatgcgtac   10800
ctagagcaga caccttgctt gtgacaatat gaaaaggata taattgagac ccgagaaga    10860
tcaggactaa gagatgtgcc tccttctcat ggaaactata tctggagaaa tacagggagc   10920
ccaaactgtg ttccttgttg ctaggcctcc ccctaatggc ctttgtttct gtgatacgaa   10980
gccatctttc taaccacagc tcagaattct tgtcatggct tggtgagata atgtcttagt   11040
acgttgtcca ggccaaccctc caatcagaga tcctctgcct cagcctccca ggtgccatta   11100
ctgttcttca gtcttgaagt ctacacatgc atggtctttg taactgttac tacctctctg   11160
tgccttggca gttgatttcc tgaaacacaa atactaaaaa gcttattcct ttgtgcctgc   11220
atgttttgc ctctgcgtag aagcccactt ccactcgtct cattacctct gctgaaatag   11280
```

```
ctctctcctc tagatataac cttctctggc tttccatctc atgctaattg gttcttccct    11340
gggatagcgg atatcttcgg tttatatgta tttacttgag ttttatactt catgtttccc    11400
agcctctatc agaggctgtg tcattcagat tgtatctatg tgtccagtac cggtgcctgg    11460
tggtcggagc aatttaaatg aaaattgctt ctccctctgc tctgccttac agtgtgacgc    11520
tcaagagtga atcaagaag ctgatctacg tacatctggt catatggctg ctgttggttg    11580
ccaagatgtg tgtgggacac ctgaggctct tgtcacatga ccaagtggct atgccctatc    11640
agtgggaata tccatattta ttgagcattg tgccctctct cttgggcctt ctctccttcc    11700
ctcgaaacaa cattagctac ctggtgctct ccatgatcag catggggctc ttctccatcg    11760
ctcccctcat ttatggcagc atggagatgt ccctgccgc ccagcaactc taccgccatg     11820
gcaaggccta ccgcttcctg tttggtttct ccgctgtctc cgtcatgtac ctagtgttga    11880
tactggcagt ccaagttcat gcctggcaac tgtactacag taagaaactc ttagactctt    11940
ggttcaccag cacacaggag aagaaacgta aatgaagcct gcctgatgga cacatgaagg    12000
gagctgttca gaatctccat ggactgtggc atctgtgatg ttggcaccta gtgcacacta    12060
tcctcagatt ttggccttga gttctctgtt accatctgct gagatgacaa atctgtagtg    12120
tttaatttat tcttgactag ccacaaaccg gatgaccgat gtctgtggaa cacttcaagt    12180
tgaggccctc cagactgagc cttatccttg ccttctcttg gtcaaattcc ttacttccat    12240
ttatcacctc ttcatcaccg atactaaaag agatctggaa taaatcagtg cagaaattct    12300
acttcaatct gtaggtcatg gggcaagcaa catttgggaa gttgctcccc taaaggctac    12360
tctgtttact gcaaaccatt ttaattaaaa aagaacttca ataaagttaa gactgtcctg    12420
tgctttgtgt ttgagatttg attgaatttc aaagttgtat tgctctagag gacttagaca    12480
ttatgagaag aatagatgtt tcctgagaac atgggactgg cgctggagga gagacagtgt    12540
gaagagtctt aagtcagctg cagccctcta gctcttaggt gagaacaacc ctgggatggg    12600
ggttgctgga ggaatggctc aggggttaag agcactgaca gaggacacag gtttagttct    12660
cagcacccaa atggtgactt aaaaccattt gtaactactg tcccagggca tttgacgcct    12720
tcttgcctcc ggatgcacta ggcagacatg aggtacaaaa acaaacatgc aagcaaaaca    12780
ctcaaaaaat taaaaaaaaa aaacatggtc tctcaatgta gctgtggatg tactagaact    12840
cactaagtag agcaatctgg gctcaaactc acagagatcc tcctgccttt gcctaccaag    12900
tacagggatt taaggtatgt gccaccacac ttagcaatat atatttggcc agacatttaa    12960
tctccaccca taaagcagct tatttggctt ggattatgag ctcccctttt tatgcttgtt    13020
tgagacaggg cttctctata gctctggctg tcctggaact tgcttcgtgg accagactgg    13080
catcaaactc aaatccacct gcctctgcct cccacgtgct ggcattaaag gtgtgtgcat    13140
cactgcccag ctgggttacg agctttctat ttggttattt atgtttatta gacttttatg    13200
tgtctaaaac tgagtaataa tacccaaaaa gaatctgctt gttggggcta taattttcca    13260
gtaactgaca aataaacctg agtcaaaata agaagaaagg ggtttgagtt cttttttccct   13320 tttagtttct gtcattgatt attccttggc ctgcttgttt ggggaatgtg caaaggaagc    13380
tgctaactct atggaagcca gaaaagaaa aaggtgagat tccagtgtcg ccactagggg    13440
cagactgcca gtgacgtaac ttcttcactc agcccctccc aaagcttcct ccacctccaa    13500
aaatgtcaag gactggtaac tagtacatgg gcctttgaga aaagatagca gggagcttcc    13560
agtcttgggg gaatgtgcag tgaacataac atctaattgt gtgagagacc cacagctgag    13620
```

```
atacagttta agagtcacac ctagaagtct tcacagtaaa taaggcagca aaggtgtgca    13680 tcccttgca ctggacttta ttatgcctag atgatgctca gatctgtaac tgcagagatc    13740
tggccactac agttgtaatt cttttgtcct ggaaatgtgt tgcttgtaca gtctgcaaag    13800
ctaattcctc cagctatccc actgatcatt tctttggagc aggggcagtt ccagacaga     13860 atttctctgt gtagtcctcg ctatcctgga actcagagat ctgcctgctg tgtgctggga    13920
ctaaaggcat gtaccaccat gcccagctcc tactgatcat ttcaaagata acttcttgtg    13980
cctcaggcct attgctgttc ctgcttcctg tgtttacggg aacacagctc tggatcatcc    14040
accctgcaag tttaagtccg tccccactcc atatacacac tgcctattcg gtgaacctcc    14100
tatagatacc ctgataagtt ccctagcttc tcagtttaac acttagaact ctccctactt    14160
aaggggaggc ctctcagtgg tgaagtgctc ctctagcatg caccgaggcc tgggtgtgac    14220
tccctcgtaa caacaaataa aaacaaacct tttctgctct tacattcctt tattaatctt    14280
taagatgcca cttgtatgaa aattcctcaa ttttcaattc ctcaatttga agaacaactt    14340
taatttgtct ggttgctttc accttattcc tttattatta ttttctaaca agacagagcc    14400
cagaatgacc ttaagctatg tggctgagga tgactttgaa ctcctgatgc tttgtctcta    14460
cttcctaagt gctaggatta caagtatgca ccatcactcc tggcttatat tactcgtccc    14520 ccaccccac cccatagacc aagccttgac ctttattttt aaaagctgca tatttattct     14580
gctttctgac ttagtgtttg tgccttcaac actttcacaa ccctttctc ttcctcaata     14640 aggaaagcct gcttgatcct gtcacggaca cacttggcac acaaggagcc accacagccc    14700
ctgctgacgt gcttctttgt ctagacagtc tcataaggac tttgggtctc acagcatgaa    14760
ccccttcaag tctgcctggg cacacaccac atggggattc aggtgctttc ccagtcttct    14820
tggtataaag gtaaacaatc ctgttgccag gggttcgaga cagcctagtt tcgttagagg    14880
ctgtattgta ggaaagccta caatggtatg tcaaacactg gaccattcga gtgcctctaa    14940
gcaccatccc tggaagagga agagctgtat tatttgtttt atattgacag aattgctact    15000
ttgtatgtct tctgtagctc attagtgttc actctgagct tattgaatga attaacttgc    15060
ccttttgagg acaaaggtct gtatttcaca gaaaacagaa ctggactgaa gcagaaagaa    15120
gcccatggac aagggagttt gtcatgagct tagctgaggc acacattgct aacttcaaac    15180
aactgtgatg caaacaatta aaactgcagt gcagaccccc ctgctttctc caataaaatt    15240
ttccacataa gttctgtccc cccccaaaa aaaaaacctg ttagcacatt attagtcaaa      15300
gagctaaaac ctgttttttgg tcatcagaat agtgttttac tgaaagtctt tgaatacctt    15360
gtagactaat ttcactcatt gtgaaattag tcaacagttt taaaacacta tcatgccaac    15420
atcagttttt gttagttttg tgcttggaat tctgcttttc tagccttttc ctataacttt    15480
tttctgcctc atggttatgg tgttcacaag tcctcttgat ttagtgggaa gaatgctatt    15540
tgggttagaa agttcagctg gtatgggggg tacatgtcta atcccaacct ttggcaggtt    15600
gaggcagcag gaatactctg agtttgaggc cagcctgaca tacatacata catacataca    15660
tacatacata catacataca tacaaacact atctcaaaaa acaaagttgg agttaaagta    15720
tcaaccacag gactaagatc aacctgcctg ttcacaggtt gctttaaagc tccaatagcc    15780
ggttggagag atggctcaga ggttaagagc actggctgct cttccagagg tcctgagttc    15840
aattcccagc aaccacatag tggctcacag ccatccatta tgaggtcagg tgccctcttc    15900
tggtgtgcag atgtacatgg aagcagaatg ttgttcacata ataaatacat aaaatcttaa    15960
aaaaaaaaaa ctccaatagc caaagtatta tgaaggcatt ctaaaatttt taatttattt    16020
```

```
tcattttatt tttggagaca cagtttctct gtgtaaaaac cccaactgtc ctggaactca   16080
ctctagacca gactggcctc caactcacag agataaacct acctctgcct cccaagtact   16140
gggattaggc cgggcagtgg tatcgcccac ctttaatccc aacactcgag aggcagaggt   16200
tggtggatct ctgtgagttt gagaccagcc tggtctgcaa gagctagttc taggacagcc   16260
tccaaagcca cagagaaacc ctgtcttgaa aaaacaaaa aacaaacaaa agcaagtta    16320 atctggaatt aaaagtgtat gccaccacac ctgatgtaaa tttaaattt ttttaaatt    16380 aattttctta tacacaggtg ttttgccagc atgtatgttt gtatagcaca tgtgaacctg   16440
gtgcctaaaa agccaaaaga gtgcatctga tcccctggga ctggagttac aaatggagtg   16500
ctgccatgtg ggtgctgaga attaaaacca aatcttctag aagagcagcc agtgagtgcc   16560
cttaactgct gcagcatctt tctggctctt gtgaaggcat tttatggagt ctgtaacacc   16620
atatgggtat caaaagccgt gtggtcacct gatctttgca gcaagacagg agagagaagg   16680
tgtttgagag acttgaggga tggtctagac accaaagaaa ggtttgtgtg ttgtgagcaa   16740
tgactgatta ttaggttgag attctagcca gggagtttac tatctcttgt ttgatttatt   16800
acattttatt gccatcctag gaattaaata gggttttaca tttgctaagc aagtgttctc   16860
tcaacatcct tatatcccct ccccgatttc tgacacttac tatagctcag cttgtccttg   16920
aactcagcaa tcctgcctcc atagtgccgg gattatggat gtttccactc ccagctgagc   16980
ctgttcttca tgtgttgcat gggcattgca gatctctccc attgctgtga ggctgaaata   17040
aatgtggatg aactttgtag tacatagtcg tttacatatc aagatgcctt tccttggtaa   17100
acagtgttat gcttgcctct caaattggga gtgtcttcct gttttaagaa taatcctctt   17160
ccctcttttc ttcctctctc ctccttcccc ctccttctga cagggtctct ttatagaata   17220
ttcctgcctc tctctgcctt ccaaatgttg tgtaggtgta catcaccatg cctgcctagt   17280
tagaatgacg tctcagaatg ctggaggtta atttcacatt cttagtccac attatcctga   17340
ctggtatgtt caaggtgccc tgacagtagg tacagaccca gcagacctca ggaagtgacc   17400
attacagcaa gatcctgtag ctgctactca tagcctgttg ggagcccgtg cataggaaag   17460
aatggcaaga aaaatggct gccagagggc gtccccatag tatactctgt cactaagcat    17520
gcatgcttca gagcttgcca aaacctcctg agtccctggc ttggtcccca aataaaggtc   17580
attagagcat gaagtcttgg tcaactgatt gagactcctt tggagagtgc aaggcttcta   17640
tgtagatgcc cctgttgcct cctattctgt ctaatttctt actctccctg ttgacagctg   17700
ccaatctcct ttctcctagg actgtgccca ctcatcactc actgtgataa gaccccttc    17760 cttttctttg ttccttcctg gtctgcctgc ctgctccccc cccacctct ccctttcat    17820 ggtctcatga aaactgctct cagactcact atgtagctaa ggatgactgg agctcccaat   17880
cctcctgccc ctacttccct aattctggga ttacaagttt atgccaccac attccacttt   17940
ctgatttcct tccttacatc ttaattccac tagctttatc acactgctaa agctaaaact   18000
ttctttgcaa aatgagatcc agaaacccac agactctcca tagtaggttc tgacagggaa   18060
acagctgaca ttgtatggtg ttctgccttc ccatttcttt gctgtgtgtg ttttggaca    18120 agtctcggtc ttcctgtatt tccttccttc cttccttcct tccttccttc ttttccatt    18180 ttttatttga attataaaca cgattgtttt acatgttaat cccagttccc tctccctccc   18240
ctcctcccct accaccatcc ccaactaaaa ccctacctat cacatatcct ttctgctccc   18300
cagggagggt gaggccttcc atagggtcc tcagggtccg tcatatcctt tgggataggg    18360
```

```
cctaggccca cctccgtgta tcttggctca gggagtatcc ctctatgtgg aatgggctcc   18420
caaagtccac acctatgcta aggataagta ctgctctact acaagaggct ccatggattt   18480
ctgaggtctc ctcactaaca cccacattca ggggtctgga tcagttccat gctggtttcc   18540
cagctatcag tctggggacc aagagctccc tgttgttcag gtcagctgtt tctgtgggtt   18600
tcaccagcct ggtctggacc cctttgctct tcattcatcc ttctctgcaa ctgtattcca   18660
gttcagttta gtgtttagct gtgggtgtct gcttctactt cttccagctg ctggatgaag   18720
gctataggat ggcatataag tcagtcatca atgtcattat caggggaggg catttaaagc   18780
agcctctcct ctgttgctta gattgttagt tggtgtcatc tttgtagctc tccaggcatt   18840
tccctagtgc ctgatttctc tgtaaaccta aaattttccc tctattatgg tatctcttat   18900
cttgttttct tctattcttc ccccaactca acctttctgc tccctcatat actcatcttc   18960
ccttctcatt ctcctagctc cttcctcccc ttcccaattt gctcaggaga tctggtccct   19020 ttcccttct ccaggggacc atgtatgtct ctcttagagt cctccttgtt acctagcttc   19080
tctggctttt ttttttttt taagatttat ttattatgtg tacagtgttc tgcctgcagg   19140
tcagaagagg gcaccagatc ccattacaga tggttgtgag ccaccatgtg gttgctggga   19200
attgaactcc ggacctttgg aagagcagtc agtgctctta accgctgagc catctctcca   19260
gcccttctta aaactggaca ttagcctagc ctcaagggtt gtgatgctaa caatacaagc   19320
taaagagagc aatgggcatg atccaaagcc agatagttca gcaaatattg atttcatccc   19380
ttcccttttc ggaacagact ccagccacac caaatatgta aaccagcaag acaaaaaaca   19440
gcaggctatc ttttcccact ttttgctttg tctatgtttg ttggacaatg tcaaactatg   19500
tagcccagac ccttctgta actttccatg tagaccaggc tggcctccaa ctcaaattcc   19560
cagcaatcta cctgtctctg cctctggagt tctgggaata aaggtgtgca tcaccatgcc   19620
tggcctcaat aagtccttgt cttatggtct tcttttctcc tcctttactt cttatcctcc   19680
tccctctctc ttcccttttcc ctttatcttt atttctttat tgtcaccgtt tctttttctgc   19740 ttctcttacc atgctttaac aaccatcagg aagcaactaa ccaaatgttc tcatcttgag   19800
agtcaggtca gaagatctag gagtcaagaa agacacgtgt aaaatagagc tcacatacca   19860
agcattagaa aactcgcagt ggcactaaaa gatggctcag gggataagaa cacttacatg   19920
gtgactcaca accatttgta attccagttg cagacaattc aatatctcct tctgatctct   19980
aagggcaccc agaatgtaca tacatacatt caggtaaaac gttcatatac attaaaaata   20040 ataagccttta agaattagaa aagagggctg gagagatggc tcagaggtta agagcaccga   20100
ctgctcttcc agaggtcctg agttcaattc ccagcaacca catggtggct cacaaccatc   20160
tgtaatgaga tctggtgccc tcttctggtg tgcagatata catggaagct gaatgttgta   20220
tacatattaa ataaataaaa tcttaaaaaa agagaattag aaaagaaaaa aaagcttcat   20280
gtgtgtgtgg aaacctccat gaggtagaat gggataaaag ctcttgattc tatgcttagt   20340
ctggctagat caccctctcct gttctctgga tctctctgac ttgactgtag aggttggctc   20400
tgtacaaggc agcactgtca gcagatcctg ttggttcaaa gaggtaggtg aagccaagag   20460
actacaggtg acagcagatt gggagggccc agcacaggtg cagctcactg gaagggtcca   20520
gcacaggtgc agctcactgg aagggcccag cacaagcgca gcaccttggg ctatagactt   20580
tgaccttgac caaatcactt tcctctctgc ttccttattt ctctccttac gaaattaaac   20640
aaataatcct catttacctg cctcacaagt tgtttagagg gatcaaatat tgctgttgct   20700
ttgtgaactg taagtagata agctatttag atgagatata tcatgattga cattcactca   20760
```

```
gccatgaagc acaggcttcc tgacaggcac tgctaggtga tggagaagaa caaatgagtc   20820
tctccatctc tcttttctca gcactaggat tgaacccagg gccttgcata cactaagcaa   20880
gtgcactgcc gccgagctta tctgttttta cctcctttta aaatattgt ttatgagctg    20940 ggtggtggtg gcacacttct ttaatcccag cacttgagag gcagaggcag ggggagctct   21000
gtgacttcga ggccagcctg gtctgtagag tgagttccaa gacagccagg gctacaaaat   21060
aaaaccctgt ctcaaaaaac aaaaacaaaa acaaaaacaa aatcaacaaa atgtatgaat   21120
gcaaaaacaa aaggatactt tagggtcgca ggtagattgg gaacttcaaa tgtgggccaa   21180
aagaaggctg tggccctgct tctgaaggat ggtccagacc gaatctcaga aggacaaagt   21240 gtcgggcta agatgtagct tcgttgatag agttcatgca tgcctagcac gaaatcctgg     21300
gttcagtctc cagccctgaa gaaactggat atggtggttc acgcccgtaa cctcagcact   21360
tgggaggtag aggtagaagg accaggagtt taaggaccgg gcccagccta cgatacgtga    21420
gaacctgtct tgatgatgat gataatggga ctggagagat ggctcctgtg taaagtgctg   21480
cataaacacg aggacctgag ttctggtccc cagcaccagc atgataccag gccatggcag   21540
aatatacctc tagctccagt atcgagtaga ggagacaggt ggaccctggg gcttgcctcc   21600
ccaccagctt agctgagaca gcaaggtcta ggttcaatga gagatcctgt ctcaaaacaa   21660
aatagagata aatcaggaag acaccctggt gtcagctctg gcctccacac gagcctgcaa   21720
gcacacctgc ccatacaaca cacacacaca cacacacaca cacacacaca cacacacaca   21780
cacacacaca cacacacaca ccctggtgtc agctctggcc tccacacgag cctgcaagca   21840
cacctgccca tacaacacac acacacacac acacacacac aaacacacac acacacacac   21900
acacacacac acacacctaa attttttttaa ttaatttaaa agaagagac aatagcaata    21960 ccaagatgca atgacccagt ggacatgccc ctaactgtcc tcccatcgtg gagattgcca   22020
aggtgaggct gaagcagcta aagtctccat gaatgagagg aagctgtgag atgatgggga   22080
gggtccccac aaagcctgga gccttgtcag ccttttttcc tgcaccggaa accacaggaa   22140
accaggtcag tgtgtgtggc tgctccctct gctccagagc tcagctgtca gttttgggc    22200 ttcctgagca agctgtatta tttagtttgt ccttgaagct agagaccact ttgacctgga   22260
gtcgagaaga gttggaaagc cagctagctg gggagccaga gtgtacatgg ataacacaag   22320
aagtttattt gtgttatatg ttggcctatt tttttgccta actttaaatg atgtaccaat   22380 tgcttctta tcttcagcat tcagtataga caagtgccga atagctgtta attctcaaaa    22440
tggaagatgt gtaactgtct atgacagatc caagttctag aacatgctaa taggcgtgcc   22500
agatctgcag tgtttgagga gggttaagaa atgggtgcat ttccacaaca gggtgctggt   22560
ccctttcctg ttacctctcc gccacaccaa gagcccctg tgacgtgaga gcagtaaggc    22620
tttctaccaa acaggtggac aagtgaatta gtgttcacca gtgccctggc tcaggagaag   22680
gaatgtgacc cagcctgctg gttaggatag aggaggagct tcaggcagg gtggatccag    22740 ggcagggctt ggtgagagcg cctgctggta ctgtgtgctc ctcacagctc cagggccagg   22800
ccctgctgcc ctgctgccct cctgcaaaca acaaagccat ggtctctgtg ccctgatcct   22860
gcagaagctt atggggagcc ccagactgac aacctggttc ctgcctctcc tcttactgct   22920
cttcagcctg tctatgtctg ctgaggttgg ctgtccctac ctgccacgct ggaccagcca   22980
ctgtctactg gcttcccatg tggtaaggtc ctgctgctag gtgggggaca cttgcttggc   23040
acagagtaga aactccccag tctcctgtct gcccttccct acctctgaaa tccctgtgat   23100
```

```
ctagtggcag cctctctgtg tccaccatgt ggtcctgaag gttctgttgg gctgaggtcc    23160
ttggaaggat gagaagaaaa cagctggggt ggatggacag tgggctgtgg gtctcagaac    23220
cggatgatcg gcacaaagag ttcagggagc atgcacctcc tgcagttccc ttctaaccac    23280
acctctctca tttcttttcc gcactgggct ctgtacctcc aggataagaa ttctgccggt    23340
gagtcctgtt tcttgttctg cttcactccc catgctcccc tgagttccag gtcccagtga    23400
gccatccatg gccattttgg ttcccagcct ggggagtagt ctagtatcaa tgggaaagtg    23460
cgggactagt gaagatttgc attgtaattc tgcctcagac gctatgactg cttttcactc    23520
tcccatctga ccctcggtct ctgagcacag gagaagagga gaaatgatta tgcgatgagg    23580
acagtgttgc tctctaccaa tggggaggat aaaatgagca ccatggctaa tctccaggca    23640
ctctggacaa gctggctctt cttatcaccg gtacctcact tgaccaggaa caataatcat    23700
ctttcatact ttattgtgca ttctgcttta ccaagctttc ccccatgcct tatgtcactt    23760
ggtccttatg acaaacccac tttgagcagt ctggcacctg cccaataact taaccaagat    23820
tgtacctgta agctatatca gagcccagcc cgaaatccag tttggagaag gtaggtggga    23880 cccccttaggc cctaccattt ttcttgttcc tctttttgtt tttgttttga gatagggcct    23940
cactatgtaa taacaaagcc tccataatta tttatttact tattttggtt cttcaagata    24000
gtgtttctct gtgtagtcct ggctgacctg gaactcactt tgtagactag gctggccatg    24060
aactcacaga gatccacctg cccctgcctc ctgagtgcta ggatcaaagg catacgccat    24120
caccacccag ctgcctccat cttttaatcc ttccatctca gcctcccaag gaatagctta    24180
cagccatgtg ttattgtgcc gactttctat catacacagg aagttctgtt caaactccct    24240
gccctaccct cctagccacg aagccttggc actggctctg ctgtttgtgc ctgcgtctga    24300
tgtcacggcc ttcaggtaag aaaagcagcc tttgagccat tcttagtgaa ggcatgaatc    24360
agggacagtt gaaataact agctaggctg acacaagtgt caattgtcat attgggacat    24420
atatttgtct tgttaacctc aagagggact tagagcatcc tagaataaca catcatgaca    24480
gacattcatg ggaccactat atctttgtgg aggtgccatc tttcatctgg cactaattcc    24540
taaaagccat gtgttctgta gacttgctat tgttaccttc cctctgtaaa atgggactgc    24600
cactctgctg cttcattgcc tcacttggta catacggaac acacacttta aaaccagcag    24660
tcataggcgg atgaaagat agcttagcca tcaagagtac tagatgctct tgcagaggac    24720
ctaagttcaa ttcccagcac ccatatcagg cagcatacaa ctgtaggtaa ctccaactct    24780
aaggaatctg atgtttctga tctcttaagc ctcatttata tgtgccaata catagatata    24840
catacacatg caagtaatta aacataaaat aaaatcacaa aaagttagtt taaaattgtt    24900
caccattagc tgagtgctag tggcgcacgc ctttaatccc agcactcggg aggcagcggc    24960
aggaggatct ctgtgatttt gaggcccgcc tgttctatag aatgagttct aggacaggct    25020
ccaaaacaat acagagaaac cctgtctcaa ataaataaat aaataataa ataaataaat    25080 aaataaacaa acaaactaag aaagaaatca tgctacaatt aacactgctt ttgtgggagg    25140
tgtgtgtgtt tgtgtgtgtg tgcgtgtctg tcttttttct ttgttttatt ttatttttta    25200
aatatcttat gttagaggtg gagagatggc tcagttgttg agacagttgc tgcccttcca    25260
gaggatctgt attagattcc cagtaccctc atagtggctg tatacacaat tgtctgtaac    25320
tgtagttcag ggaatccagt gccttctttt gacctcagca ggcaccaggc atgcgcatgg    25380
tgtacattca tatgtgcagg taaaaccttc atacacataa aataaaataa ataaacctaa    25440
atatttaaaa aagaaatgaa atatctttta tttattgttt gacagtctca tacatgcaga    25500
```

```
caatctatct tggtcaaaac cacccacaat tcctccctcc catgcacttg gataactccc   25560
aatacatcac tgctccacat tcatgtctct tttaagatct tgtgtgtatg agtgctttgc   25620
ctgcatgtat atatgtgtat tacattcatg tagtactcat ggaagcatca aatccctgta   25680
gcactggagt tatagatggt tgggagccgc catgtgggtg ctgggaacca atcctgaatc   25740
taagaacatc aagtaggctg aactgctgat ccatcttcac acacacacac acacacacac   25800
acacacacac acacacgcac gcacgcacgc acgcacgcac gcacgcacgc acacagagag   25860
ccatcaaatt ttgagacaga ggcttactgt gtagtcctgg ctcacctgga acttgcagag   25920
tagaccaggc aggtgtcaaa atcaagagat cagcctgcct ctgcttctca atacaagtat   25980
aaaaccacgc cttgctctgt ttgttttgta aattcacgga gtccagctat gagtctgcct   26040
gctggaatgt tgactgatct ggttggcttg accttgtgca gttcctgtgc aggtaaccac   26100
agctgcagtg ggttcatgaa cacgacagtc atgccatgtc tagaagactt caaaacactc   26160
ttccacatct tctggctctc acattctttc tgccctgtct tctgcatttg ctgaaccttg   26220
aaggggctta attctgtttt ttactgaatc ataattttttg ccaccaaaga agctcaatat   26280
cattgctacc cttgatttct ataaacattc tacccaacat tgggccacat ctccagatag   26340
gacaggggcc aagaatgccc aggtaagaag tgtgtttccc tcccacaggc cttcagtgga   26400
actggtttcc tctcttggtg aagaaatcta aaagtcctcc taagtctgaa ttctactgga   26460
ggcgtagaag gccagcatcg tcccaggtac cctatcattt acaacactat ggccctcagc   26520
ccctttcttt cttgccccctt attttgttct tcagcaacaa gagggagttt gaaaatgtgg   26580
agattacgca ctaagggaaa ctgaggccaa aggaatttga acaacttgcc tgttaaatta   26640
atttgtctct cagggttcag aggcagagtt agaaagcaca cttcctggat cctggcagac   26700
ttcctggatc ctggctcaca tccactttgt tctctgcttg cagaggaagc tgctaagcag   26760
cctttccctg tctcaggaag accatagcat ttccaacccc ttcccagcca tctcccatgg   26820
agggccacac tgcaaaagga cccagccttt ggacaccgga ggagtagaac attttcctag   26880
agcaggttca cagaagcgtg gaggtaggtg cgaggagcaa caagctggtg gtctcagcct   26940
tgcctgagcc agtctctgag tcgtccttct ccctaggacc tgaattctcc tttgatttgc   27000
tgcctgaggc acaggctatt cgggtgacta ttcctccagg cccagaggct agtgtgcgtc   27060
tttgttacca gtgggcactg gaatgtgaag acatgagcag tccttttgat acccaggtat   27120
ggagttccat gccttgcaaa gagacagatt acacaatttc tcagcaaatg ggatggggtg   27180 gggggggttgg ggcccagaca aggaaagtaa ttgtccaaaa cttccttaca aaatgagata   27240
agtagcatta aaaacttgtt gggggcgggg gaggactaga tagaaaagat ggtgggctat   27300
gttacttgag aagagagacc agaaagaaat gagaatggta tgtattgcca gggagaggac   27360
tcttggtgtg attcgggtca aattaagaga ctttgctaag ggctggggac atacccgttg   27420
gtagaatgtt tacctagcat gcttgatctc tggcactgca cagatggagt gggaggtgga   27480
agcaggagaa tcagaagttc aaagtcttcc ttagatatat aatgagtctg aggtctgttt   27540
ggagtacgtg agtcttaaga gaaaaaaaaa aaaaagctt tgttatttcc tcaggaggtt   27600
gttccctgaa aatttgacaa aactgtcata tgtgtcttgg tacttttccc tttcataccct   27660 tttgtctagc cctcagaaat gatattcccc agtctcacaa tccaggtctt gacagcctac   27720
tttaactgcc actcctcaca gatgccattg tatgtagctg gcatcacat gcagagactg   27780 gagtccttca gcttgcttca tgtctacaat ggctatacct tctaacaata ccagccttta   27840
```

```
gtagaattga tgcttctaat actgcatggc atacagctgg aactcaagaa atgtatcgcc   27900
tcttccctaa ccctactgct tgtagagtac ctcaagaaaa tggccaggat atagaaccta   27960
tgagagggag aaataagttc catggagtag gaaagtaagg tatattgtcc aaggtcccgg   28020
cttcatcctg ccttgtccat agtgtccatg cttttcctta ggtgtctctt tttctttccc   28080
tttgtggttt tatcaacaga aaattgtgtc cgggggccac actgtagacc tgccttatga   28140
attcctcctg ccctgcatgt gtatagaggt gagcacaggg aaatgtggat tagccatggc   28200
tccttgtcca accgcatctc cagtaagtca acttagaaag gactcgggaa ggatggagat   28260
gacttggtga tagagcaggc cgtacacact aaggagagac tccaaaaaaa ccgggctact   28320
gggatgctta ggaagctggt gctggctagg ctatgagcca caccagaggt ggaagggtcc   28380
taggcaattc cacctcagcc ctgcctggat gctgtcttct ctggtccaga tttggcttca   28440
gctcacagac acagagtaga cagccatcat cgctgtgttc ttgagagcca aggttgcata   28500
tccctctcaa agtcatgttc tttccaaccc tccatttctc cttgtaagtc tgaagataaa   28560
gatgttttgg acattttag ggggaagaca ggtactaaaa gaagggtatg gacagagacc   28620
tgggaaacaa gaagctgaca gaggagacaa ccagtggact ggactcgtag ggagtccaga   28680
gtgaggagtc aacacagggt actgggtact tgagaaagtc aacaatggag ctcagagagc   28740
ctaaaattga gtgatgcaac ctcgggaatt ctctgctgct gggaacagtt ctttggagac   28800
aggaggggtc atccctctc atttgccact ccctcctatg ctctggaacc ccaacactta   28860
cacacactcc acagtgctgc ccattattgt ctgacagctc aagctgtttg atgacagtaa   28920
gccagagcca gaatgaagat gttaggaaag ccatttctaa caaacactct ctatgctccc   28980
caggcctcct acctgcaaga ggacaccgtg agatgcaaaa agtgtccctt ccagagctgg   29040
cctgaagcct gtgagtgttg tttgtattaa tcccgatgca cattcatact cccctgctg   29100 tgtgtgtgtg tgtgtgtgtg tgtgtgtgtg tgtgtgtgtg tgtgtgtgtg atggaggaag   29160
accccagatg gcaggaggac attttcttca ggagccaggg gaagatgcca cagctgtcag   29220
ccaacagatg agctcctgag tgctgaacat tatgaatgga aaaggatcgc ccagcgagtg   29280
tgtgagaggg ccaactgtag acctaggctc acttctcagt tctgccatag gttatcccca   29340
tagcccctcc cctttccctc atctgtaaaa tcccaaactg tttttgaggc ttgaatgaaa   29400
tattttaggg gaaagtggct ggtgttgtct ggagtgctgt atgtagaatg gtgaccttga   29460
ggagagagga cacttagaca caagtaacaa agtctaacgt acataggcag ggttatcatc   29520
aagggtatca gcccaggaca ggagaagccc agagacactg ttgtgagcag agagggtgtc   29580
acaggatggc acttgactga gctcaggaac tggacaggaa ttagaaagaa gaagcagggg   29640
gaagacagac tctgtgagga gcctacacag attctggata caggcgacag taagggctgt   29700
tcagtgtgga ggcctggatg gaaaggtaaa gccaaggaag ctgggtagaa agggagggag   29760
cgtggagtgc ttgcctgttg aggacctgtg aagcctggaa ttgtgctgga acattggtat   29820
tttctcctgg tgtcctgggg tggggtgggg agatggagtt acagctgggc tatggcctca   29880
ctcttgcacc tgccacctgc ccagatggct cggacttctg gaagtcagta cacttcactg   29940
actacagcca gaacaaccag atggtcatgg ctgtgacact                         29980
```

<210> SEQ ID NO 6
<211> LENGTH: 47
<212> TYPE: DNA
<213> ORGANISM: Cricetulus griseus
<220> FEATURE:
<221> NAME/KEY: misc_feature

```
<222> LOCATION: (1)..(47)
<223> OTHER INFORMATION: consensus sequence of group 1 ERVs

<400> SEQUENCE: 6
gcccccgcca tatccgccac tgccgccccc accagaggca gaagcgg                47

<210> SEQ ID NO 7
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: Myr2 5'-3 target site

<400> SEQUENCE: 7
tcctaagcct agaaactatg                                              20

<210> SEQ ID NO 8
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: Myr4 5'-3 target site

<400> SEQUENCE: 8
catagtttct aggcttagga                                              20

<210> SEQ ID NO 9
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: Myr8 5'-3 target site

<400> SEQUENCE: 9
gagtgttagg gacaaaggag                                              20

<210> SEQ ID NO 10
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: PPYP5 5'-3 target site

<400> SEQUENCE: 10
gttggttgat ctattaacgg                                              20

<210> SEQ ID NO 11
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: PYPP6 5'-3 target site

<400> SEQUENCE: 11
gccactgccg cccccaccag                                              20

<210> SEQ ID NO 12
```

```
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: PPYP7 5'-3 target site

<400> SEQUENCE: 12
gcccccacca gaggcagaag                                                 20

<210> SEQ ID NO 13
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: PPYP13 5'-3 target site

<400> SEQUENCE: 13
ggcagtggcg gatatggcgg                                                 20

<210> SEQ ID NO 14
<211> LENGTH: 20
<212> TYPE: DNA
<213> ORGANISM: Cricetulus griseus
<220> FEATURE:
<221> NAME/KEY: misc_feature
<222> LOCATION: (1)..(20)
<223> OTHER INFORMATION: PPYP20 5'-3 target site

<400> SEQUENCE: 14
gcttctgcct ctggtggggg                                                 20

<210> SEQ ID NO 15
<211> LENGTH: 21
<212> TYPE: DNA
<213> ORGANISM: Artificial Sequence
<220> FEATURE:
<223> OTHER INFORMATION: modified Myr2 target sequence

<400> SEQUENCE: 15
gtcctaagcc tagaaactat g                                               21

<210> SEQ ID NO 16
<211> LENGTH: 27
<212> TYPE: DNA
<213> ORGANISM: Artificial Sequence
<220> FEATURE:
<223> OTHER INFORMATION: Myr2 primer 1

<400> SEQUENCE: 16
acaccgtcct aagcctagaa actatgg                                         27

<210> SEQ ID NO 17
<211> LENGTH: 27
<212> TYPE: DNA
<213> ORGANISM: Artificial Sequence
<220> FEATURE:
<223> OTHER INFORMATION: Myr2 primer 2

<400> SEQUENCE: 17
aaaaccatag tttctaggct taggacg                                         27

<210> SEQ ID NO 18
<211> LENGTH: 21
```

```
<212> TYPE: DNA
<213> ORGANISM: Artificial Sequence
<220> FEATURE:
<223> OTHER INFORMATION: modified Myr4 5' 3' target sequence

<400> SEQUENCE: 18
gcatagtttc taggcttagg a                                              21

<210> SEQ ID NO 19
<211> LENGTH: 27
<212> TYPE: DNA
<213> ORGANISM: Artificial Sequence
<220> FEATURE:
<223> OTHER INFORMATION: Myr4 primer 1

<400> SEQUENCE: 19
acaccgcata gtttctaggc ttaggag                                        27

<210> SEQ ID NO 20
<211> LENGTH: 27
<212> TYPE: DNA
<213> ORGANISM: Artificial Sequence
<220> FEATURE:
<223> OTHER INFORMATION: Myr4 primer 2

<400> SEQUENCE: 20
aaaactccta agcctagaaa ctatgcg                                        27

<210> SEQ ID NO 21
<211> LENGTH: 26
<212> TYPE: DNA
<213> ORGANISM: Artificial Sequence
<220> FEATURE:
<223> OTHER INFORMATION: Myr8 primer 1

<400> SEQUENCE: 21
acaccgagtg ttagggacaa aggagg                                         26

<210> SEQ ID NO 22
<211> LENGTH: 26
<212> TYPE: DNA
<213> ORGANISM: Artificial Sequence
<220> FEATURE:
<223> OTHER INFORMATION: Myr8 primer 2

<400> SEQUENCE: 22
aaaacctcct ttgtccctaa cactcg                                         26

<210> SEQ ID NO 23
<211> LENGTH: 26
<212> TYPE: DNA
<213> ORGANISM: Artificial Sequence
<220> FEATURE:
<223> OTHER INFORMATION: PPYP5 primer 1

<400> SEQUENCE: 23
acaccgttgg ttgatctatt aacggg                                         26

<210> SEQ ID NO 24
<211> LENGTH: 26
<212> TYPE: DNA
<213> ORGANISM: Artificial Sequence
<220> FEATURE:
<223> OTHER INFORMATION: PPYP5 primer 2

<400> SEQUENCE: 24
```
aaaacccgtt aatagatcaa ccaacg                                              26

<210> SEQ ID NO 25
<211> LENGTH: 26
<212> TYPE: DNA
<213> ORGANISM: Artificial Sequence
<220> FEATURE:
<223> OTHER INFORMATION: PPYP6 primer 1

<400> SEQUENCE: 25
acaccgccac tgccgccccc accagg                                              26

<210> SEQ ID NO 26
<211> LENGTH: 26
<212> TYPE: DNA
<213> ORGANISM: Artificial Sequence
<220> FEATURE:
<223> OTHER INFORMATION: PPYP6 primer 2

<400> SEQUENCE: 26
aaaacctggt gggggcggca gtggcg                                              26

<210> SEQ ID NO 27
<211> LENGTH: 26
<212> TYPE: DNA
<213> ORGANISM: Artificial Sequence
<220> FEATURE:
<223> OTHER INFORMATION: PPYP7 primer 1

<400> SEQUENCE: 27
acaccgcccc caccagaggc agaagg                                              26

<210> SEQ ID NO 28
<211> LENGTH: 26
<212> TYPE: DNA
<213> ORGANISM: Artificial Sequence
<220> FEATURE:
<223> OTHER INFORMATION: PPYP7 primer 2

<400> SEQUENCE: 28
aaaaccttct gcctctggtg ggggcg                                              26

<210> SEQ ID NO 29
<211> LENGTH: 26
<212> TYPE: DNA
<213> ORGANISM: Artificial Sequence
<220> FEATURE:
<223> OTHER INFORMATION: PPYP13 primer 1

<400> SEQUENCE: 29
acaccggcag tggcggatat ggcggg                                              26

<210> SEQ ID NO 30
<211> LENGTH: 26
<212> TYPE: DNA
<213> ORGANISM: Artificial Sequence
<220> FEATURE:
<223> OTHER INFORMATION: PPYP13 primer 2

<400> SEQUENCE: 30
aaaacccgcc atatccgcca ctgccg                                              26

<210> SEQ ID NO 31
<211> LENGTH: 26
<212> TYPE: DNA
<213> ORGANISM: Artificial Sequence

```
<220> FEATURE:
<223> OTHER INFORMATION: PPYP20 primer 1

<400> SEQUENCE: 31
acaccgcttc tgcctctggt gggggg                                          26

<210> SEQ ID NO 32
<211> LENGTH: 26
<212> TYPE: DNA
<213> ORGANISM: Artificial Sequence
<220> FEATURE:
<223> OTHER INFORMATION: PPYP20 primer 2

<400> SEQUENCE: 32
aaaacccccc accagaggca gaagcg                                          26

<210> SEQ ID NO 33
<211> LENGTH: 55
<212> TYPE: DNA
<213> ORGANISM: Artificial Sequence
<220> FEATURE:
<223> OTHER INFORMATION: Myr_Fa_3 forward primer

<400> SEQUENCE: 33
tcgtcggcag cgtcagatgt gtataagaga cagaccgctt gaaggatttg caatc          55

<210> SEQ ID NO 34
<211> LENGTH: 52
<212> TYPE: DNA
<213> ORGANISM: Artificial Sequence
<220> FEATURE:
<223> OTHER INFORMATION: Myr_Fb_0 forward primer

<400> SEQUENCE: 34
tcgtcggcag cgtcagatgt gtataagaga caggcttgag ggatttgcaa tc             52

<210> SEQ ID NO 35
<211> LENGTH: 53
<212> TYPE: DNA
<213> ORGANISM: Artificial Sequence
<220> FEATURE:
<223> OTHER INFORMATION: Myr_Fb_1 forward primer

<400> SEQUENCE: 35
tcgtcggcag cgtcagatgt gtataagaga cagtgcttga gggatttgca atc            53

<210> SEQ ID NO 36
<211> LENGTH: 54
<212> TYPE: DNA
<213> ORGANISM: Artificial Sequence
<220> FEATURE:
<223> OTHER INFORMATION: Myr_Fb_2 forward primer

<400> SEQUENCE: 36
tcgtcggcag cgtcagatgt gtataagaga cagttgcttg agggatttgc aatc           54

<210> SEQ ID NO 37
<211> LENGTH: 55
<212> TYPE: DNA
<213> ORGANISM: Artificial Sequence
<220> FEATURE:
<223> OTHER INFORMATION: Myr_Fb_3 forward primer

<400> SEQUENCE: 37
tcgtcggcag cgtcagatgt gtataagaga cagactgctt gagggatttg caatc          55
```

<210> SEQ ID NO 38
<211> LENGTH: 54
<212> TYPE: DNA
<213> ORGANISM: Artificial Sequence
<220> FEATURE:
<223> OTHER INFORMATION: Myr_Fc_2 forward primer

<400> SEQUENCE: 38
tcgtcggcag cgtcagatgt gtataagaga caggtgcttg agggatttgt aatc    54

<210> SEQ ID NO 39
<211> LENGTH: 55
<212> TYPE: DNA
<213> ORGANISM: Artificial Sequence
<220> FEATURE:
<223> OTHER INFORMATION: Myr_R_0 reverse primer

<400> SEQUENCE: 39
gtctcgtggg ctcggagatg tgtataagag acagacaaag agtaatccat ttgcg    55

<210> SEQ ID NO 40
<211> LENGTH: 56
<212> TYPE: DNA
<213> ORGANISM: Artificial Sequence
<220> FEATURE:
<223> OTHER INFORMATION: Myr_R_1 reverse primer

<400> SEQUENCE: 40
gtctcgtggg ctcggagatg tgtataagag acaggacaaa gagtaatcca tttgcg    56

<210> SEQ ID NO 41
<211> LENGTH: 57
<212> TYPE: DNA
<213> ORGANISM: Artificial Sequence
<220> FEATURE:
<223> OTHER INFORMATION: Myr_R_2 reverse primer

<400> SEQUENCE: 41
gtctcgtggg ctcggagatg tgtataagag acagcgacaa agagtaatcc atttgcg    57

<210> SEQ ID NO 42
<211> LENGTH: 58
<212> TYPE: DNA
<213> ORGANISM: Artificial Sequence
<220> FEATURE:
<223> OTHER INFORMATION: Myr_R_3 reverse primer

<400> SEQUENCE: 42
gtctcgtggg ctcggagatg tgtataagag acagaagaca aagagtaatc catttgcg    58

<210> SEQ ID NO 43
<211> LENGTH: 52
<212> TYPE: DNA
<213> ORGANISM: Artificial Sequence
<220> FEATURE:
<223> OTHER INFORMATION: PPYP_Fa_0 forward primer

<400> SEQUENCE: 43
tcgtcggcag cgtcagatgt gtataagaga cagactccag cctttaccct ac    52

<210> SEQ ID NO 44
<211> LENGTH: 53
<212> TYPE: DNA
<213> ORGANISM: Artificial Sequence
<220> FEATURE:
<223> OTHER INFORMATION: PPYP_Fa_1 forward primer

```
<400> SEQUENCE: 44
tcgtcggcag cgtcagatgt gtataagaga cagaactcca gcctttaccc tac         53

<210> SEQ ID NO 45
<211> LENGTH: 52
<212> TYPE: DNA
<213> ORGANISM: Artificial Sequence
<220> FEATURE:
<223> OTHER INFORMATION: PPYP_Fb_0 forward primer

<400> SEQUENCE: 45
tcgtcggcag cgtcagatgt gtataagaga cagattccaa cctttaccct ac          52

<210> SEQ ID NO 46
<211> LENGTH: 53
<212> TYPE: DNA
<213> ORGANISM: Artificial Sequence
<220> FEATURE:
<223> OTHER INFORMATION: PPYP_Fb_1 forward primer

<400> SEQUENCE: 46
tcgtcggcag cgtcagatgt gtataagaga caggattcca acctttaccc tac         53

<210> SEQ ID NO 47
<211> LENGTH: 54
<212> TYPE: DNA
<213> ORGANISM: Artificial Sequence
<220> FEATURE:
<223> OTHER INFORMATION: PPYP_Fb_2 forward primer

<400> SEQUENCE: 47
tcgtcggcag cgtcagatgt gtataagaga cagtgattcc aacctttacc ctac        54

<210> SEQ ID NO 48
<211> LENGTH: 55
<212> TYPE: DNA
<213> ORGANISM: Artificial Sequence
<220> FEATURE:
<223> OTHER INFORMATION: PPYP_Fb_3 forward primer

<400> SEQUENCE: 48
tcgtcggcag cgtcagatgt gtataagaga cagcttattc caacctttac cctac       55

<210> SEQ ID NO 49
<211> LENGTH: 53
<212> TYPE: DNA
<213> ORGANISM: Artificial Sequence
<220> FEATURE:
<223> OTHER INFORMATION: PPYP_Ra_1 reverse primer

<400> SEQUENCE: 49
gtctcgtggg ctcggagatg tgtataagag acagggtct gatgctgaga atg          53

<210> SEQ ID NO 50
<211> LENGTH: 52
<212> TYPE: DNA
<213> ORGANISM: Artificial Sequence
<220> FEATURE:
<223> OTHER INFORMATION: PPYP_Rb_0 reverse primer

<400> SEQUENCE: 50
gtctcgtggg ctcggagatg tgtataagag acagggtccg atgctgagaa tg          52

<210> SEQ ID NO 51
```

```
<211> LENGTH: 53
<212> TYPE: DNA
<213> ORGANISM: Artificial Sequence
<220> FEATURE:
<223> OTHER INFORMATION: PPYP_Rb_1 reverse primer

<400> SEQUENCE: 51
gtctcgtggg ctcggagatg tgtataagag acagtggtcc gatgctgaga atg        53

<210> SEQ ID NO 52
<211> LENGTH: 54
<212> TYPE: DNA
<213> ORGANISM: Artificial Sequence
<220> FEATURE:
<223> OTHER INFORMATION: PPYP_Rb_2 reverse primer

<400> SEQUENCE: 52
gtctcgtggg ctcggagatg tgtataagag acaggtggtc cgatgctgag aatg       54

<210> SEQ ID NO 53
<211> LENGTH: 55
<212> TYPE: DNA
<213> ORGANISM: Artificial Sequence
<220> FEATURE:
<223> OTHER INFORMATION: PPYP_Rb_3 reverse primer

<400> SEQUENCE: 53
gtctcgtggg ctcggagatg tgtataagag acagaagggt ccgatgctga gaatg      55

<210> SEQ ID NO 54
<211> LENGTH: 23
<212> TYPE: DNA
<213> ORGANISM: Artificial Sequence
<220> FEATURE:
<223> OTHER INFORMATION: PCR  ERV Type 1 validation primer

<400> SEQUENCE: 54
ctctggttct tgcctgctga gct                                         23

<210> SEQ ID NO 55
<211> LENGTH: 22
<212> TYPE: DNA
<213> ORGANISM: Artificial Sequence
<220> FEATURE:
<223> OTHER INFORMATION: PCR  ERV Type 1 validation primer

<400> SEQUENCE: 55
tggtcaatgt atatgaggcg ct                                          22

<210> SEQ ID NO 56
<211> LENGTH: 22
<212> TYPE: DNA
<213> ORGANISM: Artificial Sequence
<220> FEATURE:
<223> OTHER INFORMATION: qPCR Type1 ERV specific LTR primer

<400> SEQUENCE: 56
gggaattgag tctgctgtac ca                                          22

<210> SEQ ID NO 57
<211> LENGTH: 22
<212> TYPE: DNA
<213> ORGANISM: Artificial Sequence
<220> FEATURE:
<223> OTHER INFORMATION: qPCR Type1 ERV specific LTR primer

<400> SEQUENCE: 57
```
acagagtctt tcaaatgagg cg                                                  22

<210> SEQ ID NO 58
<211> LENGTH: 22
<212> TYPE: DNA
<213> ORGANISM: Artificial Sequence
<220> FEATURE:
<223> OTHER INFORMATION: qPCR reference GAPDH primer 1

<400> SEQUENCE: 58
gcgacttcaa cagtgactcc ca                                                  22

<210> SEQ ID NO 59
<211> LENGTH: 22
<212> TYPE: DNA
<213> ORGANISM: Artificial Sequence
<220> FEATURE:
<223> OTHER INFORMATION: qPCR reference GAPDH primer 2

<400> SEQUENCE: 59
tgaggtccac cactctgttg ct                                                  22

<210> SEQ ID NO 60
<211> LENGTH: 22
<212> TYPE: DNA
<213> ORGANISM: Artificial Sequence
<220> FEATURE:
<223> OTHER INFORMATION: qPCR Type 2 ERV specific primer 1

<400> SEQUENCE: 60
gaataaaagg tcagggcgtt gg                                                  22

<210> SEQ ID NO 61
<211> LENGTH: 22
<212> TYPE: DNA
<213> ORGANISM: Artificial Sequence
<220> FEATURE:
<223> OTHER INFORMATION: qPCR Type 2 ERV specific primer 2

<400> SEQUENCE: 61
ctgacttggc tctatcttgg gt                                                  22

<210> SEQ ID NO 62
<211> LENGTH: 20
<212> TYPE: DNA
<213> ORGANISM: Artificial Sequence
<220> FEATURE:
<223> OTHER INFORMATION: qPCR Type 1 ERV specific Gag primer 1

<400> SEQUENCE: 62
tgacgatata agccacttga                                                     20

<210> SEQ ID NO 63
<211> LENGTH: 23
<212> TYPE: DNA
<213> ORGANISM: Artificial Sequence
<220> FEATURE:
<223> OTHER INFORMATION: qPCR Type 1 ERV specific Gag primer 2

<400> SEQUENCE: 63
acccccagac tatattccag ata                                                 23

<210> SEQ ID NO 64
<211> LENGTH: 20
<212> TYPE: DNA

```
<213> ORGANISM: Artificial Sequence
<220> FEATURE:
<223> OTHER INFORMATION: qPCR Type1 ERV specific Env primer 1

<400> SEQUENCE: 64
ctatgtgctg ccctcaagga                                              20

<210> SEQ ID NO 65
<211> LENGTH: 20
<212> TYPE: DNA
<213> ORGANISM: Artificial Sequence
<220> FEATURE:
<223> OTHER INFORMATION: qPCR Type1 ERV specific Env primer 2

<400> SEQUENCE: 65
gcctctccct aagtttggcc                                              20

<210> SEQ ID NO 66
<211> LENGTH: 21
<212> TYPE: DNA
<213> ORGANISM: Artificial Sequence
<220> FEATURE:
<223> OTHER INFORMATION: PCR locus ERV Type 1 validation 2 primer

<400> SEQUENCE: 66
taagccattg gtgaagggtc a                                            21

<210> SEQ ID NO 67
<211> LENGTH: 23
<212> TYPE: DNA
<213> ORGANISM: Artificial Sequence
<220> FEATURE:
<223> OTHER INFORMATION: PCR locus ERV Type 1 validation 4 primer

<400> SEQUENCE: 67
ttttctggtg ccctcttgcc tgg                                          23

<210> SEQ ID NO 68
<211> LENGTH: 23
<212> TYPE: DNA
<213> ORGANISM: Artificial Sequence
<220> FEATURE:
<223> OTHER INFORMATION: PCR locus ERV Type 1 validation primer without
      ERV

<400> SEQUENCE: 68
ttgtggagct gtgtgagtgg tgg                                          23

<210> SEQ ID NO 69
<211> LENGTH: 63
<212> TYPE: DNA
<213> ORGANISM: Cricetulus griseus
<220> FEATURE:
<221> NAME/KEY: misc_feature
<222> LOCATION: (1)..(2)
<223> OTHER INFORMATION: genomic Myr2 sgRNA target sequence

<400> SEQUENCE: 69
ctgtcatttg tgccctccta agcctagaaa ctatggggca aactgtcacc actcctttgt   60
ccc                                                                63

<210> SEQ ID NO 70
<211> LENGTH: 64
<212> TYPE: DNA
<213> ORGANISM: Artificial Sequence
<220> FEATURE:
```

<223> OTHER INFORMATION: cloned sequence of Myr2 mutated mRNA juction

<400> SEQUENCE: 70
ctgtcatttg tgccctccta agcctagaaa cttatggggc aaactgtcac cactcctttg    60
tccc    64

<210> SEQ ID NO 71
<211> LENGTH: 51
<212> TYPE: DNA
<213> ORGANISM: Artificial Sequence
<220> FEATURE:
<223> OTHER INFORMATION: cloned sequence of Myr2 mutated mRNA junction

<400> SEQUENCE: 71
ctgtcatttg tgccctccta agcctagaaa ctgtcaccac tcctttgtcc c    51

<210> SEQ ID NO 72
<211> LENGTH: 222
<212> TYPE: DNA
<213> ORGANISM: Cricetulus griseus
<220> FEATURE:
<221> NAME/KEY: misc_feature
<222> LOCATION: (1)..(222)
<223> OTHER INFORMATION: genomic PPYP6 sgRNA target sequence

<400> SEQUENCE: 72
cctttgattc ctcccaaccc cccttcccat tccaaccttt accctaccgt gatgaaagac    60
actaaggcta aagaaaagaa gacacctaag gtactccctc cgggagaaga ccagttggtt    120
gatctattaa cggaggagcc cccgccatat ccgccatgcc gccccacca gaggcagaag    180 cggactccgc cgctgccttg gcggaagcgg ccctgaccc tt    222

<210> SEQ ID NO 73
<211> LENGTH: 168
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 73
cctttgattc ctcccaaccc cccttcccat tccaaccttt accctaccgt gatgaaagac    60
actaaggcta aagaaaagaa gacacctaag gtactccctc cgggagaaga ccccccgcca    120
tatccgccat atccgccgct gccttggcgg aagcggcccc tgacccctt    168

<210> SEQ ID NO 74
<211> LENGTH: 64
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic PPYP6 sgRNA target sequence

<400> SEQUENCE: 74
gcccccgcca tatccgccac tgccgccccc accagaggca gaagcggact ccgccgctgc    60
cttg    64

<210> SEQ ID NO 75
<211> LENGTH: 65
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 75
gcccccgcca tatccgccac tgccgccccc acccagaggc agaagcggac tccgccgctg    60
ccttg    65

<210> SEQ ID NO 76
<211> LENGTH: 117
<212> TYPE: DNA
<213> ORGANISM: Cricetulus griseus
<220> FEATURE:
<221> NAME/KEY: misc_feature
<222> LOCATION: (1)..(117)
<223> OTHER INFORMATION: genomic PPYP6 sgRNA target sequence

<400> SEQUENCE: 76
tccgggagaa gaccagttgg ttgatctatt aacggaggag cccccgccat atccgccact    60
gccgccccca ccagaggcag aagcggactc cgccgctgcc ttggcggaag cggcccc      117

<210> SEQ ID NO 77
<211> LENGTH: 113
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 77
tccgggagaa gaccagttgg ttgatctatt aacggaggag cccccgccat atccgccact    60
gccgccccag aggcagaagc ggactccgcc gctgccttgg cggaagcggc ccc          113

<210> SEQ ID NO 78
<211> LENGTH: 382
<212> TYPE: DNA
<213> ORGANISM: Cricetulus griseus
<220> FEATURE:
<221> NAME/KEY: misc_feature
<222> LOCATION: (1)..(382)
<223> OTHER INFORMATION: genomic PPYP6 sgRNA target sequence

<400> SEQUENCE: 78
atggatcctg gaccacacgg gcatcccgat caagtggctt atatcgtcac ttgggaggct    60
ttggttcagg accccctcc ctgggtacgt cctttcttac atcccaaggg cccctctctc   120 cttccccct ctaaccgctc caaccgaccc attccttcgg ccccctacacc tcccactcct  180 ttgattcctc ccaaccccccc ttcccattcc aaccttttacc ctaccgtgat gaaagacact   240
aaggctaaag aaaagaagac acctaaggta ctccctccgg gagaagacca gttggttgat   300
ctattaacgg aggagccccc gccatatccg ccactgccgc ccccaccaga ggcagaagcg   360
gactccgccg ctgccttggc gg                                            382

<210> SEQ ID NO 79
<211> LENGTH: 399
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 79
atggatcctg gaccacacgg gcatcccgat caagtggctt atatcgtcac ttgggaggct    60
ttggttcagg accccctcc ctgggtacgt cctttcttac atcccaaggg cccctctctc   120 cttccccct ctaaccgctc caaccgaccc attccttcgg ccccctacacc tcccactcct  180

```
ttgattcctc caacccccc ttcccattcc aacctttacc ctaccgtgat gaaagacact    240
aaggctaaag aaaagaagac acctaaggta ctccctccgg gagaagacca gttggttgat    300
ctattaacgg aggagccccc gccatatccg ccactgccgc ccccaagtga cgatataagc    360
cacttgatcg ggatgcggac tccgccgctg ccttggcgg                           399
```

<210> SEQ ID NO 80
<211> LENGTH: 110
<212> TYPE: DNA
<213> ORGANISM: Cricetulus griseus
<220> FEATURE:
<221> NAME/KEY: misc_feature
<222> LOCATION: (1)..(110)
<223> OTHER INFORMATION: genomic PPYP13 sgRNA target sequence

<400> SEQUENCE: 80

```
ttaacggagg agcccccgcc atatccgcca ctgccgcccc caccagaggc agaagcggac     60
tccgccgctg ccttggcgga agcggcccct gacccttcac caatggctta               110
```

<210> SEQ ID NO 81
<211> LENGTH: 122
<212> TYPE: DNA
<213> ORGANISM: Artificial Sequence
<220> FEATURE:
<223> OTHER INFORMATION: cloned sequence of PPYP13 mutated mRNA junction

<400> SEQUENCE: 81

```
ttaacggagg agcccccgcc atatccgcca ctgccgcccc caccagaggc agaagcggac     60
tccgccgctg ccttggcgga agcggcccca gatccaccac ctgacccttc accaatggct    120
ta                                                                   122
```

<210> SEQ ID NO 82
<211> LENGTH: 81
<212> TYPE: DNA
<213> ORGANISM: Cricetulus griseus
<220> FEATURE:
<221> NAME/KEY: misc_feature
<222> LOCATION: (1)..(81)
<223> OTHER INFORMATION: genomic Myr2 sgRNA target sequence

<400> SEQUENCE: 82

```
tgtcatttgt gccctcctaa gcctagaaac tatggggcaa actgtcacca ctcctttgtc     60
cctaacactc tcccactgga a                                               81
```

<210> SEQ ID NO 83
<211> LENGTH: 79
<212> TYPE: DNA
<213> ORGANISM: Artificial Sequence
<220> FEATURE:
<223> OTHER INFORMATION: cloned sequence of Myr2 mutated mRNA junction

<400> SEQUENCE: 83

```
tgtcatttgt gccctcctaa gcctagaaac tggggcaaac tgtcaccact cctttgtccc     60
taacactctc ccactggaa                                                  79
```

<210> SEQ ID NO 84
<211> LENGTH: 53
<212> TYPE: DNA
<213> ORGANISM: Cricetulus griseus
<220> FEATURE:
<221> NAME/KEY: misc_feature
<222> LOCATION: (1)..(53)
<223> OTHER INFORMATION: 5' and 3' end of genomic Myr2 sgRNA target

```
      sequence
<220> FEATURE:
<221> NAME/KEY: misc_feature
<222> LOCATION: (18)..(19)
<223> OTHER INFORMATION: site of 75 bp additon in Myr2 sgRNA target
      sequence

<400> SEQUENCE: 84
cgactctctc tcaattcctg aaactatggg gcaaactgtc accactcctt tgt            53

<210> SEQ ID NO 85
<211> LENGTH: 33
<212> TYPE: DNA
<213> ORGANISM: Artificial Sequence
<220> FEATURE:
<223> OTHER INFORMATION: cloned sequence of Myr2 mutated mRNA junction

<400> SEQUENCE: 85
cgactctctc tcaaactgtc accactcctt tgt                                  33

<210> SEQ ID NO 86
<211> LENGTH: 127
<212> TYPE: DNA
<213> ORGANISM: Cricetulus griseus
<220> FEATURE:
<221> NAME/KEY: misc_feature
<222> LOCATION: (1)..(127)
<223> OTHER INFORMATION: genomic Myr2 sgRNA target sequence

<400> SEQUENCE: 86
tctttgtctt gtagctgtca tttgtgccct cctaagccta gaaactatgg ggcaaactgt     60
caccactcct ttgtccctaa cactctccca ctggaaagat gtacaggaat atgctcataa    120
ccaatct                                                              127

<210> SEQ ID NO 87
<211> LENGTH: 100
<212> TYPE: DNA
<213> ORGANISM: Artificial Sequence
<220> FEATURE:
<223> OTHER INFORMATION: cloned sequence of Myr2 mutated mRNA junction

<400> SEQUENCE: 87
tctttgtctt gtagctgtca tggggcaaac tgtcaccact cctttgtccc taacactctc     60
ccactggaaa gatgtacagg aatatgctca taaccaatct                          100

<210> SEQ ID NO 88
<211> LENGTH: 65
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic Myr2 sgRNA target sequence

<400> SEQUENCE: 88
agctgtcatt tgtgccctcc taagcctaga aactatgggg caaactgtca ccactccttt     60
gtccc                                                                65

<210> SEQ ID NO 89
<211> LENGTH: 62
<212> TYPE: DNA
<213> ORGANISM: Artificial Sequence
<220> FEATURE:
<223> OTHER INFORMATION: cloned sequence of Myr2 mutated mRNA junction
```

```
<400> SEQUENCE: 89
agctgtcatt tgtgccctcc taagcctaga tatggggcaa actgtcacca ctcctttgtc    60
cc                                                                   62

<210> SEQ ID NO 90
<211> LENGTH: 41
<212> TYPE: DNA
<213> ORGANISM: Cricetulus griseus
<220> FEATURE:
<221> NAME/KEY: misc_feature
<222> LOCATION: (1)..(41)
<223> OTHER INFORMATION: genomic Myr2 sgRNA target sequence

<400> SEQUENCE: 90
ctcctaagcc tagaaactat ggggcaaact gtcaccactc c                        41

<210> SEQ ID NO 91
<211> LENGTH: 42
<212> TYPE: DNA
<213> ORGANISM: Artificial Sequence
<220> FEATURE:
<223> OTHER INFORMATION: cloned sequence of Myr2 mutated mRNA junction

<400> SEQUENCE: 91
ctcctaagcc tagaaactta tggggcaaac tgtcaccact cc                       42

<210> SEQ ID NO 92
<211> LENGTH: 71
<212> TYPE: DNA
<213> ORGANISM: Cricetulus griseus
<220> FEATURE:
<221> NAME/KEY: misc_feature
<222> LOCATION: (1)..(71)
<223> OTHER INFORMATION: genomic PPYP6 sgRNA target sequence

<400> SEQUENCE: 92
cccccgccat atccgccact gccgccccca ccagaggcag aagcggactc cgccgctgcc    60
ttggcggaag c                                                         71

<210> SEQ ID NO 93
<211> LENGTH: 61
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 93
cccccgccat atccgccact gccgccccac tgcttctgtc cgccgctgcc ttggcggaag    60
c                                                                    61

<210> SEQ ID NO 94
<211> LENGTH: 65
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic PPYP6 sgRNA target sequence

<400> SEQUENCE: 94
cccccgccat atccgccact gccgccccca ccagaggcag aagcggactc cgccgctgcc    60
ttggc                                                                65
```

```
<210> SEQ ID NO 95
<211> LENGTH: 58
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 95
cccccgccat atccgccact gccgccccca cagaagcgga ctccgccgct gccttggc      58

<210> SEQ ID NO 96
<211> LENGTH: 66
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 96
cccccgccat atccgccact gccgccccca cccagaggca gaagcggact ccgccgctgc    60
cttggc                                                                66

<210> SEQ ID NO 97
<211> LENGTH: 91
<212> TYPE: DNA
<213> ORGANISM: Cricetulus griseus
<220> FEATURE:
<221> NAME/KEY: misc_feature
<222> LOCATION: (1)..(91)
<223> OTHER INFORMATION: genomic PPYP6 sgRNA target sequence

<400> SEQUENCE: 97
ggagaagacc agttggttga tctattaacg gaggagcccc ccgccatatc cgccactgcc    60
gcccccacca gaggcagaag cggactccgc c                                    91

<210> SEQ ID NO 98
<211> LENGTH: 82
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 98
ggagaagacc agttggttga tctattaacg gaggagcccc ccgccatatc cgccactgcc    60
gcccccagaa gcggactccg cc                                              82

<210> SEQ ID NO 99
<211> LENGTH: 65
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic PPYP6 sgRNA target sequence

<400> SEQUENCE: 99 agccccgcc atatccgcca ctgccgcccc caccagaggc agaagcggac tccgccgctg     60
ccttg                                                                 65

<210> SEQ ID NO 100
<211> LENGTH: 28
<212> TYPE: DNA
<213> ORGANISM: Artificial Sequence
<220> FEATURE:
<223> OTHER INFORMATION: cloned sequence of PPYP6 mutated mRNA junction
```

```
<400> SEQUENCE: 100
agcccccgcc atatccgccg ctgccttg                                        28

<210> SEQ ID NO 101
<211> LENGTH: 65
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic PPYP6 sgRNA target sequence

<400> SEQUENCE: 101
cccccgccat atccgccact gccgccccca ccagaggcag aagcggactc cgccgctgcc    60
ttggc                                                                 65

<210> SEQ ID NO 102
<211> LENGTH: 62
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 102
cccccgccat atccgccact gccgccccca gaggcagaag cggactccgc cgctgccttg    60
gc                                                                    62

<210> SEQ ID NO 103
<211> LENGTH: 73
<212> TYPE: DNA
<213> ORGANISM: Cricetulus griseus
<220> FEATURE:
<221> NAME/KEY: misc_feature
<222> LOCATION: (1)..(73)
<223> OTHER INFORMATION: genomic PPYP6 sgRNA target sequence

<400> SEQUENCE: 103
cccccgccat atccgccact gccgccccca ccagaggcag aagcggactc cgccgctgcc    60
ttggcggaag cgg                                                        73

<210> SEQ ID NO 104
<211> LENGTH: 51
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 104
cccccgccat atccgccact gcggactccg ccgctgcctt ggcggaagcg g              51

<210> SEQ ID NO 105
<211> LENGTH: 60
<212> TYPE: DNA
<213> ORGANISM: Cricetulus griseus
<220> FEATURE:
<221> NAME/KEY: misc_feature
<222> LOCATION: (1)..(60)
<223> OTHER INFORMATION: genomic PPYP6 sgRNA target sequence

<400> SEQUENCE: 105
cccccgccat atccgccact gccgccccca ccagaggcag aagcggactc cgccgctgcc    60

<210> SEQ ID NO 106
<211> LENGTH: 59
```

```
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 106
cccccgccat atccgccact gccgccccca cagaggcaga agcggactcc gccgctgcc        59

<210> SEQ ID NO 107
<211> LENGTH: 65
<212> TYPE: DNA
<213> ORGANISM: Cricetulus griseus
<220> FEATURE:
<221> NAME/KEY: misc_feature
<222> LOCATION: (1)..(65)
<223> OTHER INFORMATION: genomic PPYP6 sgRNA target sequence

<400> SEQUENCE: 107
ttaacggagg agccccgcc atatccgcca ctgccgcccc caccagaggc agaagcggac        60
tccgc                                                                  65

<210> SEQ ID NO 108
<211> LENGTH: 63
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 108
ttaacggagg agccccgcc atatccgcca ctgccgcccc cacaaggcag aagcggactc        60
cgc                                                                    63

<210> SEQ ID NO 109
<211> LENGTH: 90
<212> TYPE: DNA
<213> ORGANISM: Cricetulus griseus
<220> FEATURE:
<221> NAME/KEY: misc_feature
<222> LOCATION: (1)..(90)
<223> OTHER INFORMATION: genomic PPYP6 sgRNA target sequence

<400> SEQUENCE: 109
aggagccccc gccatatccg ccactgccgc ccccaccaga ggcagaagcg gactcccccg        60
ccatatccgc ggaagcggcc cctgaccctt                                        90

<210> SEQ ID NO 110
<211> LENGTH: 77
<212> TYPE: DNA
<213> ORGANISM: Artificial Sequence
<220> FEATURE:
<223> OTHER INFORMATION: cloned sequence of PPYP6 mutated mRNA junction

<400> SEQUENCE: 110
aggagccccc gccatatccg ccactgccgc agaagcggac tccgccgctg ccttggcgga        60
agcggcccct gaccctt                                                     77
```